(12) United States Patent
Taylor et al.

(10) Patent No.: US 10,526,380 B2
(45) Date of Patent: Jan. 7, 2020

(54) FUSION PROTEIN AND NUCLEIC ACID MOLECULE FOR LIGHT-DEPENDENT STRESS GRANULE ASSEMBLY

(71) Applicant: St. Jude Children's Research Hospital, Memphis, TN (US)

(72) Inventors: Joseph Paul Taylor, Memphis, TN (US); Peipei Zhang, Memphis, NC (US)

(73) Assignee: St. Jude Children's Research Hospital, Memphis, TN (US)

( * ) Notice: Subject to any disclaimer, the term of this patent is extended or adjusted under 35 U.S.C. 154(b) by 0 days.

(21) Appl. No.: 15/794,503

(22) Filed: Oct. 26, 2017

(65) Prior Publication Data

US 2019/0127428 A1 May 2, 2019

(51) Int. Cl.
| | |
|---|---|
| *C12N 15/82* | (2006.01) |
| *C07K 14/415* | (2006.01) |
| *C12N 9/14* | (2006.01) |
| *C12N 13/00* | (2006.01) |

(52) U.S. Cl.
CPC .............. *C07K 14/415* (2013.01); *C12N 9/14* (2013.01); *C12N 13/00* (2013.01); *C12Y 306/04012* (2013.01); *C12Y 306/04013* (2013.01); *C07K 2319/00* (2013.01)

(58) Field of Classification Search
None
See application file for complete search history.

(56) References Cited

U.S. PATENT DOCUMENTS

2015/0284439 A1* 10/2015 Heo .................... C07K 14/325
                                                          435/29

FOREIGN PATENT DOCUMENTS

| WO | WO 2011/130540 A1 | 10/2011 | | |
|---|---|---|---|---|
| WO | WO-2011130540 A1 | * 10/2011 | ........... | C07K 14/415 |
| WO | WO-2013115482 A1 | * 8/2013 | ........... | C07K 14/705 |

OTHER PUBLICATIONS

Li et al., Photochemistry and Photobiology, 83:94-101; 2007.*
Xuhong et al., (The Plant Cell; 21:118-130, 2009.*
Aala A. Abulfaraj;PhD Thesis; Investigating the Role of the *Arabidopsis* Homologue of the Human G3BP in RNA Metabolism, Cellular Stress Responses and Innate Immunity; King Abdullah University of Science and Technology; Department Biological and Environmental Sciences and Engineering (BESE) 2018; [Abstract Only].*
Tourri'ere et al. (The Journal of Cell Biology; 160:823-831; Published 2003).*
Aulas et al. (Molecular Neurodegeneration, 7:54, pp. 1-14; Published 2012).*
Shanner et al., Nat. Biotechnol ., 22: 1567-1572, 2004.*
Theologis et al. (GenBank Sequence Accession No. NM_100320; Published 2013).*
Shin et al. "Spatiotemporal Control of Intracellular Phase Transitions Using Light-Activated optoDroplets" Cell 2017 168:1-13.
Tourrière et al. "The RasGAP-associated Endoribonuclease G3BP Assembles Stress Granules" The Journal of Cell Biology 2003 160(6) :823-831.

* cited by examiner

*Primary Examiner* — Vinod Kumar
(74) *Attorney, Agent, or Firm* — Licata & Tyrrell P.C.

(57) ABSTRACT

A nucleic acid molecule encoding a fusion protein composed of a plant cryptochrome at the amino terminus, and a GTPase-Activating Protein SH3 Domain-Binding Protein (G3BP) is provided for light-dependent, G3BP-mediated stress granule formation.

4 Claims, 15 Drawing Sheets

Specification includes a Sequence Listing.

```
P1   MVMEKPSPLLVGREEFVRQYYTLLNQAPDMLHRFYGKNSSYVHGGLDSNGKPADAVYGQKE
P2A  MVMEKPSPLLVGREEFVRQYYTLLNKAPEYLHRFYGRNSSYVHGGVDASGKPQEAVYGQND
P2B  MVMEKPSPLLVGREEFVRQYYTLLNKAPEYLHRFYGRNSSYVHGGVDASGKPQEAVYGQND

P1   IHRKVMSQNFTNCHTKIRHVDAHATLNDGVVVQVMGLLSNNNQALRRFMQTFVLAPEGSV
P2A  IHHKVLSLNFSECHTKIRHVDAHATLSDGVVVQVMGLLSNSGQPERKFMQTFVLAPEGSV
P2B  IHHKVLSLNFSECHTKIRHVDAHATLSDGVVVQVMGLLSNSGQPERKFMQTFVLAPEGSV

P1   ANKFYVHNDIFRYQDEVFGGFVTEPQEESEEVE-EPEERQQTPEVVPDDSGT-FYDQAV
P2A  PNKFYVHNDMFRYEDEVFGDSEPELDEESEDEVEEEQEERQPSPEPVQENANSGYYEAHP
P2B  PNKFYVHNDMFRYEDEVFGDSEPELDEESEDEVEEEQEERQPSPEPVQENANSGYYEAHP

P1   VSNDMEEHLEEPVAEPEPDPEPEPEQEPVSEIQEEKPEPVLEETAPEDAQKSSSPAPADI
P2A  VTNGIEEPLEESSHEPEPEPESETKTEELKPQVEEKNLEELEE------KSTTPPPAEP
P2B  VTNGIEEPLEESSHEPEPEPESETKTEELKPQVEEKNLEELEE------KSTTPPPAEP

P1   AQTVQEDLRTFSWASVTSKNLPPSGAVPVTGIPPHVVKVPASQRPRESKPESQIPPPQRPQ
P2A  VSLPQEPPKAFSWASVTSKNLPPSGTVSSSGIPPHV-KAPVSQPRVEAKPEVQSQPPR-V
P2B  VSLPQEPPK--------------------------PRVEAKPEVQSQPPR-V

P1   RDQRVREQRINIPPQRGPRPIREAGEQGDIEPRRMVRHPDSHQLFIGNLPHEVDKSELKD
P2A  REQRPRE-RPGFPP-RGPRPGRGDMEQNDSDNRRIIRYPDSHQLFVGNLPHDIDENELKE
P2B  REQRPRE-RPGFPP-RGPRPGRGDMEQNDSDNRRIIRYPDSHQLFVGNLPHDIDENELKE
```

FIG. 1A

```
P1   FFQSYGNVVELRLINS---GGKL PNFGFVV FDDSEPVQKVLSNRPIMFRGEVRLNVEEKKT
P2A  FFMSFGNVVELRINTKGVGGKL PNFGFVV FDDSEPVQRILIAKPIMFRGEVRLNVEEKKT
P2B  FFMSFGNVVELRINTKGVGGKL PNFGFVV FDDSEPVQRILIAKPIMFRGEVRLNVEEKKT
                              ***    ***  ***     ***       ***

P1   RAARE------GDRRDNRL--RGPGGPRGGLGGGM------RGPP-RGGMVQKPGFGVG
P2A  RAARERETRGGGDDRRDIRRNDRGPGGPRGIVGGGMMRDRDGRGPPPRGGMAQKLGSGRG
P2B  RAARERETRGGGDDRRDIRRNDRGPGGPRGIVGGGMMRDRDGRGPPPRGGMAQKLGSGRG
     **

P1   RG-----LAPRQ    (SEQ ID NO:1)
P2A  TGQMEGRFTGQRR   (SEQ ID NO:2)
P2B  TGQMEGRFTGQRR   (SEQ ID NO:3)
```

FIG. 1B

| | |
|---|---|
| RAT | MVMEKPSPLLVGREFVRQYYTLLNQAPDMLHRFYGKNSSYAHGGLDSNGKPADAVYGQKE |
| MOUSE | MVMEKPSPLLVGREFVRQYYTLLNQAPDMLHRFYGKNSSYAHGGLDSNGKPADAVYGQKE |
| MONKEY | MVMEKPSPLLVGREFVRQYYTLLNQAPDMLHRFYGKNSSYVHGGLDSNGKPADAVYGQKE |
| HUMAN | MVMEKPSPLLVGREFVRQYYTLLNQAPDMLHRFYGKNSSYVHGGLDSNGKPADAVYGQKE |
| CHIMP | MVMEKPSPLLVGREFVRQYYTLLNQAPDMLHRFYGKNSSYVHGGLDSNGKPADAVYGQKE |
| COW | MVMEKPSPLLVGREFVRQYYTLLNQAPDMLHRFYGKNSSYVHGGLDSNGKPADAVYGQKE |
| DOG | MVMEKPSPLLVGREFVRQYYTLLNQAPDMLHRFYGKNSSYVHGGLDSNGKPADAVYGQKE |
| | **********************************************:******* |
| RAT | IHRKVMSQNFTNCHTKIRHVDAHATLNDGVVVQVMGLLSNNNQALRRFMQTFVLAPEGSV |
| MOUSE | IHRKVMSQNFTNCHTKIRHVDAHATLNDGVVVQVMGLLSNNNQALRRFMQTFVLAPEGSV |
| MONKEY | IHRKVMSQNFTNCHTKIRHVDAHATLNDGVVVQVMGLLSNNNQALRRFMQTFVLAPEGSV |
| HUMAN | IHRKVMSQNFTNCHTKIRHVDAHATLNDGVVVQVMGLLSNNNQALRRFMQTFVLAPEGSV |
| CHIMP | IHRKVMSQNFTNCHTKIRHVDAHATLNDGVVVQVMGLLSNNNQALRRFMQTFVLAPEGSV |
| COW | IHRKVMSQNFTNCHTKIRHVDAHATLNDGVVVQVMGLLSNNNQALRRFMQTFVLAPEGSV |
| DOG | IHRKVMSQNFTNCHTKIRHVDAHATLNDGVVVQVMGLLSNNNQALRRFMQTFVLAPEGSV |
| | ************************************************************ |
| RAT | ANKFYVHNDIFRYQDEVFGGFVTEPQEESEEEVEEPEERQQSPEVVADDSGTFYDQT-VS |
| MOUSE | ANKFYVHNDIFRYQDEVFGGFVTEPQEESEEEVEEPEERQQTPEVVPDDSGTFYDQT-VS |
| MONKEY | ANKFYVHNDIFRYQDEVFGGFVTEPQEESEEEVEEPEERQQTPEVVPDDSGTFYDQAVVS |
| HUMAN | ANKFYVHNDIFRYQDEVFGGFVTEPQEESEEEVEEPEERQQTPEVVPDDSGTFYDQAVVS |
| CHIMP | ANKFYVHNDIFRYQDEVFGGFVTEPQEESEEEVEEPEERQQTPEVVPDDSGTFYDQAVVS |
| COW | ANKFYVHNDIFRYQDEVFGGFITEPQEESEEEVEEPEERQQTPEVVPDDSGTFYDQT-VS |
| DOG | ANKFYVHNDIFRYQDEVFGGFVTEPQEESEEEVEEPEERQQTPEVVPDDSGTFYDQS-VS |
| | ********************:*************************:  |

FIG. 2A

```
RAT     NDLEEHLEEPVVEPEPEPEPEPEPEPEPEPEPVSDIQEDKPEPALEEAAPEDVQKSASPAPADVAP
MOUSE   NDLEEHLEEPVVEPEPEPEPEPEPEPEPEPEPVSDIQEDKPEAALEEAAPDDVQKSTSPAPADVAP
MONKEY  NDMEEHLEEPVAEPEPDPEPEPEPEQEPVSEIQEEKPEPVLEETAPEDTQKSSSPAPADIAQ
HUMAN   NDMEEHLEEPVAEPEPDPEPEPEPEQEPVSEIQEEKPEPVLEETAPEDAQKSSSPAPADIAQ
CHIMP   NDVEEHLEEPVAEPEPDPEPEPEPEQEPVSEIQEEKPEPVLEETAPEDAQKSSSPAPADIAQ
COW     NDLEEHLEEPVAEPEPEPEPEPEPEQEPVSEVQEEKSEPVLEETAPEDVQKSSSPAPADIAQ
DOG     NDLEEHLEEPVAEPEPDPEPEPEPEQEPVSEIQEEKSEPVLEETAPEDTQKSSSPAPTDIAQ
        **:*:******* :**** *******::****** ****:*.****:.*:.:******:***

RAT     -AQEDLRTFSWASVTSKNLPPSGAVPVTGTPPHVVKVPASQPRPESKPDSQIPPQRPQRD
MOUSE   -AQEDLRTFSWASVTSKNLPPSGAVPVTGTPPHVVKVPASQPRPESKPDSQIPPQRPQRD
MONKEY  TVQEDLRTFSWASVTSKNLPPSGAVPVTGIPPHVVKVPASQPRPESKPESQIPPQRPQRD
HUMAN   TVQEDLRTFSWASVTSKNLPPSGAVPVTGIPPHVVKVPASQPRPESKPESQIPPQRPQRD
CHIMP   TVQEDLRTFSWASVTSKNLPPSGAVPVTGIPPHVVKVPASQPRPESKPESQIPPQRPQRD
COW     TVQEDLRTFSWASVTSKNLPPSGAVPVTGIPPHVVKVPASQPRPESKPESQIPLQRPQRD
DOG     TVQEDLRTFSWASVTSKNLPPSGAVPVTGIPPHVVKVPASQPRPESKPESQIPPQRPQRD
         *********************** ********************:****:****

RAT     QRAREQRINIPPQRGPRPIREAGEPGDVEPRRMVRHPDSHQLFIGNLPHEVDKSELKDFF
MOUSE   QRVREQRINIPPQRGPRPIREAGEPGDVEPRRMVRHPDSHQLFIGNLPHEVDKSELKDFF
MONKEY  QRVREQRINIPPQRGPRPIREAGEQGDIEPRRMVRHPDSHQLFIGNLPHEVDKSELKDFF
HUMAN   QRVREQRINIPPQRGPRPIREAGEQGDIEPRRMVRHPDSHQLFIGNLPHEVDKSELKDFF
CHIMP   QRVREQRINIPPQRGPRPIREAGEQGDIEPRRMVRHPDSHQLFIGNLPHEVDKSELKDFF
COW     QRVREQRINVPPQRGPRPVREAGEQGDVEPRRIVRHPDSHQLFIGNLPHEVDKSELKDFF
DOG     QRVREQRINIPPQRGPRPIREAGEQGDVEPRRIVRHPDSHQLFIGNLPHEVDKSELKDFF
        **.******:********:******:**:***:***************************
```

*FIG. 2B*

| | | |
|---|---|---|
| RAT | QSYGNVVELRINSGGKLPNFGFVVFDDSEPVQKVLNNRPIMFRGAVRLNVEEKKTRAARE | |
| MOUSE | QNFGNVVELRINSGGKLPNFGFVVFDDSEPVQKVLNNRPIMFRGAVRLNVEEKKTRAARE | |
| MONKEY | QNYGNVVELRINSGGKLPNFGFVVFDDSEPVQKVLSNRPIMFRGEVRLNVEEKKTRAARE | |
| HUMAN | QSYGNVVELRINSGGKLPNFGFVVFDDSEPVQKVLSNRPIMFRGEVRLNVEEKKTRAARE | |
| CHIMP | QSYGNVVELRINSGGKLPNFGFVVFDDSEPVQKVLSNRPIMFRGEVRLNVEEKKTRAARE | |
| COW | QNYGNVVELRINSGGKLPNFGFVVFDDSEPVQKVLSNRPIMFRGEVRLNVEEKKTRAARE | |
| DOG | QSYGNVVELRINSGGKLPNFGFVVFDDSEPVQKVLSNRPIMFRGEVRLNVEEKKTRAARE | |
| | * :*******************************:*******:******** | |
| RAT | GDRRDNRLRGPGGPRGGPSGGMRGPPRGGMVQKPGFGVGRGITTPRQ | (SEQ ID NO:4) |
| MOUSE | GDRRDNRLRGPGGPRGGPSGGMRGPPRGGMVQKPGFGVGRGITTPRQ | (SEQ ID NO:5) |
| MONKEY | GDRRDNRLRGPGGPRGGLGGMRGPPRGGMVQKPGFGVGRGLAPRQ- | (SEQ ID NO:6) |
| HUMAN | GDRRDNRLRGPGGPRGGLGGMRGPPRGGMVQKPGFGVGRGLAPRQ- | (SEQ ID NO:1) |
| CHIMP | GDRRDNRLRGPGGPRGGLGGMRGPPRGGMVQKPGFGVGRGLAPRQ- | (SEQ ID NO:7) |
| COW | GDRRDNRLRGPGGPRGGLGGMRGPPRGGMVQKPGFGVGRGRSIAPRQ- | (SEQ ID NO:8) |
| DOG | GDRRDNRLRGPGGPRGGLGGMRGPSRGGMVQKPGFGVGRGIAPRQ- | (SEQ ID NO:9) |
| | *************.***.*****************  : | |

*FIG. 2C*

| | |
|---|---|
| MOUSE A | MVMEKPSPLLVGREFVRQYYTLLNKAPEYLHRFYGRNSSYVHGGVDASGKPQEAVYGQND |
| MOUSE B | MVMEKPSPLLVGREFVRQYYTLLNKAPEYLHRFYGRNSSYVHGGVDASGKPQEAVYGQND |
| RAT B | MVMEKPSPLLVGREFVRQYYTLLNKAPEYLHRFYGRNSSYVHGGVDASGKPQEAVYGQND |
| RAT A | MVMEKPSPLLVGREFVRQYYTLLNKAPEYLHRFYGRNSSYVHGGVDASGKPQEAVYGQND |
| COW B | MVMEKPSPLLVGREFVRQYYTLLNKAPEYLHRFYGRNSSYVHGGVDASGKPQEAVYGQND |
| COW A | MVMEKPSPLLVGREFVRQYYTLLNKAPEYLHRFYGRNSSYVHGGVDASGKPQEAVYGQND |
| DOG B | MVMEKPSPLLVGREFVRQYYTLLNKAPEYLHRFYGRNSSYVHGGVDASGKPQEAVYGQND |
| DOG A | MVMEKPSPLLVGREFVRQYYTLLNKAPEYLHRFYGRNSSYVHGGVDASGKPQEAVYGQND |
| MONKEY B | MVMEKPSPLLVGREFVRQYYTLLNKAPEYLHRFYGRNSSYVHGGVDASGKPQEAVYGQND |
| CHIMP B | MVMEKPSPLLVGREFVRQYYTLLNKAPEYLHRFYGRNSSYVHGGVDASGKPQEAVYGQND |
| HUMAN B | MVMEKPSPLLVGREFVRQYYTLLNKAPEYLHRFYGRNSSYVHGGVDASGKPQEAVYGQND |
| HUMAN A | MVMEKPSPLLVGREFVRQYYTLLNKAPEYLHRFYGRNSSYVHGGVDASGKPQEAVYGQND |
| CHIMP A | MVMEKPSPLLVGREFVRQYYTLLNKAPEYLHRFYGRNSSYVHGGVDASGKPQEAVYGQND |
| MONKEY A | MVMEKPSPLLVGREFVRQYYTLLNKAPEYLHRFYGRNSSYVHGGVDASGKPQEAVYGQND |
| | ************************************************************ |

| | |
|---|---|
| MOUSE A | IHHKVLSLNFSECHTKIRHVDAHATLSDGVVVQVMGLLSNSGQPERKFMQTFVLAPEGSV |
| MOUSE B | IHHKVLSLNFSECHTKIRHVDAHATLSDGVVVQVMGLLSNSGQPERKFMQTFVLAPEGSV |
| RAT B | IHHKVLSLNFSECHTKIRHVDAHATLSDGVVVQVMGLLSNSGQPERKFMQTFVLAPEGSV |
| RAT A | IHHKVLSLNFSECHTKIRHVDAHATLSDGVVVQVMGLLSNSGQPERKFMQTFVLAPEGSV |
| COW B | IHHKVLSLNFSECHTKIRHVDAHATLSDGVVVQVMGLLSNSGQPERKFMQTFVLAPEGSV |
| COW A | IHHKVLSLNFSECHTKIRHVDAHATLSDGVVVQVMGLLSNSGQPERKFMQTFVLAPEGSV |
| DOG B | IHHKVLSLNFSECHTKIRHVDAHATLSDGVVVQVMGLLSNSGQPERKFMQTFVLAPEGSV |
| DOG A | IHHKVLSLNFSECHTKIRHVDAHATLSDGVVVQVMGLLSNSGQPERKFMQTFVLAPEGSV |
| MONKEY B | IHHKVLSLNFSECHTKIRHVDAHATLSDGVVVQVMGLLSNSGQPERKFMQTFVLAPEGSV |
| CHIMP B | IHHKVLSLNFSECHTKIRHVDAHATLSDGVVVQVMGLLSNSGQPERKFMQTFVLAPEGSV |
| HUMAN B | IHHKVLSLNFSECHTKIRHVDAHATLSDGVVVQVMGLLSNSGQPERKFMQTFVLAPEGSV |
| HUMAN A | IHHKVLSLNFSECHTKIRHVDAHATLSDGVVVQVMGLLSNSGQPERKFMQTFVLAPEGSV |
| CHIMP A | IHHKVLSLNFSECHTKIRHVDAHATLSDGVVVQVMGLLSNSGQPERKFMQTFVLAPEGSV |
| MONKEY A | IHHKVLSLNFSECHTKIRHVDAHATLSDGVVVQVMGLLSNSGQPERKFMQTFVLAPEGSV |
| | ************************************************************ |

FIG. 3A

| | |
|---|---|
| MOUSE A | PNKFYVHNDMFRYEDEVFGDSEPELDEESEDEVEEEQEDRQPSPEPVQENANSAYYDAHP |
| MOUSE B | PNKFYVHNDMFRYEDEVFGDSEPELDEESEDEVEEEQEDRQPSPEPVQENANSAYYDAHP |
| RAT B | PNKFYVHNDMFRYEDEVFGDSEPELDEESEDEVEEEQEDRQPSPEPVQENANSAYYEAHP |
| RAT A | PNKFYVHNDMFRYEDEVFGDSEPELDEESEDEVEEEQEDRQPSPEPVQENANSAYYEAHP |
| COW B | PNKFYVHNDMFRYEDEVFGDSEPELDEESEDEVEEEQEERQPSPEPVQENANSGYYEAHP |
| COW A | PNKFYVHNDMFRYEDEVFGDSEPELDEESEDEVEEEQEERQPSPEPVQENANSGYYEAHP |
| DOG B | PNKFYVHNDMFRYEDEVFGDSEPELDEESEDEVEEEQEERQPSPEPVQENADSGYYEAHP |
| DOG A | PNKFYVHNDMFRYEDEVFGDSEPELDEESEDEVEEEQEERQPSPEPVQENADSGYYEAHP |
| MONKEY B | PNKFYVHNDMFRYEDEVFGDSEPELDEESEDEVEEEQEERQPSPEPVQENANSGYYEAHP |
| CHIMP B | PNKFYVHNDMFRYEDEVFGDSEPELDEESEDEVEEEQEERQPSPEPVQENANSGYYEAHP |
| HUMAN B | PNKFYVHNDMFRYEDEVFGDSEPELDEESEDEVEEEQEERQPSPEPVQENANSGYYEAHP |
| HUMAN A | PNKFYVHNDMFRYEDEVFGDSEPELDEESEDEVEEEQEERQPSPEPVQENANSGYYEAHP |
| CHIMP A | PNKFYVHNDMFRYEDEVFGDSEPELDEESEDEVEEEQEERQPSPEPVQENANSGYYEAHP |
| MONKEY A | PNKFYVHNDMFRYEDEVFGDSEPELDEESEDEVEEEQEERQPSPEPVQENANSGYYEAHP |
| | ****************************************:.*:*********:* |

| | |
|---|---|
| MOUSE A | VTNGIEEPLEESSHEPEPEPESETKTEELKPQVEEKHLEELEEKSATPPAEPASLPQEP |
| MOUSE B | VTNGIEEPLEESSHEPEPEPESETKTEELKPQVEEKHLEELEEKSATPPAEPASLPQEP |
| RAT B | VTNGIEEPLEESSHEPEPEPESETKTEELKPQAEEKHLEELEEKSATPPTEPASLPQEP |
| RAT A | VTNGIEEPLEESSHEPEPEPESETKTEELKPQAEEKHLEELEEKSATPPTEPASLPQEP |
| COW B | VTNGIEEPLEESSHEPEPEPESETKTEELKPPVEEKNLEELEEKSASPPPAEPVSLPQEP |
| COW A | VTNGIEEPLEESSHEPEPEPESETKTEELKPPVEEKNLEELEEKSASPPPAEPVSLPQEP |
| DOG B | VANGIEEPLEESSHEPEPEPDSETKTEELKPQVEEKNLEELEEKSTSPPPAEPVSLPQEP |
| DOG A | VANGIEEPLEESSHEPEPEPDSETKTEELKPQVEEKNLEELEEKSTSPPPAEPVSLPQEP |
| MONKEY B | VTNGIEEPLEESSHEPEPEPESETKTEELKPQVEEKNLEELEEKSTTPPPAEPVSLPQEP |
| CHIMP B | VTNGIEEPLEESSHEPEPEPESETKTEELKPQVEEKNLEELEEKSTTPPPAEPVSLPQEP |
| HUMAN B | VTNGIEEPLEESSHEPEPEPESETKTEELKPQVEEKNLEELEEKSTTPPPAEPVSLPQEP |
| HUMAN A | VTNGIEEPLEESSHEPEPEPESETKTEELKPQVEEKNLEELEEKSTTPPPAEPVSLPQEP |
| CHIMP A | VTNGIEEPLEESSHEPETESETKTEELKPQVEEKNLEELEEKSTTPPPAEPVSLPQEP |
| MONKEY A | VTNGIEEPLEESSHEPEPETESETKTEELKPQVEEKNLEELEEKSTTPPPAEPVSLPQEP |
| | *:*************   ******* ::***:.* *:** |

*FIG. 3B*

```
MOUSE   A    PKAFSWASVTSKNLPPSGTVSSSGIPPHVKAPVSQPPRVDAKPEVQSQPPRVREQRPRERP
MOUSE   B    PK----------------------------------PRVDAKPEVQSQPPRVREQRPRERP
RAT     B    PK----------------------------------PRVDAKPEVQSQPPRVREQRPRERP
RAT     A    PKAFSWASVTSKNLPPSGTVSSSGIPPHVKAPVSQPPRVDAKPEVQSQPPRVREQRPRERP
COW     B    PK----------------------------------PRVEAKPEVQSQPPRVREQRPRERP
COW     A    PKAFSWASVTSKNLPPSGTVSSSGIPPHVKAPVSQPPRVEAKPEVQSQPPRVREQRPRERP
DOG     B    PK----------------------------------PRVEAKPEVQSQPPRVREQRPRERP
DOG     A    PKAFSWASVTSKNLPPSGTVSSSGIPPHVKAPVSQPPRVEAKPEVQSQPPRVREQRPRERP
MONKEY  B    PK----------------------------------PRVEAKPEVQSQPPRVREQRPRERP
CHIMP   B    PK----------------------------------PRVEAKPEVQSQPPRVREQRPRERP
HUMAN   B    PK----------------------------------PRVEAKPEVQSQPPRVREQRPRERP
HUMAN   A    PKAFSWASVTSKNLPPSGTVSSSGIPPHVKAPVSQPPRVEAKPEVQSQPPRVREQRPRERP
CHIMP   A    PKAFSWASVTSKNLPPSGTVSSSGIPPHVKAPVSQPPRVEAKPEVQSQPPRVREQRPRERP
MONKEY  A    PKAFSWASVTSKNLPPSGTVSSSGIPPHVKAPVSQPPRVEAKPEVQSQPPRVREQRPRERP
             **                                  ***:************************

MOUSE   A    GFPPRGPRPGRGDMEQNDSDNRRIIRYPDSHQLFVGNLPHDIDENELKEFFMSFGNVVEL
MOUSE   B    GFPPRGPRPGRGDMEQNDSDNRRIIRYPDSHQLFVGNLPHDIDENELKEFFMSFGNVVEL
RAT     B    GFPPRGPRPGRGDTEQNDSDNRRIIRYPDSHQLFVGNLPHDIDENELKEFFMSFGNVVEL
RAT     A    GFPPRGPRPGRGDTEQNDSDNRRIIRYPDSHQLFVGNLPHDIDENELKEFFMSFGNVVEL
COW     B    GFPPRGPRPGRGDIEQNESDNRRIIRYPDSHQLFVGNLPHDIDENELKEFFMSFGNVVEL
COW     A    GFPPRGPRPGRGDIEQNESDNRRIIRYPDSHQLFVGNLPHDIDENELKEFFMSFGNVVEL
DOG     B    GFPPRGPRPGRGDLEQNESDNRRIIRYPDSHQLFVGNLPHDIDENELKEFFMSFGNVVEL
DOG     A    GFPPRGPRPGRGDLEQNESDNRRIIRYPDSHQLFVGNLPHDIDENELKEFFMSFGNVVEL
MONKEY  B    GFPPRGPRPGRGDMEQNDSDNRRIIRYPDSHQLFVGNLPHDIDENELKEFFMSFGNVVEL
CHIMP   B    GFPPRGPRPGRGDMEQNDSDNRRIIRYPDSHQLFVGNLPHDIDENELKEFFMSFGNVVEL
HUMAN   B    GFPPRGPRPGRGDMEQNDSDNRRIIRYPDSHQLFVGNLPHDIDENELKEFFMSFGNVVEL
HUMAN   A    GFPPRGPRPGRGDMEQNDSDNRRIIRYPDSHQLFVGNLPHDIDENELKEFFMSFGNVVEL
CHIMP   A    GFPPRGPRPGRGDMEQNDSDNRRIIRYPDSHQLFVGNLPHDIDENELKEFFMSFGNVVEL
MONKEY  A    GFPPRGPRPGRGDMEQNDSDNRRIIRYPDSHQLFVGNLPHDIDENELKEFFMSFGNVVEL
             ************ ***:*******************************************
```

FIG. 3C

| | | |
|---|---|---|
| MOUSE A | RINTKGVGGKLPNFGFVVFDDSEPVQRILIAKPIMFRGEVRLNVEEKKTRAARERETRGG | (SEQ ID NO:10) |
| MOUSE B | RINTKGVGGKLPNFGFVVFDDSEPVQRILIAKPIMFRGEVRLNVEEKKTRAARERETRGG | (SEQ ID NO:11) |
| RAT B | RINTKGVGGKLPNFGFVVFDDSEPVQRILIAKPIMFRGEVRLNVEEKKTRAARERETRGG | (SEQ ID NO:12) |
| RAT A | RINTKGVGGKLPNFGFVVFDDSEPVQRILIAKPIMFRGEVRLNVEEKKTRAARERETRGG | (SEQ ID NO:13) |
| COW B | RINTKGVGGKLPNFGFVVFDDSEPVQRILIAKPIMFRGEVRLNVEEKKTRAARERETRGG | (SEQ ID NO:14) |
| COW A | RINTKGVGGKLPNFGFVVFDDSEPVQRILIAKPIMFRGEVRLNVEEKKTRAARERETRGG | (SEQ ID NO:15) |
| DOG B | RINTKGVGGKLPNFGFVVFDDSEPVQRILIAKPIMFRGEVRLNVEEKKTRAARERETRGG | (SEQ ID NO:16) |
| DOG A | RINTKGVGGKLPNFGFVVFDDSEPVQRILIAKPIMFRGEVRLNVEEKKTRAARERETRGG | (SEQ ID NO:17) |
| MONKEY B | RINTKGVGGKLPNFGFVVFDDSEPVQRILIAKPIMFRGEVRLNVEEKKTRAARERETRGG | (SEQ ID NO:18) |
| CHIMP B | RINTKGVGGKLPNFGFVVFDDSEPVQRILIAKPIMFRGEVRLNVEEKKTRAARERETRGG | (SEQ ID NO:19) |
| HUMAN B | RINTKGVGGKLPNFGFVVFDDSEPVQRILIAKPIMFRGEVRLNVEEKKTRAARERETRGG | (SEQ ID NO:3) |
| HUMAN A | RINTKGVGGKLPNFGFVVFDDSEPVQRILIAKPIMFRGEVRLNVEEKKTRAARERETRGG | (SEQ ID NO:2) |
| CHIMP A | RINTKGVGGKLPNFGFVVFDDSEPVQRILIAKPIMFRGEVRLNVEEKKTRAARERETRGG | (SEQ ID NO:20) |
| MONKEY A | RINTKGVGGKLPNFGFVVFDDSEPVQRILIAKPIMFRGEVRLNVEEKKTRAARERETRGG | (SEQ ID NO:21) |
| | ************************************************************ | |

| | | |
|---|---|---|
| MOUSE A | GDDRRDIRRNDRGPGGPRGIVGGMMRDRDGRGPPPRGGMTQKLGSGRGTGQMEGRFTGQRR | |
| MOUSE B | GDDRRDIRRNDRGPGGPRGIVGGMMRDRDGRGPPPRGGMTQKLGSGRGTGQMEGRFTGQRR | |
| RAT B | GDDRRDIRRNDRGPGGPRGIVGGMMRDRDGRGPPPRGGMTQKLGSGRGTGQMEGRFTGQRR | |
| RAT A | GDDRRDIRRSDRGPGGPRGIVGGMMRDRDGRGPPPRGGMTQKLGSGRGTGQMEGRFTGQRR | |
| COW B | GDDRRDIRRSDRGPGGPRGIVGGMMRDRDGRGPPPRGGMAQKLGSGRGAGQMEGRFTGQRR | |
| COW A | GDDRRDIRRNDRGPGGPRGIVGGMMRDRDGRGPPPRGGMAQKLGSGRGAGQMEGRFTGQRR | |
| DOG B | GDDRRDIRRNDRGPGGPRGIVGGMMRDRDGRGPPPRGGMAQKLGSGRGTGQMEGRFTGQRR | |
| DOG A | GDDRRDIRRNDRGPGGPRGIVGGMMRDRDGRGPPPRGGMAQKLGSGRGTGQMEGRFTGQRR | |
| MONKEY B | GDDRRDIRRNDRGPGGPRGIVGGMMRDRDGRGPPPRGGMAQKLGSGRGTGQMEGRFTGQRR | |
| CHIMP B | GDDRRDIRRNDRGPGGPRGIVGGMMRDRDGRGPPPRGGMAQKLGSGRGTGQMEGRFTGQRR | |
| HUMAN B | GDDRRDIRRNDRGPGGPRGIVGGMMRDRDGRGPPPRGGMAQKLGSGRGTGQMEGRFTGQRR | |
| HUMAN A | GDDRRDIRRNDRGPGGPRGIVGGMMRDRDGRGPPPRGGMAQKLGSGRGTGQMEGRFTGQRR | |
| CHIMP A | GDDRRDIRRNDRGPGGPRGIVGGMMRDRDGRGPPPRGGMAQKLGSGRGTGQMEGRFTGQRR | |
| MONKEY A | GDDRRDIRRNDRGPGGPRGIVGGMMRDRDGRGPPPRGGMAQKLGSGRGTGQMEGRFTGQRR | |
| | *******.***********************:****:********* | |

FIG. 3D

```
OS1  MSASPSSMSGAGAGEAGVRTVVWFRRDLRVEDNPALAAAARAAGEVVPVYVWAPEEDGPY
SB2  MSASSSS---LCGGDPAMRSVVWFRRDLRVEDNPALAAAARAGGEVVPAYVWSPEEEGPY
AT1  MSGSV---SGCG-----SGGCSIVWFRRDLRVEDNPALAAAVRA-GPVIALFVWAPEEGHY
LE1  --------MS---GGGCSIVWFRRDLRVEDNPALAAGVRA-GAVIAVFIYAPEEEGHY
GM1  --------MS---GGGCSIVWFRRDLRVEDNPALAAGVRA-GAVISVFIWAPEEEGQY
PP1  -----------MAACTIVWFRRDLREDNPALIAAARA-GTVVPVFVWSPAEDGQF
SB1  -----------MAGSGKTVVWFRRDLRIHDNPALAAAAKE-GSVLPLFIWCPADYEQY
OS2  -----------MAGSERTVVWFRRDLRIDDNPALASAARD-GAVLPVFIWCPADEGQF
AT2  -----------MKMDKKTIVWFRRDLRIEDNPALAAAAHE-GSVFPVFIWCPEEEGQF
GM2  -----------MGSNRTIVWFRRDLRIEDNPALTAAAKE-GSVLPVYVWCPKEEGQF
                 :*:*****: ..*:::  .: * .  ..  :   ..

OS1  M
SB2  YPGRVSRWWLSQSLKHLDASLRRLGASRLVTRRSADAVVALIELVRSIGATHLFFNHLYD
AT1  YPGRVSRWWISQSLKRLDASLRRLGAGKLVTRRSADAVVALLQLVRDTGATHVYFNHLYD
LE1  HPGRVSRWWLKNSLAQLDSSLRSLGTC-LITKRSTDSVASLLDVVKSTGASQIFFNHLYD
GM1  YPGRVSRWWLKQSLAHLDSSLKSLGTS-LITKRSTDSISSLLEVVKSTGATQLFFNHLYD
PP1  YPGRVSRWWLKQSLAHLDSSLRNLGSP-LITKRSTNSISSLLEVVKSTGATQLFFNHLYD
SB1  HPGRVSRWWLKQSLTHLELSLKKLGSLELLGCPLVLIRAEDSTLATLLECVHCISATRVVYNRLYD
OS2  YPGRCSRWMLKQSLAHLQSLPHLSQSLESLGCPLVLIRAE-STLEALLRCIDSVGATRLVYNHLYD
AT2  YPGRCSRWMLKQSLAHLSQSLKALGSDLTLIKTH-NTISAILDCIRVTGATKVVFNHLYD
GM2  YPGRASRWWMKQSLAHLDQSLKSLGSRLVLIKTH-STAVALVECVKAIQATKVVFNHLYD
         *.**:*:.:: . *    *       *    :.  ** *:*:***
```

FIG. 4A

```
      MM
OS1   PLSLVRDHRVKALLTAEGIAVQSFNADLLYEPWEVVDDDGCPFTMFAPFWDRCLCMP-DP
SB2   PISLVRDHRLKEMLAAEGIVVQSFNADLLYEPWEVVDDEGQPFTMFTAFWNRCLSMQYDP
AT1   PLSLVRDHRAKDVLTAQGIAVRSFNADLLYEPWEVTDELGRPFSMFAAFWERCLSMPYDP
LE1   PISLVRDHRTKEILTAQGISVRSFNADLLYEPWEVNDDEGRPFTTFSAFWEKCLSMPYDP
GM1   PLSLVRDHRAKEVLTAQGITVRSFNSDLLYEPWDVNDAHGQPFTTFSAFWERCLSMPYDP
PP1   PVSLVRDHRVKQGLSQRGIVVHTFNGDLLYEPWEVYDEEGQAFTVYEAFWKKCMSMPFEP
SB1   PISLVLDDKIKNELSAHGISVQSFNGDLLYEPWDVYDENGQAFTSFNKYWEKCMNVPIEI
OS2   PVSLVRDDKIKKELSALGISIQSFNGDLLYEPWEIYDDSGLAFTTFNMYWEKCMELPIDA
AT2   PVSLVRDHTVKEKLVERGISVQSYNGDLLYEPWEIYCEKGKPFTSFNSYWKKCLDMSIES
GM2   PVSLVRDHNIKEKLVEQGISVQSYNGDLLYEPWEVNSESGRAFTTFNAFWKKCLHMQMDI
       *:****.  *    .  :* ** :*******  .     .:* * *. ::

OS1   AAPLLPPKRIAPGEL---PARRCPSDELVFEDES-ERGSNALLARAWSPGWQNADKALAA
SB2   PAPLLPPKKINSGDL---S--MCPSEDLIFEDDS-ERGSNALLARAWTPGWQNADKALTA
AT1   ESPLLPPKKIISGDV---S--KCVADPLVFEDDS-EKGSNALLARAWSPGWSNADKALTT
LE1   EAPLLPPKRIISGDA---S--RCPSDNLVFEDES-EKGSNALLARAWSPGWSNADKALTT
GM1   QAPLLPPKRIIPGDV---P--RCPSDTLVFEDEL-EKASNALLARAWSPGWSNADKALTA
PP1   EAPLLPPRRLTGP----IGKIVGCNAEELGLEDEF-EKSSNALLARAWCPGWGFANKSLDS
SB1   SQ-YLAPTRLVAAPGLA-NVRCCSIDDLGLESSKDVESSNALLSRAWSPGWRNAENMLEE
OS2   SP-SLAPWKLVPVPGLE-SVRSCSVDDLGLESSKDEESSNALLMRAWSPGWRNAEKMLEE
AT2   VM-LPPPWRLMPITAAAEAIWACSIEELGLENEA-EKPSNALLTRAWSPGWSNADKLLNE
GM2   VS-VVPPWQLIPAEG---KIEECSLEELGLENES-EKPSNALLGRAWSPGWRNADKALRE
       .  :          *    :        .      ***** *** ***  *
```

FIG. 4B

```
            F                       FFFFF
OS1  FLNGPLMDYSVNRKKAD---SASTSLLSPYLHFGELSVRKVFHQVRMKQLMWSNEGNHAG
SB2  FLNGPLADYSVNRKKAD---SASTSLLSPHLHFGELSVRKVFHLVRMKQLVWSNEGNHAA
AT1  FINGPLLEYSKNRRKAD----SATTSFLSPHLHFGEVSVRKVFHLVRIKQVAWANEGNEAG
LE1  FVNGPLLEYSQNRRKAD----SATTSFLSPHLHFGEVSVRKVFHFVRIKQVLMANEGNKAG
GM1  FVNGALIEYSKNRRKAD----SATTSFLSPHLHFGELSVRKVFHLVRIKQVFWANEGNKAG
PP1  FLRSPLIDYARDRQKADGASGTPTSLLSPHLHFGELSVRKIFHEVRKRQITWAREGNAGG
SB1  FLSCGLLEYSKHGMKVG---GTTTSLLSPYLHFGELSVRKVYQLVTMHHVKWQNEGKSEA
OS2  FVSHGLLEYSKHGMKVE---GATTSLLSPYLHFGEVSVRKVYQLVRMQQIKWENEGTSEA
AT2  FIEKQLIDYAKNSKKVV---GNSTSLLSPYLHFGEISVRHVFQCARMKQIIWARDKNSEG
GM2  FVELHLLHYSKKRLKVG---GESTSLLSPYLHFGELSARKVFQVTCMKQILWTNEGNSAG
     *  :           .    :*:: ****     :: . ::  .  :  : ::.  .
                                  $
              F        F               MM
OS1  DESCVLFLRSIGLREYSRYLTFNHPCSLEKPLLAHLRFFPWVDEVYFKVWRQGRTGYPL
SB2  EESCTLFLRSIGLREYSRYLSFNHPSSHERPLLAHLRFFPWVNESYFKIWRQGRTGYPL
AT1  EESVNLFLKSIGLREYSRYISFNHPYSHERPLLGHLKFFPWAVDENYFKAWRQGRTGYPL
LE1  EESVNLFLKSIGLREYSRYMSFNHPYSHERPLLGHLRYFPWVDEGYFKAWRQGRTGYPL
GM1  EESVNLFLKSIGLREYSRYISFNHPYSHERPLLAHLKFFPWVNEGYFKAWRQGRTGYPL
PP1  EASVNMFLRALGFREYSRYLSFHFPFTHERSLLANLKSFPWRADEGYFKAWRQGRTGYPL
SB1  EESVRLFLRSIGFREYSRYLCFNFPFTHERSFLGNLKHYPWLLDEDRFKSWRQGMTGYPL
OS2  EESIHFFMRSIGLREYSRYLCFNFPFTHEKSLLGNLKHYPWKDEERFKSWRQGMTGYPL
AT2  EESADLFLRGIGLREYSRYICFNFPFTHEQSLLSHLRFFPWDADVDKFKAWRQGRTGYPL
GM2  EESANLFLRAIGLREYSRYLCFNFPFTHERALLGHLKFFPWNPDPDIFKTWRQGRTGFPL
     :*  :* : *:****** .*:. .:.    :* **    : *.**. *  **
```

*FIG. 4C*

```
             F  F                           $            F  FM  F       $              F   FM  F               $
OS1  VDAGMRELWATGWLHDRIRVVVSSFFVKVLQLPWRWGMKYFWDTLLDADLESDALGWQYI
SB2  VDAGMRELWATGWLHDRIRVVVSSFFVKVLQLPWRWGMKYFWDTLLDADLESDALGWQYI
AT1  VDAGMRELWATGWLHDRIRVVVSSFFVKVLQLPWRWGMKYFWDTLLDADLESDALGWQYI
LE1  VDAGMRELWATGWLHDRIRVVVSSFFVKVLQLPWRWGMKYFWDTLLDADLESDALGWQYI
GM1  VDAGMRELWATGWLHDRIRVVVSSFFVKVLQLPWRWGMKYFWDTLLDADLESDALGWQYI
PP1  VDAGMRELWATGWAHNRIRVVVASFSVKFLQLPWRWGMKYFWDVLLDADLECDVLGWQYI
SB1  VDAGMRELWATGWTHNRIRVIVSSFAVKCLQIPWIWGMKYFWDVLLDADLESDILGWQYI
OS2  VDAGMRELWATGWTHNRIRVIISSFAVKFLLIPWTWGMKYFWDVLLDADLESDILGWQYI
AT2  VDAGMRELWATGWMHNRIRVIVSSFAVKFLLLPWKWGMKYFWDTLLDADLECDILGWQYI
GM2  VDAGMRELWATGWIHNRIRVIVSSFAVKMLLLPWKWGMKYFWDTLLDADLESDILGWQYI
     *********** : ***:.:::*** * * .: *** *** :******* ****.****

OS1  SGSLPDGRELDRIDNPQLEGYKFDPHGEYVRRWLPELARLPTEWIHHPWDAPESVLQAAG
SB2  TGSLPDSRELDRIDNPQFEGYKFDPHGEYVRRWLPELVRLPTEWIHHPWDAPVSVLQAAG
AT1  TGTLPDSREFDRIDNPQFEGYKFDPNGEYVRRWLPELSRLPTDWIHHPNAPESVLQAAG
LE1  SGTLPDGRELDRIDNPQFVGYKCDPHGEYVRRWLPELARLPTEWIHHPNAPESVLEAAG
GM1  SGTLPDGRELDRIDNPQFEGYKCDPNGEYVRRWLPELARLPTEWIHHPWNAPESVLQAAG
PP1  SGSLPDGHELDRIENPEVEGYRFDPDGDYVRRWLPELARLPNEWVHHPWDAPPSALRAAG
SB1  SGSLPDGHELSRLDNPEVQGYQKYDPDGEYVRTWIPELARMPTEWIHCPWSAPNSILQVAG
OS2  SGSLPDGHELSRLDNPEVQGYQKYDPDGVYVRTWIPELARMPTEWIHHPWDAPSCILEVAG
AT2  SGSIPDGHELDRLDNPALQGAKYDPEGEYIRQWLPELARLPTEWIHHPWDAPLTVLKASG
GM2  SGGLPDGHELERLDNPEIQGAKFDPEGEYVRQWLPELARMPTEWIHHPWDAPLTVLRAAG
     :* :***::*  : *:**   *  **.* : *:***:*.:*** *:*:   .*  *

FIG. 4D
```

| | |
|---|---|
| OS1 | IELGSNYPLPIVELDAAKTRLQDALSEMWELEAASRAAMENGMEEGLGDSSDV--PPIAF |
| SB2 | IELGSNYPLPIVELDAAKARLQEALSEMWQLEAASRATMNNGMEEGLGDSSEV-P---F |
| AT1 | IELGSNYPLPIVGLDEAKARLHEALSQMWQLEAASRAAIENGSEEGLGDSAEVEEAPIEF |
| LE1 | IELGSNYPLPIVEIDSAKVRLEQALSQMWQNDAAARAAIENGMEEGHGDSAD---SPIAF |
| GM1 | IELGSNYPLPIVGIDAAEVRLQEALIQMWQQEAASRAAMENGTEEGLGDSAE--SAPIAF |
| PP1 | VELGTNYPRPIVEIGAARERLQASLAEMWERDAAMKAALANGLEEGLGETVEVAGT--GG |
| SB1 | VELGFNYPKPIVELHMARECLDDAISTMWQLDTAAKLA--ALDGEVV------DD--NL |
| OS2 | VELGFNYPKPIVDLHIARECLDDSISTMWQLDTAEKLA--ELDGEVV------ED--NL |
| AT2 | VELGTNYAKPIVDIDTARELLAKAISRTREAQIMI---GAAP-DEIV------AD--SF |
| GM2 | VELGQNYPKPIIDIDLARERLTEAIFKMWESEAAAKAAGSEPRDEVV------VD--NS |
| | :.*.*..:.*.......*......:..:....::.........* |
| | |
| OS1 | PPELQMEVDRAPAQPTVHGPTTAGRRREDQMVPSMTSSLVRAETEL------SADFDNS- |
| SB2 | PEELQMEVDRATANVV------MTVRRREDQMVPTMTSSLNRAETEV------SADLGNS- |
| AT1 | PRDITMEETE-PTR------LNPNRRYEDQMVPSITSSLIRPEEDEES----SLNLRNSV |
| LE1 | PQAMHMEMDHEPVRNNP---VIVTVRRYEDQMVPSMTSSLFRAED-EEN------SVDIRNSV |
| GM1 | PQDIQMEERPEPVRNNL---PHGTRRYQDQMVPSITSSHVRVEE-EET----SSDLRNSA |
| PP1 | PEHERMDVPRVMVHMQRDADMSCNSSRRDQLVPEIVPNQFHIRAHESIMNRSAAMVEDGE |
| SB1 | NNIRSFDIPKVVLKKK----LSPSTSSMNKRVLSTNGKNEKSQPT---EVKAPYK---- |
| OS2 | SNIKTFDIPKVVLRET----SPCALPIDQRVPHASSKDHNLKSK---VLKASNR---- |
| AT2 | ---EALGAN--TIKEP---GLCPSVSSNDQQVPSAVRYNGS-K------RVKPEEE--EER |
| GM2 | HTVENLDTQKVVVLGK---APCATISANDQKVPALQDSKNE-PPT---RKRPKHMIEEGQ |
| | ..:..........:.........*........*:: |

FIG. 4E

```
OS1  MDSRPEVPSQVLFQPRMEREETVDGGGGGMVGRSNGGGHQGQHQQQHNFQTTIHRARG
SB2  EDTRAQVPFHAHFHPRVEREDMIQNTEGPALR--INGT-HQHN-----IFQQPQNHRREA
AT1  GDSRAEVPRNMVNTNQAQQ-RRAE--------------PASNQVTAMIPEFNIRIVAEST
LE1  VESRAEVPTDINVAEVHRR-DTRDQA---------------VMQTARTNATPHFNFAVGRRNS
GM1  ADSRAEVPINVTTQQIARE-TVNQGV-------------LLNANRNTRVQNNATTWLRNAA
PP1  EAGRAAVPMVFAS------VRRGMGGNYGGHHVEGN-GGEVAQASAP---IQWPTVTAVDYE
SB1  -QI--------------------IRDDMINASN------------------MD------D
OS2  -SS--------------------ICVDMIRSSK------------------ME------A
AT2  D-------------------------MKKSRG-------------------FD---ERE
GM2  NQD------------------HSQNHNKDTG--------------------LSSIDQD

OS1  VAPSTSEASSNWT----GREGGVVPVWSPPAASGPSDHYAADE-ADIT-SRSYLDR-HPQ
SB2  LAPSVSEASSSWT----GREGAVVPVWSPPAASGHSETFAADE-ADVS-SRSYLDR-HPR
AT1  EDSTAESSSSGRR----ERSGGIVPEWSPG---YSEQFPSEE-NGIGGGSTTSSY-LQN
LE1  EDSTAES-SSSTR----ERDGGVVPTWSPSSS-NYSDQYVGDD-NGIGTSSSYLQR-HPQ
GM1  EDSTAESSSSTRR----ERDGGVVPVWSPPAS-NFSEQFVDDE-NGIGAGSSYLQRQHPQ
PP1  LDSTAESASVTGRGGSEG---GTVPVWSQSVSARTPIQVREGLVPEVRRGPGLSRRQLQA
SB1  TGSTANLQVTRKR----SRSDSAFNVPSSSSSLVMESRIHDNDSCSV------RYSGY-LQQ
OS2  TSSVANSPVSRKR----SFCETAFHVPSYSSSAEVHSHIQDHGGSLV------GPSRY-LLQ
AT2  LFSTAESS---------SSSSVFFVSQSCSLASEGKN----------------LEG--I--
GM2  ICSTADSSSCKKQCASTSSYSFSVPQQCSSSSNLKW--------------------PW----
              *                       .

OS1  SHT-----------------LMNWSQLSQSLTTGWEVEN    (SEQ ID NO:47)
SB2  SYR-----------------LMNWSQLSQSL--------    (SEQ ID NO:48)
AT1  HHE-----------------ILNWRRLSQTG--------    (SEQ ID NO:49)
LE1  SHQ-----------------LMNWQRLSQTG--------    (SEQ ID NO:50)
GM1  SHQ-----------------LMNWTRLPQTG--------    (SEQ ID NO:51)
PP1  SVQRVNLEGMTSNKQAEEEDFYVPKLIVKWTQPRKRRVKQDG-   (SEQ ID NO:52)
SB1  TADRDDTDKVEDNDSEDS----GTSISRPSKRPA--------    (SEQ ID NO:53)
OS2  EAGRNYVDEVEDSSTADS----GSSISRQRKAA---------    (SEQ ID NO:54)
AT2  ---QDSSDQITTSLGKNG----CK-----------------    (SEQ ID NO:55)
GM2  ---QEKIDMEQSSSKDG-----AM-----------------    (SEQ ID NO:56)
```

FIG. 4F

SEQUENCE LISTING

```
<160> NUMBER OF SEQ ID NOS: 74

<210> SEQ ID NO 1
<211> LENGTH: 466
<212> TYPE: PRT
<213> ORGANISM: Homo sapiens

<400> SEQUENCE: 1

Met Val Met Glu Lys Pro Ser Pro Leu Leu Val Gly Arg Glu Phe Val
1               5                   10                  15

Arg Gln Tyr Tyr Thr Leu Leu Asn Gln Ala Pro Asp Met Leu His Arg
            20                  25                  30

Phe Tyr Gly Lys Asn Ser Ser Tyr Val His Gly Gly Leu Asp Ser Asn
        35                  40                  45

Gly Lys Pro Ala Asp Ala Val Tyr Gly Gln Lys Glu Ile His Arg Lys
    50                  55                  60

Val Met Ser Gln Asn Phe Thr Asn Cys His Thr Lys Ile Arg His Val
65                  70                  75                  80

Asp Ala His Ala Thr Leu Asn Asp Gly Val Val Val Gln Val Met Gly
                85                  90                  95

Leu Leu Ser Asn Asn Asn Gln Ala Leu Arg Arg Phe Met Gln Thr Phe
            100                 105                 110

Val Leu Ala Pro Glu Gly Ser Val Ala Asn Lys Phe Tyr Val His Asn
        115                 120                 125

Asp Ile Phe Arg Tyr Gln Asp Glu Val Phe Gly Gly Phe Val Thr Glu
    130                 135                 140

Pro Gln Glu Glu Ser Glu Glu Val Glu Pro Glu Glu Arg Gln
145                 150                 155                 160

Gln Thr Pro Glu Val Val Pro Asp Asp Ser Gly Thr Phe Tyr Asp Gln
                165                 170                 175

Ala Val Val Ser Asn Asp Met Glu Glu His Leu Glu Glu Pro Val Ala
            180                 185                 190

Glu Pro Glu Pro Asp Pro Glu Pro Glu Pro Glu Gln Glu Pro Val Ser
        195                 200                 205

Glu Ile Gln Glu Glu Lys Pro Glu Pro Val Leu Glu Glu Thr Ala Pro
    210                 215                 220

Glu Asp Ala Gln Lys Ser Ser Pro Ala Pro Ala Asp Ile Ala Gln
225                 230                 235                 240

Thr Val Gln Glu Asp Leu Arg Thr Phe Ser Trp Ala Ser Val Thr Ser
                245                 250                 255

Lys Asn Leu Pro Pro Ser Gly Ala Val Pro Val Thr Gly Ile Pro Pro
            260                 265                 270

His Val Val Lys Val Pro Ala Ser Gln Pro Arg Pro Glu Ser Lys Pro
```

```
                    275                 280                 285
Glu Ser Gln Ile Pro Gln Arg Pro Gln Arg Asp Gln Arg Val Arg
    290                 295                 300
Glu Gln Arg Ile Asn Ile Pro Pro Gln Arg Gly Pro Arg Pro Ile Arg
305                 310                 315                 320
Glu Ala Gly Glu Gln Gly Asp Ile Glu Pro Arg Arg Met Val Arg His
                    325                 330                 335
Pro Asp Ser His Gln Leu Phe Ile Gly Asn Leu Pro His Glu Val Asp
                340                 345                 350
Lys Ser Glu Leu Lys Asp Phe Phe Gln Ser Tyr Gly Asn Val Val Glu
                355                 360                 365
Leu Arg Ile Asn Ser Gly Gly Lys Leu Pro Asn Phe Gly Phe Val Val
                370                 375                 380
Phe Asp Asp Ser Glu Pro Val Gln Lys Val Leu Ser Asn Arg Pro Ile
385                 390                 395                 400
Met Phe Arg Gly Glu Val Arg Leu Asn Val Glu Glu Lys Lys Thr Arg
                405                 410                 415
Ala Ala Arg Glu Gly Asp Arg Arg Asp Asn Arg Leu Arg Gly Pro Gly
                420                 425                 430
Gly Pro Arg Gly Gly Leu Gly Gly Met Arg Gly Pro Pro Arg Gly
            435                 440                 445
Gly Met Val Gln Lys Pro Gly Phe Gly Val Gly Arg Gly Leu Ala Pro
450                 455                 460
Arg Gln
465

<210> SEQ ID NO 2
<211> LENGTH: 482
<212> TYPE: PRT
<213> ORGANISM: Homo sapiens

<400> SEQUENCE: 2

Met Val Met Glu Lys Pro Ser Pro Leu Leu Val Gly Arg Glu Phe Val
1               5                   10                  15
Arg Gln Tyr Tyr Thr Leu Leu Asn Lys Ala Pro Glu Tyr Leu His Arg
            20                  25                  30
Phe Tyr Gly Arg Asn Ser Ser Tyr Val His Gly Gly Val Asp Ala Ser
        35                  40                  45
Gly Lys Pro Gln Glu Ala Val Tyr Gly Gln Asn Asp Ile His His Lys
    50                  55                  60
Val Leu Ser Leu Asn Phe Ser Glu Cys His Thr Lys Ile Arg His Val
65                  70                  75                  80
Asp Ala His Ala Thr Leu Ser Asp Gly Val Val Val Gln Val Met Gly
                85                  90                  95
Leu Leu Ser Asn Ser Gly Gln Pro Glu Arg Lys Phe Met Gln Thr Phe
            100                 105                 110
Val Leu Ala Pro Glu Gly Ser Val Pro Asn Lys Phe Tyr Val His Asn
        115                 120                 125
Asp Met Phe Arg Tyr Glu Asp Glu Val Phe Gly Asp Ser Glu Pro Glu
    130                 135                 140
Leu Asp Glu Glu Ser Glu Asp Glu Val Glu Glu Gln Glu Glu Arg
145                 150                 155                 160
Gln Pro Ser Pro Glu Pro Val Gln Glu Asn Ala Asn Ser Gly Tyr Tyr
                165                 170                 175
```

Glu Ala His Pro Val Thr Asn Gly Ile Glu Pro Leu Glu Glu Ser
            180                 185                 190

Ser His Glu Pro Glu Pro Glu Pro Ser Glu Thr Lys Thr Glu Glu
        195                 200                 205

Leu Lys Pro Gln Val Glu Glu Lys Asn Leu Glu Glu Leu Glu Lys
    210                 215                 220

Ser Thr Thr Pro Pro Ala Glu Pro Val Ser Leu Pro Gln Glu Pro
225                 230                 235                 240

Pro Lys Ala Phe Ser Trp Ala Ser Val Thr Ser Lys Asn Leu Pro
                245                 250                 255

Ser Gly Thr Val Ser Ser Gly Ile Pro Pro His Val Lys Ala Pro
            260                 265                 270

Val Ser Gln Pro Arg Val Glu Ala Lys Pro Glu Val Gln Ser Gln Pro
        275                 280                 285

Pro Arg Val Arg Glu Gln Arg Pro Arg Glu Arg Pro Gly Phe Pro Pro
    290                 295                 300

Arg Gly Pro Arg Pro Gly Arg Gly Asp Met Glu Gln Asn Asp Ser Asp
305                 310                 315                 320

Asn Arg Arg Ile Ile Arg Tyr Pro Asp Ser His Gln Leu Phe Val Gly
                325                 330                 335

Asn Leu Pro His Asp Ile Asp Glu Asn Glu Leu Lys Glu Phe Phe Met
            340                 345                 350

Ser Phe Gly Asn Val Val Glu Leu Arg Ile Asn Thr Lys Gly Val Gly
        355                 360                 365

Gly Lys Leu Pro Asn Phe Gly Phe Val Val Phe Asp Asp Ser Glu Pro
    370                 375                 380

Val Gln Arg Ile Leu Ile Ala Lys Pro Ile Met Phe Arg Gly Glu Val
385                 390                 395                 400

Arg Leu Asn Val Glu Glu Lys Lys Thr Arg Ala Ala Arg Glu Arg Glu
                405                 410                 415

Thr Arg Gly Gly Gly Asp Asp Arg Asp Ile Arg Arg Asn Asp Arg
            420                 425                 430

Gly Pro Gly Gly Pro Arg Gly Ile Val Gly Gly Gly Met Met Arg Asp
    435                 440                 445

Arg Asp Gly Arg Gly Pro Pro Arg Gly Gly Met Ala Gln Lys Leu
450                 455                 460

Gly Ser Gly Arg Gly Thr Gly Gln Met Glu Gly Arg Phe Thr Gly Gln
465                 470                 475                 480

Arg Arg

<210> SEQ ID NO 3
<211> LENGTH: 449
<212> TYPE: PRT
<213> ORGANISM: Homo sapiens

<400> SEQUENCE: 3

Met Val Met Glu Lys Pro Ser Pro Leu Leu Val Gly Arg Glu Phe Val
1               5                   10                  15

Arg Gln Tyr Tyr Thr Leu Leu Asn Lys Ala Pro Glu Tyr Leu His Arg
            20                  25                  30

Phe Tyr Gly Arg Asn Ser Ser Tyr Val His Gly Gly Val Asp Ala Ser
        35                  40                  45

Gly Lys Pro Gln Glu Ala Val Tyr Gly Gln Asn Asp Ile His His Lys
    50                  55                  60

```
Val Leu Ser Leu Asn Phe Ser Glu Cys His Thr Lys Ile Arg His Val
 65                  70                  75                  80

Asp Ala His Ala Thr Leu Ser Asp Gly Val Val Gln Val Met Gly
                 85                  90                  95

Leu Leu Ser Asn Ser Gly Gln Pro Glu Arg Lys Phe Met Gln Thr Phe
            100                 105                 110

Val Leu Ala Pro Glu Gly Ser Val Pro Asn Lys Phe Tyr Val His Asn
        115                 120                 125

Asp Met Phe Arg Tyr Glu Asp Glu Val Phe Gly Asp Ser Glu Pro Glu
    130                 135                 140

Leu Asp Glu Glu Ser Glu Asp Glu Val Glu Glu Gln Glu Glu Arg
145                 150                 155                 160

Gln Pro Ser Pro Glu Pro Val Gln Glu Asn Ala Asn Ser Gly Tyr Tyr
                165                 170                 175

Glu Ala His Pro Val Thr Asn Gly Ile Glu Glu Pro Leu Glu Glu Ser
            180                 185                 190

Ser His Glu Pro Glu Pro Glu Pro Glu Ser Glu Thr Lys Thr Glu Glu
        195                 200                 205

Leu Lys Pro Gln Val Glu Glu Lys Asn Leu Glu Glu Leu Glu Glu Lys
    210                 215                 220

Ser Thr Thr Pro Pro Pro Ala Glu Pro Val Ser Leu Pro Gln Glu Pro
225                 230                 235                 240

Pro Lys Pro Arg Val Glu Ala Lys Pro Glu Val Gln Ser Gln Pro Pro
                245                 250                 255

Arg Val Arg Glu Gln Arg Pro Arg Glu Arg Pro Gly Phe Pro Pro Arg
            260                 265                 270

Gly Pro Arg Pro Gly Arg Gly Asp Met Glu Gln Asn Asp Ser Asp Asn
        275                 280                 285

Arg Arg Ile Ile Arg Tyr Pro Asp Ser His Gln Leu Phe Val Gly Asn
    290                 295                 300

Leu Pro His Asp Ile Asp Glu Asn Glu Leu Lys Glu Phe Phe Met Ser
305                 310                 315                 320

Phe Gly Asn Val Val Glu Leu Arg Ile Asn Thr Lys Gly Val Gly Gly
                325                 330                 335

Lys Leu Pro Asn Phe Gly Phe Val Val Phe Asp Asp Ser Glu Pro Val
            340                 345                 350

Gln Arg Ile Leu Ile Ala Lys Pro Ile Met Phe Arg Gly Glu Val Arg
        355                 360                 365

Leu Asn Val Glu Glu Lys Lys Thr Arg Ala Ala Arg Glu Arg Glu Thr
    370                 375                 380

Arg Gly Gly Gly Asp Asp Arg Arg Asp Ile Arg Arg Asn Asp Arg Gly
385                 390                 395                 400

Pro Gly Gly Pro Arg Gly Ile Val Gly Gly Met Met Arg Asp Arg
                405                 410                 415

Asp Gly Arg Gly Pro Pro Arg Gly Gly Met Ala Gln Lys Leu Gly
            420                 425                 430

Ser Gly Arg Gly Thr Gly Gln Met Glu Gly Arg Phe Thr Gly Gln Arg
        435                 440                 445

Arg

<210> SEQ ID NO 4
<211> LENGTH: 465
<212> TYPE: PRT
<213> ORGANISM: Rattus norvegicus
```

<400> SEQUENCE: 4

```
Met Val Met Glu Lys Pro Ser Pro Leu Leu Val Gly Arg Glu Phe Val
1               5                   10                  15

Arg Gln Tyr Tyr Thr Leu Leu Asn Gln Ala Pro Asp Met Leu His Arg
            20                  25                  30

Phe Tyr Gly Lys Asn Ser Ser Tyr Ala His Gly Gly Leu Asp Ser Asn
        35                  40                  45

Gly Lys Pro Ala Asp Ala Val Tyr Gly Gln Lys Glu Ile His Arg Lys
    50                  55                  60

Val Met Ser Gln Asn Phe Thr Asn Cys His Thr Lys Ile Arg His Val
65                  70                  75                  80

Asp Ala His Ala Thr Leu Asn Asp Gly Val Val Gln Val Met Gly
                85                  90                  95

Leu Leu Ser Asn Asn Asn Gln Ala Leu Arg Arg Phe Met Gln Thr Phe
                100                 105                 110

Val Leu Ala Pro Glu Gly Ser Val Ala Asn Lys Phe Tyr Val His Asn
            115                 120                 125

Asp Ile Phe Arg Tyr Gln Asp Glu Val Phe Gly Gly Phe Val Thr Glu
        130                 135                 140

Pro Gln Glu Glu Ser Glu Glu Val Glu Glu Pro Glu Glu Arg Gln
145                 150                 155                 160

Gln Ser Pro Glu Val Val Ala Asp Asp Ser Gly Thr Phe Tyr Asp Gln
            165                 170                 175

Thr Val Ser Asn Asp Leu Glu Glu His Leu Glu Glu Pro Val Val Glu
        180                 185                 190

Pro Glu Pro Glu Pro Glu Pro Glu Pro Glu Pro Val Ser Asp
    195                 200                 205

Ile Gln Glu Asp Lys Pro Glu Pro Ala Leu Glu Glu Ala Ala Pro Glu
210                 215                 220

Asp Val Gln Lys Ser Ala Ser Pro Ala Pro Ala Asp Val Ala Pro Ala
225                 230                 235                 240

Gln Glu Asp Leu Arg Thr Phe Ser Trp Ala Ser Val Thr Ser Lys Asn
            245                 250                 255

Leu Pro Pro Ser Gly Ala Val Pro Val Thr Gly Thr Pro Pro His Val
        260                 265                 270

Val Lys Val Pro Ala Ser Gln Pro Arg Pro Glu Ser Lys Pro Asp Ser
    275                 280                 285

Gln Ile Pro Pro Gln Arg Pro Gln Arg Asp Gln Arg Ala Arg Glu Gln
    290                 295                 300

Arg Ile Asn Ile Pro Pro Gln Arg Gly Pro Arg Pro Ile Arg Glu Ala
305                 310                 315                 320

Gly Glu Pro Gly Asp Val Glu Pro Arg Arg Met Val Arg His Pro Asp
                325                 330                 335

Ser His Gln Leu Phe Ile Gly Asn Leu Pro His Glu Val Asp Lys Ser
            340                 345                 350

Glu Leu Lys Asp Phe Phe Gln Ser Tyr Gly Asn Val Val Glu Leu Arg
        355                 360                 365

Ile Asn Ser Gly Gly Lys Leu Pro Asn Phe Gly Phe Val Val Phe Asp
    370                 375                 380

Asp Ser Glu Pro Val Gln Lys Val Leu Asn Asn Arg Pro Ile Met Phe
385                 390                 395                 400

Arg Gly Ala Val Arg Leu Asn Val Glu Glu Lys Lys Thr Arg Ala Ala
```

```
                    405                 410                 415
Arg Glu Gly Asp Arg Asp Asn Arg Leu Arg Gly Pro Gly Pro
            420                 425                 430

Arg Gly Gly Pro Ser Gly Gly Met Arg Gly Pro Pro Arg Gly Gly Met
            435                 440                 445

Val Gln Lys Pro Gly Phe Gly Val Gly Arg Gly Ile Thr Thr Pro Arg
    450                 455                 460

Gln
465

<210> SEQ ID NO 5
<211> LENGTH: 465
<212> TYPE: PRT
<213> ORGANISM: Mus musculus

<400> SEQUENCE: 5

Met Val Met Glu Lys Pro Ser Pro Leu Leu Val Gly Arg Glu Phe Val
1               5                   10                  15

Arg Gln Tyr Tyr Thr Leu Leu Asn Gln Ala Pro Asp Met Leu His Arg
            20                  25                  30

Phe Tyr Gly Lys Asn Ser Ser Tyr Ala His Gly Gly Leu Asp Ser Asn
        35                  40                  45

Gly Lys Pro Ala Asp Ala Val Tyr Gly Gln Lys Glu Ile His Arg Lys
    50                  55                  60

Val Met Ser Gln Asn Phe Thr Asn Cys His Thr Lys Ile Arg His Val
65                  70                  75                  80

Asp Ala His Ala Thr Leu Asn Asp Gly Val Val Gln Val Met Gly
            85                  90                  95

Leu Leu Ser Asn Asn Asn Gln Ala Leu Arg Arg Phe Met Gln Thr Phe
                100                 105                 110

Val Leu Ala Pro Glu Gly Ser Val Ala Asn Lys Phe Tyr Val His Asn
            115                 120                 125

Asp Ile Phe Arg Tyr Gln Asp Glu Val Phe Gly Gly Phe Val Thr Glu
        130                 135                 140

Pro Gln Glu Glu Ser Glu Glu Val Glu Glu Pro Glu Glu Arg Gln
145                 150                 155                 160

Gln Thr Pro Glu Val Val Pro Asp Asp Ser Gly Thr Phe Tyr Asp Gln
                165                 170                 175

Thr Val Ser Asn Asp Leu Glu Glu His Leu Glu Glu Pro Val Val Glu
            180                 185                 190

Pro Glu Pro Glu Pro Glu Pro Glu Pro Glu Pro Val Ser Asp
        195                 200                 205

Ile Gln Glu Asp Lys Pro Glu Ala Ala Leu Glu Ala Ala Pro Asp
    210                 215                 220

Asp Val Gln Lys Ser Thr Ser Pro Ala Pro Ala Asp Val Ala Pro Ala
225                 230                 235                 240

Gln Glu Asp Leu Arg Thr Phe Ser Trp Ala Ser Val Thr Ser Lys Asn
                245                 250                 255

Leu Pro Pro Ser Gly Ala Val Pro Val Thr Gly Thr Pro Pro His Val
            260                 265                 270

Val Lys Val Pro Ala Ser Gln Pro Arg Pro Glu Ser Lys Pro Asp Ser
        275                 280                 285

Gln Ile Pro Pro Gln Arg Pro Gln Arg Asp Gln Arg Val Arg Glu Gln
    290                 295                 300
```

```
Arg Ile Asn Ile Pro Pro Gln Arg Gly Pro Arg Pro Ile Arg Glu Ala
305                 310                 315                 320

Gly Glu Pro Gly Asp Val Glu Pro Arg Arg Met Val Arg His Pro Asp
            325                 330                 335

Ser His Gln Leu Phe Ile Gly Asn Leu Pro His Glu Val Asp Lys Ser
            340                 345                 350

Glu Leu Lys Asp Phe Phe Gln Asn Phe Gly Asn Val Val Glu Leu Arg
        355                 360                 365

Ile Asn Ser Gly Gly Lys Leu Pro Asn Phe Gly Phe Val Val Phe Asp
        370                 375                 380

Asp Ser Glu Pro Val Gln Lys Val Leu Ser Asn Arg Pro Ile Met Phe
385                 390                 395                 400

Arg Gly Ala Val Arg Leu Asn Val Glu Glu Lys Lys Thr Arg Ala Ala
            405                 410                 415

Arg Glu Gly Asp Arg Arg Asp Asn Arg Leu Arg Gly Pro Gly Gly Pro
            420                 425                 430

Arg Gly Gly Pro Ser Gly Gly Met Arg Gly Pro Pro Arg Gly Gly Met
        435                 440                 445

Val Gln Lys Pro Gly Phe Gly Val Gly Arg Gly Ile Thr Thr Pro Arg
    450                 455                 460

Gln
465

<210> SEQ ID NO 6
<211> LENGTH: 466
<212> TYPE: PRT
<213> ORGANISM: Macaca mulatta

<400> SEQUENCE: 6

Met Val Met Glu Lys Pro Ser Pro Leu Leu Val Gly Arg Glu Phe Val
1               5                   10                  15

Arg Gln Tyr Tyr Thr Leu Leu Asn Gln Ala Pro Asp Met Leu His Arg
            20                  25                  30

Phe Tyr Gly Lys Asn Ser Ser Tyr Val His Gly Gly Leu Asp Ser Asn
        35                  40                  45

Gly Lys Pro Ala Asp Ala Val Tyr Gly Gln Lys Glu Ile His Arg Lys
    50                  55                  60

Val Met Ser Gln Asn Phe Thr Asn Cys His Thr Lys Ile Arg His Val
65                  70                  75                  80

Asp Ala His Ala Thr Leu Asn Asp Gly Val Val Val Gln Val Met Gly
                85                  90                  95

Leu Leu Ser Asn Asn Asn Gln Ala Leu Arg Arg Phe Met Gln Thr Phe
            100                 105                 110

Val Leu Ala Pro Glu Gly Ser Val Ala Asn Lys Phe Tyr Val His Asn
        115                 120                 125

Asp Ile Phe Arg Tyr Gln Asp Glu Val Phe Gly Gly Phe Val Thr Glu
    130                 135                 140

Pro Gln Glu Glu Ser Glu Glu Val Glu Glu Pro Glu Glu Arg Gln
145                 150                 155                 160

Gln Thr Pro Glu Val Val Pro Asp Asp Ser Gly Thr Phe Tyr Asp Gln
            165                 170                 175

Ala Val Val Ser Asn Asp Met Glu Glu His Leu Glu Glu Pro Val Ala
        180                 185                 190

Glu Pro Glu Pro Asp Pro Glu Pro Glu Pro Glu Gln Glu Pro Val Ser
    195                 200                 205
```

-continued

Glu Ile Gln Glu Glu Lys Pro Glu Pro Val Leu Glu Thr Ala Pro
    210                 215                 220

Glu Asp Thr Gln Lys Ser Ser Pro Ala Pro Ala Asp Ile Ala Gln
225                 230                 235                 240

Thr Val Gln Glu Asp Leu Arg Thr Phe Ser Trp Ala Ser Val Thr Ser
                245                 250                 255

Lys Asn Leu Pro Pro Ser Gly Ala Val Pro Val Thr Gly Ile Pro Pro
                260                 265                 270

His Val Val Lys Val Pro Ala Ser Gln Pro Arg Pro Glu Ser Lys Pro
            275                 280                 285

Glu Ser Gln Ile Pro Pro Gln Arg Pro Gln Arg Asp Gln Arg Val Arg
    290                 295                 300

Glu Gln Arg Ile Asn Ile Pro Pro Gln Arg Gly Pro Arg Pro Ile Arg
305                 310                 315                 320

Glu Ala Gly Glu Gln Gly Asp Ile Glu Pro Arg Arg Met Val Arg His
                325                 330                 335

Pro Asp Ser His Gln Leu Phe Ile Gly Asn Leu Pro His Glu Val Asp
                340                 345                 350

Lys Ser Glu Leu Lys Asp Phe Phe Gln Asn Tyr Gly Asn Val Val Glu
            355                 360                 365

Leu Arg Ile Asn Ser Gly Gly Lys Leu Pro Asn Phe Gly Phe Val Val
    370                 375                 380

Phe Asp Asp Ser Glu Pro Val Gln Lys Val Leu Ser Asn Arg Pro Ile
385                 390                 395                 400

Met Phe Arg Gly Glu Val Arg Leu Asn Val Glu Glu Lys Lys Thr Arg
                405                 410                 415

Ala Ala Arg Glu Gly Asp Arg Arg Asp Asn Arg Leu Arg Gly Pro Gly
            420                 425                 430

Gly Pro Arg Gly Gly Leu Gly Gly Met Arg Gly Pro Pro Arg Gly
        435                 440                 445

Gly Met Val Gln Lys Pro Gly Phe Gly Val Gly Arg Gly Leu Ala Pro
    450                 455                 460

Arg Gln
465

<210> SEQ ID NO 7
<211> LENGTH: 466
<212> TYPE: PRT
<213> ORGANISM: Pan troglodytes

<400> SEQUENCE: 7

Met Val Met Glu Lys Pro Ser Pro Leu Leu Val Gly Arg Glu Phe Val
1               5                   10                  15

Arg Gln Tyr Tyr Thr Leu Leu Asn Gln Ala Pro Asp Met Leu His Arg
            20                  25                  30

Phe Tyr Gly Lys Asn Ser Ser Tyr Val His Gly Gly Leu Asp Ser Asn
        35                  40                  45

Gly Lys Pro Ala Asp Ala Val Tyr Gly Gln Lys Glu Ile His Arg Lys
    50                  55                  60

Val Met Ser Gln Asn Phe Thr Asn Cys His Thr Lys Ile Arg His Val
65                  70                  75                  80

Asp Ala His Ala Thr Leu Asn Asp Gly Val Val Val Gln Val Met Gly
                85                  90                  95

Leu Leu Ser Asn Asn Asn Gln Ala Leu Arg Arg Phe Met Gln Thr Phe

```
            100                 105                 110
Val Leu Ala Pro Glu Gly Ser Val Ala Asn Lys Phe Tyr Val His Asn
        115                 120                 125

Asp Ile Phe Arg Tyr Gln Asp Glu Val Phe Gly Gly Phe Val Thr Glu
        130                 135                 140

Pro Gln Glu Glu Ser Glu Glu Val Glu Glu Pro Glu Glu Arg Gln
145                 150                 155                 160

Gln Thr Pro Glu Val Val Pro Asp Asp Ser Gly Thr Phe Tyr Asp Gln
                165                 170                 175

Ala Val Val Ser Asn Asp Val Glu Glu His Leu Glu Glu Pro Val Ala
                180                 185                 190

Glu Pro Glu Pro Asp Pro Glu Pro Glu Gln Glu Pro Val Ser
        195                 200                 205

Glu Ile Gln Glu Glu Lys Pro Glu Pro Val Leu Glu Glu Thr Ala Pro
        210                 215                 220

Glu Asp Ala Gln Lys Ser Ser Ser Pro Ala Pro Ala Asp Ile Ala Gln
225                 230                 235                 240

Thr Val Gln Glu Asp Leu Arg Thr Phe Ser Trp Ala Ser Val Thr Ser
                245                 250                 255

Lys Asn Leu Pro Pro Ser Gly Ala Val Pro Val Thr Gly Ile Pro Pro
                260                 265                 270

His Val Val Lys Val Pro Ala Ser Gln Pro Arg Pro Glu Ser Lys Pro
                275                 280                 285

Glu Ser Gln Ile Pro Pro Gln Arg Pro Gln Arg Asp Gln Arg Val Arg
        290                 295                 300

Glu Gln Arg Ile Asn Ile Pro Pro Gln Arg Gly Pro Arg Pro Ile Arg
305                 310                 315                 320

Glu Ala Gly Glu Gln Gly Asp Ile Glu Pro Arg Arg Met Val Arg His
                325                 330                 335

Pro Asp Ser His Gln Leu Phe Ile Gly Asn Leu Pro His Glu Val Asp
                340                 345                 350

Lys Ser Glu Leu Lys Asp Phe Phe Gln Ser Tyr Gly Asn Val Val Glu
                355                 360                 365

Leu Arg Ile Asn Ser Gly Gly Lys Leu Pro Asn Phe Gly Phe Val Val
        370                 375                 380

Phe Asp Asp Ser Glu Pro Val Gln Lys Val Leu Ser Asn Arg Pro Ile
385                 390                 395                 400

Met Phe Arg Gly Glu Val Arg Leu Asn Val Glu Glu Lys Lys Thr Arg
                405                 410                 415

Ala Ala Arg Glu Gly Asp Arg Asp Asn Arg Leu Arg Gly Pro Gly
                420                 425                 430

Gly Pro Arg Gly Gly Leu Gly Gly Met Arg Gly Pro Pro Arg Gly
        435                 440                 445

Gly Met Val Gln Lys Pro Gly Phe Gly Val Gly Arg Gly Leu Ala Pro
        450                 455                 460

Arg Gln
465

<210> SEQ ID NO 8
<211> LENGTH: 465
<212> TYPE: PRT
<213> ORGANISM: Bos taurus

<400> SEQUENCE: 8
```

-continued

```
Met Val Met Glu Lys Pro Ser Pro Leu Leu Val Gly Arg Glu Phe Val
1               5                   10                  15

Arg Gln Tyr Tyr Thr Leu Leu Asn Gln Ala Pro Asp Met Leu His Arg
            20                  25                  30

Phe Tyr Gly Lys Asn Ser Ser Tyr Val His Gly Gly Leu Asp Ser Asn
            35                  40                  45

Gly Lys Pro Ala Asp Ala Val Tyr Gly Gln Lys Glu Ile His Arg Lys
    50                  55                  60

Val Met Ser Gln Asn Phe Thr Asn Cys His Thr Lys Ile Arg His Val
65                  70                  75                  80

Asp Ala His Ala Thr Leu Asn Asp Gly Val Val Gln Val Met Gly
                85                  90                  95

Leu Leu Ser Asn Asn Asn Gln Ala Leu Arg Arg Phe Met Gln Thr Phe
            100                 105                 110

Val Leu Ala Pro Glu Gly Ser Val Ala Asn Lys Phe Tyr Val His Asn
            115                 120                 125

Asp Ile Phe Arg Tyr Gln Asp Glu Val Phe Gly Gly Phe Ile Thr Glu
        130                 135                 140

Pro Gln Glu Glu Ser Glu Glu Val Glu Glu Pro Glu Glu Arg Gln
145                 150                 155                 160

Gln Thr Pro Glu Val Val Pro Asp Asp Ser Gly Thr Phe Tyr Asp Gln
            165                 170                 175

Thr Val Ser Asn Asp Leu Glu Glu His Leu Glu Glu Pro Val Ala Glu
            180                 185                 190

Pro Glu Pro Glu Pro Glu Pro Glu Gln Glu Pro Val Ser Glu
        195                 200                 205

Val Gln Glu Glu Lys Ser Glu Pro Val Leu Glu Glu Thr Ala Pro Glu
    210                 215                 220

Asp Val Gln Lys Ser Ser Pro Ala Pro Ala Asp Ile Ala Gln Thr
225                 230                 235                 240

Val Gln Glu Asp Leu Arg Thr Phe Ser Trp Ala Ser Val Thr Ser Lys
            245                 250                 255

Asn Leu Pro Pro Ser Gly Ala Val Pro Val Thr Gly Ile Pro Pro His
            260                 265                 270

Val Val Lys Val Pro Ala Ser Gln Pro Arg Pro Glu Ser Lys Pro Glu
    275                 280                 285

Ser Gln Ile Pro Leu Gln Arg Pro Gln Arg Asp Gln Arg Val Arg Glu
    290                 295                 300

Gln Arg Ile Asn Val Pro Pro Gln Arg Gly Pro Arg Pro Val Arg Glu
305                 310                 315                 320

Ala Gly Glu Gln Gly Asp Val Glu Pro Arg Arg Ile Val Arg His Pro
            325                 330                 335

Asp Ser His Gln Leu Phe Ile Gly Asn Leu Pro His Glu Val Asp Lys
            340                 345                 350

Ser Glu Leu Lys Asp Phe Gln Asn Tyr Gly Asn Val Val Glu Leu
    355                 360                 365

Arg Ile Asn Ser Gly Gly Lys Leu Pro Asn Phe Gly Phe Val Val Phe
    370                 375                 380

Asp Asp Ser Glu Pro Val Gln Lys Val Leu Ser Asn Arg Pro Ile Met
385                 390                 395                 400

Phe Arg Gly Glu Val Arg Leu Asn Val Glu Glu Lys Lys Thr Arg Ala
            405                 410                 415

Ala Arg Glu Gly Asp Arg Arg Asp Asn Arg Leu Arg Gly Pro Gly Gly
```

```
                420             425              430
Pro Arg Gly Gly Leu Gly Gly Gly Met Arg Gly Pro Pro Arg Gly Gly
            435              440             445

Met Val Gln Lys Pro Gly Phe Gly Val Gly Arg Ser Ile Ala Pro Arg
            450              455             460

Gln
465

<210> SEQ ID NO 9
<211> LENGTH: 465
<212> TYPE: PRT
<213> ORGANISM: Canis lupus

<400> SEQUENCE: 9

Met Val Met Glu Lys Pro Ser Pro Leu Leu Val Gly Arg Glu Phe Val
1               5                   10                  15

Arg Gln Tyr Tyr Thr Leu Leu Asn Gln Ala Pro Asp Met Leu His Arg
            20                  25                  30

Phe Tyr Gly Lys Asn Ser Ser Tyr Val His Gly Gly Leu Asp Ser Asn
            35                  40                  45

Gly Lys Pro Ala Asp Ala Val Tyr Gly Gln Lys Glu Ile His Arg Lys
50                  55                  60

Val Met Ser Gln Asn Phe Thr Asn Cys His Thr Lys Ile Arg His Val
65                  70                  75                  80

Asp Ala His Ala Thr Leu Asn Asp Gly Val Val Gln Val Met Gly
            85                  90                  95

Leu Leu Ser Asn Asn Gln Ala Leu Arg Arg Phe Met Gln Thr Phe
            100                 105                 110

Val Leu Ala Pro Glu Gly Ser Val Ala Asn Lys Phe Tyr Val His Asn
            115                 120                 125

Asp Ile Phe Arg Tyr Gln Asp Glu Val Phe Gly Gly Phe Val Thr Glu
130                 135                 140

Pro Gln Glu Glu Ser Glu Glu Val Glu Glu Pro Glu Glu Arg Gln
145                 150                 155                 160

Gln Thr Pro Glu Val Val Pro Asp Asp Ser Gly Thr Phe Tyr Asp Gln
            165                 170                 175

Ser Val Ser Asn Asp Leu Glu Glu His Leu Glu Glu Pro Val Ala Glu
            180                 185                 190

Pro Glu Pro Asp Pro Glu Pro Glu Gln Glu Pro Val Ser Glu
            195                 200                 205

Ile Gln Glu Glu Lys Ser Glu Pro Val Leu Glu Glu Thr Ala Pro Glu
210                 215                 220

Asp Thr Gln Lys Ser Ser Pro Ala Pro Thr Asp Ile Ala Gln Thr
225                 230                 235                 240

Val Gln Glu Asp Leu Arg Thr Phe Ser Trp Ala Ser Val Thr Ser Lys
            245                 250                 255

Asn Leu Pro Pro Ser Gly Ala Val Pro Val Thr Gly Ile Pro Pro His
            260                 265                 270

Val Val Lys Val Pro Ala Ser Gln Pro Arg Pro Glu Ser Lys Pro Glu
            275                 280                 285

Ser Gln Ile Pro Pro Gln Arg Pro Gln Arg Asp Gln Arg Val Arg Glu
            290                 295                 300

Gln Arg Ile Asn Ile Pro Pro Gln Arg Gly Pro Arg Pro Ile Arg Glu
305                 310                 315                 320
```

Ala Gly Glu Gln Gly Asp Val Glu Pro Arg Ile Val Arg His Pro
            325                 330                 335

Asp Ser His Gln Leu Phe Ile Gly Asn Leu Pro His Glu Val Asp Lys
            340                 345                 350

Ser Glu Leu Lys Asp Phe Phe Gln Ser Tyr Gly Asn Val Val Glu Leu
            355                 360                 365

Arg Ile Asn Ser Gly Gly Lys Leu Pro Asn Phe Gly Phe Val Val Phe
        370                 375                 380

Asp Asp Ser Glu Pro Val Gln Lys Val Leu Ser Asn Arg Pro Ile Met
385                 390                 395                 400

Phe Arg Gly Glu Val Arg Leu Asn Val Glu Glu Lys Lys Thr Arg Ala
                405                 410                 415

Ala Arg Glu Gly Asp Arg Arg Asp Asn Arg Leu Arg Gly Pro Gly Gly
            420                 425                 430

Pro Arg Gly Gly Leu Gly Gly Gly Met Arg Gly Pro Ser Arg Gly Gly
        435                 440                 445

Met Val Gln Lys Pro Gly Phe Gly Val Gly Arg Gly Ile Ala Pro Arg
    450                 455                 460

Gln
465

<210> SEQ ID NO 10
<211> LENGTH: 482
<212> TYPE: PRT
<213> ORGANISM: Mus musculus

<400> SEQUENCE: 10

Met Val Met Glu Lys Pro Ser Pro Leu Leu Val Gly Arg Glu Phe Val
1               5                   10                  15

Arg Gln Tyr Tyr Thr Leu Leu Asn Lys Ala Pro Glu Tyr Leu His Arg
            20                  25                  30

Phe Tyr Gly Arg Asn Ser Ser Tyr Val His Gly Gly Val Asp Ala Ser
        35                  40                  45

Gly Lys Pro Gln Glu Ala Val Tyr Gly Gln Asn Asp Ile His His Lys
    50                  55                  60

Val Leu Ser Leu Asn Phe Ser Glu Cys His Thr Lys Ile Arg His Val
65                  70                  75                  80

Asp Ala His Ala Thr Leu Ser Asp Gly Val Val Val Gln Val Met Gly
                85                  90                  95

Leu Leu Ser Asn Ser Gly Gln Pro Glu Arg Lys Phe Met Gln Thr Phe
            100                 105                 110

Val Leu Ala Pro Glu Gly Ser Val Pro Asn Lys Phe Tyr Val His Asn
        115                 120                 125

Asp Met Phe Arg Tyr Glu Asp Glu Val Phe Gly Asp Ser Glu Pro Glu
    130                 135                 140

Leu Asp Glu Glu Ser Glu Asp Glu Val Glu Glu Gln Glu Asp Arg
145                 150                 155                 160

Gln Pro Ser Pro Glu Pro Val Gln Glu Asn Ala Asn Ser Ala Tyr Tyr
                165                 170                 175

Asp Ala His Pro Val Thr Asn Gly Ile Glu Glu Pro Leu Glu Glu Ser
            180                 185                 190

Ser His Glu Pro Glu Pro Glu Pro Glu Ser Glu Thr Lys Thr Glu Glu
        195                 200                 205

Leu Lys Pro Gln Val Glu Glu Lys His Leu Glu Glu Leu Glu Glu Lys
    210                 215                 220

```
Ser Ala Thr Pro Pro Ala Glu Pro Ala Ser Leu Pro Gln Glu Pro
225                 230                 235                 240

Pro Lys Ala Phe Ser Trp Ala Ser Val Thr Ser Lys Asn Leu Pro Pro
            245                 250                 255

Ser Gly Thr Val Ser Ser Ser Gly Ile Pro Pro His Val Lys Ala Pro
                260                 265                 270

Val Ser Gln Pro Arg Val Asp Ala Lys Pro Glu Val Gln Ser Gln Pro
            275                 280                 285

Pro Arg Val Arg Glu Gln Arg Pro Arg Glu Arg Pro Gly Phe Pro Pro
        290                 295                 300

Arg Gly Pro Arg Pro Gly Arg Gly Asp Met Glu Gln Asn Asp Ser Asp
305                 310                 315                 320

Asn Arg Arg Ile Ile Arg Tyr Pro Asp Ser His Gln Leu Phe Val Gly
                325                 330                 335

Asn Leu Pro His Asp Ile Asp Glu Asn Glu Leu Lys Glu Phe Phe Met
            340                 345                 350

Ser Phe Gly Asn Val Val Glu Leu Arg Ile Asn Thr Lys Gly Val Gly
        355                 360                 365

Gly Lys Leu Pro Asn Phe Gly Phe Val Val Phe Asp Asp Ser Glu Pro
    370                 375                 380

Val Gln Arg Ile Leu Ile Ala Lys Pro Ile Met Phe Arg Gly Glu Val
385                 390                 395                 400

Arg Leu Asn Val Glu Glu Lys Lys Thr Arg Ala Ala Arg Glu Arg Glu
                405                 410                 415

Thr Arg Gly Gly Gly Asp Asp Arg Arg Asp Ile Arg Arg Asn Asp Arg
            420                 425                 430

Gly Pro Gly Gly Pro Arg Gly Ile Val Gly Gly Met Met Arg Asp
        435                 440                 445

Arg Asp Gly Arg Gly Pro Pro Pro Arg Gly Met Thr Gln Lys Leu
    450                 455                 460

Gly Ser Gly Arg Gly Thr Gly Gln Met Glu Gly Arg Phe Thr Gly Gln
465                 470                 475                 480

Arg Arg

<210> SEQ ID NO 11
<211> LENGTH: 449
<212> TYPE: PRT
<213> ORGANISM: Mus musculus

<400> SEQUENCE: 11

Met Val Met Glu Lys Pro Ser Pro Leu Leu Val Gly Arg Glu Phe Val
1               5                   10                  15

Arg Gln Tyr Tyr Thr Leu Leu Asn Lys Ala Pro Glu Tyr Leu His Arg
                20                  25                  30

Phe Tyr Gly Arg Asn Ser Ser Tyr Val His Gly Gly Val Asp Ala Ser
            35                  40                  45

Gly Lys Pro Gln Glu Ala Val Tyr Gly Gln Asn Asp Ile His His Lys
        50                  55                  60

Val Leu Ser Leu Asn Phe Ser Glu Cys His Thr Lys Ile Arg His Val
65                  70                  75                  80

Asp Ala His Ala Thr Leu Ser Asp Gly Val Val Gln Val Met Gly
                85                  90                  95

Leu Leu Ser Asn Ser Gly Gln Pro Glu Arg Lys Phe Met Gln Thr Phe
            100                 105                 110
```

Val Leu Ala Pro Glu Gly Ser Val Pro Asn Lys Phe Tyr Val His Asn
            115                 120                 125

Asp Met Phe Arg Tyr Glu Asp Glu Val Phe Gly Asp Ser Glu Pro Glu
            130                 135                 140

Leu Asp Glu Glu Ser Glu Asp Glu Val Glu Glu Gln Glu Asp Arg
145                 150                 155                 160

Gln Pro Ser Pro Glu Pro Val Gln Glu Asn Ala Asn Ser Ala Tyr Tyr
            165                 170                 175

Asp Ala His Pro Val Thr Asn Gly Ile Glu Glu Pro Leu Glu Glu Ser
            180                 185                 190

Ser His Glu Pro Glu Pro Glu Ser Glu Thr Lys Thr Glu Glu
            195                 200                 205

Leu Lys Pro Gln Val Glu Glu Lys His Leu Glu Glu Leu Glu Glu Lys
            210                 215                 220

Ser Ala Thr Pro Pro Pro Ala Glu Pro Ala Ser Leu Pro Gln Glu Pro
225                 230                 235                 240

Pro Lys Pro Arg Val Asp Ala Lys Pro Glu Val Gln Ser Gln Pro Pro
            245                 250                 255

Arg Val Arg Glu Gln Arg Pro Glu Arg Pro Gly Phe Pro Pro Arg
            260                 265                 270

Gly Pro Arg Pro Gly Arg Gly Asp Met Glu Gln Asn Asp Ser Asp Asn
            275                 280                 285

Arg Arg Ile Ile Arg Tyr Pro Asp Ser His Gln Leu Phe Val Gly Asn
            290                 295                 300

Leu Pro His Asp Ile Asp Glu Asn Glu Leu Lys Glu Phe Phe Met Ser
305                 310                 315                 320

Phe Gly Asn Val Val Glu Leu Arg Ile Asn Thr Lys Gly Val Gly Gly
            325                 330                 335

Lys Leu Pro Asn Phe Gly Phe Val Val Phe Asp Asp Ser Glu Pro Val
            340                 345                 350

Gln Arg Ile Leu Ile Ala Lys Pro Ile Met Phe Arg Gly Glu Val Arg
            355                 360                 365

Leu Asn Val Glu Glu Lys Lys Thr Arg Ala Ala Arg Glu Arg Glu Thr
            370                 375                 380

Arg Gly Gly Gly Asp Asp Arg Arg Asp Ile Arg Arg Asn Asp Arg Gly
385                 390                 395                 400

Pro Gly Gly Pro Arg Gly Ile Val Gly Gly Met Met Arg Asp Arg
            405                 410                 415

Asp Gly Arg Gly Pro Pro Arg Gly Met Thr Gln Lys Leu Gly
            420                 425                 430

Ser Gly Arg Gly Thr Gly Gln Met Glu Gly Arg Phe Thr Gly Gln Arg
            435                 440                 445

Arg

<210> SEQ ID NO 12
<211> LENGTH: 449
<212> TYPE: PRT
<213> ORGANISM: Rattus norvegicus

<400> SEQUENCE: 12

Met Val Met Glu Lys Pro Ser Pro Leu Leu Val Gly Arg Glu Phe Val
1               5                   10                  15

Arg Gln Tyr Tyr Thr Leu Leu Asn Lys Ala Pro Glu Tyr Leu His Arg
            20                  25                  30

```
Phe Tyr Gly Arg Asn Ser Ser Tyr Val His Gly Gly Val Asp Ala Ser
        35                  40                  45

Gly Lys Pro Gln Glu Ala Val Tyr Gly Gln Asn Asp Ile His His Lys
    50                  55                  60

Val Leu Ser Leu Asn Phe Ser Glu Cys His Thr Lys Ile Arg His Val
65                  70                  75                  80

Asp Ala His Ala Thr Leu Ser Asp Gly Val Val Gln Val Met Gly
                85                  90                  95

Leu Leu Ser Asn Ser Gly Gln Pro Glu Arg Lys Phe Met Gln Thr Phe
            100                 105                 110

Val Leu Ala Pro Glu Gly Ser Val Pro Asn Lys Phe Tyr Val His Asn
            115                 120                 125

Asp Met Phe Arg Tyr Glu Asp Glu Val Phe Gly Asp Ser Glu Pro Glu
        130                 135                 140

Leu Asp Glu Glu Ser Glu Asp Glu Val Glu Glu Gln Glu Asp Arg
145                 150                 155                 160

Gln Pro Ser Pro Glu Pro Val Gln Glu Asn Ala Asn Ser Ala Tyr Tyr
                165                 170                 175

Glu Ala His Pro Val Thr Asn Gly Ile Glu Glu Pro Leu Glu Glu Ser
            180                 185                 190

Ser His Glu Pro Glu Pro Glu Pro Glu Ser Glu Thr Lys Thr Glu Glu
        195                 200                 205

Leu Lys Pro Gln Ala Glu Glu Lys His Leu Glu Glu Leu Glu Glu Lys
    210                 215                 220

Ser Ala Thr Pro Pro Thr Glu Pro Ala Ser Leu Pro Gln Glu Pro
225                 230                 235                 240

Pro Lys Pro Arg Val Asp Ala Lys Pro Glu Val Gln Ser Gln Pro Pro
                245                 250                 255

Arg Val Arg Glu Gln Arg Pro Arg Glu Arg Pro Gly Phe Pro Pro Arg
            260                 265                 270

Gly Pro Arg Pro Gly Arg Gly Asp Thr Glu Gln Asn Asp Ser Asp Asn
        275                 280                 285

Arg Arg Ile Ile Arg Tyr Pro Asp Ser His Gln Leu Phe Val Gly Asn
    290                 295                 300

Leu Pro His Asp Ile Asp Glu Asn Glu Leu Lys Glu Phe Phe Met Ser
305                 310                 315                 320

Phe Gly Asn Val Val Glu Leu Arg Ile Asn Thr Lys Gly Val Gly Gly
                325                 330                 335

Lys Leu Pro Asn Phe Gly Phe Val Val Phe Asp Asp Ser Glu Pro Val
            340                 345                 350

Gln Arg Ile Leu Ile Ala Lys Pro Ile Met Phe Arg Gly Glu Val Arg
        355                 360                 365

Leu Asn Val Glu Glu Lys Lys Thr Arg Ala Ala Arg Glu Arg Glu Thr
    370                 375                 380

Arg Gly Gly Gly Asp Asp Arg Asp Ile Arg Arg Asn Asp Arg Gly
385                 390                 395                 400

Pro Gly Gly Pro Arg Gly Ile Val Gly Gly Met Met Arg Asp Arg
                405                 410                 415

Asp Gly Arg Gly Pro Pro Arg Gly Gly Met Thr Gln Lys Leu Gly
            420                 425                 430

Ser Gly Arg Gly Thr Gly Gln Met Glu Gly Arg Phe Thr Gly Gln Arg
        435                 440                 445
```

Arg

<210> SEQ ID NO 13
<211> LENGTH: 482
<212> TYPE: PRT
<213> ORGANISM: Rattus norvegicus

<400> SEQUENCE: 13

```
Met Val Met Glu Lys Pro Ser Pro Leu Leu Val Gly Arg Glu Phe Val
1               5                   10                  15
Arg Gln Tyr Tyr Thr Leu Leu Asn Lys Ala Pro Glu Tyr Leu His Arg
            20                  25                  30
Phe Tyr Gly Arg Asn Ser Ser Tyr Val His Gly Gly Val Asp Ala Ser
        35                  40                  45
Gly Lys Pro Gln Glu Ala Val Tyr Gly Gln Asn Asp Ile His His Lys
    50                  55                  60
Val Leu Ser Leu Asn Phe Ser Glu Cys His Thr Lys Ile Arg His Val
65                  70                  75                  80
Asp Ala His Ala Thr Leu Ser Asp Gly Val Val Gln Val Met Gly
                85                  90                  95
Leu Leu Ser Asn Ser Gly Gln Pro Glu Arg Lys Phe Met Gln Thr Phe
            100                 105                 110
Val Leu Ala Pro Glu Gly Ser Val Pro Asn Lys Phe Tyr Val His Asn
        115                 120                 125
Asp Met Phe Arg Tyr Glu Asp Glu Val Phe Gly Asp Ser Glu Pro Glu
    130                 135                 140
Leu Asp Glu Glu Ser Glu Asp Glu Val Glu Glu Gln Glu Asp Arg
145                 150                 155                 160
Gln Pro Ser Pro Glu Pro Val Gln Glu Asn Ala Asn Ser Ala Tyr Tyr
                165                 170                 175
Glu Ala His Pro Val Thr Asn Gly Ile Glu Glu Pro Leu Glu Glu Ser
            180                 185                 190
Ser His Glu Pro Glu Pro Glu Ser Glu Thr Lys Thr Glu Glu
        195                 200                 205
Leu Lys Pro Gln Ala Glu Glu Lys His Leu Glu Leu Glu Glu Lys
    210                 215                 220
Ser Ala Thr Pro Pro Thr Glu Pro Ala Ser Leu Pro Gln Glu Pro
225                 230                 235                 240
Pro Lys Ala Phe Ser Trp Ala Ser Val Thr Ser Lys Asn Leu Pro Pro
                245                 250                 255
Ser Gly Thr Val Ser Ser Ser Gly Ile Pro Pro His Val Lys Ala Pro
            260                 265                 270
Val Ser Gln Pro Arg Val Asp Ala Lys Pro Glu Val Gln Ser Gln Pro
        275                 280                 285
Pro Arg Val Arg Glu Gln Arg Pro Arg Glu Arg Pro Gly Phe Pro Pro
    290                 295                 300
Arg Gly Pro Arg Pro Gly Arg Gly Asp Thr Glu Gln Asn Asp Ser Asp
305                 310                 315                 320
Asn Arg Arg Ile Ile Arg Tyr Pro Asp Ser His Gln Leu Phe Val Gly
                325                 330                 335
Asn Leu Pro His Asp Ile Asp Glu Asn Glu Leu Lys Glu Phe Phe Met
            340                 345                 350
Ser Phe Gly Asn Val Val Glu Leu Arg Ile Asn Thr Lys Gly Val Gly
        355                 360                 365
```

-continued

```
Gly Lys Leu Pro Asn Phe Gly Phe Val Val Phe Asp Asp Ser Glu Pro
    370             375             380
Val Gln Arg Ile Leu Ile Ala Lys Pro Ile Met Phe Arg Gly Glu Val
385             390             395             400
Arg Leu Asn Val Glu Glu Lys Lys Thr Arg Ala Ala Arg Glu Arg Glu
            405             410             415
Thr Arg Gly Gly Gly Asp Asp Arg Arg Asp Ile Arg Arg Asn Asp Arg
            420             425             430
Gly Pro Gly Gly Pro Arg Gly Ile Val Gly Gly Met Met Arg Asp
            435             440             445
Arg Asp Gly Arg Gly Pro Pro Arg Gly Gly Met Thr Gln Lys Leu
450             455             460
Gly Ser Gly Arg Gly Thr Gly Gln Met Glu Gly Arg Phe Thr Gly Gln
465             470             475             480
Arg Arg
```

<210> SEQ ID NO 14
<211> LENGTH: 449
<212> TYPE: PRT
<213> ORGANISM: Bos taurus

<400> SEQUENCE: 14

```
Met Val Met Glu Lys Pro Ser Pro Leu Leu Val Gly Arg Glu Phe Val
1               5                   10                  15
Arg Gln Tyr Tyr Thr Leu Leu Asn Lys Ala Pro Glu Tyr Leu His Arg
            20                  25                  30
Phe Tyr Gly Arg Asn Ser Ser Tyr Val His Gly Gly Val Asp Ala Ser
        35                  40                  45
Gly Lys Pro Gln Glu Ala Val Tyr Gly Gln Asn Asp Ile His His Lys
    50                  55                  60
Val Leu Ser Leu Asn Phe Ser Glu Cys His Thr Lys Ile Arg His Val
65                  70                  75                  80
Asp Ala His Ala Thr Leu Ser Asp Gly Val Val Gln Val Met Gly
            85                  90                  95
Leu Leu Ser Asn Ser Gly Gln Pro Glu Arg Lys Phe Met Gln Thr Phe
            100                 105                 110
Val Leu Ala Pro Glu Gly Ser Val Pro Asn Lys Phe Tyr Val His Asn
        115                 120                 125
Asp Met Phe Arg Tyr Glu Asp Glu Val Phe Gly Asp Ser Glu Pro Glu
    130                 135                 140
Leu Asp Glu Glu Ser Glu Asp Glu Val Glu Glu Gln Glu Glu Arg
145                 150                 155                 160
Gln Pro Ser Pro Glu Pro Val Gln Glu Asn Ala Asn Ser Gly Tyr Tyr
            165                 170                 175
Glu Ala His Pro Val Thr Asn Gly Ile Glu Glu Pro Leu Glu Glu Ser
        180                 185                 190
Ser His Glu Pro Glu Pro Glu Ser Glu Thr Lys Thr Glu Glu
    195                 200                 205
Leu Lys Pro Pro Val Glu Glu Lys Asn Leu Glu Glu Leu Glu Glu Lys
    210                 215                 220
Ser Ala Ser Pro Pro Ala Glu Pro Val Ser Leu Pro Gln Glu Pro
225                 230                 235                 240
Pro Lys Pro Arg Val Glu Ala Lys Pro Glu Val Gln Ser Gln Pro Pro
            245                 250                 255
```

```
Arg Val Arg Glu Gln Arg Pro Arg Glu Arg Pro Gly Phe Pro Pro Arg
            260                 265                 270

Gly Pro Arg Pro Gly Arg Gly Asp Ile Glu Gln Asn Glu Ser Asp Asn
            275                 280                 285

Arg Arg Ile Ile Arg Tyr Pro Asp Ser His Gln Leu Phe Val Gly Asn
        290                 295                 300

Leu Pro His Asp Ile Asp Glu Asn Glu Leu Lys Glu Phe Phe Met Ser
305                 310                 315                 320

Phe Gly Asn Val Val Glu Leu Arg Ile Asn Thr Lys Gly Val Gly Gly
                325                 330                 335

Lys Leu Pro Asn Phe Gly Phe Val Val Phe Asp Asp Ser Glu Pro Val
            340                 345                 350

Gln Arg Ile Leu Ile Ala Lys Pro Ile Met Phe Arg Gly Glu Val Arg
            355                 360                 365

Leu Asn Val Glu Glu Lys Lys Thr Arg Ala Ala Arg Glu Arg Glu Thr
        370                 375                 380

Arg Gly Gly Gly Asp Asp Arg Arg Asp Ile Arg Arg Ser Asp Arg Gly
385                 390                 395                 400

Pro Gly Gly Pro Arg Gly Ile Val Gly Gly Met Met Arg Asp Arg
            405                 410                 415

Asp Gly Arg Gly Pro Pro Arg Gly Gly Met Ala Gln Lys Leu Gly
            420                 425                 430

Ser Gly Arg Gly Ala Gly Gln Met Glu Gly Arg Phe Thr Gly Gln Arg
            435                 440                 445

Arg

<210> SEQ ID NO 15
<211> LENGTH: 482
<212> TYPE: PRT
<213> ORGANISM: Bos taurus

<400> SEQUENCE: 15

Met Val Met Glu Lys Pro Ser Pro Leu Leu Val Gly Arg Glu Phe Val
1               5                   10                  15

Arg Gln Tyr Tyr Thr Leu Leu Asn Lys Ala Pro Glu Tyr Leu His Arg
            20                  25                  30

Phe Tyr Gly Arg Asn Ser Ser Tyr Val His Gly Gly Val Asp Ala Ser
        35                  40                  45

Gly Lys Pro Gln Glu Ala Val Tyr Gly Gln Asn Asp Ile His His Lys
    50                  55                  60

Val Leu Ser Leu Asn Phe Ser Glu Cys His Thr Lys Ile Arg His Val
65                  70                  75                  80

Asp Ala His Ala Thr Leu Ser Asp Gly Val Val Gln Val Met Gly
                85                  90                  95

Leu Leu Ser Asn Ser Gly Gln Pro Glu Arg Lys Phe Met Gln Thr Phe
                100                 105                 110

Val Leu Ala Pro Glu Gly Ser Val Pro Asn Lys Phe Tyr Val His Asn
            115                 120                 125

Asp Met Phe Arg Tyr Glu Asp Glu Val Phe Gly Asp Ser Glu Pro Glu
        130                 135                 140

Leu Asp Glu Glu Ser Glu Asp Glu Val Glu Glu Gln Glu Glu Arg
145                 150                 155                 160

Gln Pro Ser Pro Glu Pro Val Gln Glu Asn Ala Asn Ser Gly Tyr Tyr
            165                 170                 175
```

```
Glu Ala His Pro Val Thr Asn Gly Ile Glu Pro Leu Glu Glu Ser
            180                 185                 190
Ser His Glu Pro Glu Pro Glu Pro Ser Glu Thr Lys Thr Glu Glu
        195                 200                 205
Leu Lys Pro Pro Val Glu Glu Lys Asn Leu Glu Glu Leu Glu Lys
    210                 215                 220
Ser Ala Ser Pro Pro Ala Glu Pro Val Ser Leu Pro Gln Glu Pro
225                 230                 235                 240
Pro Lys Ala Phe Ser Trp Ala Ser Val Thr Ser Lys Asn Leu Pro Pro
            245                 250                 255
Ser Gly Thr Val Ser Ser Gly Ile Pro Pro His Val Lys Ala Pro
        260                 265                 270
Val Ser Gln Pro Arg Val Glu Ala Lys Pro Glu Val Gln Ser Gln Pro
    275                 280                 285
Pro Arg Val Arg Glu Gln Arg Pro Arg Glu Arg Pro Gly Phe Pro Pro
290                 295                 300
Arg Gly Pro Arg Pro Gly Arg Gly Asp Ile Glu Gln Asn Glu Ser Asp
305                 310                 315                 320
Asn Arg Arg Ile Ile Arg Tyr Pro Asp Ser His Gln Leu Phe Val Gly
            325                 330                 335
Asn Leu Pro His Asp Ile Asp Glu Asn Glu Leu Lys Glu Phe Phe Met
        340                 345                 350
Ser Phe Gly Asn Val Val Glu Leu Arg Ile Asn Thr Lys Gly Val Gly
        355                 360                 365
Gly Lys Leu Pro Asn Phe Gly Phe Val Val Phe Asp Asp Ser Glu Pro
    370                 375                 380
Val Gln Arg Ile Leu Ile Ala Lys Pro Ile Met Phe Arg Gly Glu Val
385                 390                 395                 400
Arg Leu Asn Val Glu Glu Lys Lys Thr Arg Ala Ala Arg Glu Arg Glu
            405                 410                 415
Thr Arg Gly Gly Gly Asp Asp Arg Arg Asp Ile Arg Arg Ser Asp Arg
        420                 425                 430
Gly Pro Gly Gly Pro Arg Gly Ile Val Gly Gly Gly Met Met Arg Asp
    435                 440                 445
Arg Asp Gly Arg Gly Pro Pro Arg Gly Gly Met Ala Gln Lys Leu
450                 455                 460
Gly Ser Gly Arg Gly Ala Gly Gln Met Glu Gly Arg Phe Thr Gly Gln
465                 470                 475                 480
Arg Arg

<210> SEQ ID NO 16
<211> LENGTH: 449
<212> TYPE: PRT
<213> ORGANISM: Canis lupus

<400> SEQUENCE: 16

Met Val Met Glu Lys Pro Ser Pro Leu Leu Val Gly Arg Glu Phe Val
1               5                   10                  15
Arg Gln Tyr Tyr Thr Leu Leu Asn Lys Ala Pro Glu Tyr Leu His Arg
            20                  25                  30
Phe Tyr Gly Arg Asn Ser Ser Tyr Val His Gly Gly Val Asp Ala Ser
        35                  40                  45
Gly Lys Pro Gln Glu Ala Val Tyr Gly Gln Asn Asp Ile His His Lys
    50                  55                  60
```

Val Leu Ser Leu Asn Phe Ser Glu Cys His Thr Lys Ile Arg His Val
65                  70                  75                  80

Asp Ala His Ala Thr Leu Ser Asp Gly Val Val Gln Val Met Gly
            85                  90                  95

Leu Leu Ser Asn Ser Gly Gln Pro Glu Arg Lys Phe Met Gln Thr Phe
            100                 105                 110

Val Leu Ala Pro Glu Gly Ser Val Pro Asn Lys Phe Tyr Val His Asn
            115                 120                 125

Asp Met Phe Arg Tyr Glu Asp Glu Val Phe Gly Asp Ser Glu Pro Glu
    130                 135                 140

Leu Asp Glu Glu Ser Glu Asp Glu Val Glu Glu Gln Glu Glu Arg
145                 150                 155                 160

Gln Pro Ser Pro Glu Pro Val Gln Glu Asn Ala Asp Ser Gly Tyr Tyr
                165                 170                 175

Glu Ala His Pro Val Ala Asn Gly Ile Glu Glu Pro Leu Glu Glu Ser
            180                 185                 190

Ser His Glu Pro Glu Pro Glu Pro Asp Ser Glu Thr Lys Thr Glu Glu
        195                 200                 205

Leu Lys Pro Gln Val Glu Glu Lys Asn Leu Glu Glu Leu Glu Glu Lys
    210                 215                 220

Ser Thr Ser Pro Pro Pro Ala Glu Pro Val Ser Leu Pro Gln Glu Pro
225                 230                 235                 240

Pro Lys Pro Arg Val Glu Ala Lys Pro Glu Val Gln Ser Gln Pro Pro
                245                 250                 255

Arg Val Arg Glu Gln Arg Pro Glu Arg Pro Gly Phe Pro Pro Arg
                260                 265                 270

Gly Pro Arg Pro Gly Arg Gly Asp Leu Glu Gln Asn Glu Ser Asp Asn
            275                 280                 285

Arg Arg Ile Ile Arg Tyr Pro Asp Ser His Gln Leu Phe Val Gly Asn
        290                 295                 300

Leu Pro His Asp Ile Asp Glu Asn Glu Leu Lys Glu Phe Phe Met Ser
305                 310                 315                 320

Phe Gly Asn Val Val Glu Leu Arg Ile Asn Thr Lys Gly Val Gly Gly
                325                 330                 335

Lys Leu Pro Asn Phe Gly Phe Val Val Phe Asp Asp Ser Glu Pro Val
            340                 345                 350

Gln Arg Ile Leu Ile Ala Lys Pro Ile Met Phe Arg Gly Glu Val Arg
        355                 360                 365

Leu Asn Val Glu Glu Lys Lys Thr Arg Ala Ala Arg Glu Arg Glu Thr
    370                 375                 380

Arg Gly Gly Gly Asp Asp Arg Arg Asp Ile Arg Arg Asn Asp Arg Gly
385                 390                 395                 400

Pro Gly Gly Pro Arg Gly Ile Val Gly Gly Met Met Arg Asp Arg
                405                 410                 415

Asp Gly Arg Gly Pro Pro Arg Gly Gly Met Ala Gln Lys Leu Gly
            420                 425                 430

Ser Gly Arg Gly Thr Gly Gln Met Glu Gly Arg Phe Thr Gly Gln Arg
        435                 440                 445

Arg

<210> SEQ ID NO 17
<211> LENGTH: 482
<212> TYPE: PRT
<213> ORGANISM: Canis lupus

<400> SEQUENCE: 17

| Met | Val | Met | Glu | Lys | Pro | Ser | Pro | Leu | Leu | Val | Gly | Arg | Glu | Phe | Val |
| 1 | | | | 5 | | | | | 10 | | | | | 15 | |

| Arg | Gln | Tyr | Tyr | Thr | Leu | Leu | Asn | Lys | Ala | Pro | Glu | Tyr | Leu | His | Arg |
| | | | 20 | | | | | 25 | | | | | 30 | | |

| Phe | Tyr | Gly | Arg | Asn | Ser | Ser | Tyr | Val | His | Gly | Gly | Val | Asp | Ala | Ser |
| | | 35 | | | | | 40 | | | | | 45 | | | |

| Gly | Lys | Pro | Gln | Glu | Ala | Val | Tyr | Gly | Gln | Asn | Asp | Ile | His | His | Lys |
| | 50 | | | | | 55 | | | | | 60 | | | | |

| Val | Leu | Ser | Leu | Asn | Phe | Ser | Glu | Cys | His | Thr | Lys | Ile | Arg | His | Val |
| 65 | | | | | 70 | | | | | 75 | | | | | 80 |

| Asp | Ala | His | Ala | Thr | Leu | Ser | Asp | Gly | Val | Val | Gln | Val | Met | Gly |
| | | | | 85 | | | | | 90 | | | | | 95 |

| Leu | Leu | Ser | Asn | Ser | Gly | Gln | Pro | Glu | Arg | Lys | Phe | Met | Gln | Thr | Phe |
| | | | | 100 | | | | | 105 | | | | | 110 | |

| Val | Leu | Ala | Pro | Glu | Gly | Ser | Val | Pro | Asn | Lys | Phe | Tyr | Val | His | Asn |
| | | | 115 | | | | | 120 | | | | | 125 | | |

| Asp | Met | Phe | Arg | Tyr | Glu | Asp | Glu | Val | Phe | Gly | Asp | Ser | Glu | Pro | Glu |
| | 130 | | | | | 135 | | | | | 140 | | | | |

| Leu | Asp | Glu | Glu | Ser | Glu | Asp | Glu | Val | Glu | Glu | Gln | Glu | Glu | Arg |
| 145 | | | | | 150 | | | | | 155 | | | | | 160 |

| Gln | Pro | Ser | Pro | Glu | Pro | Val | Gln | Glu | Asn | Ala | Asp | Ser | Gly | Tyr | Tyr |
| | | | | 165 | | | | | 170 | | | | | 175 | |

| Glu | Ala | His | Pro | Val | Ala | Asn | Gly | Ile | Glu | Glu | Pro | Leu | Glu | Glu | Ser |
| | | | 180 | | | | | 185 | | | | | 190 | | |

| Ser | His | Glu | Pro | Glu | Pro | Glu | Pro | Asp | Ser | Glu | Thr | Lys | Thr | Glu | Glu |
| | | 195 | | | | | 200 | | | | | 205 | | | |

| Leu | Lys | Pro | Gln | Val | Glu | Glu | Lys | Asn | Leu | Glu | Glu | Leu | Glu | Glu | Lys |
| | 210 | | | | | 215 | | | | | 220 | | | | |

| Ser | Thr | Ser | Pro | Pro | Ala | Glu | Pro | Val | Ser | Leu | Pro | Gln | Glu | Pro |
| 225 | | | | | 230 | | | | | 235 | | | | | 240 |

| Pro | Lys | Ala | Phe | Ser | Trp | Ala | Ser | Val | Thr | Ser | Lys | Asn | Leu | Pro | Pro |
| | | | | 245 | | | | | 250 | | | | | 255 | |

| Ser | Gly | Thr | Val | Ser | Ser | Gly | Ile | Pro | Pro | His | Val | Lys | Ala | Pro |
| | | | 260 | | | | | 265 | | | | | 270 | | |

| Val | Ser | Gln | Pro | Arg | Val | Glu | Ala | Lys | Pro | Glu | Val | Gln | Ser | Gln | Pro |
| | | 275 | | | | | 280 | | | | | 285 | | | |

| Pro | Arg | Val | Arg | Glu | Gln | Arg | Pro | Arg | Glu | Arg | Pro | Gly | Phe | Pro | Pro |
| | 290 | | | | | 295 | | | | | 300 | | | | |

| Arg | Gly | Pro | Arg | Pro | Gly | Arg | Gly | Asp | Leu | Glu | Gln | Asn | Glu | Ser | Asp |
| 305 | | | | | 310 | | | | | 315 | | | | | 320 |

| Asn | Arg | Arg | Ile | Ile | Arg | Tyr | Pro | Asp | Ser | His | Gln | Leu | Phe | Val | Gly |
| | | | | 325 | | | | | 330 | | | | | 335 | |

| Asn | Leu | Pro | His | Asp | Ile | Asp | Glu | Asn | Glu | Leu | Lys | Glu | Phe | Phe | Met |
| | | | 340 | | | | | 345 | | | | | 350 | | |

| Ser | Phe | Gly | Asn | Val | Val | Glu | Leu | Arg | Ile | Asn | Thr | Lys | Gly | Val | Gly |
| | | 355 | | | | | 360 | | | | | 365 | | | |

| Gly | Lys | Leu | Pro | Asn | Phe | Gly | Phe | Val | Phe | Asp | Asp | Ser | Glu | Pro |
| | 370 | | | | | 375 | | | | | 380 | | | | |

| Val | Gln | Arg | Ile | Leu | Ile | Ala | Lys | Pro | Ile | Met | Phe | Arg | Gly | Glu | Val |
| 385 | | | | | 390 | | | | | 395 | | | | | 400 |

| Arg | Leu | Asn | Val | Glu | Glu | Lys | Lys | Thr | Arg | Ala | Ala | Arg | Glu | Arg | Glu |

```
                        405                 410                 415
Thr Arg Gly Gly Gly Asp Asp Arg Arg Asp Ile Arg Arg Asn Asp Arg
                420                 425                 430
Gly Pro Gly Gly Pro Arg Gly Ile Val Gly Gly Met Met Arg Asp
            435                 440                 445
Arg Asp Gly Arg Gly Pro Pro Arg Gly Gly Met Ala Gln Lys Leu
        450                 455                 460
Gly Ser Gly Arg Gly Thr Gly Gln Met Glu Gly Arg Phe Thr Gly Gln
465                 470                 475                 480
Arg Arg

<210> SEQ ID NO 18
<211> LENGTH: 449
<212> TYPE: PRT
<213> ORGANISM: Macaca mulatta

<400> SEQUENCE: 18

Met Val Met Glu Lys Pro Ser Pro Leu Leu Val Gly Arg Glu Phe Val
1               5                   10                  15
Arg Gln Tyr Tyr Thr Leu Leu Asn Lys Ala Pro Glu Tyr Leu His Arg
            20                  25                  30
Phe Tyr Gly Arg Asn Ser Ser Tyr Val His Gly Gly Val Asp Ala Ser
        35                  40                  45
Gly Lys Pro Gln Glu Ala Val Tyr Gly Gln Asn Asp Ile His His Lys
    50                  55                  60
Val Leu Ser Leu Asn Phe Ser Glu Cys His Thr Lys Ile Arg His Val
65                  70                  75                  80
Asp Ala His Ala Thr Leu Ser Asp Gly Val Val Val Gln Val Met Gly
                85                  90                  95
Leu Leu Ser Asn Ser Gly Gln Pro Glu Arg Lys Phe Met Gln Thr Phe
            100                 105                 110
Val Leu Ala Pro Glu Gly Ser Val Pro Asn Lys Phe Tyr Val His Asn
        115                 120                 125
Asp Met Phe Arg Tyr Glu Asp Glu Val Phe Gly Asp Ser Glu Pro Glu
    130                 135                 140
Leu Asp Glu Glu Ser Glu Asp Glu Val Glu Glu Gln Glu Glu Arg
145                 150                 155                 160
Gln Pro Ser Pro Glu Pro Val Gln Glu Asn Ala Asn Ser Gly Tyr Tyr
                165                 170                 175
Glu Ala His Pro Val Thr Asn Gly Ile Glu Glu Pro Leu Glu Glu Ser
            180                 185                 190
Ser His Glu Pro Glu Pro Glu Thr Glu Ser Glu Thr Lys Thr Glu Glu
        195                 200                 205
Leu Lys Pro Gln Val Glu Glu Lys Asn Leu Glu Glu Leu Glu Glu Lys
    210                 215                 220
Ser Thr Thr Pro Pro Ala Glu Pro Val Ser Leu Pro Gln Glu Pro
225                 230                 235                 240
Pro Lys Pro Arg Val Glu Ala Lys Pro Glu Val Gln Ser Gln Pro Pro
                245                 250                 255
Arg Val Arg Glu Gln Arg Pro Arg Glu Arg Pro Gly Phe Pro Pro Arg
            260                 265                 270
Gly Pro Arg Pro Gly Arg Gly Asp Met Glu Gln Asn Asp Ser Asp Asn
        275                 280                 285
Arg Arg Ile Ile Arg Tyr Pro Asp Ser His Gln Leu Phe Val Gly Asn
```

-continued

```
            290                 295                 300
Leu Pro His Asp Ile Asp Glu Asn Glu Leu Lys Glu Phe Phe Met Ser
305                 310                 315                 320

Phe Gly Asn Val Val Glu Leu Arg Ile Asn Thr Lys Gly Val Gly Gly
                325                 330                 335

Lys Leu Pro Asn Phe Gly Phe Val Phe Asp Asp Ser Glu Pro Val
            340                 345                 350

Gln Arg Ile Leu Ile Ala Lys Pro Ile Met Phe Arg Gly Glu Val Arg
            355                 360                 365

Leu Asn Val Glu Glu Lys Lys Thr Arg Ala Ala Arg Glu Arg Glu Thr
        370                 375                 380

Arg Gly Gly Gly Asp Asp Arg Arg Asp Ile Arg Arg Asn Asp Arg Gly
385                 390                 395                 400

Pro Gly Gly Pro Arg Gly Ile Val Gly Gly Met Met Arg Asp Arg
            405                 410                 415

Asp Gly Arg Gly Pro Pro Arg Gly Gly Met Ala Gln Lys Leu Gly
            420                 425                 430

Ser Gly Arg Gly Thr Gly Gln Met Glu Gly Arg Phe Thr Gly Gln Arg
        435                 440                 445

Arg

<210> SEQ ID NO 19
<211> LENGTH: 449
<212> TYPE: PRT
<213> ORGANISM: Pan troglodytes

<400> SEQUENCE: 19

Met Val Met Glu Lys Pro Ser Pro Leu Leu Val Gly Arg Glu Phe Val
1               5                   10                  15

Arg Gln Tyr Tyr Thr Leu Leu Asn Lys Ala Pro Glu Tyr Leu His Arg
            20                  25                  30

Phe Tyr Gly Arg Asn Ser Ser Tyr Val His Gly Gly Val Asp Ala Ser
        35                  40                  45

Gly Lys Pro Gln Glu Ala Val Tyr Gly Gln Asn Asp Ile His His Lys
    50                  55                  60

Val Leu Ser Leu Asn Phe Ser Glu Cys His Thr Lys Ile Arg His Val
65                  70                  75                  80

Asp Ala His Ala Thr Leu Ser Asp Gly Val Val Gln Val Met Gly
            85                  90                  95

Leu Leu Ser Asn Ser Gly Gln Pro Glu Arg Lys Phe Met Gln Thr Phe
                100                 105                 110

Val Leu Ala Pro Glu Gly Ser Val Pro Asn Lys Phe Tyr Val His Asn
            115                 120                 125

Asp Met Phe Arg Tyr Glu Asp Glu Val Phe Gly Asp Ser Glu Pro Glu
130                 135                 140

Leu Asp Glu Glu Ser Glu Asp Glu Val Glu Glu Gln Glu Glu Arg
145                 150                 155                 160

Gln Pro Ser Pro Glu Pro Val Gln Glu Asn Ala Asn Ser Gly Tyr Tyr
                165                 170                 175

Glu Ala His Pro Val Thr Asn Gly Ile Glu Glu Pro Leu Glu Glu Ser
            180                 185                 190

Ser His Glu Pro Glu Pro Glu Pro Glu Ser Glu Thr Lys Thr Glu Glu
        195                 200                 205

Leu Lys Pro Gln Val Glu Glu Lys Asn Leu Glu Glu Leu Glu Glu Lys
```

Ser Thr Thr Pro Pro Ala Glu Pro Val Ser Leu Pro Gln Glu Pro
225                 230                 235                 240

Pro Lys Pro Arg Val Glu Ala Lys Pro Glu Val Gln Ser Gln Pro Pro
                245                 250                 255

Arg Val Arg Glu Gln Arg Pro Arg Glu Arg Pro Gly Phe Pro Pro Arg
            260                 265                 270

Gly Pro Arg Pro Arg Gly Asp Met Glu Gln Asn Asp Ser Asp Asn
        275                 280                 285

Arg Arg Ile Ile Arg Tyr Pro Asp Ser His Gln Leu Phe Val Gly Asn
    290                 295                 300

Leu Pro His Asp Ile Asp Glu Asn Glu Leu Lys Glu Phe Phe Met Ser
305                 310                 315                 320

Phe Gly Asn Val Val Glu Leu Arg Ile Asn Thr Lys Gly Val Gly Gly
                325                 330                 335

Lys Leu Pro Asn Phe Gly Phe Val Val Phe Asp Asp Ser Glu Pro Val
                340                 345                 350

Gln Arg Ile Leu Ile Ala Lys Pro Ile Met Phe Arg Gly Glu Val Arg
            355                 360                 365

Leu Asn Val Glu Glu Lys Lys Thr Arg Ala Ala Arg Glu Arg Glu Thr
        370                 375                 380

Arg Gly Gly Gly Asp Asp Arg Arg Asp Ile Arg Arg Asn Asp Arg Gly
385                 390                 395                 400

Pro Gly Gly Pro Arg Gly Ile Val Gly Gly Met Met Arg Asp Arg
                405                 410                 415

Asp Gly Arg Gly Pro Pro Arg Gly Gly Met Ala Gln Lys Leu Gly
                420                 425                 430

Ser Gly Arg Gly Thr Gly Gln Met Glu Gly Arg Phe Thr Gly Gln Arg
            435                 440                 445

Arg

<210> SEQ ID NO 20
<211> LENGTH: 482
<212> TYPE: PRT
<213> ORGANISM: Pan troglodytes

<400> SEQUENCE: 20

Met Val Met Glu Lys Pro Ser Pro Leu Leu Val Gly Arg Glu Phe Val
1               5                   10                  15

Arg Gln Tyr Tyr Thr Leu Leu Asn Lys Ala Pro Glu Tyr Leu His Arg
            20                  25                  30

Phe Tyr Gly Arg Asn Ser Ser Tyr Val His Gly Gly Val Asp Ala Ser
        35                  40                  45

Gly Lys Pro Gln Glu Ala Val Tyr Gly Gln Asn Asp Ile His His Lys
    50                  55                  60

Val Leu Ser Leu Asn Phe Ser Glu Cys His Thr Lys Ile Arg His Val
65                  70                  75                  80

Asp Ala His Ala Thr Leu Ser Asp Gly Val Val Gln Val Met Gly
                85                  90                  95

Leu Leu Ser Asn Ser Gly Gln Pro Glu Arg Lys Phe Met Gln Thr Phe
            100                 105                 110

Val Leu Ala Pro Glu Gly Ser Val Pro Asn Lys Phe Tyr Val His Asn
        115                 120                 125

Asp Met Phe Arg Tyr Glu Asp Glu Val Phe Gly Asp Ser Glu Pro Glu

```
                    130                135                140
Leu Asp Glu Glu Ser Glu Asp Glu Val Glu Glu Gln Glu Glu Arg
145                 150                155                160

Gln Pro Ser Pro Glu Pro Val Gln Glu Asn Ala Asn Ser Gly Tyr Tyr
                165                170                175

Glu Ala His Pro Val Thr Asn Gly Ile Glu Glu Pro Leu Glu Glu Ser
            180                185                190

Ser His Glu Pro Glu Pro Glu Pro Glu Ser Gly Thr Lys Thr Glu Glu
                195                200                205

Leu Lys Pro Gln Val Glu Glu Lys Asn Leu Glu Glu Leu Glu Glu Lys
            210                215                220

Ser Thr Thr Pro Pro Ala Glu Pro Val Ser Leu Pro Gln Glu Pro
225                 230                235                240

Pro Lys Ala Phe Ser Trp Ala Ser Val Thr Ser Lys Asn Leu Pro Pro
                245                250                255

Ser Gly Thr Val Ser Ser Gly Ile Pro Pro His Val Lys Ala Pro
            260                265                270

Val Ser Gln Pro Arg Val Glu Ala Lys Pro Glu Val Gln Ser Gln Pro
                275                280                285

Pro Arg Val Arg Glu Gln Arg Pro Arg Glu Arg Pro Gly Phe Pro Pro
            290                295                300

Arg Gly Pro Arg Pro Gly Arg Gly Asp Met Glu Gln Asn Asp Ser Asp
305                 310                315                320

Asn Arg Arg Ile Ile Arg Tyr Pro Asp Ser His Gln Leu Phe Val Gly
                325                330                335

Asn Leu Pro His Asp Ile Asp Glu Asn Glu Leu Lys Glu Phe Phe Met
            340                345                350

Ser Phe Gly Asn Val Val Glu Leu Arg Ile Asn Thr Lys Gly Val Gly
                355                360                365

Gly Lys Leu Pro Asn Phe Gly Phe Val Val Phe Asp Asp Ser Glu Pro
            370                375                380

Val Gln Arg Ile Leu Ile Ala Lys Pro Ile Met Phe Arg Gly Glu Val
385                 390                395                400

Arg Leu Asn Val Glu Glu Lys Lys Thr Arg Ala Ala Arg Glu Arg Glu
                405                410                415

Thr Arg Gly Gly Gly Asp Asp Arg Arg Asp Ile Arg Arg Asn Asp Arg
            420                425                430

Gly Pro Gly Gly Pro Arg Gly Ile Val Gly Gly Met Met Arg Asp
            435                440                445

Arg Asp Gly Arg Gly Pro Pro Arg Gly Gly Met Ala Gln Lys Leu
    450                455                460

Gly Ser Gly Arg Gly Thr Gly Gln Met Glu Gly Arg Phe Thr Gly Gln
465                 470                475                480

Arg Arg

<210> SEQ ID NO 21
<211> LENGTH: 482
<212> TYPE: PRT
<213> ORGANISM: Macaca mulatta

<400> SEQUENCE: 21

Met Val Met Glu Lys Pro Ser Pro Leu Leu Val Gly Arg Glu Phe Val
1                   5                  10                 15

Arg Gln Tyr Tyr Thr Leu Leu Asn Lys Ala Pro Glu Tyr Leu His Arg
```

```
            20                  25                  30
Phe Tyr Gly Arg Asn Ser Ser Tyr Val His Gly Gly Val Asp Ala Ser
         35                  40                  45
Gly Lys Pro Gln Glu Ala Val Tyr Gly Gln Asn Asp Ile His His Lys
 50                  55                  60
Val Leu Ser Leu Asn Phe Ser Glu Cys His Thr Lys Ile Arg His Val
 65                  70                  75                  80
Asp Ala His Ala Thr Leu Ser Asp Gly Val Val Gln Val Met Gly
                 85                  90                  95
Leu Leu Ser Asn Ser Gly Gln Pro Glu Arg Lys Phe Met Gln Thr Phe
            100                 105                 110
Val Leu Ala Pro Glu Gly Ser Val Pro Asn Lys Phe Tyr Val His Asn
            115                 120                 125
Asp Met Phe Arg Tyr Glu Asp Glu Val Phe Gly Asp Ser Glu Pro Glu
            130                 135                 140
Leu Asp Glu Glu Ser Glu Asp Glu Val Glu Glu Gln Glu Glu Arg
145                 150                 155                 160
Gln Pro Ser Pro Glu Pro Val Gln Glu Asn Ala Asn Ser Gly Tyr Tyr
                 165                 170                 175
Glu Ala His Pro Val Thr Asn Gly Ile Glu Glu Pro Leu Glu Glu Ser
            180                 185                 190
Ser His Glu Pro Glu Pro Glu Thr Glu Ser Glu Thr Lys Thr Glu Glu
            195                 200                 205
Leu Lys Pro Gln Val Glu Glu Lys Asn Leu Glu Glu Leu Glu Glu Lys
            210                 215                 220
Ser Thr Thr Pro Pro Pro Ala Glu Pro Val Ser Leu Pro Gln Glu Pro
225                 230                 235                 240
Pro Lys Ala Phe Ser Trp Ala Ser Val Thr Ser Lys Asn Leu Pro Pro
                 245                 250                 255
Ser Gly Thr Val Ser Ser Ser Gly Ile Pro Pro His Val Lys Ala Pro
                 260                 265                 270
Val Ser Gln Pro Arg Val Glu Ala Lys Pro Glu Val Gln Ser Gln Pro
            275                 280                 285
Pro Arg Val Arg Glu Gln Arg Pro Arg Glu Arg Pro Gly Phe Pro Pro
            290                 295                 300
Arg Gly Pro Arg Pro Gly Arg Gly Asp Met Glu Gln Asn Asp Ser Asp
305                 310                 315                 320
Asn Arg Arg Ile Ile Arg Tyr Pro Asp Ser His Gln Leu Phe Val Gly
                 325                 330                 335
Asn Leu Pro His Asp Ile Asp Glu Asn Glu Leu Lys Glu Phe Phe Met
            340                 345                 350
Ser Phe Gly Asn Val Val Glu Leu Arg Ile Asn Thr Lys Gly Val Gly
            355                 360                 365
Gly Lys Leu Pro Asn Phe Gly Phe Val Val Phe Asp Asp Ser Glu Pro
            370                 375                 380
Val Gln Arg Ile Leu Ile Ala Lys Pro Ile Met Phe Arg Gly Glu Val
385                 390                 395                 400
Arg Leu Asn Val Glu Glu Lys Lys Thr Arg Ala Ala Arg Glu Arg Glu
                 405                 410                 415
Thr Arg Gly Gly Gly Asp Asp Arg Arg Asp Ile Arg Arg Asn Asp Arg
            420                 425                 430
Gly Pro Gly Gly Pro Arg Gly Ile Val Gly Gly Met Met Arg Asp
            435                 440                 445
```

Arg Asp Gly Arg Gly Pro Pro Pro Arg Gly Gly Met Ala Gln Lys Leu
            450                 455                 460

Gly Ser Gly Arg Gly Thr Gly Gln Met Glu Gly Arg Phe Thr Gly Gln
465                 470                 475                 480

Arg Arg

<210> SEQ ID NO 22
<211> LENGTH: 482
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (243)..(243)
<223> OTHER INFORMATION: X is present or absent and when present denotes
      Ala
<220> FEATURE:
<221> NAME/KEY: MISC_FEATURE
<222> LOCATION: (244)..(244)
<223> OTHER INFORMATION: X is present or absent and when present denotes
      Phe
<220> FEATURE:
<221> NAME/KEY: MISC_FEATURE
<222> LOCATION: (245)..(245)
<223> OTHER INFORMATION: X is present or absent and when present denotes
      Ser
<220> FEATURE:
<221> NAME/KEY: MISC_FEATURE
<222> LOCATION: (246)..(246)
<223> OTHER INFORMATION: X is present or absent and when present denotes
      Trp
<220> FEATURE:
<221> NAME/KEY: MISC_FEATURE
<222> LOCATION: (247)..(247)
<223> OTHER INFORMATION: X is present or absent and when present denotes
      Ala
<220> FEATURE:
<221> NAME/KEY: MISC_FEATURE
<222> LOCATION: (248)..(248)
<223> OTHER INFORMATION: X is present or absent and when present denotes
      Ser
<220> FEATURE:
<221> NAME/KEY: MISC_FEATURE
<222> LOCATION: (249)..(249)
<223> OTHER INFORMATION: X is present or absent and when present denotes
      Val
<220> FEATURE:
<221> NAME/KEY: MISC_FEATURE
<222> LOCATION: (250)..(250)
<223> OTHER INFORMATION: X is present or absent and when present denotes
      Thr
<220> FEATURE:
<221> NAME/KEY: MISC_FEATURE
<222> LOCATION: (251)..(251)
<223> OTHER INFORMATION: X is present or absent and when present denotes
      Ser
<220> FEATURE:
<221> NAME/KEY: MISC_FEATURE
<222> LOCATION: (252)..(252)
<223> OTHER INFORMATION: X is present or absent and when present denotes
      Lys
<220> FEATURE:
<221> NAME/KEY: MISC_FEATURE
<222> LOCATION: (253)..(253)
<223> OTHER INFORMATION: X is present or absent and when present denotes
      Asn
<220> FEATURE:
<221> NAME/KEY: MISC_FEATURE
<222> LOCATION: (254)..(254)
<223> OTHER INFORMATION: X is present or absent and when present denotes
      Leu
<220> FEATURE:
<221> NAME/KEY: MISC_FEATURE
<222> LOCATION: (255)..(255)

```
<223> OTHER INFORMATION: X is present or absent and when present denotes
      Pro
<220> FEATURE:
<221> NAME/KEY: MISC_FEATURE
<222> LOCATION: (256)..(256)
<223> OTHER INFORMATION: X is present or absent and when present denotes
      Pro
<220> FEATURE:
<221> NAME/KEY: MISC_FEATURE
<222> LOCATION: (257)..(257)
<223> OTHER INFORMATION: X is present or absent and when present denotes
      Ser
<220> FEATURE:
<221> NAME/KEY: MISC_FEATURE
<222> LOCATION: (258)..(258)
<223> OTHER INFORMATION: X is present or absent and when present denotes
      Gly
<220> FEATURE:
<221> NAME/KEY: MISC_FEATURE
<222> LOCATION: (259)..(259)
<223> OTHER INFORMATION: X is present or absent and when present denotes
      Thr
<220> FEATURE:
<221> NAME/KEY: MISC_FEATURE
<222> LOCATION: (260)..(260)
<223> OTHER INFORMATION: X is present or absent and when present denotes
      Val
<220> FEATURE:
<221> NAME/KEY: MISC_FEATURE
<222> LOCATION: (261)..(261)
<223> OTHER INFORMATION: X is present or absent and when present denotes
      Ser
<220> FEATURE:
<221> NAME/KEY: MISC_FEATURE
<222> LOCATION: (262)..(262)
<223> OTHER INFORMATION: X is present or absent and when present denotes
      Ser
<220> FEATURE:
<221> NAME/KEY: MISC_FEATURE
<222> LOCATION: (263)..(263)
<223> OTHER INFORMATION: X is present or absent and when present denotes
      Ser
<220> FEATURE:
<221> NAME/KEY: MISC_FEATURE
<222> LOCATION: (264)..(264)
<223> OTHER INFORMATION: X is present or absent and when present denotes
      Gly
<220> FEATURE:
<221> NAME/KEY: MISC_FEATURE
<222> LOCATION: (265)..(265)
<223> OTHER INFORMATION: X is present or absent and when present denotes
      Ile
<220> FEATURE:
<221> NAME/KEY: MISC_FEATURE
<222> LOCATION: (266)..(266)
<223> OTHER INFORMATION: X is present or absent and when present denotes
      Pro
<220> FEATURE:
<221> NAME/KEY: MISC_FEATURE
<222> LOCATION: (267)..(267)
<223> OTHER INFORMATION: X is present or absent and when present denotes
      Pro
<220> FEATURE:
<221> NAME/KEY: MISC_FEATURE
<222> LOCATION: (268)..(268)
<223> OTHER INFORMATION: X is present or absent and when present denotes
      His
<220> FEATURE:
<221> NAME/KEY: MISC_FEATURE
<222> LOCATION: (269)..(269)
<223> OTHER INFORMATION: X is present or absent and when present denotes
      Val
<220> FEATURE:
<221> NAME/KEY: MISC_FEATURE
<222> LOCATION: (270)..(270)
<223> OTHER INFORMATION: X is present or absent and when present denotes
      Lys
<220> FEATURE:
<221> NAME/KEY: MISC_FEATURE
```

```
<222> LOCATION: (271)..(271)
<223> OTHER INFORMATION: X is present or absent and when present denotes
      Ala
<220> FEATURE:
<221> NAME/KEY: MISC_FEATURE
<222> LOCATION: (272)..(272)
<223> OTHER INFORMATION: X is present or absent and when present denotes
      Pro
<220> FEATURE:
<221> NAME/KEY: MISC_FEATURE
<222> LOCATION: (273)..(273)
<223> OTHER INFORMATION: X is present or absent and when present denotes
      Val
<220> FEATURE:
<221> NAME/KEY: MISC_FEATURE
<222> LOCATION: (274)..(274)
<223> OTHER INFORMATION: X is present or absent and when present denotes
      Ser
<220> FEATURE:
<221> NAME/KEY: MISC_FEATURE
<222> LOCATION: (275)..(275)
<223> OTHER INFORMATION: X is present or absent and when present denotes
      Gln

<400> SEQUENCE: 22

Met Val Met Glu Lys Pro Ser Pro Leu Leu Val Gly Arg Glu Phe Val
1               5                   10                  15

Arg Gln Tyr Tyr Thr Leu Leu Asn Lys Ala Pro Glu Tyr Leu His Arg
            20                  25                  30

Phe Tyr Gly Arg Asn Ser Ser Tyr Val His Gly Gly Val Asp Ala Ser
        35                  40                  45

Gly Lys Pro Gln Glu Ala Val Tyr Gly Gln Asn Asp Ile His His Lys
    50                  55                  60

Val Leu Ser Leu Asn Phe Ser Glu Cys His Thr Lys Ile Arg His Val
65                  70                  75                  80

Asp Ala His Ala Thr Leu Ser Asp Gly Val Val Gln Val Met Gly
                85                  90                  95

Leu Leu Ser Asn Ser Gly Gln Pro Glu Arg Lys Phe Met Gln Thr Phe
            100                 105                 110

Val Leu Ala Pro Glu Gly Ser Val Pro Asn Lys Phe Tyr Val His Asn
        115                 120                 125

Asp Met Phe Arg Tyr Glu Asp Glu Val Phe Gly Asp Ser Glu Pro Glu
    130                 135                 140

Leu Asp Glu Glu Ser Glu Asp Glu Val Glu Glu Gln Glu Glu Arg
145                 150                 155                 160

Gln Pro Ser Pro Glu Pro Val Gln Glu Asn Ala Asn Ser Gly Tyr Tyr
                165                 170                 175

Glu Ala His Pro Val Thr Asn Gly Ile Glu Glu Pro Leu Glu Glu Ser
            180                 185                 190

Ser His Glu Pro Glu Pro Glu Ser Glu Thr Lys Thr Glu Glu
        195                 200                 205

Leu Lys Pro Gln Val Glu Glu Lys Asn Leu Glu Glu Leu Glu Glu Lys
    210                 215                 220

Ser Thr Thr Pro Pro Ala Glu Pro Val Ser Leu Pro Gln Glu Pro
225                 230                 235                 240

Pro Lys Xaa Xaa Xaa Xaa Xaa Xaa Xaa Xaa Xaa Xaa Xaa Xaa
                245                 250                 255

Xaa Xaa Xaa Xaa Xaa Xaa Xaa Xaa Xaa Xaa Xaa Xaa Xaa
            260                 265                 270

Xaa Xaa Xaa Pro Arg Val Glu Ala Lys Pro Glu Val Gln Ser Gln Pro
        275                 280                 285
```

```
Pro Arg Val Arg Glu Gln Arg Pro Arg Glu Arg Pro Gly Phe Pro Pro
    290                 295                 300

Arg Gly Pro Arg Pro Gly Arg Gly Asp Met Glu Gln Asn Asp Ser Asp
305                 310                 315                 320

Asn Arg Arg Ile Ile Arg Tyr Pro Asp Ser His Gln Leu Phe Val Gly
                325                 330                 335

Asn Leu Pro His Asp Ile Asp Glu Asn Glu Leu Lys Glu Phe Phe Met
            340                 345                 350

Ser Phe Gly Asn Val Val Glu Leu Arg Ile Asn Thr Lys Gly Val Gly
        355                 360                 365

Gly Lys Leu Pro Asn Phe Gly Phe Val Val Phe Asp Asp Ser Glu Pro
    370                 375                 380

Val Gln Arg Ile Leu Ile Ala Lys Pro Ile Met Phe Arg Gly Glu Val
385                 390                 395                 400

Arg Leu Asn Val Glu Glu Lys Lys Thr Arg Ala Ala Arg Glu Arg Glu
                405                 410                 415

Thr Arg Gly Gly Gly Asp Asp Arg Asp Ile Arg Arg Asn Asp Arg
            420                 425                 430

Gly Pro Gly Gly Pro Arg Gly Ile Val Gly Gly Met Met Arg Asp
    435                 440                 445

Arg Asp Gly Arg Gly Pro Pro Arg Gly Met Ala Gln Lys Leu
    450                 455                 460

Gly Ser Gly Arg Gly Thr Gln Met Glu Gly Arg Phe Thr Gly Gln
465                 470                 475                 480

Arg Arg

<210> SEQ ID NO 23
<211> LENGTH: 6
<212> TYPE: PRT
<213> ORGANISM: Artificial Sequence
<220> FEATURE:
<223> OTHER INFORMATION: Synthetic peptide

<400> SEQUENCE: 23

Leu Phe Ile Gly Asn Leu
1               5

<210> SEQ ID NO 24
<211> LENGTH: 8
<212> TYPE: PRT
<213> ORGANISM: Artificial Sequence
<220> FEATURE:
<223> OTHER INFORMATION: Synthetic peptide

<400> SEQUENCE: 24

Pro Asn Phe Gly Phe Val Val Phe
1               5

<210> SEQ ID NO 25
<211> LENGTH: 324
<212> TYPE: PRT
<213> ORGANISM: Homo sapiens

<400> SEQUENCE: 25

Thr Glu Pro Gln Glu Glu Ser Glu Glu Glu Val Glu Glu Pro Glu Glu
1               5                   10                  15

Arg Gln Gln Thr Pro Glu Val Val Pro Asp Asp Ser Gly Thr Phe Tyr
            20                  25                  30
```

```
Asp Gln Ala Val Val Ser Asn Asp Met Glu Glu His Leu Glu Glu Pro
            35                  40                  45

Val Ala Glu Pro Glu Pro Asp Pro Glu Pro Glu Gln Glu Pro
 50                  55                  60

Val Ser Glu Ile Gln Glu Lys Pro Glu Pro Val Leu Glu Thr
 65                  70                  75                  80

Ala Pro Glu Asp Ala Gln Lys Ser Ser Pro Ala Pro Ala Asp Ile
                 85                  90                  95

Ala Gln Thr Val Gln Glu Asp Leu Arg Thr Phe Ser Trp Ala Ser Val
                100                 105                 110

Thr Ser Lys Asn Leu Pro Pro Ser Gly Ala Val Pro Val Thr Gly Ile
                115                 120                 125

Pro Pro His Val Val Lys Val Pro Ala Ser Gln Pro Arg Pro Glu Ser
        130                 135                 140

Lys Pro Glu Ser Gln Ile Pro Pro Gln Arg Pro Gln Arg Asp Gln Arg
145                 150                 155                 160

Val Arg Glu Gln Arg Ile Asn Ile Pro Pro Gln Arg Gly Pro Arg Pro
                165                 170                 175

Ile Arg Glu Ala Gly Glu Gln Gly Asp Ile Glu Pro Arg Arg Met Val
                180                 185                 190

Arg His Pro Asp Ser His Gln Leu Phe Ile Gly Asn Leu Pro His Glu
        195                 200                 205

Val Asp Lys Ser Glu Leu Lys Asp Phe Phe Gln Ser Tyr Gly Asn Val
        210                 215                 220

Val Glu Leu Arg Ile Asn Ser Gly Gly Lys Leu Pro Asn Phe Gly Phe
225                 230                 235                 240

Val Val Phe Asp Asp Ser Glu Pro Val Gln Lys Val Leu Ser Asn Arg
                245                 250                 255

Pro Ile Met Phe Arg Gly Glu Val Arg Leu Asn Val Glu Glu Lys Lys
                260                 265                 270

Thr Arg Ala Ala Arg Glu Gly Asp Arg Arg Asp Asn Arg Leu Arg Gly
                275                 280                 285

Pro Gly Gly Pro Arg Gly Gly Leu Gly Gly Met Arg Gly Pro Pro
        290                 295                 300

Arg Gly Gly Met Val Gln Lys Pro Gly Phe Gly Val Gly Arg Gly Leu
305                 310                 315                 320

Ala Pro Arg Gln

<210> SEQ ID NO 26
<211> LENGTH: 340
<212> TYPE: PRT
<213> ORGANISM: Homo sapiens

<400> SEQUENCE: 26

Pro Glu Leu Asp Glu Glu Ser Glu Asp Glu Val Glu Glu Gln Glu
 1               5                  10                  15

Glu Arg Gln Pro Ser Pro Glu Pro Val Gln Glu Asn Ala Asn Ser Gly
                20                  25                  30

Tyr Tyr Glu Ala His Pro Val Thr Asn Gly Ile Glu Glu Pro Leu Glu
            35                  40                  45

Glu Ser Ser His Glu Pro Glu Pro Glu Ser Glu Thr Lys Thr
         50                  55                  60

Glu Glu Leu Lys Pro Gln Val Glu Glu Lys Asn Leu Glu Glu Leu Glu
 65                  70                  75                  80
```

```
Glu Lys Ser Thr Thr Pro Pro Ala Glu Pro Val Ser Leu Pro Gln
                85                  90                  95

Glu Pro Pro Lys Ala Phe Ser Trp Ala Ser Val Thr Ser Lys Asn Leu
            100                 105                 110

Pro Pro Ser Gly Thr Val Ser Ser Gly Ile Pro Pro His Val Lys
            115                 120                 125

Ala Pro Val Ser Gln Pro Arg Val Glu Ala Lys Pro Glu Val Gln Ser
130                 135                 140

Gln Pro Pro Arg Val Arg Gln Arg Pro Glu Arg Pro Gly Phe
145                 150                 155                 160

Pro Pro Arg Gly Pro Arg Pro Gly Arg Gly Asp Met Glu Gln Asn Asp
                165                 170                 175

Ser Asp Asn Arg Arg Ile Ile Arg Tyr Pro Asp Ser His Gln Leu Phe
            180                 185                 190

Val Gly Asn Leu Pro His Asp Ile Asp Glu Asn Glu Leu Lys Glu Phe
            195                 200                 205

Phe Met Ser Phe Gly Asn Val Val Glu Leu Arg Ile Asn Thr Lys Gly
    210                 215                 220

Val Gly Gly Lys Leu Pro Asn Phe Gly Phe Val Val Phe Asp Asp Ser
225                 230                 235                 240

Glu Pro Val Gln Arg Ile Leu Ile Ala Lys Pro Ile Met Phe Arg Gly
                245                 250                 255

Glu Val Arg Leu Asn Val Glu Glu Lys Lys Thr Arg Ala Ala Arg Glu
            260                 265                 270

Arg Glu Thr Arg Gly Gly Gly Asp Asp Arg Arg Asp Ile Arg Arg Asn
            275                 280                 285

Asp Arg Gly Pro Gly Gly Pro Arg Gly Ile Val Gly Gly Gly Met Met
290                 295                 300

Arg Asp Arg Asp Gly Arg Gly Pro Pro Arg Gly Gly Met Ala Gln
305                 310                 315                 320

Lys Leu Gly Ser Gly Arg Gly Thr Gly Gln Met Glu Gly Arg Phe Thr
                325                 330                 335

Gly Gln Arg Arg
            340

<210> SEQ ID NO 27
<211> LENGTH: 307
<212> TYPE: PRT
<213> ORGANISM: Homo sapiens

<400> SEQUENCE: 27

Pro Glu Leu Asp Glu Glu Ser Glu Asp Glu Val Glu Glu Gln Glu
1               5                   10                  15

Glu Arg Gln Pro Ser Pro Glu Pro Val Gln Glu Asn Ala Asn Ser Gly
            20                  25                  30

Tyr Tyr Glu Ala His Pro Val Thr Asn Gly Ile Glu Glu Pro Leu Glu
        35                  40                  45

Glu Ser Ser His Glu Pro Glu Pro Glu Pro Glu Ser Glu Thr Lys Thr
    50                  55                  60

Glu Glu Leu Lys Pro Gln Val Glu Glu Lys Asn Leu Glu Glu Leu Glu
65                  70                  75                  80

Glu Lys Ser Thr Thr Pro Pro Ala Glu Pro Val Ser Leu Pro Gln
                85                  90                  95

Glu Pro Pro Lys Pro Arg Val Glu Ala Lys Pro Glu Val Gln Ser Gln
            100                 105                 110
```

```
Pro Pro Arg Val Arg Glu Gln Arg Pro Arg Glu Arg Pro Gly Phe Pro
        115                 120                 125

Pro Arg Gly Pro Arg Pro Gly Arg Gly Asp Met Glu Gln Asn Asp Ser
    130                 135                 140

Asp Asn Arg Arg Ile Ile Arg Tyr Pro Asp Ser His Gln Leu Phe Val
145                 150                 155                 160

Gly Asn Leu Pro His Asp Ile Asp Glu Asn Glu Leu Lys Glu Phe Phe
                165                 170                 175

Met Ser Phe Gly Asn Val Val Glu Leu Arg Ile Asn Thr Lys Gly Val
            180                 185                 190

Gly Gly Lys Leu Pro Asn Phe Gly Phe Val Val Phe Asp Asp Ser Glu
        195                 200                 205

Pro Val Gln Arg Ile Leu Ile Ala Lys Pro Ile Met Phe Arg Gly Glu
    210                 215                 220

Val Arg Leu Asn Val Glu Glu Lys Lys Thr Arg Ala Ala Arg Glu Arg
225                 230                 235                 240

Glu Thr Arg Gly Gly Gly Asp Asp Arg Asp Ile Arg Arg Asn Asp
                245                 250                 255

Arg Gly Pro Gly Gly Pro Arg Gly Ile Val Gly Gly Gly Met Met Arg
            260                 265                 270

Asp Arg Asp Gly Arg Gly Pro Pro Arg Gly Gly Met Ala Gln Lys
    275                 280                 285

Leu Gly Ser Gly Arg Gly Thr Gly Gln Met Glu Gly Arg Phe Thr Gly
        290                 295                 300

Gln Arg Arg
305

<210> SEQ ID NO 28
<211> LENGTH: 340
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (101)..(101)
<223> OTHER INFORMATION: Xaa is present or absent and when present is
      Ala
<220> FEATURE:
<221> NAME/KEY: MISC_FEATURE
<222> LOCATION: (102)..(102)
<223> OTHER INFORMATION: Xaa is present or absent and when present is
      Phe
<220> FEATURE:
<221> NAME/KEY: MISC_FEATURE
<222> LOCATION: (103)..(103)
<223> OTHER INFORMATION: Xaa is present or absent and when present is
      Ser
<220> FEATURE:
<221> NAME/KEY: MISC_FEATURE
<222> LOCATION: (104)..(104)
<223> OTHER INFORMATION: Xaa is present or absent and when present is
      Trp
<220> FEATURE:
<221> NAME/KEY: MISC_FEATURE
<222> LOCATION: (105)..(105)
<223> OTHER INFORMATION: Xaa is present or absent and when present is
      Ala
<220> FEATURE:
<221> NAME/KEY: MISC_FEATURE
<222> LOCATION: (106)..(106)
<223> OTHER INFORMATION: Xaa is present or absent and when present is
      Ser
<220> FEATURE:
<221> NAME/KEY: MISC_FEATURE
```

```
<222> LOCATION: (107)..(107)
<223> OTHER INFORMATION: Xaa is present or absent and when present is
      Val
<220> FEATURE:
<221> NAME/KEY: MISC_FEATURE
<222> LOCATION: (108)..(108)
<223> OTHER INFORMATION: Xaa is present or absent and when present is
      Thr
<220> FEATURE:
<221> NAME/KEY: MISC_FEATURE
<222> LOCATION: (109)..(109)
<223> OTHER INFORMATION: Xaa is present or absent and when present is
      Ser
<220> FEATURE:
<221> NAME/KEY: MISC_FEATURE
<222> LOCATION: (110)..(110)
<223> OTHER INFORMATION: Xaa is present or absent and when present is
      Lys
<220> FEATURE:
<221> NAME/KEY: MISC_FEATURE
<222> LOCATION: (111)..(111)
<223> OTHER INFORMATION: Xaa is present or absent and when present is
      Asn
<220> FEATURE:
<221> NAME/KEY: MISC_FEATURE
<222> LOCATION: (112)..(112)
<223> OTHER INFORMATION: Xaa is present or absent and when present is
      Leu
<220> FEATURE:
<221> NAME/KEY: MISC_FEATURE
<222> LOCATION: (113)..(113)
<223> OTHER INFORMATION: Xaa is present or absent and when present is
      Pro
<220> FEATURE:
<221> NAME/KEY: MISC_FEATURE
<222> LOCATION: (114)..(114)
<223> OTHER INFORMATION: Xaa is present or absent and when present is
      Pro
<220> FEATURE:
<221> NAME/KEY: MISC_FEATURE
<222> LOCATION: (115)..(115)
<223> OTHER INFORMATION: Xaa is present or absent and when present is
      Ser
<220> FEATURE:
<221> NAME/KEY: MISC_FEATURE
<222> LOCATION: (116)..(116)
<223> OTHER INFORMATION: Xaa is present or absent and when present is
      Gly
<220> FEATURE:
<221> NAME/KEY: MISC_FEATURE
<222> LOCATION: (117)..(117)
<223> OTHER INFORMATION: Xaa is present or absent and when present is
      Thr
<220> FEATURE:
<221> NAME/KEY: MISC_FEATURE
<222> LOCATION: (118)..(118)
<223> OTHER INFORMATION: Xaa is present or absent and when present is
      Val
<220> FEATURE:
<221> NAME/KEY: MISC_FEATURE
<222> LOCATION: (119)..(119)
<223> OTHER INFORMATION: Xaa is present or absent and when present is
      Ser
<220> FEATURE:
<221> NAME/KEY: MISC_FEATURE
<222> LOCATION: (120)..(120)
<223> OTHER INFORMATION: Xaa is present or absent and when present is
      Ser
<220> FEATURE:
<221> NAME/KEY: MISC_FEATURE
<222> LOCATION: (121)..(121)
<223> OTHER INFORMATION: Xaa is present or absent and when present is
      Ser
<220> FEATURE:
<221> NAME/KEY: MISC_FEATURE
<222> LOCATION: (122)..(122)
<223> OTHER INFORMATION: Xaa is present or absent and when present is
      Gly
<220> FEATURE:
```

```
<221> NAME/KEY: MISC_FEATURE
<222> LOCATION: (123)..(123)
<223> OTHER INFORMATION: Xaa is present or absent and when present is
      Ile
<220> FEATURE:
<221> NAME/KEY: MISC_FEATURE
<222> LOCATION: (124)..(124)
<223> OTHER INFORMATION: Xaa is present or absent and when present is
      Pro
<220> FEATURE:
<221> NAME/KEY: MISC_FEATURE
<222> LOCATION: (125)..(125)
<223> OTHER INFORMATION: Xaa is present or absent and when present is
      Pro
<220> FEATURE:
<221> NAME/KEY: MISC_FEATURE
<222> LOCATION: (126)..(126)
<223> OTHER INFORMATION: Xaa is present or absent and when present is
      His
<220> FEATURE:
<221> NAME/KEY: MISC_FEATURE
<222> LOCATION: (127)..(127)
<223> OTHER INFORMATION: Xaa is present or absent and when present is
      Val
<220> FEATURE:
<221> NAME/KEY: MISC_FEATURE
<222> LOCATION: (128)..(128)
<223> OTHER INFORMATION: Xaa is present or absent and when present is
      Lys
<220> FEATURE:
<221> NAME/KEY: MISC_FEATURE
<222> LOCATION: (129)..(129)
<223> OTHER INFORMATION: Xaa is present or absent and when present is
      Ala
<220> FEATURE:
<221> NAME/KEY: MISC_FEATURE
<222> LOCATION: (130)..(130)
<223> OTHER INFORMATION: Xaa is present or absent and when present is
      Pro
<220> FEATURE:
<221> NAME/KEY: MISC_FEATURE
<222> LOCATION: (131)..(131)
<223> OTHER INFORMATION: Xaa is present or absent and when present is
      Val
<220> FEATURE:
<221> NAME/KEY: MISC_FEATURE
<222> LOCATION: (132)..(132)
<223> OTHER INFORMATION: Xaa is present or absent and when present is
      Ser
<220> FEATURE:
<221> NAME/KEY: MISC_FEATURE
<222> LOCATION: (133)..(133)
<223> OTHER INFORMATION: Xaa is present or absent and when present is
      Gln

<400> SEQUENCE: 28

Pro Glu Leu Asp Glu Glu Ser Glu Asp Glu Val Glu Glu Gln Glu
1               5                   10                  15

Glu Arg Gln Pro Ser Pro Glu Pro Val Gln Glu Asn Ala Asn Ser Gly
            20                  25                  30

Tyr Tyr Glu Ala His Pro Val Thr Asn Gly Ile Glu Glu Pro Leu Glu
        35                  40                  45

Glu Ser Ser His Glu Pro Glu Pro Glu Pro Glu Ser Glu Thr Lys Thr
    50                  55                  60

Glu Glu Leu Lys Pro Gln Val Glu Glu Lys Asn Leu Glu Glu Leu Glu
65                  70                  75                  80

Glu Lys Ser Thr Thr Pro Pro Pro Ala Glu Pro Val Ser Leu Pro Gln
                85                  90                  95

Glu Pro Pro Lys Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa
```

```
            115                 120                 125
Xaa Xaa Xaa Xaa Xaa Pro Arg Val Glu Ala Lys Pro Glu Val Gln Ser
        130                 135                 140

Gln Pro Pro Arg Val Arg Glu Gln Arg Pro Arg Glu Arg Pro Gly Phe
145                 150                 155                 160

Pro Pro Arg Gly Pro Arg Pro Gly Arg Gly Asp Met Glu Gln Asn Asp
                165                 170                 175

Ser Asp Asn Arg Arg Ile Ile Arg Tyr Pro Asp Ser His Gln Leu Phe
            180                 185                 190

Val Gly Asn Leu Pro His Asp Ile Asp Glu Asn Glu Leu Lys Glu Phe
        195                 200                 205

Phe Met Ser Phe Gly Asn Val Val Glu Leu Arg Ile Asn Thr Lys Gly
210                 215                 220

Val Gly Gly Lys Leu Pro Asn Phe Gly Phe Val Val Phe Asp Asp Ser
225                 230                 235                 240

Glu Pro Val Gln Arg Ile Leu Ile Ala Lys Pro Ile Met Phe Arg Gly
                245                 250                 255

Glu Val Arg Leu Asn Val Glu Glu Lys Lys Thr Arg Ala Ala Arg Glu
            260                 265                 270

Arg Glu Thr Arg Gly Gly Gly Asp Arg Arg Asp Ile Arg Arg Asn
        275                 280                 285

Asp Arg Gly Pro Gly Gly Pro Arg Gly Ile Val Gly Gly Met Met
290                 295                 300

Arg Asp Arg Asp Gly Arg Gly Pro Pro Arg Gly Met Ala Gln
305                 310                 315                 320

Lys Leu Gly Ser Gly Arg Gly Thr Gly Gln Met Glu Gly Arg Phe Thr
                325                 330                 335

Gly Gln Arg Arg
        340

<210> SEQ ID NO 29
<211> LENGTH: 323
<212> TYPE: PRT
<213> ORGANISM: Rattus norvegicus

<400> SEQUENCE: 29

Thr Glu Pro Gln Glu Glu Ser Glu Glu Val Glu Glu Pro Glu Glu
1               5                   10                  15

Arg Gln Gln Ser Pro Glu Val Val Ala Asp Asp Ser Gly Thr Phe Tyr
            20                  25                  30

Asp Gln Thr Val Ser Asn Asp Leu Glu Glu His Leu Glu Glu Pro Val
        35                  40                  45

Val Glu Pro Glu Pro Glu Pro Glu Pro Glu Pro Glu Pro Val
50                  55                  60

Ser Asp Ile Gln Glu Asp Lys Pro Glu Pro Ala Leu Glu Glu Ala Ala
65                  70                  75                  80

Pro Glu Asp Val Gln Lys Ser Ala Ser Pro Ala Pro Ala Asp Val Ala
                85                  90                  95

Pro Ala Gln Glu Asp Leu Arg Thr Phe Ser Trp Ala Ser Val Thr Ser
            100                 105                 110

Lys Asn Leu Pro Pro Ser Gly Ala Val Pro Val Thr Gly Thr Pro Pro
        115                 120                 125

His Val Val Lys Val Pro Ala Ser Gln Pro Arg Pro Glu Ser Lys Pro
130                 135                 140
```

Asp Ser Gln Ile Pro Pro Gln Arg Pro Gln Asp Gln Arg Ala Arg
145                 150                 155                 160

Glu Gln Arg Ile Asn Ile Pro Pro Gln Arg Gly Pro Arg Pro Ile Arg
            165                 170                 175

Glu Ala Gly Glu Pro Gly Asp Val Glu Pro Arg Arg Met Val Arg His
        180                 185                 190

Pro Asp Ser His Gln Leu Phe Ile Gly Asn Leu Pro His Glu Val Asp
    195                 200                 205

Lys Ser Glu Leu Lys Asp Phe Phe Gln Ser Tyr Gly Asn Val Val Glu
210                 215                 220

Leu Arg Ile Asn Ser Gly Gly Lys Leu Pro Asn Phe Gly Phe Val Val
225                 230                 235                 240

Phe Asp Asp Ser Glu Pro Val Gln Lys Val Leu Asn Asn Arg Pro Ile
                245                 250                 255

Met Phe Arg Gly Ala Val Arg Leu Asn Val Glu Glu Lys Lys Thr Arg
            260                 265                 270

Ala Ala Arg Glu Gly Asp Arg Arg Asp Asn Arg Leu Arg Gly Pro Gly
        275                 280                 285

Gly Pro Arg Gly Gly Pro Ser Gly Gly Met Arg Gly Pro Pro Arg Gly
    290                 295                 300

Gly Met Val Gln Lys Pro Gly Phe Gly Val Gly Arg Gly Ile Thr Thr
305                 310                 315                 320

Pro Arg Gln

<210> SEQ ID NO 30
<211> LENGTH: 323
<212> TYPE: PRT
<213> ORGANISM: Mus musculus

<400> SEQUENCE: 30

Thr Glu Pro Gln Glu Glu Ser Glu Glu Val Glu Glu Pro Glu Glu
1               5                   10                  15

Arg Gln Gln Thr Pro Glu Val Val Pro Asp Asp Ser Gly Thr Phe Tyr
            20                  25                  30

Asp Gln Thr Val Ser Asn Asp Leu Glu Glu His Leu Glu Glu Pro Val
        35                  40                  45

Val Glu Pro Glu Pro Glu Pro Glu Pro Glu Pro Glu Pro Glu Pro Val
    50                  55                  60

Ser Asp Ile Gln Glu Asp Lys Pro Glu Ala Ala Leu Glu Glu Ala Ala
65                  70                  75                  80

Pro Asp Asp Val Gln Lys Ser Thr Ser Pro Ala Pro Ala Asp Val Ala
                85                  90                  95

Pro Ala Gln Glu Asp Leu Arg Thr Phe Ser Trp Ala Ser Val Thr Ser
            100                 105                 110

Lys Asn Leu Pro Pro Ser Gly Ala Val Pro Val Thr Gly Thr Pro Pro
        115                 120                 125

His Val Val Lys Val Pro Ala Ser Gln Pro Arg Pro Glu Ser Lys Pro
    130                 135                 140

Asp Ser Gln Ile Pro Pro Gln Arg Pro Gln Arg Asp Gln Arg Val Arg
145                 150                 155                 160

Glu Gln Arg Ile Asn Ile Pro Pro Gln Arg Gly Pro Arg Pro Ile Arg
            165                 170                 175

Glu Ala Gly Glu Pro Gly Asp Val Glu Pro Arg Arg Met Val Arg His
        180                 185                 190

-continued

```
Pro Asp Ser His Gln Leu Phe Ile Gly Asn Leu Pro His Glu Val Asp
            195                 200                 205

Lys Ser Glu Leu Lys Asp Phe Phe Gln Asn Phe Gly Asn Val Val Glu
210                 215                 220

Leu Arg Ile Asn Ser Gly Gly Lys Leu Pro Asn Phe Gly Phe Val Val
225                 230                 235                 240

Phe Asp Asp Ser Glu Pro Val Gln Lys Val Leu Ser Asn Arg Pro Ile
                245                 250                 255

Met Phe Arg Gly Ala Val Arg Leu Asn Val Glu Glu Lys Lys Thr Arg
            260                 265                 270

Ala Ala Arg Glu Gly Asp Arg Arg Asp Asn Arg Leu Arg Gly Pro Gly
        275                 280                 285

Gly Pro Arg Gly Gly Pro Ser Gly Gly Met Arg Gly Pro Pro Arg Gly
    290                 295                 300

Gly Met Val Gln Lys Pro Gly Phe Gly Val Gly Arg Gly Ile Thr Thr
305                 310                 315                 320

Pro Arg Gln
```

<210> SEQ ID NO 31
<211> LENGTH: 323
<212> TYPE: PRT
<213> ORGANISM: Bos taurus

<400> SEQUENCE: 31

```
Thr Glu Pro Gln Glu Glu Ser Glu Glu Val Glu Glu Pro Glu Glu
1               5                   10                  15

Arg Gln Gln Thr Pro Glu Val Val Pro Asp Asp Ser Gly Thr Phe Tyr
                20                  25                  30

Asp Gln Thr Val Ser Asn Asp Leu Glu Glu His Leu Glu Glu Pro Val
            35                  40                  45

Ala Glu Pro Glu Pro Glu Pro Glu Pro Glu Gln Glu Pro Val
        50                  55                  60

Ser Glu Val Gln Glu Glu Lys Ser Glu Pro Val Leu Glu Glu Thr Ala
65                  70                  75                  80

Pro Glu Asp Val Gln Lys Ser Ser Pro Ala Pro Ala Asp Ile Ala
                85                  90                  95

Gln Thr Val Gln Glu Asp Leu Arg Thr Phe Ser Trp Ala Ser Val Thr
            100                 105                 110

Ser Lys Asn Leu Pro Pro Ser Gly Ala Val Pro Val Thr Gly Ile Pro
        115                 120                 125

Pro His Val Val Lys Val Pro Ala Ser Gln Pro Arg Pro Glu Ser Lys
    130                 135                 140

Pro Glu Ser Gln Ile Pro Leu Gln Arg Pro Gln Arg Asp Gln Arg Val
145                 150                 155                 160

Arg Glu Gln Arg Ile Asn Val Pro Pro Gln Arg Gly Pro Arg Pro Val
                165                 170                 175

Arg Glu Ala Gly Glu Gln Gly Asp Val Glu Pro Arg Arg Ile Val Arg
            180                 185                 190

His Pro Asp Ser His Gln Leu Phe Ile Gly Asn Leu Pro His Glu Val
        195                 200                 205

Asp Lys Ser Glu Leu Lys Asp Phe Phe Gln Asn Tyr Gly Asn Val Val
    210                 215                 220

Glu Leu Arg Ile Asn Ser Gly Gly Lys Leu Pro Asn Phe Gly Phe Val
225                 230                 235                 240
```

```
Val Phe Asp Asp Ser Glu Pro Val Gln Lys Val Leu Ser Asn Arg Pro
                245                 250                 255

Ile Met Phe Arg Gly Glu Val Arg Leu Asn Val Glu Glu Lys Lys Thr
            260                 265                 270

Arg Ala Ala Arg Glu Gly Asp Arg Arg Asp Asn Arg Leu Arg Gly Pro
        275                 280                 285

Gly Gly Pro Arg Gly Gly Leu Gly Gly Gly Met Arg Gly Pro Pro Arg
290                 295                 300

Gly Gly Met Val Gln Lys Pro Gly Phe Gly Val Gly Arg Ser Ile Ala
305                 310                 315                 320

Pro Arg Gln

<210> SEQ ID NO 32
<211> LENGTH: 324
<212> TYPE: PRT
<213> ORGANISM: Macaca mulatta

<400> SEQUENCE: 32

Thr Glu Pro Gln Glu Glu Ser Glu Glu Val Glu Glu Pro Glu Glu
1               5                   10                  15

Arg Gln Gln Thr Pro Glu Val Val Pro Asp Asp Ser Gly Thr Phe Tyr
                20                  25                  30

Asp Gln Ala Val Val Ser Asn Asp Met Glu Glu His Leu Glu Glu Pro
            35                  40                  45

Val Ala Glu Pro Glu Pro Asp Pro Glu Pro Glu Pro Glu Gln Glu Pro
        50                  55                  60

Val Ser Glu Ile Gln Glu Lys Pro Glu Pro Val Leu Glu Glu Thr
65                  70                  75                  80

Ala Pro Glu Asp Thr Gln Lys Ser Ser Ser Pro Ala Pro Ala Asp Ile
                85                  90                  95

Ala Gln Thr Val Gln Glu Asp Leu Arg Thr Phe Ser Trp Ala Ser Val
            100                 105                 110

Thr Ser Lys Asn Leu Pro Pro Ser Gly Ala Val Pro Val Thr Gly Ile
        115                 120                 125

Pro Pro His Val Val Lys Val Pro Ala Ser Gln Pro Arg Pro Glu Ser
    130                 135                 140

Lys Pro Glu Ser Gln Ile Pro Pro Gln Arg Pro Gln Arg Asp Gln Arg
145                 150                 155                 160

Val Arg Glu Gln Arg Ile Asn Ile Pro Pro Gln Arg Gly Pro Arg Pro
                165                 170                 175

Ile Arg Glu Ala Gly Glu Gln Gly Asp Ile Glu Pro Arg Arg Met Val
            180                 185                 190

Arg His Pro Asp Ser His Gln Leu Phe Ile Gly Asn Leu Pro His Glu
        195                 200                 205

Val Asp Lys Ser Glu Leu Lys Asp Phe Phe Gln Asn Tyr Gly Asn Val
    210                 215                 220

Val Glu Leu Arg Ile Asn Ser Gly Gly Lys Leu Pro Asn Phe Gly Phe
225                 230                 235                 240

Val Val Phe Asp Asp Ser Glu Pro Val Gln Lys Val Leu Ser Asn Arg
                245                 250                 255

Pro Ile Met Phe Arg Gly Glu Val Arg Leu Asn Val Glu Glu Lys Lys
            260                 265                 270

Thr Arg Ala Ala Arg Glu Gly Asp Arg Arg Asp Asn Arg Leu Arg Gly
        275                 280                 285
```

-continued

Pro Gly Gly Pro Arg Gly Gly Leu Gly Gly Gly Met Arg Gly Pro Pro
290                 295                 300

Arg Gly Gly Met Val Gln Lys Pro Gly Phe Gly Val Gly Arg Gly Leu
305                 310                 315                 320

Ala Pro Arg Gln

<210> SEQ ID NO 33
<211> LENGTH: 324
<212> TYPE: PRT
<213> ORGANISM: Pan troglodytes

<400> SEQUENCE: 33

Thr Glu Pro Gln Glu Glu Ser Glu Glu Val Glu Glu Pro Glu Glu
1               5                   10                  15

Arg Gln Gln Thr Pro Glu Val Val Pro Asp Asp Ser Gly Thr Phe Tyr
                20                  25                  30

Asp Gln Ala Val Val Ser Asn Asp Val Glu Glu His Leu Glu Glu Pro
            35                  40                  45

Val Ala Glu Pro Glu Pro Asp Pro Glu Pro Glu Pro Glu Gln Glu Pro
50                  55                  60

Val Ser Glu Ile Gln Glu Glu Lys Pro Glu Pro Val Leu Glu Glu Thr
65                  70                  75                  80

Ala Pro Glu Asp Ala Gln Lys Ser Ser Ser Pro Ala Pro Ala Asp Ile
                85                  90                  95

Ala Gln Thr Val Gln Glu Asp Leu Arg Thr Phe Ser Trp Ala Ser Val
            100                 105                 110

Thr Ser Lys Asn Leu Pro Pro Ser Gly Ala Val Pro Val Thr Gly Ile
            115                 120                 125

Pro Pro His Val Val Lys Val Pro Ala Ser Gln Pro Arg Pro Glu Ser
130                 135                 140

Lys Pro Glu Ser Gln Ile Pro Pro Gln Arg Pro Gln Arg Asp Gln Arg
145                 150                 155                 160

Val Arg Glu Gln Arg Ile Asn Ile Pro Pro Gln Arg Gly Pro Arg Pro
                165                 170                 175

Ile Arg Glu Ala Gly Glu Gln Gly Asp Ile Glu Pro Arg Arg Met Val
            180                 185                 190

Arg His Pro Asp Ser His Gln Leu Phe Ile Gly Asn Leu Pro His Glu
            195                 200                 205

Val Asp Lys Ser Glu Leu Lys Asp Phe Phe Gln Ser Tyr Gly Asn Val
210                 215                 220

Val Glu Leu Arg Ile Asn Ser Gly Gly Lys Leu Pro Asn Phe Gly Phe
225                 230                 235                 240

Val Val Phe Asp Asp Ser Glu Pro Val Gln Lys Val Leu Ser Asn Arg
                245                 250                 255

Pro Ile Met Phe Arg Gly Glu Val Arg Leu Asn Val Glu Glu Lys Lys
            260                 265                 270

Thr Arg Ala Ala Arg Glu Gly Asp Arg Arg Asp Asn Arg Leu Arg Gly
            275                 280                 285

Pro Gly Gly Pro Arg Gly Gly Leu Gly Gly Gly Met Arg Gly Pro Pro
290                 295                 300

Arg Gly Gly Met Val Gln Lys Pro Gly Phe Gly Val Gly Arg Gly Leu
305                 310                 315                 320

Ala Pro Arg Gln

-continued

```
<210> SEQ ID NO 34
<211> LENGTH: 323
<212> TYPE: PRT
<213> ORGANISM: Canis lupus

<400> SEQUENCE: 34
```

Thr Glu Pro Gln Glu Glu Ser Glu Glu Val Glu Glu Pro Glu Glu
1               5                   10                  15

Arg Gln Gln Thr Pro Glu Val Val Pro Asp Ser Gly Thr Phe Tyr
            20                  25                  30

Asp Gln Ser Val Ser Asn Asp Leu Glu Glu His Leu Glu Glu Pro Val
            35                  40                  45

Ala Glu Pro Glu Pro Asp Pro Glu Pro Glu Pro Glu Gln Glu Pro Val
        50                  55                  60

Ser Glu Ile Gln Glu Glu Lys Ser Glu Pro Val Leu Glu Glu Thr Ala
65                  70                  75                  80

Pro Glu Asp Thr Gln Lys Ser Ser Pro Ala Pro Thr Asp Ile Ala
                85                  90                  95

Gln Thr Val Gln Glu Asp Leu Arg Thr Phe Ser Trp Ala Ser Val Thr
            100                 105                 110

Ser Lys Asn Leu Pro Pro Ser Gly Ala Val Pro Val Thr Gly Ile Pro
        115                 120                 125

Pro His Val Val Lys Val Pro Ala Ser Gln Pro Arg Pro Glu Ser Lys
    130                 135                 140

Pro Glu Ser Gln Ile Pro Pro Gln Arg Pro Gln Arg Asp Gln Arg Val
145                 150                 155                 160

Arg Glu Gln Arg Ile Asn Ile Pro Pro Gln Arg Gly Pro Arg Pro Ile
                165                 170                 175

Arg Glu Ala Gly Glu Gln Gly Asp Val Glu Pro Arg Arg Ile Val Arg
            180                 185                 190

His Pro Asp Ser His Gln Leu Phe Ile Gly Asn Leu Pro His Glu Val
        195                 200                 205

Asp Lys Ser Glu Leu Lys Asp Phe Phe Gln Ser Tyr Gly Asn Val Val
    210                 215                 220

Glu Leu Arg Ile Asn Ser Gly Gly Lys Leu Pro Asn Phe Gly Phe Val
225                 230                 235                 240

Val Phe Asp Asp Ser Glu Pro Val Gln Lys Val Leu Ser Asn Arg Pro
                245                 250                 255

Ile Met Phe Arg Gly Glu Val Arg Leu Asn Val Glu Glu Lys Lys Thr
            260                 265                 270

Arg Ala Ala Arg Glu Gly Asp Arg Asp Asn Arg Leu Arg Gly Pro
        275                 280                 285

Gly Gly Pro Arg Gly Gly Leu Gly Gly Gly Met Arg Gly Pro Ser Arg
    290                 295                 300

Gly Gly Met Val Gln Lys Pro Gly Phe Gly Val Gly Arg Gly Ile Ala
305                 310                 315                 320

Pro Arg Gln

```
<210> SEQ ID NO 35
<211> LENGTH: 340
<212> TYPE: PRT
<213> ORGANISM: Mus musculus

<400> SEQUENCE: 35
```

Pro Glu Leu Asp Glu Glu Ser Glu Asp Glu Val Glu Glu Glu Gln Glu
1               5                   10                  15

Asp Arg Gln Pro Ser Pro Glu Pro Val Gln Glu Asn Ala Asn Ser Ala
            20                  25                  30

Tyr Tyr Asp Ala His Pro Val Thr Asn Gly Ile Glu Glu Pro Leu Glu
            35                  40                  45

Glu Ser Ser His Glu Pro Glu Pro Glu Pro Ser Glu Thr Lys Thr
 50                  55                  60

Glu Glu Leu Lys Pro Gln Val Glu Glu Lys His Leu Glu Glu Leu Glu
 65                  70                  75                  80

Glu Lys Ser Ala Thr Pro Pro Ala Glu Pro Ala Ser Leu Pro Gln
                 85                  90                  95

Glu Pro Pro Lys Ala Phe Ser Trp Ala Ser Val Thr Ser Lys Asn Leu
            100                 105                 110

Pro Pro Ser Gly Thr Val Ser Ser Gly Ile Pro Pro His Val Lys
             115                 120                 125

Ala Pro Val Ser Gln Pro Arg Val Asp Ala Lys Pro Glu Val Gln Ser
130                 135                 140

Gln Pro Pro Arg Val Arg Glu Gln Arg Pro Glu Arg Pro Gly Phe
145                 150                 155                 160

Pro Pro Arg Gly Pro Arg Pro Gly Arg Gly Asp Met Glu Gln Asn Asp
             165                 170                 175

Ser Asp Asn Arg Arg Ile Ile Arg Tyr Pro Asp Ser His Gln Leu Phe
             180                 185                 190

Val Gly Asn Leu Pro His Asp Ile Asp Glu Asn Glu Leu Lys Glu Phe
             195                 200                 205

Phe Met Ser Phe Gly Asn Val Val Glu Leu Arg Ile Asn Thr Lys Gly
    210                 215                 220

Val Gly Gly Lys Leu Pro Asn Phe Gly Phe Val Val Phe Asp Asp Ser
225                 230                 235                 240

Glu Pro Val Gln Arg Ile Leu Ile Ala Lys Pro Ile Met Phe Arg Gly
             245                 250                 255

Glu Val Arg Leu Asn Val Glu Glu Lys Lys Thr Arg Ala Ala Arg Glu
             260                 265                 270

Arg Glu Thr Arg Gly Gly Gly Asp Asp Arg Arg Asp Ile Arg Arg Asn
             275                 280                 285

Asp Arg Gly Pro Gly Pro Arg Gly Ile Val Gly Gly Met Met
290                 295                 300

Arg Asp Arg Asp Gly Arg Gly Pro Pro Arg Gly Gly Met Thr Gln
305                 310                 315                 320

Lys Leu Gly Ser Gly Arg Gly Thr Gly Gln Met Glu Gly Arg Phe Thr
                 325                 330                 335

Gly Gln Arg Arg
            340

<210> SEQ ID NO 36
<211> LENGTH: 307
<212> TYPE: PRT
<213> ORGANISM: Mus musculus

<400> SEQUENCE: 36

Pro Glu Leu Asp Glu Glu Ser Glu Asp Glu Val Glu Glu Gln Glu
1               5                   10                  15

Asp Arg Gln Pro Ser Pro Glu Pro Val Gln Glu Asn Ala Asn Ser Ala
            20                  25                  30

Tyr Tyr Asp Ala His Pro Val Thr Asn Gly Ile Glu Glu Pro Leu Glu

```
                35                  40                  45
Glu Ser Ser His Glu Pro Glu Pro Glu Ser Glu Thr Lys Thr
         50                  55                  60
Glu Glu Leu Lys Pro Gln Val Glu Lys His Leu Glu Glu Leu Glu
 65                  70                  75                  80
Glu Lys Ser Ala Thr Pro Pro Ala Glu Pro Ala Ser Leu Pro Gln
                 85                  90                  95
Glu Pro Pro Lys Pro Arg Val Asp Ala Lys Pro Glu Val Gln Ser Gln
                100                 105                 110
Pro Pro Arg Val Arg Glu Gln Arg Pro Arg Glu Arg Pro Gly Phe Pro
            115                 120                 125
Pro Arg Gly Pro Arg Pro Gly Arg Gly Asp Met Glu Gln Asn Asp Ser
        130                 135                 140
Asp Asn Arg Arg Ile Ile Arg Tyr Pro Asp Ser His Gln Leu Phe Val
145                 150                 155                 160
Gly Asn Leu Pro His Asp Ile Asp Glu Asn Glu Leu Lys Glu Phe Phe
                165                 170                 175
Met Ser Phe Gly Asn Val Val Glu Leu Arg Ile Asn Thr Lys Gly Val
            180                 185                 190
Gly Gly Lys Leu Pro Asn Phe Gly Phe Val Val Phe Asp Asp Ser Glu
        195                 200                 205
Pro Val Gln Arg Ile Leu Ile Ala Lys Pro Ile Met Phe Arg Gly Glu
    210                 215                 220
Val Arg Leu Asn Val Glu Glu Lys Lys Thr Arg Ala Ala Arg Glu Arg
225                 230                 235                 240
Glu Thr Arg Gly Gly Gly Asp Asp Arg Arg Asp Ile Arg Arg Asn Asp
                245                 250                 255
Arg Gly Pro Gly Gly Pro Arg Gly Ile Val Gly Gly Met Met Arg
            260                 265                 270
Asp Arg Asp Gly Arg Gly Pro Pro Arg Gly Met Thr Gln Lys
        275                 280                 285
Leu Gly Ser Gly Arg Gly Thr Gly Gln Met Glu Gly Arg Phe Thr Gly
    290                 295                 300
Gln Arg Arg
305

<210> SEQ ID NO 37
<211> LENGTH: 307
<212> TYPE: PRT
<213> ORGANISM: Rattus norvegicus

<400> SEQUENCE: 37

Pro Glu Leu Asp Glu Glu Ser Glu Asp Glu Val Glu Glu Gln Glu
 1               5                  10                  15

Asp Arg Gln Pro Ser Pro Glu Pro Val Gln Glu Asn Ala Asn Ser Ala
                 20                  25                  30

Tyr Tyr Glu Ala His Pro Val Thr Asn Gly Ile Glu Glu Pro Leu Glu
            35                  40                  45

Glu Ser Ser His Glu Pro Glu Pro Glu Ser Glu Thr Lys Thr
         50                  55                  60

Glu Glu Leu Lys Pro Gln Ala Glu Lys His Leu Glu Glu Leu Glu
 65                  70                  75                  80

Glu Lys Ser Ala Thr Pro Pro Pro Thr Glu Pro Ala Ser Leu Pro Gln
                 85                  90                  95
```

-continued

```
Glu Pro Pro Lys Pro Arg Val Asp Ala Lys Pro Glu Val Gln Ser Gln
            100                 105                 110

Pro Pro Arg Val Arg Glu Gln Arg Pro Arg Glu Arg Pro Gly Phe Pro
        115                 120                 125

Pro Arg Gly Pro Arg Pro Gly Arg Gly Asp Thr Glu Gln Asn Asp Ser
    130                 135                 140

Asp Asn Arg Arg Ile Ile Arg Tyr Pro Asp Ser His Gln Leu Phe Val
145                 150                 155                 160

Gly Asn Leu Pro His Asp Ile Asp Glu Asn Glu Leu Lys Glu Phe Phe
                165                 170                 175

Met Ser Phe Gly Asn Val Val Glu Leu Arg Ile Asn Thr Lys Gly Val
            180                 185                 190

Gly Gly Lys Leu Pro Asn Phe Gly Phe Val Val Phe Asp Asp Ser Glu
        195                 200                 205

Pro Val Gln Arg Ile Leu Ile Ala Lys Pro Ile Met Phe Arg Gly Glu
    210                 215                 220

Val Arg Leu Asn Val Glu Glu Lys Lys Thr Arg Ala Ala Arg Glu Arg
225                 230                 235                 240

Glu Thr Arg Gly Gly Gly Asp Asp Arg Asp Ile Arg Arg Asn Asp
                245                 250                 255

Arg Gly Pro Gly Gly Pro Arg Gly Ile Val Gly Gly Gly Met Met Arg
            260                 265                 270

Asp Arg Asp Gly Arg Gly Pro Pro Arg Gly Gly Met Thr Gln Lys
        275                 280                 285

Leu Gly Ser Gly Arg Gly Thr Gly Gln Met Glu Gly Arg Phe Thr Gly
    290                 295                 300

Gln Arg Arg
305

<210> SEQ ID NO 38
<211> LENGTH: 340
<212> TYPE: PRT
<213> ORGANISM: Rattus norvegicus

<400> SEQUENCE: 38

Pro Glu Leu Asp Glu Glu Ser Glu Asp Glu Val Glu Glu Gln Glu
1               5                   10                  15

Asp Arg Gln Pro Ser Pro Glu Pro Val Gln Glu Asn Ala Asn Ser Ala
            20                  25                  30

Tyr Tyr Glu Ala His Pro Val Thr Asn Gly Ile Glu Glu Pro Leu Glu
        35                  40                  45

Glu Ser Ser His Glu Pro Glu Pro Glu Pro Glu Ser Glu Thr Lys Thr
    50                  55                  60

Glu Glu Leu Lys Pro Gln Ala Glu Glu Lys His Leu Glu Glu Leu Glu
65                  70                  75                  80

Glu Lys Ser Ala Thr Pro Pro Thr Glu Pro Ala Ser Leu Pro Gln
            85                  90                  95

Glu Pro Pro Lys Ala Phe Ser Trp Ala Ser Val Thr Ser Lys Asn Leu
        100                 105                 110

Pro Pro Ser Gly Thr Val Ser Ser Gly Ile Pro Pro His Val Lys
    115                 120                 125

Ala Pro Val Ser Gln Pro Arg Val Asp Ala Lys Pro Glu Val Gln Ser
    130                 135                 140

Gln Pro Pro Arg Val Arg Glu Gln Arg Pro Arg Glu Arg Pro Gly Phe
145                 150                 155                 160
```

```
Pro Pro Arg Gly Pro Arg Pro Gly Arg Gly Asp Thr Glu Gln Asn Asp
                165                 170                 175

Ser Asp Asn Arg Arg Ile Ile Arg Tyr Pro Asp Ser His Gln Leu Phe
            180                 185                 190

Val Gly Asn Leu Pro His Asp Ile Asp Glu Asn Glu Leu Lys Glu Phe
            195                 200                 205

Phe Met Ser Phe Gly Asn Val Val Glu Leu Arg Ile Asn Thr Lys Gly
    210                 215                 220

Val Gly Gly Lys Leu Pro Asn Phe Gly Phe Val Val Phe Asp Asp Ser
225                 230                 235                 240

Glu Pro Val Gln Arg Ile Leu Ile Ala Lys Pro Ile Met Phe Arg Gly
                245                 250                 255

Glu Val Arg Leu Asn Val Glu Glu Lys Lys Thr Arg Ala Ala Arg Glu
            260                 265                 270

Arg Glu Thr Arg Gly Gly Gly Asp Arg Arg Asp Ile Arg Arg Asn
            275                 280                 285

Asp Arg Gly Pro Gly Pro Arg Gly Ile Val Gly Gly Met Met
    290                 295                 300

Arg Asp Arg Asp Gly Arg Gly Pro Pro Arg Gly Met Thr Gln
305                 310                 315                 320

Lys Leu Gly Ser Gly Arg Gly Thr Gly Gln Met Glu Gly Arg Phe Thr
                325                 330                 335

Gly Gln Arg Arg
            340

<210> SEQ ID NO 39
<211> LENGTH: 307
<212> TYPE: PRT
<213> ORGANISM: Canis lupus

<400> SEQUENCE: 39

Pro Glu Leu Asp Glu Glu Ser Glu Asp Glu Val Glu Glu Glu Gln Glu
1               5                   10                  15

Glu Arg Gln Pro Ser Pro Glu Pro Val Gln Glu Asn Ala Asp Ser Gly
            20                  25                  30

Tyr Tyr Glu Ala His Pro Val Ala Asn Gly Ile Glu Glu Pro Leu Glu
            35                  40                  45

Glu Ser Ser His Glu Pro Glu Pro Glu Pro Asp Ser Glu Thr Lys Thr
        50                  55                  60

Glu Glu Leu Lys Pro Gln Val Glu Glu Lys Asn Leu Glu Glu Leu Glu
65                  70                  75                  80

Glu Lys Ser Thr Ser Pro Pro Ala Glu Pro Val Ser Leu Pro Gln
                85                  90                  95

Glu Pro Pro Lys Pro Arg Val Glu Ala Lys Pro Glu Val Gln Ser Gln
                100                 105                 110

Pro Pro Arg Val Arg Glu Gln Arg Pro Arg Glu Arg Pro Gly Phe Pro
            115                 120                 125

Pro Arg Gly Pro Arg Pro Gly Arg Gly Asp Leu Glu Gln Asn Glu Ser
    130                 135                 140

Asp Asn Arg Arg Ile Ile Arg Tyr Pro Asp Ser His Gln Leu Phe Val
145                 150                 155                 160

Gly Asn Leu Pro His Asp Ile Asp Glu Asn Glu Leu Lys Glu Phe Phe
                165                 170                 175

Met Ser Phe Gly Asn Val Val Glu Leu Arg Ile Asn Thr Lys Gly Val
```

```
                180             185                 190
Gly Gly Lys Leu Pro Asn Phe Gly Phe Val Phe Asp Asp Ser Glu
            195                 200             205

Pro Val Gln Arg Ile Leu Ile Ala Lys Pro Ile Met Phe Arg Gly Glu
    210                 215                 220

Val Arg Leu Asn Val Glu Lys Lys Thr Arg Ala Ala Arg Glu Arg
225             230                 235                 240

Glu Thr Arg Gly Gly Asp Arg Arg Asp Ile Arg Arg Asn Asp
            245                 250                 255

Arg Gly Pro Gly Gly Pro Arg Gly Ile Val Gly Gly Met Met Arg
            260                 265                 270

Asp Arg Asp Gly Arg Gly Pro Pro Arg Gly Gly Met Ala Gln Lys
            275                 280                 285

Leu Gly Ser Gly Arg Gly Thr Gly Gln Met Glu Gly Arg Phe Thr Gly
            290                 295                 300

Gln Arg Arg
305

<210> SEQ ID NO 40
<211> LENGTH: 340
<212> TYPE: PRT
<213> ORGANISM: Canis lupus

<400> SEQUENCE: 40

Pro Glu Leu Asp Glu Glu Ser Glu Asp Glu Val Glu Glu Gln Glu
1               5                   10                  15

Glu Arg Gln Pro Ser Pro Glu Pro Val Gln Glu Asn Ala Asp Ser Gly
            20                  25                  30

Tyr Tyr Glu Ala His Pro Val Ala Asn Gly Ile Glu Glu Pro Leu Glu
            35                  40                  45

Glu Ser Ser His Glu Pro Glu Pro Glu Pro Asp Ser Glu Thr Lys Thr
50                  55                  60

Glu Glu Leu Lys Pro Gln Val Glu Glu Lys Asn Leu Glu Glu Leu Glu
65                  70                  75                  80

Glu Lys Ser Thr Ser Pro Pro Ala Glu Pro Val Ser Leu Pro Gln
            85                  90                  95

Glu Pro Pro Lys Ala Phe Ser Trp Ala Ser Val Thr Ser Lys Asn Leu
            100                 105                 110

Pro Pro Ser Gly Thr Val Ser Ser Gly Ile Pro Pro His Val Lys
            115                 120                 125

Ala Pro Val Ser Gln Pro Arg Val Glu Ala Lys Pro Glu Val Gln Ser
            130                 135                 140

Gln Pro Pro Arg Val Arg Glu Gln Arg Pro Arg Glu Arg Pro Gly Phe
145                 150                 155                 160

Pro Pro Arg Gly Pro Arg Pro Gly Arg Gly Asp Leu Glu Gln Asn Glu
            165                 170                 175

Ser Asp Asn Arg Arg Ile Ile Arg Tyr Pro Asp Ser His Gln Leu Phe
            180                 185                 190

Val Gly Asn Leu Pro His Asp Ile Asp Glu Asn Glu Leu Lys Glu Phe
            195                 200                 205

Phe Met Ser Phe Gly Asn Val Val Glu Leu Arg Ile Asn Thr Lys Gly
            210                 215                 220

Val Gly Gly Lys Leu Pro Asn Phe Gly Phe Val Val Phe Asp Asp Ser
225                 230                 235                 240
```

```
Glu Pro Val Gln Arg Ile Leu Ile Ala Lys Pro Ile Met Phe Arg Gly
                245                 250                 255

Glu Val Arg Leu Asn Val Glu Glu Lys Lys Thr Arg Ala Ala Arg Glu
            260                 265                 270

Arg Glu Thr Arg Gly Gly Gly Asp Asp Arg Arg Asp Ile Arg Arg Asn
        275                 280                 285

Asp Arg Gly Pro Gly Gly Pro Arg Gly Ile Val Gly Gly Met Met
    290                 295                 300

Arg Asp Arg Asp Gly Arg Gly Pro Pro Arg Gly Gly Met Ala Gln
305                 310                 315                 320

Lys Leu Gly Ser Gly Arg Gly Thr Gly Gln Met Glu Gly Arg Phe Thr
                325                 330                 335

Gly Gln Arg Arg
            340

<210> SEQ ID NO 41
<211> LENGTH: 307
<212> TYPE: PRT
<213> ORGANISM: Bos taurus

<400> SEQUENCE: 41

Pro Glu Leu Asp Glu Glu Ser Glu Asp Glu Val Glu Glu Gln Glu
1               5                   10                  15

Glu Arg Gln Pro Ser Pro Glu Pro Val Gln Glu Asn Ala Asn Ser Gly
            20                  25                  30

Tyr Tyr Glu Ala His Pro Val Thr Asn Gly Ile Glu Glu Pro Leu Glu
        35                  40                  45

Glu Ser Ser His Glu Pro Glu Pro Glu Pro Glu Ser Glu Thr Lys Thr
    50                  55                  60

Glu Glu Leu Lys Pro Pro Val Glu Glu Lys Asn Leu Glu Glu Leu Glu
65                  70                  75                  80

Glu Lys Ser Ala Ser Pro Pro Ala Glu Pro Val Ser Leu Pro Gln
                85                  90                  95

Glu Pro Pro Lys Pro Arg Val Glu Ala Lys Pro Glu Val Gln Ser Gln
            100                 105                 110

Pro Pro Arg Val Arg Glu Gln Arg Pro Arg Glu Arg Pro Gly Phe Pro
        115                 120                 125

Pro Arg Gly Pro Arg Pro Gly Arg Gly Asp Ile Glu Gln Asn Glu Ser
    130                 135                 140

Asp Asn Arg Arg Ile Ile Arg Tyr Pro Asp Ser His Gln Leu Phe Val
145                 150                 155                 160

Gly Asn Leu Pro His Asp Ile Asp Glu Asn Glu Leu Lys Glu Phe Phe
                165                 170                 175

Met Ser Phe Gly Asn Val Val Glu Leu Arg Ile Asn Thr Lys Gly Val
            180                 185                 190

Gly Gly Lys Leu Pro Asn Phe Gly Phe Val Val Phe Asp Asp Ser Glu
        195                 200                 205

Pro Val Gln Arg Ile Leu Ile Ala Lys Pro Ile Met Phe Arg Gly Glu
    210                 215                 220

Val Arg Leu Asn Val Glu Glu Lys Lys Thr Arg Ala Ala Arg Glu Arg
225                 230                 235                 240

Glu Thr Arg Gly Gly Gly Asp Asp Arg Asp Ile Arg Arg Ser Asp
                245                 250                 255

Arg Gly Pro Gly Gly Pro Arg Gly Ile Val Gly Gly Met Met Arg
            260                 265                 270
```

```
Asp Arg Asp Gly Arg Gly Pro Pro Arg Gly Gly Met Ala Gln Lys
        275                 280                 285

Leu Gly Ser Gly Arg Gly Ala Gly Gln Met Glu Gly Arg Phe Thr Gly
    290                 295                 300

Gln Arg Arg
305

<210> SEQ ID NO 42
<211> LENGTH: 340
<212> TYPE: PRT
<213> ORGANISM: Bos taurus

<400> SEQUENCE: 42

Pro Glu Leu Asp Glu Glu Ser Glu Asp Glu Val Glu Glu Gln Glu
1               5                   10                  15

Glu Arg Gln Pro Ser Pro Glu Pro Val Gln Glu Asn Ala Asn Ser Gly
                20                  25                  30

Tyr Tyr Glu Ala His Pro Val Thr Asn Gly Ile Glu Glu Pro Leu Glu
            35                  40                  45

Glu Ser Ser His Glu Pro Glu Pro Glu Pro Glu Ser Glu Thr Lys Thr
50                  55                  60

Glu Glu Leu Lys Pro Pro Val Glu Glu Lys Asn Leu Glu Glu Leu Glu
65                  70                  75                  80

Glu Lys Ser Ala Ser Pro Pro Ala Glu Pro Val Ser Leu Pro Gln
                85                  90                  95

Glu Pro Pro Lys Ala Phe Ser Trp Ala Ser Val Thr Ser Lys Asn Leu
            100                 105                 110

Pro Pro Ser Gly Thr Val Ser Ser Gly Ile Pro Pro His Val Lys
            115                 120                 125

Ala Pro Val Ser Gln Pro Arg Val Glu Ala Lys Pro Glu Val Gln Ser
130                 135                 140

Gln Pro Pro Arg Val Arg Glu Gln Arg Pro Arg Glu Arg Pro Gly Phe
145                 150                 155                 160

Pro Pro Arg Gly Pro Arg Pro Gly Arg Gly Asp Ile Glu Gln Asn Glu
                165                 170                 175

Ser Asp Asn Arg Arg Ile Ile Arg Tyr Pro Asp Ser His Gln Leu Phe
            180                 185                 190

Val Gly Asn Leu Pro His Asp Ile Asp Glu Asn Glu Leu Lys Glu Phe
        195                 200                 205

Phe Met Ser Phe Gly Asn Val Val Glu Leu Arg Ile Asn Thr Lys Gly
    210                 215                 220

Val Gly Gly Lys Leu Pro Asn Phe Gly Phe Val Val Phe Asp Asp Ser
225                 230                 235                 240

Glu Pro Val Gln Arg Ile Leu Ile Ala Lys Pro Ile Met Phe Arg Gly
                245                 250                 255

Glu Val Arg Leu Asn Val Glu Glu Lys Lys Thr Arg Ala Ala Arg Glu
            260                 265                 270

Arg Glu Thr Arg Gly Gly Gly Asp Asp Arg Arg Asp Ile Arg Arg Ser
        275                 280                 285

Asp Arg Gly Pro Gly Gly Pro Arg Gly Ile Val Gly Gly Met Met
        290                 295                 300

Arg Asp Arg Asp Gly Arg Gly Pro Pro Arg Gly Gly Met Ala Gln
305                 310                 315                 320

Lys Leu Gly Ser Gly Arg Gly Ala Gly Gln Met Glu Gly Arg Phe Thr
```

```
                        325                 330                 335

Gly Gln Arg Arg
            340

<210> SEQ ID NO 43
<211> LENGTH: 340
<212> TYPE: PRT
<213> ORGANISM: Pan troglodytes

<400> SEQUENCE: 43

Pro Glu Leu Asp Glu Glu Ser Glu Asp Glu Val Glu Glu Gln Glu
1               5                   10                  15

Glu Arg Gln Pro Ser Pro Glu Pro Val Gln Glu Asn Ala Asn Ser Gly
                20                  25                  30

Tyr Tyr Glu Ala His Pro Val Thr Asn Gly Ile Glu Glu Pro Leu Glu
            35                  40                      45

Glu Ser Ser His Glu Pro Glu Pro Glu Pro Glu Ser Glu Thr Lys Thr
        50                  55                  60

Glu Glu Leu Lys Pro Gln Val Glu Glu Lys Asn Leu Glu Glu Leu Glu
65              70                  75                  80

Glu Lys Ser Thr Thr Pro Pro Pro Ala Glu Pro Val Ser Leu Pro Gln
                85                  90                      95

Glu Pro Pro Lys Ala Phe Ser Trp Ala Ser Val Thr Ser Lys Asn Leu
                100                 105                 110

Pro Pro Ser Gly Thr Val Ser Ser Gly Ile Pro Pro His Val Lys
                115                 120                 125

Ala Pro Val Ser Gln Pro Arg Val Glu Ala Lys Pro Glu Val Gln Ser
            130                 135                 140

Gln Pro Pro Arg Val Arg Glu Gln Arg Pro Arg Glu Arg Pro Gly Phe
145                 150                 155                 160

Pro Pro Arg Gly Pro Arg Pro Gly Arg Gly Asp Met Glu Gln Asn Asp
                165                 170                 175

Ser Asp Asn Arg Arg Ile Ile Arg Tyr Pro Asp Ser His Gln Leu Phe
                180                 185                 190

Val Gly Asn Leu Pro His Asp Ile Asp Glu Asn Glu Leu Lys Glu Phe
            195                 200                 205

Phe Met Ser Phe Gly Asn Val Val Glu Leu Arg Ile Asn Thr Lys Gly
        210                 215                 220

Val Gly Gly Lys Leu Pro Asn Phe Gly Phe Val Val Phe Asp Asp Ser
225                 230                 235                 240

Glu Pro Val Gln Arg Ile Leu Ile Ala Lys Pro Ile Met Phe Arg Gly
                245                 250                 255

Glu Val Arg Leu Asn Val Glu Glu Lys Lys Thr Arg Ala Ala Arg Glu
                260                 265                 270

Arg Glu Thr Arg Gly Gly Gly Asp Asp Arg Asp Ile Arg Arg Asn
            275                 280                 285

Asp Arg Gly Pro Gly Gly Pro Arg Gly Ile Val Gly Gly Met Met
290                 295                 300

Arg Asp Arg Asp Gly Arg Gly Pro Pro Arg Gly Gly Met Ala Gln
305                 310                 315                 320

Lys Leu Gly Ser Gly Arg Gly Thr Gly Gln Met Glu Gly Arg Phe Thr
                325                 330                 335

Gly Gln Arg Arg
            340
```

<210> SEQ ID NO 44
<211> LENGTH: 340
<212> TYPE: PRT
<213> ORGANISM: Macaca mulatta

<400> SEQUENCE: 44

```
Pro Glu Leu Asp Glu Ser Glu Asp Glu Val Glu Glu Gln Glu
1               5                   10                  15

Glu Arg Gln Pro Ser Pro Glu Pro Val Gln Glu Asn Ala Asn Ser Gly
                20                  25                  30

Tyr Tyr Glu Ala His Pro Val Thr Asn Gly Ile Glu Glu Pro Leu Glu
                35                  40                  45

Glu Ser Ser His Glu Pro Glu Pro Glu Thr Glu Ser Glu Thr Lys Thr
            50                  55                  60

Glu Glu Leu Lys Pro Gln Val Glu Glu Lys Asn Leu Glu Glu Leu Glu
65                  70                  75                  80

Glu Lys Ser Thr Thr Pro Pro Ala Glu Pro Val Ser Leu Pro Gln
                85                  90                  95

Glu Pro Pro Lys Ala Phe Ser Trp Ala Ser Val Thr Ser Lys Asn Leu
                100                 105                 110

Pro Pro Ser Gly Thr Val Ser Ser Gly Ile Pro Pro His Val Lys
            115                 120                 125

Ala Pro Val Ser Gln Pro Arg Val Glu Ala Lys Pro Glu Val Gln Ser
            130                 135                 140

Gln Pro Pro Arg Val Arg Glu Gln Arg Pro Arg Glu Arg Pro Gly Phe
145                 150                 155                 160

Pro Pro Arg Gly Pro Arg Pro Gly Arg Gly Asp Met Glu Gln Asn Asp
                165                 170                 175

Ser Asp Asn Arg Arg Ile Ile Arg Tyr Pro Asp Ser His Gln Leu Phe
                180                 185                 190

Val Gly Asn Leu Pro His Asp Ile Asp Glu Asn Glu Leu Lys Glu Phe
            195                 200                 205

Phe Met Ser Phe Gly Asn Val Val Glu Leu Arg Ile Asn Thr Lys Gly
210                 215                 220

Val Gly Gly Lys Leu Pro Asn Phe Gly Phe Val Val Phe Asp Asp Ser
225                 230                 235                 240

Glu Pro Val Gln Arg Ile Leu Ile Ala Lys Pro Ile Met Phe Arg Gly
                245                 250                 255

Glu Val Arg Leu Asn Val Glu Glu Lys Lys Thr Arg Ala Ala Arg Glu
                260                 265                 270

Arg Glu Thr Arg Gly Gly Gly Asp Arg Arg Asp Ile Arg Arg Asn
            275                 280                 285

Asp Arg Gly Pro Gly Gly Pro Arg Gly Ile Val Gly Gly Gly Met Met
            290                 295                 300

Arg Asp Arg Asp Gly Arg Gly Pro Pro Arg Gly Gly Met Ala Gln
305                 310                 315                 320

Lys Leu Gly Ser Gly Arg Gly Thr Gly Gln Met Glu Gly Arg Phe Thr
                325                 330                 335

Gly Gln Arg Arg
            340
```

<210> SEQ ID NO 45
<211> LENGTH: 307
<212> TYPE: PRT
<213> ORGANISM: Pan troglodytes

<400> SEQUENCE: 45

```
Pro Glu Leu Asp Glu Glu Ser Glu Asp Glu Val Glu Glu Gln Glu
1               5                   10                  15

Glu Arg Gln Pro Ser Pro Glu Pro Val Gln Glu Asn Ala Asn Ser Gly
            20                  25                  30

Tyr Tyr Glu Ala His Pro Val Thr Asn Gly Ile Glu Glu Pro Leu Glu
        35                  40                  45

Glu Ser Ser His Glu Pro Pro Glu Pro Glu Ser Glu Thr Lys Thr
    50                  55                  60

Glu Glu Leu Lys Pro Gln Val Glu Glu Lys Asn Leu Glu Glu Leu Glu
65              70                  75                  80

Glu Lys Ser Thr Thr Pro Pro Ala Glu Pro Val Ser Leu Pro Gln
            85                  90                  95

Glu Pro Pro Lys Pro Arg Val Glu Ala Lys Pro Glu Val Gln Ser Gln
                100                 105                 110

Pro Pro Arg Val Arg Glu Gln Arg Pro Arg Glu Arg Pro Gly Phe Pro
            115                 120                 125

Pro Arg Gly Pro Arg Pro Gly Arg Gly Asp Met Glu Gln Asn Asp Ser
    130                 135                 140

Asp Asn Arg Arg Ile Ile Arg Tyr Pro Asp Ser His Gln Leu Phe Val
145                 150                 155                 160

Gly Asn Leu Pro His Asp Ile Asp Glu Asn Glu Leu Lys Glu Phe Phe
                165                 170                 175

Met Ser Phe Gly Asn Val Val Glu Leu Arg Ile Asn Thr Lys Gly Val
        180                 185                 190

Gly Gly Lys Leu Pro Asn Phe Gly Phe Val Val Phe Asp Asp Ser Glu
    195                 200                 205

Pro Val Gln Arg Ile Leu Ile Ala Lys Pro Ile Met Phe Arg Gly Glu
    210                 215                 220

Val Arg Leu Asn Val Glu Glu Lys Lys Thr Arg Ala Ala Arg Glu Arg
225                 230                 235                 240

Glu Thr Arg Gly Gly Gly Asp Asp Arg Asp Ile Arg Arg Asn Asp
            245                 250                 255

Arg Gly Pro Gly Gly Pro Arg Gly Ile Val Gly Gly Met Met Arg
    260                 265                 270

Asp Arg Asp Gly Arg Gly Pro Pro Arg Gly Gly Met Ala Gln Lys
        275                 280                 285

Leu Gly Ser Gly Arg Gly Thr Gly Gln Met Gly Arg Phe Thr Gly
    290                 295                 300

Gln Arg Arg
305
```

<210> SEQ ID NO 46
<211> LENGTH: 307
<212> TYPE: PRT
<213> ORGANISM: Macaca mulatta

<400> SEQUENCE: 46

```
Pro Glu Leu Asp Glu Glu Ser Glu Asp Glu Val Glu Glu Gln Glu
1               5                   10                  15

Glu Arg Gln Pro Ser Pro Glu Pro Val Gln Glu Asn Ala Asn Ser Gly
            20                  25                  30

Tyr Tyr Glu Ala His Pro Val Thr Asn Gly Ile Glu Glu Pro Leu Glu
        35                  40                  45
```

```
Glu Ser Ser His Glu Pro Glu Pro Glu Thr Glu Ser Glu Thr Lys Thr
        50                  55                  60

Glu Glu Leu Lys Pro Gln Val Glu Glu Lys Asn Leu Glu Glu Leu Glu
 65              70                  75                  80

Glu Lys Ser Thr Thr Pro Pro Ala Glu Pro Val Ser Leu Pro Gln
                85                  90                  95

Glu Pro Pro Lys Pro Arg Val Glu Ala Lys Pro Glu Val Gln Ser Gln
                100                 105                 110

Pro Pro Arg Val Arg Glu Gln Arg Pro Arg Glu Arg Pro Gly Phe Pro
            115                 120                 125

Pro Arg Gly Pro Arg Pro Gly Arg Gly Asp Met Glu Gln Asn Asp Ser
            130                 135                 140

Asp Asn Arg Arg Ile Ile Arg Tyr Pro Asp Ser His Gln Leu Phe Val
145                 150                 155                 160

Gly Asn Leu Pro His Asp Ile Asp Glu Asn Glu Leu Lys Glu Phe Phe
                165                 170                 175

Met Ser Phe Gly Asn Val Val Glu Leu Arg Ile Asn Thr Lys Gly Val
                180                 185                 190

Gly Gly Lys Leu Pro Asn Phe Gly Phe Val Val Phe Asp Asp Ser Glu
            195                 200                 205

Pro Val Gln Arg Ile Leu Ile Ala Lys Pro Ile Met Phe Arg Gly Glu
210                 215                 220

Val Arg Leu Asn Val Glu Glu Lys Lys Thr Arg Ala Ala Arg Glu Arg
225                 230                 235                 240

Glu Thr Arg Gly Gly Gly Asp Asp Arg Gly Asp Ile Arg Arg Asn Asp
                245                 250                 255

Arg Gly Pro Gly Gly Pro Arg Gly Ile Val Gly Gly Gly Met Met Arg
            260                 265                 270

Asp Arg Asp Gly Arg Gly Pro Pro Arg Gly Gly Met Ala Gln Lys
            275                 280                 285

Leu Gly Ser Gly Arg Gly Thr Gly Gln Met Glu Gly Arg Phe Thr Gly
            290                 295                 300

Gln Arg Arg
305

<210> SEQ ID NO 47
<211> LENGTH: 718
<212> TYPE: PRT
<213> ORGANISM: Oryza sativa

<400> SEQUENCE: 47

Met Ser Ala Ser Pro Ser Ser Met Ser Gly Ala Gly Ala Gly Glu Ala
1                5                  10                  15

Gly Val Arg Thr Val Val Trp Phe Arg Arg Asp Leu Arg Val Glu Asp
                20                  25                  30

Asn Pro Ala Leu Ala Ala Ala Arg Ala Ala Gly Glu Val Val Pro
            35                  40                  45

Val Tyr Val Trp Ala Pro Glu Glu Asp Gly Pro Tyr Tyr Pro Gly Arg
         50                  55                  60

Val Ser Arg Trp Trp Leu Ser Gln Ser Leu Lys His Leu Asp Ala Ser
 65                  70                  75                  80

Leu Arg Arg Leu Gly Ala Ser Arg Leu Val Thr Arg Arg Ser Ala Asp
                85                  90                  95

Ala Val Val Ala Leu Ile Glu Leu Val Arg Ser Ile Gly Ala Thr His
```

-continued

```
                100                 105                 110
Leu Phe Phe Asn His Leu Tyr Asp Pro Leu Ser Leu Val Arg Asp His
            115                 120                 125

Arg Val Lys Ala Leu Leu Thr Ala Glu Gly Ile Ala Val Gln Ser Phe
130                 135                 140

Asn Ala Asp Leu Leu Tyr Glu Pro Trp Glu Val Val Asp Asp Asp Gly
145                 150                 155                 160

Cys Pro Phe Thr Met Phe Ala Pro Phe Trp Asp Arg Cys Leu Cys Met
                165                 170                 175

Pro Asp Pro Ala Ala Pro Leu Leu Pro Pro Lys Arg Ile Ala Pro Gly
            180                 185                 190

Glu Leu Pro Ala Arg Arg Cys Pro Ser Asp Glu Leu Val Phe Glu Asp
            195                 200                 205

Glu Ser Glu Arg Gly Ser Asn Ala Leu Leu Ala Arg Ala Trp Ser Pro
            210                 215                 220

Gly Trp Gln Asn Ala Asp Lys Ala Leu Ala Ala Phe Leu Asn Gly Pro
225                 230                 235                 240

Leu Met Asp Tyr Ser Val Asn Arg Lys Lys Ala Asp Ser Ala Ser Thr
                245                 250                 255

Ser Leu Leu Ser Pro Tyr Leu His Phe Gly Glu Leu Ser Val Arg Lys
            260                 265                 270

Val Phe His Gln Val Arg Met Lys Gln Leu Met Trp Ser Asn Glu Gly
            275                 280                 285

Asn His Ala Gly Asp Glu Ser Cys Val Leu Phe Leu Arg Ser Ile Gly
            290                 295                 300

Leu Arg Glu Tyr Ser Arg Tyr Leu Thr Phe Asn His Pro Cys Ser Leu
305                 310                 315                 320

Glu Lys Pro Leu Leu Ala His Leu Arg Phe Phe Pro Trp Val Val Asp
                325                 330                 335

Glu Val Tyr Phe Lys Val Trp Arg Gln Gly Arg Thr Gly Tyr Pro Leu
            340                 345                 350

Val Asp Ala Gly Met Arg Glu Leu Trp Ala Thr Gly Trp Leu His Asp
            355                 360                 365

Arg Ile Arg Val Val Ser Ser Phe Phe Val Lys Val Leu Gln Leu
370                 375                 380

Pro Trp Arg Trp Gly Met Lys Tyr Phe Trp Asp Thr Leu Leu Asp Ala
385                 390                 395                 400

Asp Leu Glu Ser Asp Ala Leu Gly Trp Gln Tyr Ile Ser Gly Ser Leu
                405                 410                 415

Pro Asp Gly Arg Glu Leu Asp Arg Ile Asp Asn Pro Gln Leu Glu Gly
            420                 425                 430

Tyr Lys Phe Asp Pro His Gly Glu Tyr Val Arg Arg Trp Leu Pro Glu
            435                 440                 445

Leu Ala Arg Leu Pro Thr Glu Trp Ile His His Pro Trp Asp Ala Pro
450                 455                 460

Glu Ser Val Leu Gln Ala Ala Gly Ile Glu Leu Gly Ser Asn Tyr Pro
465                 470                 475                 480

Leu Pro Ile Val Glu Leu Asp Ala Ala Lys Thr Arg Leu Gln Asp Ala
                485                 490                 495

Leu Ser Glu Met Trp Glu Leu Glu Ala Ala Ser Arg Ala Ala Met Glu
            500                 505                 510

Asn Gly Met Glu Glu Gly Leu Gly Asp Ser Ser Asp Val Pro Pro Ile
            515                 520                 525
```

```
Ala Phe Pro Pro Glu Leu Gln Met Glu Val Asp Arg Ala Pro Ala Gln
    530                 535                 540

Pro Thr Val His Gly Pro Thr Thr Ala Gly Arg Arg Glu Asp Gln
545                 550                 555                 560

Met Val Pro Ser Met Thr Ser Ser Leu Val Arg Ala Glu Thr Glu Leu
                565                 570                 575

Ser Ala Asp Phe Asp Asn Ser Met Asp Ser Arg Pro Glu Val Pro Ser
                580                 585                 590

Gln Val Leu Phe Gln Pro Arg Met Glu Arg Glu Thr Val Asp Gly
                595                 600                 605

Gly Gly Gly Gly Met Val Gly Arg Ser Asn Gly Gly His Gln
610                 615                 620

Gly Gln His Gln Gln Gln His Asn Phe Gln Thr Thr Ile His Arg
625                 630                 635                 640

Ala Arg Gly Val Ala Pro Ser Thr Ser Glu Ala Ser Ser Asn Trp Thr
                645                 650                 655

Gly Arg Glu Gly Gly Val Val Pro Val Trp Ser Pro Ala Ala Ser
                660                 665                 670

Gly Pro Ser Asp His Tyr Ala Ala Asp Glu Ala Asp Ile Thr Ser Arg
                675                 680                 685

Ser Tyr Leu Asp Arg His Pro Gln Ser His Thr Leu Met Asn Trp Ser
690                 695                 700

Gln Leu Ser Gln Ser Leu Thr Thr Gly Trp Glu Val Glu Asn
705                 710                 715

<210> SEQ ID NO 48
<211> LENGTH: 690
<212> TYPE: PRT
<213> ORGANISM: Sorghum bicolor

<400> SEQUENCE: 48

Met Ser Ala Ser Ser Ser Leu Cys Gly Gly Asp Pro Ala Met Arg
1               5                   10                  15

Ser Val Val Trp Phe Arg Arg Asp Leu Arg Val Glu Asp Asn Pro Ala
                20                  25                  30

Leu Ala Ala Ala Arg Ala Gly Gly Glu Val Val Pro Ala Tyr Val
            35                  40                  45

Trp Ser Pro Glu Glu Glu Gly Pro Tyr Tyr Pro Gly Arg Val Ser Arg
    50                  55                  60

Trp Trp Ile Ser Gln Ser Leu Lys Arg Leu Asp Ala Ser Leu Arg Arg
65                  70                  75                  80

Leu Gly Ala Gly Lys Leu Val Thr Arg Arg Ser Ala Asp Ala Val Val
                85                  90                  95

Ala Leu Leu Gln Leu Val Arg Asp Thr Gly Ala Thr His Val Tyr Phe
                100                 105                 110

Asn His Leu Tyr Asp Pro Ile Ser Leu Val Arg Asp His Arg Leu Lys
            115                 120                 125

Glu Met Leu Ala Ala Glu Gly Ile Val Val Gln Ser Phe Asn Ala Asp
130                 135                 140

Leu Leu Tyr Glu Pro Trp Glu Val Val Asp Asp Glu Gly Gln Pro Phe
145                 150                 155                 160

Thr Met Phe Thr Ala Phe Trp Asn Arg Cys Leu Ser Met Gln Tyr Asp
                165                 170                 175

Pro Pro Ala Pro Leu Leu Pro Pro Lys Lys Ile Asn Ser Gly Asp Leu
```

```
            180                 185                 190
Ser Met Cys Pro Ser Glu Asp Leu Ile Phe Glu Asp Ser Glu Arg
            195                 200                 205
Gly Ser Asn Ala Leu Leu Ala Arg Ala Trp Thr Pro Gly Trp Gln Asn
    210                 215                 220
Ala Asp Lys Ala Leu Thr Ala Phe Leu Asn Gly Pro Leu Ala Asp Tyr
225                 230                  235                 240
Ser Val Asn Arg Lys Lys Ala Asp Ser Ala Ser Thr Ser Leu Leu Ser
                245                 250                 255
Pro His Leu His Phe Gly Glu Leu Ser Val Arg Lys Val Phe His Leu
            260                 265                 270
Val Arg Met Lys Gln Leu Val Trp Ser Asn Glu Gly Asn His Ala Ala
            275                 280                 285
Glu Glu Ser Cys Thr Leu Phe Leu Arg Ser Ile Gly Leu Arg Glu Tyr
            290                 295                 300
Ser Arg Tyr Leu Ser Phe Asn His Pro Ser Ser His Glu Arg Pro Leu
305                 310                 315                 320
Leu Ala His Leu Arg Phe Phe Pro Trp Val Val Asn Glu Ser Tyr Phe
                325                 330                 335
Lys Ile Trp Arg Gln Gly Arg Thr Gly Tyr Pro Leu Val Asp Ala Gly
            340                 345                 350
Met Arg Glu Leu Trp Ala Thr Gly Trp Leu His Asp Arg Ile Arg Val
            355                 360                 365
Val Val Ser Ser Phe Phe Val Lys Val Leu Gln Leu Pro Trp Arg Trp
370                 375                 380
Gly Met Lys Tyr Phe Trp Asp Thr Leu Leu Asp Ala Asp Leu Glu Ser
385                 390                 395                 400
Asp Ala Leu Gly Trp Gln Tyr Ile Thr Gly Ser Leu Pro Asp Ser Arg
                405                 410                 415
Glu Leu Asp Arg Ile Asp Asn Pro Gln Phe Glu Gly Tyr Lys Phe Asp
            420                 425                 430
Pro His Gly Glu Tyr Val Arg Arg Trp Ile Pro Glu Leu Val Arg Leu
            435                 440                 445
Pro Thr Glu Trp Ile His His Pro Trp Asp Ala Pro Val Ser Val Leu
450                 455                 460
Gln Ala Ala Gly Ile Glu Leu Gly Ser Asn Tyr Pro Leu Pro Ile Val
465                 470                 475                 480
Glu Leu Asp Ala Ala Lys Ala Arg Leu Gln Glu Ala Leu Ser Glu Met
                485                 490                 495
Trp Gln Leu Glu Ala Ala Ser Arg Ala Thr Met Asn Asn Gly Met Glu
            500                 505                 510
Glu Gly Leu Gly Asp Ser Ser Glu Val Pro Phe Pro Glu Glu Leu Gln
            515                 520                 525
Met Glu Val Asp Arg Ala Thr Ala Asn Val Val Met Thr Val Arg Arg
            530                 535                 540
Arg Glu Asp Gln Met Val Pro Thr Met Thr Ser Ser Leu Asn Arg Ala
545                 550                 555                 560
Glu Thr Glu Val Ser Ala Asp Leu Gly Asn Ser Glu Asp Thr Arg Ala
                565                 570                 575
Gln Val Pro Phe His Ala His Phe His Pro Arg Val Glu Arg Glu Asp
            580                 585                 590
Met Ile Gln Asn Thr Glu Gly Pro Ala Leu Arg Ile Asn Gly Thr His
            595                 600                 605
```

```
Gln His Asn Ile Phe Gln Gln Pro Gln Asn His Arg Arg Glu Ala Leu
            610                 615                 620

Ala Pro Ser Val Ser Glu Ala Ser Ser Trp Thr Gly Arg Glu Gly
625                 630                 635                 640

Ala Val Val Pro Val Trp Ser Pro Pro Ala Ala Ser Gly His Ser Glu
                    645                 650                 655

Thr Phe Ala Ala Asp Glu Ala Asp Val Ser Ser Arg Ser Tyr Leu Asp
            660                 665                 670

Arg His Pro Arg Ser Tyr Arg Leu Met Asn Trp Ser Gln Leu Ser Gln
            675                 680                 685

Ser Leu
    690

<210> SEQ ID NO 49
<211> LENGTH: 681
<212> TYPE: PRT
<213> ORGANISM: Arabidopsis thaliana

<400> SEQUENCE: 49

Met Ser Gly Ser Val Ser Gly Cys Gly Ser Gly Gly Cys Ser Ile Val
1               5                   10                  15

Trp Phe Arg Arg Asp Leu Arg Val Glu Asp Asn Pro Ala Leu Ala Ala
                20                  25                  30

Ala Val Arg Ala Gly Pro Val Ile Ala Leu Phe Val Trp Ala Pro Glu
            35                  40                  45

Glu Glu Gly His Tyr His Pro Gly Arg Val Ser Arg Trp Trp Leu Lys
50                  55                  60

Asn Ser Leu Ala Gln Leu Asp Ser Ser Leu Arg Ser Leu Gly Thr Cys
65                  70                  75                  80

Leu Ile Thr Lys Arg Ser Thr Asp Ser Val Ala Ser Leu Leu Asp Val
                85                  90                  95

Val Lys Ser Thr Gly Ala Ser Gln Ile Phe Phe Asn His Leu Tyr Asp
            100                 105                 110

Pro Leu Ser Leu Val Arg Asp His Arg Ala Lys Asp Val Leu Thr Ala
            115                 120                 125

Gln Gly Ile Ala Val Arg Ser Phe Asn Ala Asp Leu Leu Tyr Glu Pro
130                 135                 140

Trp Glu Val Thr Asp Glu Leu Gly Arg Pro Phe Ser Met Phe Ala Ala
145                 150                 155                 160

Phe Trp Glu Arg Cys Leu Ser Met Pro Tyr Asp Pro Glu Ser Pro Leu
                165                 170                 175

Leu Pro Pro Lys Lys Ile Ile Ser Gly Asp Val Ser Lys Cys Val Ala
            180                 185                 190

Asp Pro Leu Val Phe Glu Asp Ser Glu Lys Gly Ser Asn Ala Leu
            195                 200                 205

Leu Ala Arg Ala Trp Ser Pro Gly Trp Ser Asn Gly Asp Lys Ala Leu
            210                 215                 220

Thr Thr Phe Ile Asn Gly Pro Leu Leu Glu Tyr Ser Lys Asn Arg Arg
225                 230                 235                 240

Lys Ala Asp Ser Ala Thr Thr Ser Phe Leu Ser Pro His Leu His Phe
                245                 250                 255

Gly Glu Val Ser Val Arg Lys Val Phe His Leu Val Arg Ile Lys Gln
            260                 265                 270

Val Ala Trp Ala Asn Glu Gly Asn Glu Ala Gly Glu Glu Ser Val Asn
```

```
                275                 280                 285
Leu Phe Leu Lys Ser Ile Gly Leu Arg Glu Tyr Ser Arg Tyr Ile Ser
    290                 295                 300

Phe Asn His Pro Tyr Ser His Glu Arg Pro Leu Leu Gly His Leu Lys
305                 310                 315                 320

Phe Phe Pro Trp Ala Val Asp Glu Asn Tyr Phe Lys Ala Trp Arg Gln
                325                 330                 335

Gly Arg Thr Gly Tyr Pro Leu Val Asp Ala Gly Met Arg Glu Leu Trp
            340                 345                 350

Ala Thr Gly Trp Leu His Asp Arg Ile Arg Val Val Ser Ser Phe
        355                 360                 365

Phe Val Lys Val Leu Gln Leu Pro Trp Arg Trp Gly Met Lys Tyr Phe
    370                 375                 380

Trp Asp Thr Leu Leu Asp Ala Asp Leu Glu Ser Asp Ala Leu Gly Trp
385                 390                 395                 400

Gln Tyr Ile Thr Gly Thr Leu Pro Asp Ser Arg Glu Phe Asp Arg Ile
                405                 410                 415

Asp Asn Pro Gln Phe Glu Gly Tyr Lys Phe Asp Pro Asn Gly Glu Tyr
            420                 425                 430

Val Arg Arg Trp Leu Pro Glu Leu Ser Arg Leu Pro Thr Asp Trp Ile
        435                 440                 445

His His Pro Trp Asn Ala Pro Glu Ser Val Leu Gln Ala Ala Gly Ile
    450                 455                 460

Glu Leu Gly Ser Asn Tyr Pro Leu Pro Ile Val Gly Leu Asp Glu Ala
465                 470                 475                 480

Lys Ala Arg Leu His Glu Ala Leu Ser Gln Met Trp Gln Leu Glu Ala
                485                 490                 495

Ala Ser Arg Ala Ala Ile Glu Asn Gly Ser Glu Glu Gly Leu Gly Asp
            500                 505                 510

Ser Ala Glu Val Glu Glu Ala Pro Ile Glu Phe Pro Arg Asp Ile Thr
        515                 520                 525

Met Glu Glu Thr Glu Pro Thr Arg Leu Asn Pro Asn Arg Arg Tyr Glu
    530                 535                 540

Asp Gln Met Val Pro Ser Ile Thr Ser Ser Leu Ile Arg Pro Glu Glu
545                 550                 555                 560

Asp Glu Glu Ser Ser Leu Asn Leu Arg Asn Ser Val Gly Asp Ser Arg
                565                 570                 575

Ala Glu Val Pro Arg Asn Met Val Asn Thr Asn Gln Ala Gln Gln Arg
            580                 585                 590

Arg Ala Glu Pro Ala Ser Asn Gln Val Thr Ala Met Ile Pro Glu Phe
        595                 600                 605

Asn Ile Arg Ile Val Ala Glu Ser Thr Glu Asp Ser Thr Ala Glu Ser
    610                 615                 620

Ser Ser Ser Gly Arg Arg Glu Arg Ser Gly Ile Val Pro Glu Trp
625                 630                 635                 640

Ser Pro Gly Tyr Ser Glu Gln Phe Pro Ser Glu Glu Asn Gly Ile Gly
                645                 650                 655

Gly Gly Ser Thr Thr Ser Ser Tyr Leu Gln Asn His His Glu Ile Leu
            660                 665                 670

Asn Trp Arg Arg Leu Ser Gln Thr Gly
        675                 680

<210> SEQ ID NO 50
```

<211> LENGTH: 679
<212> TYPE: PRT
<213> ORGANISM: Lycopersicon esculentum

<400> SEQUENCE: 50

```
Met Ser Gly Gly Gly Cys Ser Ile Val Trp Phe Arg Arg Asp Leu Arg
1               5                   10                  15

Val Glu Asp Asn Pro Ala Leu Ala Ala Gly Val Arg Ala Gly Ala Val
            20                  25                  30

Ile Ala Val Phe Ile Tyr Ala Pro Glu Glu Gly His Tyr Tyr Pro
        35                  40                  45

Gly Arg Val Ser Arg Trp Trp Leu Lys Gln Ser Leu Ala His Leu Asp
    50                  55                  60

Ser Ser Leu Lys Ser Leu Gly Thr Ser Leu Ile Thr Lys Arg Ser Thr
65                  70                  75                  80

Asp Ser Ile Ser Ser Leu Leu Glu Val Val Lys Ser Thr Gly Ala Thr
                85                  90                  95

Gln Leu Phe Phe Asn His Leu Tyr Asp Pro Ile Ser Leu Val Arg Asp
            100                 105                 110

His Arg Thr Lys Glu Ile Leu Thr Ala Gln Gly Ile Ser Val Arg Ser
        115                 120                 125

Phe Asn Ala Asp Leu Leu Tyr Glu Pro Trp Glu Val Asn Asp Asp Glu
    130                 135                 140

Gly Arg Pro Phe Thr Thr Phe Ser Ala Phe Trp Glu Lys Cys Leu Ser
145                 150                 155                 160

Met Pro Tyr Asp Pro Glu Ala Pro Leu Leu Pro Pro Lys Arg Ile Ile
                165                 170                 175

Ser Gly Asp Ala Ser Arg Cys Pro Ser Asp Asn Leu Val Phe Glu Asp
            180                 185                 190

Glu Ser Glu Lys Gly Ser Asn Ala Leu Leu Ala Arg Ala Trp Ser Pro
        195                 200                 205

Gly Trp Ser Asn Ala Asp Lys Ala Leu Thr Thr Phe Val Asn Gly Pro
    210                 215                 220

Leu Leu Glu Tyr Ser Gln Asn Arg Arg Lys Ala Asp Ser Ala Thr Thr
225                 230                 235                 240

Ser Phe Leu Ser Pro His Leu His Phe Gly Glu Val Ser Val Arg Lys
                245                 250                 255

Val Phe His Phe Val Arg Ile Lys Gln Val Leu Trp Ala Asn Glu Gly
            260                 265                 270

Asn Lys Ala Gly Glu Glu Ser Val Asn Leu Phe Leu Lys Ser Ile Gly
        275                 280                 285

Leu Arg Glu Tyr Ser Arg Tyr Met Ser Phe Asn His Pro Tyr Ser His
    290                 295                 300

Glu Arg Pro Leu Leu Gly His Leu Arg Tyr Phe Pro Trp Val Val Asp
305                 310                 315                 320

Glu Gly Tyr Phe Lys Ala Trp Arg Gln Gly Arg Thr Gly Tyr Pro Leu
                325                 330                 335

Val Asp Ala Gly Met Arg Glu Leu Trp Ala Thr Gly Trp Leu His Asp
            340                 345                 350

Arg Ile Arg Val Val Ser Phe Phe Val Lys Val Leu Gln Leu
        355                 360                 365

Pro Trp Arg Trp Gly Met Lys Tyr Phe Trp Asp Thr Leu Leu Asp Ala
    370                 375                 380

Asp Leu Glu Ser Asp Ala Leu Gly Trp Gln Tyr Ile Ser Gly Thr Leu
```

```
                385                 390                 395                 400
        Pro Asp Gly Arg Glu Leu Asp Arg Ile Asp Asn Pro Gln Phe Val Gly
                        405                 410                 415

Tyr Lys Cys Asp Pro His Gly Glu Tyr Val Arg Arg Trp Leu Pro Glu
                        420                 425                 430

Leu Ala Arg Leu Pro Thr Glu Trp Ile His Pro Trp Asn Ala Pro
                        435                 440                 445

Glu Ser Val Leu Glu Ala Ala Gly Ile Glu Leu Gly Ser Asn Tyr Pro
                        450                 455                 460

Leu Pro Ile Val Glu Ile Asp Ser Ala Lys Val Arg Leu Glu Gln Ala
        465                 470                 475                 480

Leu Ser Gln Met Trp Gln Asn Asp Ala Ala Arg Ala Ala Ile Glu
                        485                 490                 495

Asn Gly Met Glu Glu Gly His Gly Asp Ser Ala Asp Ser Pro Ile Ala
                        500                 505                 510

Phe Pro Gln Ala Met His Met Glu Met Asp His Glu Pro Val Arg Asn
                        515                 520                 525

Asn Pro Val Ile Val Thr Val Arg Arg Tyr Glu Asp Gln Met Val Pro
                530                 535                 540

Ser Met Thr Ser Ser Leu Phe Arg Ala Glu Asp Glu Asn Ser Val
        545                 550                 555                 560

Asp Ile Arg Asn Ser Val Val Glu Ser Arg Ala Glu Val Pro Thr Asp
                        565                 570                 575

Ile Asn Val Ala Glu Val His Arg Arg Asp Thr Arg Asp Gln Ala Val
                        580                 585                 590

Met Gln Thr Ala Arg Thr Asn Ala Thr Pro His Phe Asn Phe Ala Val
                        595                 600                 605

Gly Arg Arg Asn Ser Glu Asp Ser Thr Ala Glu Ser Ser Ser Ser Thr
                        610                 615                 620

Arg Glu Arg Asp Gly Gly Val Val Pro Thr Trp Ser Pro Ser Ser Ser
        625                 630                 635                 640

Asn Tyr Ser Asp Gln Tyr Val Gly Asp Asp Asn Gly Ile Gly Thr Ser
                        645                 650                 655

Ser Ser Tyr Leu Gln Arg His Pro Gln Ser His Gln Leu Met Asn Trp
                        660                 665                 670

Gln Arg Leu Ser Gln Thr Gly
                        675

<210> SEQ ID NO 51
<211> LENGTH: 681
<212> TYPE: PRT
<213> ORGANISM: Glycine max

<400> SEQUENCE: 51

Met Ser Gly Gly Gly Cys Ser Ile Val Trp Phe Arg Arg Asp Leu Arg
        1               5                   10                  15

Val Glu Asp Asn Pro Ala Leu Ala Ala Gly Val Arg Ala Gly Ala Val
                        20                  25                  30

Ile Ser Val Phe Ile Trp Ala Pro Glu Glu Glu Gly Gln Tyr Tyr Pro
                        35                  40                  45

Gly Arg Val Ser Arg Trp Trp Leu Lys Gln Ser Leu Ala His Leu Asp
                        50                  55                  60

Ser Ser Leu Arg Asn Leu Gly Ser Pro Leu Ile Thr Lys Arg Ser Thr
        65                  70                  75                  80
```

```
Asn Ser Ile Ser Ser Leu Leu Glu Val Val Lys Ser Thr Gly Ala Thr
                85                  90                  95

Gln Leu Phe Phe Asn His Leu Tyr Asp Pro Leu Ser Leu Val Arg Asp
            100                 105                 110

His Arg Ala Lys Glu Val Leu Thr Ala Gln Gly Ile Thr Val Arg Ser
            115                 120                 125

Phe Asn Ser Asp Leu Leu Tyr Glu Pro Trp Asp Val Asn Asp Ala His
        130                 135                 140

Gly Gln Pro Phe Thr Thr Phe Ser Ala Phe Trp Glu Arg Cys Leu Ser
145                 150                 155                 160

Met Pro Tyr Asp Pro Gln Ala Pro Leu Leu Pro Pro Lys Arg Ile Ile
                165                 170                 175

Pro Gly Asp Val Pro Arg Cys Pro Ser Asp Thr Leu Val Phe Glu Asp
            180                 185                 190

Glu Leu Glu Lys Ala Ser Asn Ala Leu Leu Ala Arg Ala Trp Ser Pro
            195                 200                 205

Gly Trp Ser Asn Ala Asp Lys Ala Leu Thr Ala Phe Val Asn Gly Ala
        210                 215                 220

Leu Ile Glu Tyr Ser Lys Asn Arg Arg Lys Ala Asp Ser Ala Thr Thr
225                 230                 235                 240

Ser Phe Leu Ser Pro His Leu His Phe Gly Glu Val Ser Val Lys Lys
                245                 250                 255

Val Phe His Leu Val Arg Ile Lys Gln Val Phe Trp Ala Asn Glu Gly
            260                 265                 270

Asn Lys Ala Gly Glu Glu Ser Val Asn Leu Phe Leu Lys Ser Ile Gly
        275                 280                 285

Leu Arg Glu Tyr Ser Arg Tyr Ile Ser Phe Asn His Pro Tyr Ser His
290                 295                 300

Glu Arg Pro Leu Leu Ala His Leu Lys Phe Phe Pro Trp Val Val Asn
305                 310                 315                 320

Glu Gly Tyr Phe Lys Ala Trp Arg Gln Gly Arg Thr Gly Tyr Pro Leu
                325                 330                 335

Val Asp Ala Gly Met Arg Glu Leu Trp Ala Thr Gly Trp Leu His Asp
            340                 345                 350

Arg Ile Arg Val Val Val Ser Ser Phe Phe Val Lys Val Leu Gln Leu
        355                 360                 365

Pro Trp Arg Trp Gly Met Lys Tyr Phe Trp Asp Thr Leu Leu Asp Ala
        370                 375                 380

Asp Leu Glu Ser Asp Ala Leu Gly Trp Gln Tyr Ile Ser Gly Thr Leu
385                 390                 395                 400

Pro Asp Gly Arg Glu Leu Asp Arg Ile Asp Asn Pro Gln Phe Glu Gly
                405                 410                 415

Tyr Lys Cys Asp Pro Asn Gly Glu Tyr Val Arg Arg Trp Leu Pro Glu
            420                 425                 430

Leu Ala Arg Leu Pro Thr Glu Trp Ile His His Pro Trp Asn Ala Pro
        435                 440                 445

Glu Ser Val Leu Gln Ala Ala Gly Ile Glu Leu Gly Ser Asn Tyr Pro
450                 455                 460

Leu Pro Ile Val Gly Ile Asp Ala Ala Glu Val Arg Leu Gln Glu Ala
465                 470                 475                 480

Leu Ile Gln Met Trp Gln Gln Glu Ala Ala Ser Arg Ala Ala Met Glu
                485                 490                 495

Asn Gly Thr Glu Glu Gly Leu Gly Asp Ser Ala Glu Ser Ala Pro Ile
```

```
                    500                 505                 510
Ala Phe Pro Gln Asp Ile Gln Met Glu Glu Arg Pro Glu Pro Val Arg
                515                 520                 525

Asn Asn Leu Pro His Gly Thr Arg Arg Tyr Gln Asp Gln Met Val Pro
            530                 535                 540

Ser Ile Thr Ser Ser His Val Arg Val Glu Glu Glu Thr Ser Ser
545                 550                 555                 560

Asp Leu Arg Asn Ser Ala Ala Asp Ser Arg Ala Glu Val Pro Ile Asn
                565                 570                 575

Val Thr Thr Gln Gln Ile Ala Arg Glu Thr Val Asn Gln Gly Val Leu
            580                 585                 590

Leu Asn Ala Asn Arg Asn Thr Arg Val Gln Asn Asn Ala Thr Thr Trp
        595                 600                 605

Leu Arg Asn Ala Ala Glu Asp Ser Thr Ala Glu Ser Ser Ser Ser Thr
    610                 615                 620

Arg Arg Glu Arg Asp Gly Gly Val Val Pro Val Trp Ser Pro Pro Ala
625                 630                 635                 640

Ser Asn Phe Ser Glu Gln Phe Val Asp Asp Glu Asn Gly Ile Gly Ala
                645                 650                 655

Gly Ser Ser Tyr Leu Gln Arg Gln His Pro Gln Ser His Gln Leu Met
            660                 665                 670

Asn Trp Thr Arg Leu Pro Gln Thr Gly
        675                 680

<210> SEQ ID NO 52
<211> LENGTH: 727
<212> TYPE: PRT
<213> ORGANISM: Physcomitrella patens

<400> SEQUENCE: 52

Met Ala Ala Cys Thr Ile Val Trp Phe Arg Arg Asp Leu Arg Leu Glu
1               5                   10                  15

Asp Asn Pro Ala Leu Ile Ala Ala Arg Ala Gly Thr Val Val Pro
                20                  25                  30

Val Phe Val Trp Ser Pro Ala Glu Asp Gly Gln Phe His Pro Gly Arg
            35                  40                  45

Val Ser Arg Trp Trp Leu Lys Gln Ser Leu Thr His Leu Glu Leu Ser
        50                  55                  60

Leu Lys Lys Leu Gly Ser Pro Leu Ile Leu Arg Lys Ser Pro Asp Thr
65                  70                  75                  80

Leu Ser Val Leu Leu Glu Ile Ala Glu Ala Thr Gly Ala Thr Gln Val
                85                  90                  95

Phe Tyr Asn His Leu Tyr Asp Pro Val Ser Leu Val Arg Asp His Arg
                100                 105                 110

Val Lys Gln Gly Leu Ser Gln Arg Gly Ile Val Val His Thr Phe Asn
            115                 120                 125

Gly Asp Leu Leu Tyr Glu Pro Trp Glu Val Tyr Asp Glu Glu Gly Gln
        130                 135                 140

Ala Phe Thr Val Tyr Glu Ala Phe Trp Lys Lys Cys Met Ser Met Pro
145                 150                 155                 160

Phe Glu Pro Glu Ala Pro Leu Leu Pro Pro Arg Arg Leu Thr Gly Pro
                165                 170                 175

Ile Gly Lys Ile Val Gly Cys Asn Ala Glu Glu Leu Gly Leu Glu Asp
            180                 185                 190
```

-continued

```
Glu Phe Glu Lys Ser Ser Asn Ala Leu Leu Ala Arg Ala Trp Cys Pro
            195                 200                 205

Gly Trp Gly Phe Ala Asn Lys Ser Leu Asp Ser Phe Leu Arg Ser Pro
    210                 215                 220

Leu Ile Asp Tyr Ala Arg Asp Arg Gln Lys Ala Asp Gly Ala Ser Gly
225                 230                 235                 240

Thr Pro Thr Ser Leu Leu Ser Pro His Leu His Phe Gly Glu Leu Ser
                245                 250                 255

Val Arg Lys Ile Phe His Glu Val Arg Lys Arg Gln Ile Thr Trp Ala
            260                 265                 270

Arg Glu Gly Asn Ala Gly Gly Glu Ala Ser Val Asn Met Phe Leu Arg
    275                 280                 285

Ala Leu Gly Phe Arg Glu Tyr Ser Arg Tyr Leu Ser Phe His Phe Pro
290                 295                 300

Phe Thr His Glu Arg Ser Leu Leu Ala Asn Leu Lys Ser Phe Pro Trp
305                 310                 315                 320

Arg Ala Asp Glu Gly Tyr Phe Lys Ala Trp Arg Gln Gly Arg Thr Gly
                325                 330                 335

Tyr Pro Leu Val Asp Ala Gly Met Arg Glu Leu Trp Ala Thr Gly Trp
            340                 345                 350

Ala His Asn Arg Ile Arg Val Val Ala Ser Phe Ser Val Lys Phe
    355                 360                 365

Leu Gln Leu Pro Trp Arg Trp Gly Met Lys Tyr Phe Trp Asp Val Leu
            370                 375                 380

Leu Asp Ala Asp Leu Glu Cys Asp Val Leu Gly Trp Gln Tyr Ile Ser
385                 390                 395                 400

Gly Ser Leu Pro Asp Gly His Glu Leu Asp Arg Ile Glu Asn Pro Glu
                405                 410                 415

Val Glu Gly Tyr Arg Phe Asp Pro Asp Gly Asp Tyr Val Arg Arg Trp
            420                 425                 430

Ile Pro Glu Leu Ala Arg Leu Pro Asn Glu Trp Val His His Pro Trp
            435                 440                 445

Asp Ala Pro Pro Ser Ala Leu Arg Ala Ala Gly Val Glu Leu Gly Thr
450                 455                 460

Asn Tyr Pro Arg Pro Ile Val Glu Ile Gly Ala Ala Arg Glu Arg Leu
465                 470                 475                 480

Gln Ala Ser Leu Ala Glu Met Trp Glu Arg Asp Ala Ala Met Lys Ala
                485                 490                 495

Ala Leu Ala Asn Gly Leu Glu Glu Gly Leu Gly Glu Thr Val Glu Val
            500                 505                 510

Ala Gly Thr Gly Gly Pro Glu His Glu Arg Met Asp Val Pro Arg Val
    515                 520                 525

Met Val His Met Gln Arg Asp Ala Asp Met Ser Cys Asn Ser Ser Arg
530                 535                 540

Arg Asp Gln Leu Val Pro Glu Ile Val Pro Asn Gln Phe His Ile Arg
545                 550                 555                 560

Ala His Glu Ser Ile Met Asn Arg Ser Ala Ala Met Val Glu Asp Gly
                565                 570                 575

Glu Glu Ala Gly Arg Ala Val Pro Met Val Phe Ala Ser Val Arg
            580                 585                 590

Arg Gly Met Gly Gly Asn Tyr Gly Gly His His Val Glu Gly Asn Gly
    595                 600                 605

Gly Glu Val Ala Gln Ala Ser Ala Pro Ile Gln Trp Pro Thr Val Thr
```

```
                    610                 615                 620
Ala Val Asp Tyr Glu Leu Asp Ser Thr Ala Glu Ser Ala Ser Val Thr
625                 630                 635                 640

Gly Arg Gly Gly Ser Glu Gly Thr Val Pro Val Trp Ser Gln Ser
                645                 650                 655

Val Ser Ala Arg Thr Pro Ile Gln Val Arg Glu Gly Leu Val Pro Glu
                660                 665                 670

Val Arg Arg Gly Pro Gly Leu Ser Arg Arg Gln Leu Gln Ala Ser Val
                675                 680                 685

Gln Arg Val Asn Leu Glu Gly Met Thr Ser Asn Lys Gln Ala Glu Glu
                690                 695                 700

Glu Asp Phe Tyr Val Pro Lys Leu Val Lys Trp Thr Gln Pro Arg Lys
705                 710                 715                 720

Arg Arg Val Lys Gln Asp Gly
                725

<210> SEQ ID NO 53
<211> LENGTH: 654
<212> TYPE: PRT
<213> ORGANISM: Sorghum bicolor

<400> SEQUENCE: 53

Met Ala Gly Ser Gly Lys Thr Val Val Trp Phe Arg Arg Asp Leu Arg
1               5                   10                  15

Ile His Asp Asn Pro Ala Leu Ala Ala Ala Lys Glu Gly Ser Val
                20                  25                  30

Leu Pro Leu Phe Ile Trp Cys Pro Ala Asp Tyr Glu Gln Tyr Tyr Pro
            35                  40                  45

Gly Arg Cys Ser Arg Trp Trp Leu Lys Gln Ser Leu Ala His Leu Gly
    50                  55                  60

Lys Ser Leu Glu Leu Leu Gly Cys Pro Leu Val Leu Ile Arg Ala Glu
65                  70                  75                  80

Asp Ser Thr Leu Ala Thr Leu Glu Cys Val His Cys Ile Ser Ala
                85                  90                  95

Thr Arg Val Val Tyr Asn Arg Leu Tyr Asp Pro Ile Ser Leu Val Leu
                100                 105                 110

Asp Asp Lys Ile Lys Asn Glu Leu Ser Ala His Gly Ile Ser Val Gln
            115                 120                 125

Ser Phe Asn Gly Asp Leu Leu Tyr Glu Pro Trp Asp Val Tyr Asp Glu
    130                 135                 140

Asn Gly Gln Ala Phe Thr Ser Phe Asn Lys Tyr Trp Glu Lys Cys Met
145                 150                 155                 160

Asn Val Pro Ile Glu Ile Ser Gln Tyr Leu Ala Pro Thr Arg Leu Val
                165                 170                 175

Ala Ala Pro Gly Leu Ala Asn Val Arg Cys Cys Ser Ile Asp Asp Leu
                180                 185                 190

Gly Leu Glu Ser Ser Lys Asp Val Glu Ser Ser Asn Ala Leu Leu Ser
            195                 200                 205

Arg Ala Trp Ser Pro Gly Trp Arg Asn Ala Glu Asn Met Leu Glu Glu
    210                 215                 220

Phe Leu Ser Cys Gly Leu Leu Glu Tyr Ser Lys His Gly Met Lys Val
225                 230                 235                 240

Gly Gly Thr Thr Thr Ser Leu Leu Ser Pro Tyr Leu His Phe Gly Glu
                245                 250                 255
```

```
Leu Ser Val Arg Lys Val Tyr Gln Leu Val Thr Met His His Val Lys
            260                 265                 270

Trp Gln Asn Glu Gly Lys Ser Glu Ala Glu Glu Ser Val Arg Leu Phe
        275                 280                 285

Leu Arg Ser Ile Gly Phe Arg Glu Tyr Ser Arg Tyr Leu Cys Phe Asn
    290                 295                 300

Phe Pro Phe Thr His Glu Arg Ser Phe Leu Gly Asn Leu Lys His Tyr
305                 310                 315                 320

Pro Trp Leu Leu Asp Glu Asp Arg Phe Lys Ser Trp Arg Gln Gly Met
            325                 330                 335

Thr Gly Tyr Pro Leu Val Asp Ala Gly Met Arg Glu Leu Trp Ala Thr
        340                 345                 350

Gly Trp Thr His Asn Arg Ile Arg Val Ile Val Ser Phe Ala Val
    355                 360                 365

Lys Cys Leu Gln Ile Pro Trp Ile Trp Gly Met Lys Tyr Phe Trp Asp
    370                 375                 380

Val Leu Leu Asp Ala Asp Leu Glu Ser Asp Ile Leu Gly Trp Gln Tyr
385                 390                 395                 400

Ile Ser Gly Ser Leu Pro Asp Gly His Glu Leu Ser Arg Leu Asp Asn
            405                 410                 415

Pro Glu Val Gln Gly Gln Lys Tyr Asp Pro Asp Gly Glu Tyr Val Arg
        420                 425                 430

Thr Trp Ile Pro Glu Leu Ala Arg Met Pro Thr Glu Trp Ile His Cys
    435                 440                 445

Pro Trp Ser Ala Pro Asn Ser Ile Leu Gln Val Ala Gly Val Glu Leu
450                 455                 460

Gly Phe Asn Tyr Pro Lys Pro Ile Val Glu Leu His Met Ala Arg Glu
465                 470                 475                 480

Cys Leu Asp Asp Ala Ile Ser Thr Met Trp Gln Leu Asp Thr Ala Ala
            485                 490                 495

Lys Leu Ala Ala Leu Asp Gly Glu Val Val Asp Asn Leu Asn Asn
        500                 505                 510

Ile Arg Ser Phe Asp Ile Pro Lys Val Val Lys Lys Lys Leu Ser
    515                 520                 525

Pro Ser Thr Ser Ser Met Asn Lys Arg Val Leu Ser Thr Asn Gly Lys
530                 535                 540

Asn Glu Lys Ser Gln Pro Thr Glu Val Lys Ala Pro Tyr Lys Gln Ile
545                 550                 555                 560

Ile Arg Asp Asp Met Ile Asn Ala Ser Asn Met Asp Asp Thr Gly Ser
            565                 570                 575

Thr Ala Asn Leu Gln Val Thr Arg Lys Arg Ser Arg Ser Asp Ser Ala
        580                 585                 590

Phe Asn Val Pro Ser Ser Ser Ser Leu Val Met Glu Ser Arg Ile
    595                 600                 605

His Asp Asn Asp Ser Cys Ser Val Arg Tyr Ser Gly Tyr Leu Gln Gln
    610                 615                 620

Thr Ala Asp Arg Asp Asp Thr Asp Lys Val Glu Asp Asn Asp Ser Glu
625                 630                 635                 640

Asp Ser Gly Thr Ser Ile Ser Arg Pro Ser Lys Arg Pro Ala
            645                 650

<210> SEQ ID NO 54
<211> LENGTH: 651
<212> TYPE: PRT
```

<213> ORGANISM: Oryza sativa

<400> SEQUENCE: 54

Met Ala Gly Ser Glu Arg Thr Val Val Trp Phe Arg Arg Asp Leu Arg
1               5                   10                  15

Ile Asp Asp Asn Pro Ala Leu Ala Ser Ala Ala Arg Asp Gly Ala Val
            20                  25                  30

Leu Pro Val Phe Ile Trp Cys Pro Ala Asp Glu Gly Gln Phe Tyr Pro
        35                  40                  45

Gly Arg Cys Ser Arg Trp Trp Leu Lys Gln Ser Leu Pro His Leu Ser
    50                  55                  60

Gln Ser Leu Glu Ser Leu Gly Cys Pro Leu Val Leu Ile Arg Ala Glu
65                  70                  75                  80

Ser Thr Leu Glu Ala Leu Leu Arg Cys Ile Asp Ser Val Gly Ala Thr
                85                  90                  95

Arg Leu Val Tyr Asn His Leu Tyr Asp Pro Val Ser Leu Val Arg Asp
            100                 105                 110

Asp Lys Ile Lys Lys Glu Leu Ser Ala Leu Gly Ile Ser Ile Gln Ser
        115                 120                 125

Phe Asn Gly Asp Leu Leu Tyr Glu Pro Trp Glu Ile Tyr Asp Asp Ser
130                 135                 140

Gly Leu Ala Phe Thr Thr Phe Asn Met Tyr Trp Glu Lys Cys Met Glu
145                 150                 155                 160

Leu Pro Ile Asp Ala Ser Pro Ser Leu Ala Pro Trp Lys Leu Val Pro
                165                 170                 175

Val Pro Gly Leu Glu Ser Val Arg Ser Cys Ser Val Asp Asp Leu Gly
            180                 185                 190

Leu Glu Ser Ser Lys Asp Glu Glu Ser Ser Asn Ala Leu Leu Met Arg
        195                 200                 205

Ala Trp Ser Pro Gly Trp Arg Asn Ala Glu Lys Met Leu Glu Glu Phe
210                 215                 220

Val Ser His Gly Leu Leu Glu Tyr Ser Lys His Gly Met Lys Val Glu
225                 230                 235                 240

Gly Ala Thr Thr Ser Leu Leu Ser Pro Tyr Leu His Phe Gly Glu Val
                245                 250                 255

Ser Val Arg Lys Val Tyr Gln Leu Val Arg Met Gln Gln Ile Lys Trp
            260                 265                 270

Glu Asn Glu Gly Thr Ser Glu Ala Glu Glu Ser Ile His Phe Phe Met
        275                 280                 285

Arg Ser Ile Gly Leu Arg Glu Tyr Ser Arg Tyr Leu Cys Phe Asn Phe
290                 295                 300

Pro Phe Thr His Glu Lys Ser Leu Leu Gly Asn Leu Lys His Tyr Pro
305                 310                 315                 320

Trp Lys Val Asp Glu Glu Arg Phe Lys Ser Trp Arg Gln Gly Met Thr
                325                 330                 335

Gly Tyr Pro Leu Val Asp Ala Gly Met Arg Glu Leu Trp Ala Thr Gly
            340                 345                 350

Trp Thr His Asn Arg Ile Arg Val Ile Ser Ser Phe Ala Val Lys
        355                 360                 365

Phe Leu Leu Ile Pro Trp Thr Trp Gly Met Lys Tyr Phe Trp Asp Val
370                 375                 380

Leu Leu Asp Ala Asp Leu Glu Ser Asp Ile Leu Gly Trp Gln Tyr Ile
385                 390                 395                 400

```
Ser Gly Ser Leu Pro Asp Gly His Glu Leu Ser Arg Leu Asp Asn Pro
                405                 410                 415

Glu Val Gln Gly Gln Lys Tyr Asp Pro Asp Gly Val Tyr Val Arg Thr
            420                 425                 430

Trp Ile Pro Glu Leu Ala Arg Met Pro Thr Glu Trp Ile His His Pro
        435                 440                 445

Trp Asp Ala Pro Ser Cys Ile Leu Glu Val Ala Gly Val Glu Leu Gly
    450                 455                 460

Phe Asn Tyr Pro Lys Pro Ile Val Asp Leu His Ile Ala Arg Glu Cys
465                 470                 475                 480

Leu Asp Asp Ser Ile Ser Thr Met Trp Gln Leu Asp Thr Ala Glu Lys
                485                 490                 495

Leu Ala Glu Leu Asp Gly Glu Val Val Glu Asp Asn Leu Ser Asn Ile
            500                 505                 510

Lys Thr Phe Asp Ile Pro Lys Val Val Leu Arg Glu Thr Ser Pro Cys
        515                 520                 525

Ala Leu Pro Ile Asp Gln Arg Val Pro His Ala Ser Ser Lys Asp His
    530                 535                 540

Asn Leu Lys Ser Lys Val Leu Lys Ala Ser Asn Arg Ser Ser Ile Cys
545                 550                 555                 560

Val Asp Met Ile Arg Ser Ser Lys Met Glu Ala Thr Ser Ser Val Ala
                565                 570                 575

Asn Ser Pro Val Ser Arg Lys Arg Ser Phe Cys Glu Thr Ala Phe His
            580                 585                 590

Val Pro Ser Tyr Ser Ser Ser Ala Glu Val His Ser His Ile Gln Asp
        595                 600                 605

His Gly Gly Ser Leu Val Gly Pro Ser Arg Tyr Leu Leu Gln Glu Ala
    610                 615                 620

Gly Arg Asn Tyr Val Asp Glu Val Glu Asp Ser Ser Thr Ala Asp Ser
625                 630                 635                 640

Gly Ser Ser Ile Ser Arg Gln Arg Lys Ala Ala
                645                 650

<210> SEQ ID NO 55
<211> LENGTH: 612
<212> TYPE: PRT
<213> ORGANISM: Arabidopsis thaliana

<400> SEQUENCE: 55

Met Lys Met Asp Lys Lys Thr Ile Val Trp Phe Arg Arg Asp Leu Arg
1               5                   10                  15

Ile Glu Asp Asn Pro Ala Leu Ala Ala Ala His Glu Gly Ser Val
            20                  25                  30

Phe Pro Val Phe Ile Trp Cys Pro Glu Glu Glu Gly Gln Phe Tyr Pro
        35                  40                  45

Gly Arg Ala Ser Arg Trp Trp Met Lys Gln Ser Leu Ala His Leu Ser
    50                  55                  60

Gln Ser Leu Lys Ala Leu Gly Ser Asp Leu Thr Leu Ile Lys Thr His
65                  70                  75                  80

Asn Thr Ile Ser Ala Ile Leu Asp Cys Ile Arg Val Thr Gly Ala Thr
                85                  90                  95

Lys Val Val Phe Asn His Leu Tyr Asp Pro Val Ser Leu Val Arg Asp
            100                 105                 110

His Thr Val Lys Glu Lys Leu Val Glu Arg Gly Ile Ser Val Gln Ser
        115                 120                 125
```

```
Tyr Asn Gly Asp Leu Leu Tyr Glu Pro Trp Glu Ile Tyr Cys Glu Lys
        130                 135                 140

Gly Lys Pro Phe Thr Ser Phe Asn Ser Tyr Trp Lys Lys Cys Leu Asp
145                 150                 155                 160

Met Ser Ile Glu Ser Val Met Leu Pro Pro Trp Arg Leu Met Pro
                165                 170                 175

Ile Thr Ala Ala Ala Glu Ala Ile Trp Ala Cys Ser Ile Glu Glu Leu
                180                 185                 190

Gly Leu Glu Asn Glu Ala Glu Lys Pro Ser Asn Ala Leu Leu Thr Arg
        195                 200                 205

Ala Trp Ser Pro Gly Trp Ser Asn Ala Asp Lys Leu Leu Asn Glu Phe
210                 215                 220

Ile Glu Lys Gln Leu Ile Asp Tyr Ala Lys Asn Ser Lys Lys Val Val
225                 230                 235                 240

Gly Asn Ser Thr Ser Leu Leu Ser Pro Tyr Leu His Phe Gly Glu Ile
                245                 250                 255

Ser Val Arg His Val Phe Gln Cys Ala Arg Met Lys Gln Ile Ile Trp
                260                 265                 270

Ala Arg Asp Lys Asn Ser Glu Gly Glu Glu Ser Ala Asp Leu Phe Leu
        275                 280                 285

Arg Gly Ile Gly Leu Arg Glu Tyr Ser Arg Tyr Ile Cys Phe Asn Phe
290                 295                 300

Pro Phe Thr His Glu Gln Ser Leu Leu Ser His Leu Arg Phe Phe Pro
305                 310                 315                 320

Trp Asp Ala Asp Val Asp Lys Phe Lys Ala Trp Arg Gln Gly Arg Thr
                325                 330                 335

Gly Tyr Pro Leu Val Asp Ala Gly Met Arg Glu Leu Trp Ala Thr Gly
                340                 345                 350

Trp Met His Asn Arg Ile Arg Val Ile Val Ser Ser Phe Ala Val Lys
        355                 360                 365

Phe Leu Leu Leu Pro Trp Lys Trp Gly Met Lys Tyr Phe Trp Asp Thr
370                 375                 380

Leu Leu Asp Ala Asp Leu Glu Cys Asp Ile Leu Gly Trp Gln Tyr Ile
385                 390                 395                 400

Ser Gly Ser Ile Pro Asp Gly His Glu Leu Asp Arg Leu Asp Asn Pro
                405                 410                 415

Ala Leu Gln Gly Ala Lys Tyr Asp Pro Glu Gly Glu Tyr Ile Arg Gln
        420                 425                 430

Trp Leu Pro Glu Leu Ala Arg Leu Pro Thr Glu Trp Ile His His Pro
            435                 440                 445

Trp Asp Ala Pro Leu Thr Val Leu Lys Ala Ser Gly Val Glu Leu Gly
450                 455                 460

Thr Asn Tyr Ala Lys Pro Ile Val Asp Ile Asp Thr Ala Arg Glu Leu
465                 470                 475                 480

Leu Ala Lys Ala Ile Ser Arg Thr Arg Glu Ala Gln Ile Met Ile Gly
                485                 490                 495

Ala Ala Pro Asp Glu Ile Val Ala Asp Ser Phe Glu Ala Leu Gly Ala
                500                 505                 510

Asn Thr Ile Lys Glu Pro Gly Leu Cys Pro Ser Val Ser Ser Asn Asp
        515                 520                 525

Gln Gln Val Pro Ser Ala Val Arg Tyr Asn Gly Ser Lys Arg Val Lys
530                 535                 540
```

```
Pro Glu Glu Glu Glu Arg Asp Met Lys Lys Ser Arg Gly Phe Asp
545                 550                 555                 560

Glu Arg Glu Leu Phe Ser Thr Ala Glu Ser Ser Ser Ser Ser Val
            565                 570                 575

Phe Phe Val Ser Gln Ser Cys Ser Leu Ala Ser Glu Gly Lys Asn Leu
        580                 585                 590

Glu Gly Ile Gln Asp Ser Ser Asp Gln Ile Thr Thr Ser Leu Gly Lys
        595                 600                 605

Asn Gly Cys Lys
    610
```

```
<210> SEQ ID NO 56
<211> LENGTH: 634
<212> TYPE: PRT
<213> ORGANISM: Glycine max

<400> SEQUENCE: 56

Met Gly Ser Asn Arg Thr Ile Val Trp Phe Arg Arg Asp Leu Arg Ile
1               5                   10                  15

Glu Asp Asn Pro Ala Leu Thr Ala Ala Ala Lys Glu Gly Ser Val Leu
            20                  25                  30

Pro Val Tyr Val Trp Cys Pro Lys Glu Glu Gly Gln Phe Tyr Pro Gly
        35                  40                  45

Arg Val Ser Arg Trp Trp Leu Lys Gln Ser Leu Ala His Leu Asp Gln
50                  55                  60

Ser Leu Lys Ser Leu Gly Ser Arg Leu Val Leu Ile Lys Thr His Ser
65                  70                  75                  80

Thr Ala Val Ala Leu Val Glu Cys Val Lys Ala Ile Gln Ala Thr Lys
                85                  90                  95

Val Val Phe Asn His Leu Tyr Asp Pro Val Ser Leu Val Arg Asp His
            100                 105                 110

Asn Ile Lys Glu Lys Leu Val Glu Gln Gly Ile Ser Val Gln Ser Tyr
        115                 120                 125

Asn Gly Asp Leu Leu Tyr Glu Pro Trp Glu Val Asn Ser Glu Ser Gly
130                 135                 140

Arg Ala Phe Thr Thr Phe Asn Ala Phe Trp Lys Lys Cys Leu His Met
145                 150                 155                 160

Gln Met Asp Ile Val Ser Val Pro Pro Trp Gln Leu Ile Pro Ala
                165                 170                 175

Glu Gly Lys Ile Glu Glu Cys Ser Leu Glu Glu Leu Gly Leu Glu Asn
            180                 185                 190

Glu Ser Glu Lys Pro Ser Asn Ala Leu Leu Gly Arg Ala Trp Ser Pro
        195                 200                 205

Gly Trp Arg Asn Ala Asp Lys Ala Leu Arg Glu Phe Val Glu Leu His
210                 215                 220

Leu Leu His Tyr Ser Lys Lys Arg Leu Lys Val Gly Gly Glu Ser Thr
225                 230                 235                 240

Ser Leu Leu Ser Pro Tyr Leu His Phe Gly Glu Leu Ser Ala Arg Lys
                245                 250                 255

Val Phe Gln Val Thr Cys Met Lys Gln Ile Leu Trp Thr Asn Glu Gly
            260                 265                 270

Asn Ser Ala Gly Glu Glu Ser Ala Asn Leu Phe Leu Arg Ala Ile Gly
        275                 280                 285

Leu Arg Glu Tyr Ser Arg Tyr Leu Cys Phe Asn Phe Pro Phe Thr His
290                 295                 300
```

Glu Arg Ala Leu Leu Gly His Leu Lys Phe Phe Pro Trp Asn Pro Asp
305                 310                 315                 320

Pro Asp Ile Phe Lys Thr Trp Arg Gln Gly Arg Thr Gly Phe Pro Leu
                325                 330                 335

Val Asp Ala Gly Met Arg Glu Leu Trp Ala Thr Gly Trp Ile His Asn
            340                 345                 350

Arg Ile Arg Val Ile Val Ser Ser Phe Ala Val Lys Met Leu Leu Leu
        355                 360                 365

Pro Trp Lys Trp Gly Met Lys Tyr Phe Trp Asp Thr Leu Leu Asp Ala
    370                 375                 380

Asp Leu Glu Ser Asp Ile Leu Gly Trp Gln Tyr Ile Ser Gly Gly Leu
385                 390                 395                 400

Pro Asp Gly His Glu Leu Glu Arg Leu Asp Asn Pro Glu Ile Gln Gly
                405                 410                 415

Ala Lys Phe Asp Pro Glu Gly Glu Tyr Val Arg Gln Trp Leu Pro Glu
            420                 425                 430

Leu Ala Arg Met Pro Thr Glu Trp Ile His His Pro Trp Asp Ala Pro
        435                 440                 445

Leu Thr Val Leu Arg Ala Ala Gly Val Glu Leu Gly Gln Asn Tyr Pro
    450                 455                 460

Lys Pro Ile Ile Asp Ile Asp Leu Ala Arg Glu Arg Leu Thr Glu Ala
465                 470                 475                 480

Ile Phe Lys Met Trp Glu Ser Glu Ala Ala Lys Ala Ala Gly Ser
                485                 490                 495

Glu Pro Arg Asp Glu Val Val Asp Asn Ser His Thr Val Glu Asn
            500                 505                 510

Leu Asp Thr Gln Lys Val Val Leu Gly Lys Ala Pro Cys Ala Thr
        515                 520                 525

Ile Ser Ala Asn Asp Gln Lys Val Pro Ala Leu Gln Asp Ser Lys Asn
    530                 535                 540

Glu Pro Pro Thr Arg Lys Arg Pro Lys His Met Ile Glu Glu Gly Gln
545                 550                 555                 560

Asn Gln Asp His Ser Gln Asn His Asn Lys Asp Thr Gly Leu Ser Ser
                565                 570                 575

Ile Asp Gln Asp Ile Cys Ser Thr Ala Asp Ser Ser Ser Cys Lys Lys
            580                 585                 590

Gln Cys Ala Ser Thr Ser Ser Tyr Ser Phe Ser Val Pro Gln Gln Cys
        595                 600                 605

Ser Ser Ser Ser Asn Leu Lys Trp Pro Trp Gln Glu Lys Ile Asp Met
    610                 615                 620

Glu Gln Ser Ser Ser Lys Asp Gly Ala Met
625                 630

<210> SEQ ID NO 57
<211> LENGTH: 525
<212> TYPE: PRT
<213> ORGANISM: Oryza sativa

<400> SEQUENCE: 57

Met Ser Ala Ser Pro Ser Ser Met Ser Gly Ala Gly Ala Gly Glu Ala
1               5                   10                  15

Gly Val Arg Thr Val Val Trp Phe Arg Arg Asp Leu Arg Val Glu Asp
            20                  25                  30

Asn Pro Ala Leu Ala Ala Ala Ala Arg Ala Ala Gly Glu Val Val Pro

```
            35                  40                  45
Val Tyr Val Trp Ala Pro Glu Asp Gly Pro Tyr Tyr Pro Gly Arg
            50                  55                  60
Val Ser Arg Trp Trp Leu Ser Gln Ser Leu Lys His Leu Asp Ala Ser
 65                  70                  75                  80
Leu Arg Arg Leu Gly Ala Ser Arg Leu Val Thr Arg Arg Ser Ala Asp
                85                  90                  95
Ala Val Val Ala Leu Ile Glu Leu Val Arg Ser Ile Gly Ala Thr His
                100                 105                 110
Leu Phe Phe Asn His Leu Tyr Asp Pro Leu Ser Leu Val Arg Asp His
                115                 120                 125
Arg Val Lys Ala Leu Leu Thr Ala Glu Gly Ile Ala Val Gln Ser Phe
                130                 135                 140
Asn Ala Asp Leu Leu Tyr Glu Pro Trp Glu Val Val Asp Asp Gly
145                 150                 155                 160
Cys Pro Phe Thr Met Phe Ala Pro Phe Trp Asp Arg Cys Leu Cys Met
                165                 170                 175
Pro Asp Pro Ala Ala Pro Leu Leu Pro Pro Lys Arg Ile Ala Pro Gly
                180                 185                 190
Glu Leu Pro Ala Arg Arg Cys Pro Ser Asp Glu Leu Val Phe Glu Asp
                195                 200                 205
Glu Ser Glu Arg Gly Ser Asn Ala Leu Leu Ala Arg Ala Trp Ser Pro
                210                 215                 220
Gly Trp Gln Asn Ala Asp Lys Ala Leu Ala Ala Phe Leu Asn Gly Pro
225                 230                 235                 240
Leu Met Asp Tyr Ser Val Asn Arg Lys Lys Ala Asp Ser Ala Ser Thr
                245                 250                 255
Ser Leu Leu Ser Pro Tyr Leu His Phe Gly Glu Leu Ser Val Arg Lys
                260                 265                 270
Val Phe His Gln Val Arg Met Lys Gln Leu Met Trp Ser Asn Glu Gly
                275                 280                 285
Asn His Ala Gly Asp Glu Ser Cys Val Leu Phe Leu Arg Ser Ile Gly
                290                 295                 300
Leu Arg Glu Tyr Ser Arg Tyr Leu Thr Phe Asn His Pro Cys Ser Leu
305                 310                 315                 320
Glu Lys Pro Leu Leu Ala His Leu Arg Phe Phe Pro Trp Val Val Asp
                325                 330                 335
Glu Val Tyr Phe Lys Val Trp Arg Gln Gly Arg Thr Gly Tyr Pro Leu
                340                 345                 350
Val Asp Ala Gly Met Arg Glu Leu Trp Ala Thr Gly Trp Leu His Asp
                355                 360                 365
Arg Ile Arg Val Val Val Ser Ser Phe Phe Val Lys Val Leu Gln Leu
                370                 375                 380
Pro Trp Arg Trp Gly Met Lys Tyr Phe Trp Asp Thr Leu Leu Asp Ala
385                 390                 395                 400
Asp Leu Glu Ser Asp Ala Leu Gly Trp Gln Tyr Ile Ser Gly Ser Leu
                405                 410                 415
Pro Asp Gly Arg Glu Leu Asp Arg Ile Asp Asn Pro Gln Leu Glu Gly
                420                 425                 430
Tyr Lys Phe Asp Pro His Gly Glu Tyr Val Arg Arg Trp Leu Pro Glu
                435                 440                 445
Leu Ala Arg Leu Pro Thr Glu Trp Ile His His Pro Trp Asp Ala Pro
450                 455                 460
```

```
Glu Ser Val Leu Gln Ala Ala Gly Ile Glu Leu Gly Ser Asn Tyr Pro
465                 470                 475                 480

Leu Pro Ile Val Glu Leu Asp Ala Ala Lys Thr Arg Leu Gln Asp Ala
            485                 490                 495

Leu Ser Glu Met Trp Glu Leu Glu Ala Ala Ser Arg Ala Ala Met Glu
                500                 505                 510

Asn Gly Met Glu Glu Gly Leu Gly Asp Ser Ser Asp Val
            515                 520                 525
```

<210> SEQ ID NO 58
<211> LENGTH: 521
<212> TYPE: PRT
<213> ORGANISM: Sorghum bicolor

<400> SEQUENCE: 58

```
Met Ser Ala Ser Ser Ser Leu Cys Gly Gly Asp Pro Ala Met Arg
1               5                   10                  15

Ser Val Val Trp Phe Arg Arg Asp Leu Arg Val Glu Asp Asn Pro Ala
            20                  25                  30

Leu Ala Ala Ala Arg Ala Gly Gly Glu Val Val Pro Ala Tyr Val
            35                  40                  45

Trp Ser Pro Glu Glu Gly Pro Tyr Tyr Pro Gly Arg Val Ser Arg
50                  55                  60

Trp Trp Ile Ser Gln Ser Leu Lys Arg Leu Asp Ala Ser Leu Arg Arg
65                  70                  75                  80

Leu Gly Ala Gly Lys Leu Val Thr Arg Arg Ser Ala Asp Ala Val Val
                85                  90                  95

Ala Leu Leu Gln Leu Val Arg Asp Thr Gly Ala Thr His Val Tyr Phe
            100                 105                 110

Asn His Leu Tyr Asp Pro Ile Ser Leu Val Arg Asp His Arg Leu Lys
            115                 120                 125

Glu Met Leu Ala Ala Glu Gly Ile Val Val Gln Ser Phe Asn Ala Asp
            130                 135                 140

Leu Leu Tyr Glu Pro Trp Glu Val Val Asp Asp Glu Gly Gln Pro Phe
145                 150                 155                 160

Thr Met Phe Thr Ala Phe Trp Asn Arg Cys Leu Ser Met Gln Tyr Asp
                165                 170                 175

Pro Pro Ala Pro Leu Leu Pro Pro Lys Lys Ile Asn Ser Gly Asp Leu
            180                 185                 190

Ser Met Cys Pro Ser Glu Asp Leu Ile Phe Glu Asp Asp Ser Glu Arg
            195                 200                 205

Gly Ser Asn Ala Leu Leu Ala Arg Ala Trp Thr Pro Gly Trp Gln Asn
210                 215                 220

Ala Asp Lys Ala Leu Thr Ala Phe Leu Asn Gly Pro Leu Ala Asp Tyr
225                 230                 235                 240

Ser Val Asn Arg Lys Lys Ala Asp Ser Ala Ser Thr Ser Leu Leu Ser
                245                 250                 255

Pro His Leu His Phe Gly Glu Leu Ser Val Arg Lys Val Phe His Leu
            260                 265                 270

Val Arg Met Lys Gln Leu Val Trp Ser Asn Glu Gly Asn His Ala Ala
            275                 280                 285

Glu Glu Ser Cys Thr Leu Phe Leu Arg Ser Ile Gly Leu Arg Glu Tyr
            290                 295                 300

Ser Arg Tyr Leu Ser Phe Asn His Pro Ser Ser His Glu Arg Pro Leu
```

```
            305                 310                 315                 320
Leu Ala His Leu Arg Phe Phe Pro Trp Val Val Asn Glu Ser Tyr Phe
                325                 330                 335
Lys Ile Trp Arg Gln Gly Arg Thr Gly Tyr Pro Leu Val Asp Ala Gly
                340                 345                 350
Met Arg Glu Leu Trp Ala Thr Trp Leu His Asp Arg Ile Arg Val
                355                 360                 365
Val Val Ser Ser Phe Phe Val Lys Val Leu Gln Leu Pro Trp Arg Trp
                370                 375                 380
Gly Met Lys Tyr Phe Trp Asp Thr Leu Leu Asp Ala Asp Leu Glu Ser
385                 390                 395                 400
Asp Ala Leu Gly Trp Gln Tyr Ile Thr Gly Ser Leu Pro Asp Ser Arg
                405                 410                 415
Glu Leu Asp Arg Ile Asp Asn Pro Gln Phe Gly Tyr Lys Phe Asp
                420                 425                 430
Pro His Gly Glu Tyr Val Arg Arg Trp Ile Pro Glu Leu Val Arg Leu
                435                 440                 445
Pro Thr Glu Trp Ile His His Pro Trp Asp Ala Pro Val Ser Val Leu
                450                 455                 460
Gln Ala Ala Gly Ile Glu Leu Gly Ser Asn Tyr Pro Leu Pro Ile Val
465                 470                 475                 480
Glu Leu Asp Ala Ala Lys Ala Arg Leu Gln Glu Ala Leu Ser Glu Met
                485                 490                 495
Trp Gln Leu Glu Ala Ala Ser Arg Ala Thr Met Asn Asn Gly Met Glu
                500                 505                 510
Glu Gly Leu Gly Asp Ser Ser Glu Val
                515                 520

<210> SEQ ID NO 59
<211> LENGTH: 499
<212> TYPE: PRT
<213> ORGANISM: Arabidopsis thaliana

<400> SEQUENCE: 59

Met Ser Gly Ser Val Ser Gly Cys Gly Ser Gly Cys Ser Ile Val
1               5                   10                  15
Trp Phe Arg Arg Asp Leu Arg Val Glu Asp Asn Pro Ala Leu Ala Ala
                20                  25                  30
Ala Val Arg Ala Gly Pro Val Ile Ala Leu Phe Val Trp Ala Pro Glu
                35                  40                  45
Glu Glu Gly His Tyr His Pro Gly Arg Val Ser Arg Trp Trp Leu Lys
                50                  55                  60
Asn Ser Leu Ala Gln Leu Asp Ser Ser Leu Arg Ser Leu Gly Thr Cys
65              70                  75                  80
Leu Ile Thr Lys Arg Ser Thr Asp Ser Val Ala Ser Leu Leu Asp Val
                85                  90                  95
Val Lys Ser Thr Gly Ala Ser Gln Ile Phe Phe Asn His Leu Tyr Asp
                100                 105                 110
Pro Leu Ser Leu Val Arg Asp His Arg Ala Lys Asp Val Leu Thr Ala
                115                 120                 125
Gln Gly Ile Ala Val Arg Ser Phe Asn Ala Asp Leu Leu Tyr Glu Pro
                130                 135                 140
Trp Glu Val Thr Asp Glu Leu Gly Arg Pro Phe Ser Met Phe Ala Ala
145                 150                 155                 160
```

Phe Trp Glu Arg Cys Leu Ser Met Pro Tyr Asp Pro Glu Ser Pro Leu
            165                 170                 175

Leu Pro Pro Lys Lys Ile Ile Ser Gly Asp Val Ser Lys Cys Val Ala
            180                 185                 190

Asp Pro Leu Val Phe Glu Asp Ser Glu Lys Gly Ser Asn Ala Leu
            195                 200                 205

Leu Ala Arg Ala Trp Ser Pro Gly Trp Ser Asn Gly Asp Lys Ala Leu
            210                 215                 220

Thr Thr Phe Ile Asn Gly Pro Leu Leu Glu Tyr Ser Lys Asn Arg Arg
225                 230                 235                 240

Lys Ala Asp Ser Ala Thr Thr Ser Phe Leu Ser Pro His Leu His Phe
                245                 250                 255

Gly Glu Val Ser Val Arg Lys Val Phe His Leu Val Arg Ile Lys Gln
            260                 265                 270

Val Ala Trp Ala Asn Glu Gly Asn Glu Ala Gly Glu Ser Val Asn
            275                 280                 285

Leu Phe Leu Lys Ser Ile Gly Leu Arg Glu Tyr Ser Tyr Ile Ser
            290                 295                 300

Phe Asn His Pro Tyr Ser His Glu Arg Pro Leu Leu Gly His Leu Lys
305                 310                 315                 320

Phe Phe Pro Trp Ala Val Asp Glu Asn Tyr Phe Lys Ala Trp Arg Gln
                325                 330                 335

Gly Arg Thr Gly Tyr Pro Leu Val Asp Ala Gly Met Arg Glu Leu Trp
            340                 345                 350

Ala Thr Gly Trp Leu His Asp Arg Ile Arg Val Val Val Ser Ser Phe
            355                 360                 365

Phe Val Lys Val Leu Gln Leu Pro Trp Arg Trp Gly Met Lys Tyr Phe
370                 375                 380

Trp Asp Thr Leu Leu Asp Ala Asp Leu Glu Ser Asp Ala Leu Gly Trp
385                 390                 395                 400

Gln Tyr Ile Thr Gly Thr Leu Pro Asp Ser Arg Glu Phe Asp Arg Ile
            405                 410                 415

Asp Asn Pro Gln Phe Glu Gly Tyr Lys Phe Asp Pro Asn Gly Glu Tyr
            420                 425                 430

Val Arg Arg Trp Leu Pro Glu Leu Ser Arg Leu Pro Thr Asp Trp Ile
            435                 440                 445

His His Pro Trp Asn Ala Pro Glu Ser Val Leu Gln Ala Ala Gly Ile
            450                 455                 460

Glu Leu Gly Ser Asn Tyr Pro Leu Pro Ile Val Gly Leu Asp Glu Ala
465                 470                 475                 480

Lys Ala Arg Leu His Glu Ala Leu Ser Gln Met Trp Gln Leu Glu Ala
                485                 490                 495

Ala Ser Arg

<210> SEQ ID NO 60
<211> LENGTH: 509
<212> TYPE: PRT
<213> ORGANISM: Lycopersicon esculentum
<400> SEQUENCE: 60

Met Ser Gly Gly Gly Cys Ser Ile Val Trp Phe Arg Arg Asp Leu Arg
1               5                   10                  15

Val Glu Asp Asn Pro Ala Leu Ala Ala Gly Val Arg Ala Gly Ala Val
            20                  25                  30

```
Ile Ala Val Phe Ile Tyr Ala Pro Glu Glu Gly His Tyr Tyr Pro
         35                  40                  45
Gly Arg Val Ser Arg Trp Trp Leu Lys Gln Ser Leu Ala His Leu Asp
 50                  55                  60
Ser Ser Leu Lys Ser Leu Gly Thr Ser Leu Ile Thr Lys Arg Ser Thr
 65                  70                  75                  80
Asp Ser Ile Ser Ser Leu Leu Glu Val Val Lys Ser Thr Gly Ala Thr
                 85                  90                  95
Gln Leu Phe Phe Asn His Leu Tyr Asp Pro Ile Ser Leu Val Arg Asp
                100                 105                 110
His Arg Thr Lys Glu Ile Leu Thr Ala Gln Gly Ile Ser Val Arg Ser
            115                 120                 125
Phe Asn Ala Asp Leu Leu Tyr Glu Pro Trp Glu Val Asn Asp Asp Glu
130                 135                 140
Gly Arg Pro Phe Thr Thr Phe Ser Ala Phe Trp Glu Lys Cys Leu Ser
145                 150                 155                 160
Met Pro Tyr Asp Pro Glu Ala Pro Leu Leu Pro Pro Lys Arg Ile Ile
                165                 170                 175
Ser Gly Asp Ala Ser Arg Cys Pro Ser Asp Asn Leu Val Phe Glu Asp
                180                 185                 190
Glu Ser Glu Lys Gly Ser Asn Ala Leu Leu Ala Arg Ala Trp Ser Pro
            195                 200                 205
Gly Trp Ser Asn Ala Asp Lys Ala Leu Thr Thr Phe Val Asn Gly Pro
        210                 215                 220
Leu Leu Glu Tyr Ser Gln Asn Arg Arg Lys Ala Asp Ser Ala Thr Thr
225                 230                 235                 240
Ser Phe Leu Ser Pro His Leu His Phe Gly Glu Val Ser Val Arg Lys
                245                 250                 255
Val Phe His Phe Val Arg Ile Lys Gln Val Leu Trp Ala Asn Glu Gly
                260                 265                 270
Asn Lys Ala Gly Glu Glu Ser Val Asn Leu Phe Leu Lys Ser Ile Gly
            275                 280                 285
Leu Arg Glu Tyr Ser Arg Tyr Met Ser Phe Asn His Pro Tyr Ser His
        290                 295                 300
Glu Arg Pro Leu Leu Gly His Leu Arg Tyr Phe Pro Trp Val Val Asp
305                 310                 315                 320
Glu Gly Tyr Phe Lys Ala Trp Arg Gln Gly Arg Thr Gly Tyr Pro Leu
                325                 330                 335
Val Asp Ala Gly Met Arg Glu Leu Trp Ala Thr Gly Trp Leu His Asp
            340                 345                 350
Arg Ile Arg Val Val Val Ser Ser Phe Phe Val Lys Val Leu Gln Leu
        355                 360                 365
Pro Trp Arg Trp Gly Met Lys Tyr Phe Trp Asp Thr Leu Leu Asp Ala
370                 375                 380
Asp Leu Glu Ser Asp Ala Leu Gly Trp Gln Tyr Ile Ser Gly Thr Leu
385                 390                 395                 400
Pro Asp Gly Arg Glu Leu Asp Arg Ile Asp Asn Pro Gln Phe Val Gly
                405                 410                 415
Tyr Lys Cys Asp Pro His Gly Glu Tyr Val Arg Arg Trp Leu Pro Glu
                420                 425                 430
Leu Ala Arg Leu Pro Thr Glu Trp Ile His His Pro Trp Asn Ala Pro
            435                 440                 445
Glu Ser Val Leu Glu Ala Ala Gly Ile Glu Leu Gly Ser Asn Tyr Pro
```

```
                450             455             460
Leu Pro Ile Val Glu Ile Asp Ser Ala Lys Val Arg Leu Glu Gln Ala
465                 470                 475                 480

Leu Ser Gln Met Trp Gln Asn Asp Ala Ala Arg Ala Ala Ile Glu
                485                 490                 495

Asn Gly Met Glu Glu Gly His Gly Asp Ser Ala Asp Ser
                500                 505

<210> SEQ ID NO 61
<211> LENGTH: 510
<212> TYPE: PRT
<213> ORGANISM: Glycine max

<400> SEQUENCE: 61

Met Ser Gly Gly Gly Cys Ser Ile Val Trp Phe Arg Arg Asp Leu Arg
1               5                   10                  15

Val Glu Asp Asn Pro Ala Leu Ala Ala Gly Val Arg Ala Gly Ala Val
                20                  25                  30

Ile Ser Val Phe Ile Trp Ala Pro Glu Glu Gly Gln Tyr Tyr Pro
            35                  40                  45

Gly Arg Val Ser Arg Trp Trp Leu Lys Gln Ser Leu Ala His Leu Asp
50                  55                  60

Ser Ser Leu Arg Asn Leu Gly Ser Pro Leu Ile Thr Lys Arg Ser Thr
65                  70                  75                  80

Asn Ser Ile Ser Ser Leu Leu Glu Val Val Lys Ser Thr Gly Ala Thr
                85                  90                  95

Gln Leu Phe Phe Asn His Leu Tyr Asp Pro Leu Ser Leu Val Arg Asp
            100                 105                 110

His Arg Ala Lys Glu Val Leu Thr Ala Gln Gly Ile Thr Val Arg Ser
        115                 120                 125

Phe Asn Ser Asp Leu Leu Tyr Glu Pro Trp Asp Val Asn Asp Ala His
130                 135                 140

Gly Gln Pro Phe Thr Thr Phe Ser Ala Phe Trp Glu Arg Cys Leu Ser
145                 150                 155                 160

Met Pro Tyr Asp Pro Gln Ala Pro Leu Leu Pro Pro Lys Arg Ile Ile
                165                 170                 175

Pro Gly Asp Val Pro Arg Cys Pro Ser Asp Thr Leu Val Phe Glu Asp
            180                 185                 190

Glu Leu Glu Lys Ala Ser Asn Ala Leu Leu Ala Arg Ala Trp Ser Pro
        195                 200                 205

Gly Trp Ser Asn Ala Asp Lys Ala Leu Thr Ala Phe Val Asn Gly Ala
210                 215                 220

Leu Ile Glu Tyr Ser Lys Asn Arg Arg Lys Ala Asp Ser Ala Thr Thr
225                 230                 235                 240

Ser Phe Leu Ser Pro His Leu His Phe Gly Glu Val Ser Val Lys Lys
                245                 250                 255

Val Phe His Leu Val Arg Ile Lys Gln Val Phe Trp Ala Asn Glu Gly
            260                 265                 270

Asn Lys Ala Gly Glu Glu Ser Val Asn Leu Phe Leu Lys Ser Ile Gly
        275                 280                 285

Leu Arg Glu Tyr Ser Arg Tyr Ile Ser Phe Asn His Pro Tyr Ser His
290                 295                 300

Glu Arg Pro Leu Leu Ala His Leu Lys Phe Phe Pro Trp Val Val Asn
305                 310                 315                 320
```

```
Glu Gly Tyr Phe Lys Ala Trp Arg Gln Gly Arg Thr Gly Tyr Pro Leu
            325                 330                 335

Val Asp Ala Gly Met Arg Glu Leu Trp Ala Thr Gly Trp Leu His Asp
        340                 345                 350

Arg Ile Arg Val Val Ser Ser Phe Phe Val Lys Val Leu Gln Leu
        355                 360                 365

Pro Trp Arg Trp Gly Met Lys Tyr Phe Trp Asp Thr Leu Leu Asp Ala
    370                 375                 380

Asp Leu Glu Ser Asp Ala Leu Gly Trp Gln Tyr Ile Ser Gly Thr Leu
385                 390                 395                 400

Pro Asp Gly Arg Glu Leu Asp Arg Ile Asp Asn Pro Gln Phe Glu Gly
                405                 410                 415

Tyr Lys Cys Asp Pro Asn Gly Glu Tyr Val Arg Arg Trp Leu Pro Glu
            420                 425                 430

Leu Ala Arg Leu Pro Thr Glu Trp Ile His His Pro Trp Asn Ala Pro
        435                 440                 445

Glu Ser Val Leu Gln Ala Ala Gly Ile Glu Leu Gly Ser Asn Tyr Pro
    450                 455                 460

Leu Pro Ile Val Gly Ile Asp Ala Ala Glu Val Arg Leu Gln Glu Ala
465                 470                 475                 480

Leu Ile Gln Met Trp Gln Gln Glu Ala Ala Ser Arg Ala Ala Met Glu
                485                 490                 495

Asn Gly Thr Glu Glu Gly Leu Gly Asp Ser Ala Glu Ser Ala
            500                 505                 510

<210> SEQ ID NO 62
<211> LENGTH: 522
<212> TYPE: PRT
<213> ORGANISM: Physcomitrella patens

<400> SEQUENCE: 62

Met Ala Ala Cys Thr Ile Val Trp Phe Arg Arg Asp Leu Arg Leu Glu
1               5                   10                  15

Asp Asn Pro Ala Leu Ile Ala Ala Arg Ala Gly Thr Val Val Pro
            20                  25                  30

Val Phe Val Trp Ser Pro Ala Glu Asp Gly Gln Phe His Pro Gly Arg
        35                  40                  45

Val Ser Arg Trp Trp Leu Lys Gln Ser Leu Thr His Leu Glu Leu Ser
    50                  55                  60

Leu Lys Lys Leu Gly Ser Pro Leu Ile Leu Arg Lys Ser Pro Asp Thr
65                  70                  75                  80

Leu Ser Val Leu Leu Glu Ile Ala Glu Ala Thr Gly Ala Thr Gln Val
                85                  90                  95

Phe Tyr Asn His Leu Tyr Asp Pro Val Ser Leu Val Arg Asp His Arg
            100                 105                 110

Val Lys Gln Gly Leu Ser Gln Arg Gly Ile Val Val His Thr Phe Asn
        115                 120                 125

Gly Asp Leu Leu Tyr Glu Pro Trp Glu Val Tyr Asp Glu Glu Gly Gln
    130                 135                 140

Ala Phe Thr Val Tyr Glu Ala Phe Trp Lys Lys Cys Met Ser Met Pro
145                 150                 155                 160

Phe Glu Pro Glu Ala Pro Leu Leu Pro Arg Arg Leu Thr Gly Pro
                165                 170                 175

Ile Gly Lys Ile Val Gly Cys Asn Ala Glu Glu Leu Gly Leu Glu Asp
            180                 185                 190
```

```
Glu Phe Glu Lys Ser Ser Asn Ala Leu Leu Ala Arg Ala Trp Cys Pro
            195                 200                 205

Gly Trp Gly Phe Ala Asn Lys Ser Leu Asp Ser Phe Leu Arg Ser Pro
        210                 215                 220

Leu Ile Asp Tyr Ala Arg Asp Arg Gln Lys Ala Asp Gly Ala Ser Gly
225                 230                 235                 240

Thr Pro Thr Ser Leu Leu Ser Pro His Leu His Phe Gly Glu Leu Ser
                245                 250                 255

Val Arg Lys Ile Phe His Glu Val Arg Lys Arg Gln Ile Thr Trp Ala
            260                 265                 270

Arg Glu Gly Asn Ala Gly Gly Glu Ala Ser Val Asn Met Phe Leu Arg
        275                 280                 285

Ala Leu Gly Phe Arg Glu Tyr Ser Arg Tyr Leu Ser Phe His Phe Pro
    290                 295                 300

Phe Thr His Glu Arg Ser Leu Leu Ala Asn Leu Lys Ser Phe Pro Trp
305                 310                 315                 320

Arg Ala Asp Glu Gly Tyr Phe Lys Ala Trp Arg Gln Gly Arg Thr Gly
                325                 330                 335

Tyr Pro Leu Val Asp Ala Gly Met Arg Glu Leu Trp Ala Thr Gly Trp
            340                 345                 350

Ala His Asn Arg Ile Arg Val Val Ala Ser Phe Ser Val Lys Phe
        355                 360                 365

Leu Gln Leu Pro Trp Arg Trp Gly Met Lys Tyr Phe Trp Asp Val Leu
    370                 375                 380

Leu Asp Ala Asp Leu Glu Cys Asp Val Leu Gly Trp Gln Tyr Ile Ser
385                 390                 395                 400

Gly Ser Leu Pro Asp Gly His Glu Leu Asp Arg Ile Glu Asn Pro Glu
                405                 410                 415

Val Glu Gly Tyr Arg Phe Asp Pro Asp Gly Asp Tyr Val Arg Arg Trp
            420                 425                 430

Ile Pro Glu Leu Ala Arg Leu Pro Asn Glu Trp Val His His Pro Trp
        435                 440                 445

Asp Ala Pro Pro Ser Ala Leu Arg Ala Ala Gly Val Glu Leu Gly Thr
    450                 455                 460

Asn Tyr Pro Arg Pro Ile Val Glu Ile Gly Ala Ala Arg Glu Arg Leu
465                 470                 475                 480

Gln Ala Ser Leu Ala Glu Met Trp Gly Arg Asp Ala Ala Met Lys Ala
                485                 490                 495

Ala Leu Ala Asn Gly Leu Glu Glu Gly Leu Gly Glu Thr Val Glu Val
            500                 505                 510

Ala Gly Thr Gly Gly Pro Glu His Glu Arg
        515                 520

<210> SEQ ID NO 63
<211> LENGTH: 491
<212> TYPE: PRT
<213> ORGANISM: Sorghum bicolor

<400> SEQUENCE: 63

Met Ala Gly Ser Gly Lys Thr Val Val Trp Phe Arg Arg Asp Leu Arg
1               5                   10                  15

Ile His Asp Asn Pro Ala Leu Ala Ala Ala Lys Glu Gly Ser Val
            20                  25                  30

Leu Pro Leu Phe Ile Trp Cys Pro Ala Asp Tyr Glu Gln Tyr Tyr Pro
```

```
                35                  40                  45
Gly Arg Cys Ser Arg Trp Trp Leu Lys Gln Ser Leu Ala His Leu Gly
 50                  55                  60

Lys Ser Leu Glu Leu Leu Gly Cys Pro Leu Val Leu Ile Arg Ala Glu
 65                  70                  75                  80

Asp Ser Thr Leu Ala Thr Leu Leu Glu Cys Val His Cys Ile Ser Ala
                 85                  90                  95

Thr Arg Val Val Tyr Asn Arg Leu Tyr Asp Pro Ile Ser Leu Val Leu
                100                 105                 110

Asp Asp Lys Ile Lys Asn Glu Leu Ser Ala His Gly Ile Ser Val Gln
            115                 120                 125

Ser Phe Asn Gly Asp Leu Leu Tyr Glu Pro Trp Asp Val Tyr Asp Glu
130                 135                 140

Asn Gly Gln Ala Phe Thr Ser Phe Asn Lys Tyr Trp Glu Lys Cys Met
145                 150                 155                 160

Asn Val Pro Ile Glu Ile Ser Gln Tyr Leu Ala Pro Thr Arg Leu Val
                165                 170                 175

Ala Ala Pro Gly Leu Ala Asn Val Arg Cys Cys Ser Ile Asp Asp Leu
            180                 185                 190

Gly Leu Glu Ser Ser Lys Asp Val Glu Ser Ser Asn Ala Leu Leu Ser
        195                 200                 205

Arg Ala Trp Ser Pro Gly Trp Arg Asn Ala Glu Asn Met Leu Glu Glu
210                 215                 220

Phe Leu Ser Cys Gly Leu Leu Glu Tyr Ser Lys His Gly Met Lys Val
225                 230                 235                 240

Gly Gly Thr Thr Thr Ser Leu Leu Ser Pro Tyr Leu His Phe Gly Glu
                245                 250                 255

Leu Ser Val Arg Lys Val Tyr Gln Leu Val Thr Met His His Val Lys
            260                 265                 270

Trp Gln Asn Glu Gly Lys Ser Glu Ala Glu Glu Ser Val Arg Leu Phe
        275                 280                 285

Leu Arg Ser Ile Gly Phe Arg Glu Tyr Ser Arg Tyr Leu Cys Phe Asn
290                 295                 300

Phe Pro Phe Thr His Glu Arg Ser Phe Leu Gly Asn Leu Lys His Tyr
305                 310                 315                 320

Pro Trp Leu Leu Asp Glu Asp Arg Phe Lys Ser Trp Arg Gln Gly Met
                325                 330                 335

Thr Gly Tyr Pro Leu Val Asp Ala Gly Met Arg Glu Leu Trp Ala Thr
            340                 345                 350

Gly Trp Thr His Asn Arg Ile Arg Val Ile Val Ser Ser Phe Ala Val
        355                 360                 365

Lys Cys Leu Gln Ile Pro Trp Ile Trp Gly Met Lys Tyr Phe Trp Asp
370                 375                 380

Val Leu Leu Asp Ala Asp Leu Glu Ser Asp Ile Leu Gly Trp Gln Tyr
385                 390                 395                 400

Ile Ser Gly Ser Leu Pro Asp Gly His Glu Leu Ser Arg Leu Asp Asn
                405                 410                 415

Pro Glu Val Gln Gly Gln Lys Tyr Asp Pro Asp Gly Glu Tyr Val Arg
            420                 425                 430

Thr Trp Ile Pro Glu Leu Ala Arg Met Pro Thr Glu Trp Ile His Cys
        435                 440                 445

Pro Trp Ser Ala Pro Asn Ser Ile Leu Gln Val Ala Gly Val Glu Leu
450                 455                 460
```

```
Gly Phe Asn Tyr Pro Lys Pro Ile Val Glu Leu His Met Ala Arg Glu
465                 470                 475                 480

Cys Leu Asp Asp Ala Ile Ser Thr Met Trp Gln
            485                 490

<210> SEQ ID NO 64
<211> LENGTH: 482
<212> TYPE: PRT
<213> ORGANISM: Oryza sativa

<400> SEQUENCE: 64

Met Ala Gly Ser Glu Arg Thr Val Val Trp Phe Arg Arg Asp Leu Arg
1               5                   10                  15

Ile Asp Asp Asn Pro Ala Leu Ala Ser Ala Ala Arg Asp Gly Ala Val
            20                  25                  30

Leu Pro Val Phe Ile Trp Cys Pro Ala Asp Glu Gly Gln Phe Tyr Pro
        35                  40                  45

Gly Arg Cys Ser Arg Trp Trp Leu Lys Gln Ser Leu Pro His Leu Ser
    50                  55                  60

Gln Ser Leu Glu Ser Leu Gly Cys Pro Leu Val Leu Ile Arg Ala Glu
65                  70                  75                  80

Ser Thr Leu Glu Ala Leu Leu Arg Cys Ile Asp Ser Val Gly Ala Thr
                85                  90                  95

Arg Leu Val Tyr Asn His Leu Tyr Asp Pro Val Ser Leu Val Arg Asp
            100                 105                 110

Asp Lys Ile Lys Lys Glu Leu Ser Ala Leu Gly Ile Ser Ile Gln Ser
        115                 120                 125

Phe Asn Gly Asp Leu Leu Tyr Glu Pro Trp Glu Ile Tyr Asp Asp Ser
130                 135                 140

Gly Leu Ala Phe Thr Thr Phe Asn Met Tyr Trp Glu Lys Cys Met Glu
145                 150                 155                 160

Leu Pro Ile Asp Ala Ser Pro Ser Leu Ala Pro Trp Lys Leu Val Pro
                165                 170                 175

Val Pro Gly Leu Glu Ser Val Arg Ser Cys Ser Val Asp Asp Leu Gly
            180                 185                 190

Leu Glu Ser Ser Lys Asp Glu Glu Ser Ser Asn Ala Leu Leu Met Arg
        195                 200                 205

Ala Trp Ser Pro Gly Trp Arg Asn Ala Glu Lys Met Leu Glu Glu Phe
210                 215                 220

Val Ser His Gly Leu Leu Glu Tyr Ser Lys His Gly Met Lys Val Glu
225                 230                 235                 240

Gly Ala Thr Thr Ser Leu Leu Ser Pro Tyr Leu His Phe Gly Glu Val
                245                 250                 255

Ser Val Arg Lys Val Tyr Gln Leu Val Arg Met Gln Gln Ile Lys Trp
            260                 265                 270

Glu Asn Glu Gly Thr Ser Glu Ala Glu Ser Ile His Phe Phe Met
        275                 280                 285

Arg Ser Ile Gly Leu Arg Glu Tyr Ser Arg Tyr Leu Cys Phe Asn Phe
290                 295                 300

Pro Phe Thr His Glu Lys Ser Leu Leu Gly Asn Leu Lys His Tyr Pro
305                 310                 315                 320

Trp Lys Val Asp Glu Glu Arg Phe Lys Ser Trp Arg Gln Gly Met Thr
                325                 330                 335

Gly Tyr Pro Leu Val Asp Ala Gly Met Arg Glu Leu Trp Ala Thr Gly
```

```
                340                 345                 350
Trp Thr His Asn Arg Ile Arg Val Ile Ile Ser Ser Phe Ala Val Lys
            355                 360                 365

Phe Leu Leu Ile Pro Trp Thr Trp Gly Met Lys Tyr Phe Trp Asp Val
        370                 375                 380

Leu Leu Asp Ala Asp Leu Glu Ser Asp Ile Leu Gly Trp Gln Tyr Ile
385                 390                 395                 400

Ser Gly Ser Leu Pro Asp Gly His Glu Leu Ser Arg Leu Asp Asn Pro
                405                 410                 415

Glu Val Gln Gly Gln Lys Tyr Asp Pro Asp Gly Val Tyr Val Arg Thr
            420                 425                 430

Trp Ile Pro Glu Leu Ala Arg Met Pro Thr Glu Trp Ile His His Pro
        435                 440                 445

Trp Asp Ala Pro Ser Cys Ile Leu Glu Val Ala Gly Val Glu Leu Gly
    450                 455                 460

Phe Asn Tyr Pro Lys Pro Ile Val Asp Leu His Ile Ala Arg Glu Cys
465                 470                 475                 480

Leu Asp

<210> SEQ ID NO 65
<211> LENGTH: 498
<212> TYPE: PRT
<213> ORGANISM: Arabidopsis thaliana

<400> SEQUENCE: 65

Met Lys Met Asp Lys Lys Thr Ile Val Trp Phe Arg Arg Asp Leu Arg
1               5                   10                  15

Ile Glu Asp Asn Pro Ala Leu Ala Ala Ala His Glu Gly Ser Val
            20                  25                  30

Phe Pro Val Phe Ile Trp Cys Pro Glu Glu Glu Gly Gln Phe Tyr Pro
        35                  40                  45

Gly Arg Ala Ser Arg Trp Trp Met Lys Gln Ser Leu Ala His Leu Ser
    50                  55                  60

Gln Ser Leu Lys Ala Leu Gly Ser Asp Leu Thr Leu Ile Lys Thr His
65                  70                  75                  80

Asn Thr Ile Ser Ala Ile Leu Asp Cys Ile Arg Val Thr Gly Ala Thr
                85                  90                  95

Lys Val Val Phe Asn His Leu Tyr Asp Pro Val Ser Leu Val Arg Asp
            100                 105                 110

His Thr Val Lys Glu Lys Leu Val Glu Arg Gly Ile Ser Val Gln Ser
        115                 120                 125

Tyr Asn Gly Asp Leu Leu Tyr Glu Pro Trp Glu Ile Tyr Cys Glu Lys
    130                 135                 140

Gly Lys Pro Phe Thr Ser Phe Asn Ser Tyr Trp Lys Lys Cys Leu Asp
145                 150                 155                 160

Met Ser Ile Glu Ser Val Met Leu Pro Pro Pro Trp Arg Leu Met Pro
                165                 170                 175

Ile Thr Ala Ala Ala Glu Ala Ile Trp Ala Cys Ser Ile Glu Glu Leu
            180                 185                 190

Gly Leu Glu Asn Glu Ala Glu Lys Pro Ser Asn Ala Leu Leu Thr Arg
        195                 200                 205

Ala Trp Ser Pro Gly Trp Ser Asn Ala Asp Lys Leu Leu Asn Glu Phe
    210                 215                 220

Ile Glu Lys Gln Leu Ile Asp Tyr Ala Lys Asn Ser Lys Lys Val Val
```

-continued

```
                225                 230                 235                 240
Gly Asn Ser Thr Ser Leu Leu Ser Pro Tyr Leu His Phe Gly Glu Ile
                    245                 250                 255
Ser Val Arg His Val Phe Gln Cys Ala Arg Met Lys Gln Ile Ile Trp
                260                 265                 270
Ala Arg Asp Lys Asn Ser Glu Gly Glu Ser Ala Asp Leu Phe Leu
            275                 280                 285
Arg Gly Ile Gly Leu Arg Glu Tyr Ser Arg Tyr Ile Cys Phe Asn Phe
        290                 295                 300
Pro Phe Thr His Glu Gln Ser Leu Leu Ser His Leu Arg Phe Phe Pro
305                 310                 315                 320
Trp Asp Ala Asp Val Asp Lys Phe Lys Ala Trp Arg Gln Gly Arg Thr
                325                 330                 335
Gly Tyr Pro Leu Val Asp Ala Gly Met Arg Glu Leu Trp Ala Thr Gly
                340                 345                 350
Trp Met His Asn Arg Ile Arg Val Ile Val Ser Ser Phe Ala Val Lys
                355                 360                 365
Phe Leu Leu Leu Pro Trp Lys Trp Gly Met Lys Tyr Phe Trp Asp Thr
370                 375                 380
Leu Leu Asp Ala Asp Leu Glu Cys Asp Ile Leu Gly Trp Gln Tyr Ile
385                 390                 395                 400
Ser Gly Ser Ile Pro Asp Gly His Glu Leu Asp Arg Leu Asp Asn Pro
                405                 410                 415
Ala Leu Gln Gly Ala Lys Tyr Asp Pro Glu Gly Glu Tyr Ile Arg Gln
                420                 425                 430
Trp Leu Pro Glu Leu Ala Arg Leu Pro Thr Glu Trp Ile His His Pro
                435                 440                 445
Trp Asp Ala Pro Leu Thr Val Leu Lys Ala Ser Gly Val Glu Leu Gly
                450                 455                 460
Thr Asn Tyr Ala Lys Pro Ile Val Asp Ile Asp Thr Ala Arg Glu Leu
465                 470                 475                 480
Leu Ala Lys Ala Ile Ser Arg Thr Arg Glu Ala Gln Ile Met Ile Gly
                485                 490                 495
Ala Ala

<210> SEQ ID NO 66
<211> LENGTH: 481
<212> TYPE: PRT
<213> ORGANISM: Glycine max

<400> SEQUENCE: 66

Met Gly Ser Asn Arg Thr Ile Val Trp Phe Arg Arg Asp Leu Arg Ile
1               5                   10                  15
Glu Asp Asn Pro Ala Leu Thr Ala Ala Lys Glu Gly Ser Val Leu
            20                  25                  30
Pro Val Tyr Val Trp Cys Pro Lys Glu Glu Gly Gln Phe Tyr Pro Gly
            35                  40                  45
Arg Val Ser Arg Trp Trp Leu Lys Gln Ser Leu Ala His Leu Asp Gln
        50                  55                  60
Ser Leu Lys Ser Leu Gly Ser Arg Leu Val Leu Ile Lys Thr His Ser
65                  70                  75                  80
Thr Ala Val Ala Leu Val Glu Cys Val Lys Ala Ile Gln Ala Thr Lys
                85                  90                  95
Val Val Phe Asn His Leu Tyr Asp Pro Val Ser Leu Val Arg Asp His
```

```
                    100                 105                 110
Asn Ile Lys Glu Lys Leu Val Glu Gln Gly Ile Ser Val Gln Ser Tyr
            115                 120                 125

Asn Gly Asp Leu Leu Tyr Glu Pro Trp Glu Val Asn Ser Glu Ser Gly
        130                 135                 140

Arg Ala Phe Thr Thr Phe Asn Ala Phe Trp Lys Lys Cys Leu His Met
145                 150                 155                 160

Gln Met Asp Ile Val Ser Val Val Pro Pro Trp Gln Leu Ile Pro Ala
                165                 170                 175

Glu Gly Lys Ile Glu Glu Cys Ser Leu Glu Glu Leu Gly Leu Glu Asn
            180                 185                 190

Glu Ser Glu Lys Pro Ser Asn Ala Leu Leu Gly Arg Ala Trp Ser Pro
        195                 200                 205

Gly Trp Arg Asn Ala Asp Lys Ala Leu Arg Glu Phe Val Glu Leu His
        210                 215                 220

Leu Leu His Tyr Ser Lys Lys Arg Leu Lys Val Gly Gly Glu Ser Thr
225                 230                 235                 240

Ser Leu Leu Ser Pro Tyr Leu His Phe Gly Glu Leu Ser Ala Arg Lys
                245                 250                 255

Val Phe Gln Val Thr Cys Met Lys Gln Ile Leu Trp Thr Asn Glu Gly
            260                 265                 270

Asn Ser Ala Gly Glu Glu Ser Ala Asn Leu Phe Leu Arg Ala Ile Gly
        275                 280                 285

Leu Arg Glu Tyr Ser Arg Tyr Leu Cys Phe Asn Phe Pro Phe Thr His
        290                 295                 300

Glu Arg Ala Leu Leu Gly His Leu Lys Phe Phe Pro Trp Asn Pro Asp
305                 310                 315                 320

Pro Asp Ile Phe Lys Thr Trp Arg Gln Gly Arg Thr Gly Phe Pro Leu
                325                 330                 335

Val Asp Ala Gly Met Arg Glu Leu Trp Ala Thr Gly Trp Ile His Asn
            340                 345                 350

Arg Ile Arg Val Ile Val Ser Ser Phe Ala Val Lys Met Leu Leu Leu
        355                 360                 365

Pro Trp Lys Trp Gly Met Lys Tyr Phe Trp Asp Thr Leu Leu Asp Ala
        370                 375                 380

Asp Leu Glu Ser Asp Ile Leu Gly Trp Gln Tyr Ile Ser Gly Gly Leu
385                 390                 395                 400

Pro Asp Gly His Glu Leu Glu Arg Leu Asp Asn Pro Glu Ile Gln Gly
                405                 410                 415

Ala Lys Phe Asp Pro Glu Gly Glu Tyr Val Arg Gln Trp Leu Pro Glu
            420                 425                 430

Leu Ala Arg Met Pro Thr Glu Trp Ile His His Pro Trp Asp Ala Pro
        435                 440                 445

Leu Thr Val Leu Arg Ala Ala Gly Val Glu Leu Gly Gln Asn Tyr Pro
        450                 455                 460

Lys Pro Ile Ile Asp Ile Asp Leu Ala Arg Glu Arg Leu Thr Glu Ala
465                 470                 475                 480

Ile

<210> SEQ ID NO 67
<211> LENGTH: 822
<212> TYPE: PRT
<213> ORGANISM: Artificial Sequence
<220> FEATURE:
```

<223> OTHER INFORMATION: Synthetic polypeptide

<400> SEQUENCE: 67

```
Met Lys Met Asp Lys Thr Ile Val Trp Phe Arg Arg Asp Leu Arg
1               5                   10                  15

Ile Glu Asp Asn Pro Ala Leu Ala Ala Ala His Glu Gly Ser Val
                20                  25                  30

Phe Pro Val Phe Ile Trp Cys Pro Glu Glu Gly Gln Phe Tyr Pro
            35                  40                  45

Gly Arg Ala Ser Arg Trp Trp Met Lys Gln Ser Leu Ala His Leu Ser
    50                  55                  60

Gln Ser Leu Lys Ala Leu Gly Ser Asp Leu Thr Leu Ile Lys Thr His
65                  70                  75                  80

Asn Thr Ile Ser Ala Ile Leu Asp Cys Ile Arg Val Thr Gly Ala Thr
                85                  90                  95

Lys Val Val Phe Asn His Leu Tyr Asp Pro Val Ser Leu Val Arg Asp
            100                 105                 110

His Thr Val Lys Glu Lys Leu Val Glu Arg Gly Ile Ser Val Gln Ser
            115                 120                 125

Tyr Asn Gly Asp Leu Leu Tyr Glu Pro Trp Glu Ile Tyr Cys Glu Lys
130                 135                 140

Gly Lys Pro Phe Thr Ser Phe Asn Ser Tyr Trp Lys Lys Cys Leu Asp
145                 150                 155                 160

Met Ser Ile Glu Ser Val Met Leu Pro Pro Pro Trp Arg Leu Met Pro
            165                 170                 175

Ile Thr Ala Ala Ala Glu Ala Ile Trp Ala Cys Ser Ile Glu Glu Leu
            180                 185                 190

Gly Leu Glu Asn Glu Ala Glu Lys Pro Ser Asn Ala Leu Leu Thr Arg
        195                 200                 205

Ala Trp Ser Pro Gly Trp Ser Asn Ala Asp Lys Leu Leu Asn Glu Phe
        210                 215                 220

Ile Glu Lys Gln Leu Ile Asp Tyr Ala Lys Asn Ser Lys Lys Val Val
225                 230                 235                 240

Gly Asn Ser Thr Ser Leu Leu Ser Pro Tyr Leu His Phe Gly Glu Ile
                245                 250                 255

Ser Val Arg His Val Phe Gln Cys Ala Arg Met Lys Gln Ile Ile Trp
            260                 265                 270

Ala Arg Asp Lys Asn Ser Glu Gly Glu Glu Ser Ala Asp Leu Phe Leu
        275                 280                 285

Arg Gly Ile Gly Leu Arg Glu Tyr Ser Arg Tyr Ile Cys Phe Asn Phe
        290                 295                 300

Pro Phe Thr His Glu Gln Ser Leu Leu Ser His Leu Arg Phe Phe Pro
305                 310                 315                 320

Trp Asp Ala Asp Val Asp Lys Phe Lys Ala Trp Arg Gln Gly Arg Thr
            325                 330                 335

Gly Tyr Pro Leu Val Asp Ala Gly Met Arg Glu Leu Trp Ala Thr Gly
        340                 345                 350

Trp Met His Asn Arg Ile Arg Val Ile Val Ser Ser Phe Ala Val Lys
        355                 360                 365

Phe Leu Leu Leu Pro Trp Lys Trp Gly Met Lys Tyr Phe Trp Asp Thr
370                 375                 380

Leu Leu Asp Ala Asp Leu Glu Cys Asp Ile Leu Gly Trp Gln Tyr Ile
385                 390                 395                 400
```

-continued

```
Ser Gly Ser Ile Pro Asp Gly His Glu Leu Asp Arg Leu Asp Asn Pro
                405                 410                 415
Ala Leu Gln Gly Ala Lys Tyr Asp Pro Glu Gly Glu Tyr Ile Arg Gln
            420                 425                 430
Trp Leu Pro Glu Leu Ala Arg Leu Pro Thr Glu Trp Ile His His Pro
        435                 440                 445
Trp Asp Ala Pro Leu Thr Val Leu Lys Ala Ser Gly Val Glu Leu Gly
    450                 455                 460
Thr Asn Tyr Ala Lys Pro Ile Val Asp Ile Asp Thr Ala Arg Glu Leu
465                 470                 475                 480
Leu Ala Lys Ala Ile Ser Arg Thr Arg Glu Ala Gln Ile Met Ile Gly
                485                 490                 495
Ala Ala Thr Glu Pro Gln Glu Glu Ser Glu Glu Val Glu Glu Pro
            500                 505                 510
Glu Glu Arg Gln Gln Thr Pro Glu Val Val Pro Asp Ser Gly Thr
        515                 520                 525
Phe Tyr Asp Gln Ala Val Val Ser Asn Asp Met Glu Glu His Leu Glu
    530                 535                 540
Glu Pro Val Ala Glu Pro Glu Pro Asp Pro Glu Pro Glu Pro Glu Gln
545                 550                 555                 560
Glu Pro Val Ser Glu Ile Gln Glu Glu Lys Pro Glu Pro Val Leu Glu
                565                 570                 575
Glu Thr Ala Pro Glu Asp Ala Gln Lys Ser Ser Ser Pro Ala Pro Ala
            580                 585                 590
Asp Ile Ala Gln Thr Val Gln Glu Asp Leu Arg Thr Phe Ser Trp Ala
        595                 600                 605
Ser Val Thr Ser Lys Asn Leu Pro Pro Ser Gly Ala Val Pro Val Thr
    610                 615                 620
Gly Ile Pro Pro His Val Val Lys Val Pro Ala Ser Gln Pro Arg Pro
625                 630                 635                 640
Glu Ser Lys Pro Glu Ser Gln Ile Pro Pro Gln Arg Pro Gln Arg Asp
                645                 650                 655
Gln Arg Val Arg Glu Gln Arg Ile Asn Ile Pro Pro Gln Arg Gly Pro
            660                 665                 670
Arg Pro Ile Arg Glu Ala Gly Glu Gln Gly Asp Ile Glu Pro Arg Arg
        675                 680                 685
Met Val Arg His Pro Asp Ser His Gln Leu Phe Ile Gly Asn Leu Pro
    690                 695                 700
His Glu Val Asp Lys Ser Glu Leu Lys Asp Phe Phe Gln Ser Tyr Gly
705                 710                 715                 720
Asn Val Val Glu Leu Arg Ile Asn Ser Gly Gly Lys Leu Pro Asn Phe
                725                 730                 735
Gly Phe Val Val Phe Asp Asp Ser Glu Pro Val Gln Lys Val Leu Ser
            740                 745                 750
Asn Arg Pro Ile Met Phe Arg Gly Glu Val Arg Leu Asn Val Glu Glu
        755                 760                 765
Lys Lys Thr Arg Ala Ala Arg Glu Gly Asp Arg Arg Asp Asn Arg Leu
    770                 775                 780
Arg Gly Pro Gly Gly Pro Arg Gly Gly Leu Gly Gly Met Arg Gly
785                 790                 795                 800
Pro Pro Arg Gly Gly Met Val Gln Lys Pro Gly Phe Gly Val Gly Arg
                805                 810                 815
Gly Leu Ala Pro Arg Gln
```

-continued

```
                820

<210> SEQ ID NO 68
<211> LENGTH: 1208
<212> TYPE: PRT
<213> ORGANISM: Artificial Sequence
<220> FEATURE:
<223> OTHER INFORMATION: Synthetic polypeptide

<400> SEQUENCE: 68

Met Lys Met Asp Lys Lys Thr Ile Val Trp Phe Arg Arg Asp Leu Arg
1               5                   10                  15

Ile Glu Asp Asn Pro Ala Leu Ala Ala Ala His Glu Gly Ser Val
            20                  25                  30

Phe Pro Val Phe Ile Trp Cys Pro Glu Glu Gly Gln Phe Tyr Pro
        35                  40                  45

Gly Arg Ala Ser Arg Trp Trp Met Lys Gln Ser Leu Ala His Leu Ser
    50                  55                  60

Gln Ser Leu Lys Ala Leu Gly Ser Asp Leu Thr Leu Ile Lys Thr His
65                  70                  75                  80

Asn Thr Ile Ser Ala Ile Leu Asp Cys Ile Arg Val Thr Gly Ala Thr
                85                  90                  95

Lys Val Val Phe Asn His Leu Tyr Asp Pro Val Ser Leu Val Arg Asp
            100                 105                 110

His Thr Val Lys Glu Lys Leu Val Glu Arg Gly Ile Ser Val Gln Ser
        115                 120                 125

Tyr Asn Gly Asp Leu Leu Tyr Glu Pro Trp Glu Ile Tyr Cys Glu Lys
    130                 135                 140

Gly Lys Pro Phe Thr Ser Phe Asn Ser Tyr Trp Lys Lys Cys Leu Asp
145                 150                 155                 160

Met Ser Ile Glu Ser Val Met Leu Pro Pro Pro Trp Arg Leu Met Pro
                165                 170                 175

Ile Thr Ala Ala Ala Glu Ala Ile Trp Ala Cys Ser Ile Glu Glu Leu
            180                 185                 190

Gly Leu Glu Asn Glu Ala Glu Lys Pro Ser Asn Ala Leu Leu Thr Arg
        195                 200                 205

Ala Trp Ser Pro Gly Trp Ser Asn Ala Asp Lys Leu Leu Asn Glu Phe
    210                 215                 220

Ile Glu Lys Gln Leu Ile Asp Tyr Ala Lys Asn Ser Lys Lys Val Val
225                 230                 235                 240

Gly Asn Ser Thr Ser Leu Leu Ser Pro Tyr Leu His Phe Gly Glu Ile
                245                 250                 255

Ser Val Arg His Val Phe Gln Cys Ala Arg Met Lys Gln Ile Ile Trp
            260                 265                 270

Ala Arg Asp Lys Asn Ser Glu Gly Glu Glu Ser Ala Asp Leu Phe Leu
        275                 280                 285

Arg Gly Ile Gly Leu Arg Glu Tyr Ser Arg Tyr Ile Cys Phe Asn Phe
    290                 295                 300

Pro Phe Thr His Glu Gln Ser Leu Leu Ser His Leu Arg Phe Phe Pro
305                 310                 315                 320

Trp Asp Ala Asp Val Asp Lys Phe Lys Ala Trp Arg Gln Gly Arg Thr
                325                 330                 335

Gly Tyr Pro Leu Val Asp Ala Gly Met Arg Glu Leu Trp Ala Thr Gly
            340                 345                 350

Trp Met His Asn Arg Ile Arg Val Ile Val Ser Ser Phe Ala Val Lys
```

-continued

```
              355                 360                 365
    Phe Leu Leu Leu Pro Trp Lys Trp Gly Met Lys Tyr Phe Trp Asp Thr
    370                 375                 380

Leu Leu Asp Ala Asp Leu Glu Cys Asp Ile Leu Gly Trp Gln Tyr Ile
    385                 390                 395                 400

Ser Gly Ser Ile Pro Asp Gly His Glu Leu Asp Arg Leu Asp Asn Pro
                    405                 410                 415

Ala Leu Gln Gly Ala Lys Tyr Asp Pro Glu Gly Glu Tyr Ile Arg Gln
                420                 425                 430

Trp Leu Pro Glu Leu Ala Arg Leu Pro Thr Glu Trp Ile His His Pro
                435                 440                 445

Trp Asp Ala Pro Leu Thr Val Leu Lys Ala Ser Gly Val Glu Leu Gly
                450                 455                 460

Thr Asn Tyr Ala Lys Pro Ile Val Asp Ile Asp Thr Ala Arg Glu Leu
    465                 470                 475                 480

Leu Ala Lys Ala Ile Ser Arg Thr Arg Glu Ala Gln Ile Met Ile Gly
                    485                 490                 495

Ala Ala Ala Arg Asp Pro Pro Val Ala Thr Met Val Ser Lys Gly Glu
                500                 505                 510

Glu Asp Asn Met Ala Ile Ile Lys Glu Phe Met Arg Phe Lys Val His
                515                 520                 525

Met Glu Gly Ser Val Asn Gly His Glu Phe Glu Ile Glu Gly Glu Gly
    530                 535                 540

Glu Gly Arg Pro Tyr Glu Gly Thr Gln Thr Ala Lys Leu Lys Val Thr
    545                 550                 555                 560

Lys Gly Gly Pro Leu Pro Phe Ala Trp Asp Ile Leu Ser Pro Gln Phe
                    565                 570                 575

Met Tyr Gly Ser Lys Ala Tyr Val Lys His Pro Ala Asp Ile Pro Asp
                580                 585                 590

Tyr Leu Lys Leu Ser Phe Pro Glu Gly Phe Lys Trp Glu Arg Val Met
                595                 600                 605

Asn Phe Glu Asp Gly Gly Val Val Thr Val Thr Gln Asp Ser Ser Leu
    610                 615                 620

Gln Asp Gly Glu Phe Ile Tyr Lys Val Lys Leu Arg Gly Thr Asn Phe
    625                 630                 635                 640

Pro Ser Asp Gly Pro Val Met Gln Lys Lys Thr Met Gly Trp Glu Ala
                    645                 650                 655

Ser Ser Glu Arg Met Tyr Pro Glu Asp Gly Ala Leu Lys Gly Glu Ile
                660                 665                 670

Lys Gln Arg Leu Lys Leu Lys Asp Gly Gly His Tyr Asp Ala Glu Val
                675                 680                 685

Lys Thr Thr Tyr Lys Ala Lys Lys Pro Val Gln Leu Pro Gly Ala Tyr
                690                 695                 700

Asn Val Asn Ile Lys Leu Asp Ile Thr Ser His Asn Glu Asp Tyr Thr
    705                 710                 715                 720

Ile Val Glu Gln Tyr Glu Arg Ala Glu Gly Arg His Ser Thr Gly Gly
                    725                 730                 735

Met Asp Glu Leu Tyr Lys Met Val Met Glu Lys Pro Ser Pro Leu Leu
                740                 745                 750

Val Gly Arg Glu Phe Val Arg Gln Tyr Tyr Thr Leu Leu Asn Gln Ala
                755                 760                 765

Pro Asp Met Leu His Arg Phe Tyr Gly Lys Asn Ser Ser Tyr Val His
    770                 775                 780
```

```
Gly Gly Leu Asp Ser Asn Gly Lys Pro Ala Asp Ala Val Tyr Gly Gln
785                 790                 795                 800

Lys Glu Ile His Arg Lys Val Met Ser Gln Asn Phe Thr Asn Cys His
            805                 810                 815

Thr Lys Ile Arg His Val Asp Ala His Ala Thr Leu Asn Asp Gly Val
        820                 825                 830

Val Val Gln Val Met Gly Leu Leu Ser Asn Asn Asn Gln Ala Leu Arg
    835                 840                 845

Arg Phe Met Gln Thr Phe Val Leu Ala Pro Glu Gly Ser Val Ala Asn
850                 855                 860

Lys Phe Tyr Val His Asn Asp Ile Phe Arg Tyr Gln Asp Glu Val Phe
865                 870                 875                 880

Gly Gly Phe Val Thr Glu Pro Gln Glu Glu Ser Glu Glu Glu Val Glu
                885                 890                 895

Glu Pro Glu Glu Arg Gln Gln Thr Pro Glu Val Val Pro Asp Asp Ser
            900                 905                 910

Gly Thr Phe Tyr Asp Gln Ala Val Val Ser Asn Asp Met Glu Glu His
        915                 920                 925

Leu Glu Glu Pro Val Ala Glu Pro Glu Pro Asp Pro Glu Pro Glu Pro
    930                 935                 940

Glu Gln Glu Pro Val Ser Glu Ile Gln Glu Glu Lys Pro Glu Pro Val
945                 950                 955                 960

Leu Glu Glu Thr Ala Pro Glu Asp Ala Gln Lys Ser Ser Pro Ala
                965                 970                 975

Pro Ala Asp Ile Ala Gln Thr Val Gln Glu Asp Leu Arg Thr Phe Ser
                980                 985                 990

Trp Ala Ser Val Thr Ser Lys Asn Leu Pro Pro Ser Gly Ala Val Pro
            995                 1000                1005

Val Thr Gly Ile Pro Pro His Val Val Lys Val Pro Ala Ser Gln
    1010                1015                1020

Pro Arg Pro Glu Ser Lys Pro Glu Ser Gln Ile Pro Pro Gln Arg
    1025                1030                1035

Pro Gln Arg Asp Gln Arg Val Arg Glu Gln Arg Ile Asn Ile Pro
    1040                1045                1050

Pro Gln Arg Gly Pro Arg Pro Ile Arg Glu Ala Gly Glu Gln Gly
    1055                1060                1065

Asp Ile Glu Pro Arg Arg Met Val Arg His Pro Asp Ser His Gln
    1070                1075                1080

Leu Phe Ile Gly Asn Leu Pro His Glu Val Asp Lys Ser Glu Leu
    1085                1090                1095

Lys Asp Phe Phe Gln Ser Tyr Gly Asn Val Val Glu Leu Arg Ile
    1100                1105                1110

Asn Ser Gly Gly Lys Leu Pro Asn Phe Gly Phe Val Val Phe Asp
    1115                1120                1125

Asp Ser Glu Pro Val Gln Lys Val Leu Ser Asn Arg Pro Ile Met
    1130                1135                1140

Phe Arg Gly Glu Val Arg Leu Asn Val Glu Glu Lys Lys Thr Arg
    1145                1150                1155

Ala Ala Arg Glu Gly Asp Arg Arg Asp Asn Arg Leu Arg Gly Pro
    1160                1165                1170

Gly Gly Pro Arg Gly Gly Leu Gly Gly Gly Met Arg Gly Pro Pro
    1175                1180                1185
```

Arg Gly Gly Met Val Gln Lys Pro Gly Phe Gly Val Gly Arg Gly
    1190                1195                1200

Leu Ala Pro Arg Gln
    1205

<210> SEQ ID NO 69
<211> LENGTH: 3630
<212> TYPE: DNA
<213> ORGANISM: Artificial Sequence
<220> FEATURE:
<223> OTHER INFORMATION: Synthetic polynucleotide

<400> SEQUENCE: 69

| | | |
|---|---|---|
| atgaagatgg acaaaaagac tatagtttgg tttagaagag acctaaggat tgaggataat | 60 |
| cctgcattag cagcagctgc tcacgaagga tctgttttc ctgtcttcat ttggtgtcct | 120 |
| gaagaagaag acagtttta tcctggaaga gcttcaagat ggtggatgaa acaatcactt | 180 |
| gctcacttat ctcaatcctt gaaggctctt ggatctgacc tcactttaat caaaacccac | 240 |
| aacacgattt cagcgatctt ggattgtatc cgcgttaccg tgctacaaa agtcgtcttt | 300 |
| aaccacctct atgatcctgt ttcgttagtt cgggaccata ccgtaaagga gaagctggtg | 360 |
| gaacgtggga tctctgtgca agctacaat ggagatctat tgtatgaacc gtgggagata | 420 |
| tactgcgaaa agggcaaacc ttttacgagt ttcaattctt actggaagaa atgcttagat | 480 |
| atgtcgattg aatccgttat gcttcctcct ccttggcggt tgatgccaat aactgcagcg | 540 |
| gctgaagcga tttgggcgtg ttcgattgaa gaactagggc tggagaatga ggccgagaaa | 600 |
| ccgagcaatg cgttgttaac tagagcttgg tctccaggat ggagcaatgc tgataagtta | 660 |
| ctaaatgagt tcatcgagaa gcagttgata gattatgcaa agaacagcaa gaaagttgtt | 720 |
| gggaattcta cttcactact ttctccgtat ctccatttcg gggaaataag cgtcagacac | 780 |
| gttttccagt gtgcccggat gaaacaaatt atatgggcaa gagataagaa cagtgaagga | 840 |
| gaagaaagtg cagatctttt tcttagggga tcggtttaa gagagtattc tcggtatata | 900 |
| tgtttcaact tcccgtttac tcacgagcaa tcgttgttga gtcatcttcg gttttccct | 960 |
| tgggatgctg atgttgataa gttcaaggcc tggagacaag caggaccgg ttatccgttg | 1020 |
| gtggatgccg aatgagaga gctttgggct accggatgga tgcataacag aataagagtg | 1080 |
| attgtttcaa gctttgctgt gaagtttctt ctccttccat ggaaatgggg aatgaagtat | 1140 |
| ttctgggata cacttttgga tgctgatttg aatgtgaca tccttggctg gcagtatatc | 1200 |
| tctgggagta tccccgatgg ccacgagctt gatcgcttgg acaatcccgc gttacaaggc | 1260 |
| gccaaatatg acccagaagg tgagtacata aggcaatggc ttcccgagct tgcgagattg | 1320 |
| ccaactgaat ggatccatca tccatgggac gctccttaa ccgtactcaa agcttctggt | 1380 |
| gtggaactcg gaacaaacta tgcgaaaccc attgtagaca tcgacacagc tcgtgagcta | 1440 |
| ctagctaaag ctatttcaag aacccgtgaa gcacagatca tgatcggagc agcagcccgg | 1500 |
| gatccaccgg tcgccaccat ggtgagcaag ggcgaggagg ataacatggc catcatcaag | 1560 |
| gagttcatgc gcttcaaggt gcacatggag ggctccgtga acggccacga gttcgagatc | 1620 |
| gagggcgagg gcgagggccg ccctacgag gcacccaga ccgccaagct gaaggtgacc | 1680 |
| aagggtggcc ccctgccctt cgcctgggac atcctgtccc ctcagttcat gtacggctcc | 1740 |
| aaggcctacg tgaagcaccc cgccgacatc cccgactact tgaagctgtc cttccccgag | 1800 |
| ggcttcaagt gggagcgcgt gatgaacttc gaggacggcg gcgtggtgac cgtgacccag | 1860 |
| gactcctccc tgcaggacgg cgagttcatc tacaaggtga agctgcgcgg caccaacttc | 1920 |

```
ccctccgacg gccccgtaat gcagaagaag accatgggct gggaggcctc ctccgagcgg    1980
atgtaccccg aggacggcgc cctgaagggc gagatcaagc agaggctgaa gctgaaggac    2040
ggcggccact acgacgctga ggtcaagacc acctacaagg ccaagaagcc cgtgcagctg    2100
cccgcgcct acaacgtcaa catcaagttg acatcacct cccacaacga ggactacacc     2160
atcgtggaac agtacgaacg cgccgagggc cgccactcca ccggcggcat ggacgagctg    2220
tacaagatgg tgatggagaa gcctagtccc ctgctggtcg ggcgggaatt tgtgagacag    2280
tattacacac tgctgaacca ggccccagac atgctgcata gattttatgg aaagaactct    2340
tcttatgtcc atgggggatt ggattcaaat ggaaagccag cagatgcagt ctacggacag    2400
aaagaaatcc acaggaaagt gatgtcacaa aacttccacca actgccacac caagattcgc    2460
catgttgatg ctcatgccac gctaaatgat ggtgtggtag tccaggtgat ggggcttctc    2520
tctaacaaca accaggcttt gaggagattc atgcaaacgt ttgtccttgc tcctgagggg    2580
tctgttgcaa ataaattcta tgttcacaat gatatcttca gataccaaga tgaggtcttt    2640
ggtgggtttg tcactgagcc tcaggaggag tctgaagaag aagtagagga acctgaagaa    2700
agacagcaaa cacctgaggt ggtacctgat gattctggaa ctttctatga tcaggcagtt    2760
gtcagtaatg acatggaaga acatttagag gagcctgttg ctgaaccaga gcctgatcct    2820
gaaccagaac cagaacaaga acctgtatct gaaatccaag aggaaaagcc tgagccagta    2880
ttagaagaaa ctgcccctga ggatgctcag aagagttctt ctccagcacc tgcagacata    2940
gctcagacag tacaggaaga cttgaggaca tttctctggg catctgtgac cagtaagaat    3000
cttccacca gtggagctgt tccagttact gggataccac ctcatgttgt taaagtacca    3060
gcttcacagc cccgtccaga gtctaagcct gaatctcaga ttccaccaca aagacctcag    3120
cgggatcaaa gagtgcgaga caacgaata aatattcctc cccaagggg acccagacca    3180
atccgtgagg ctggtgagca aggtgacatt gaaccccgaa gaatggtgag acaccctgac    3240
agtcaccaac tcttcattgg caacctgcct catgaagtgg acaaatcaga gcttaaagat    3300
ttctttcaaa gttatggaaa cgtggtggag ttgcgcatta acgtggtgg gaaattaccc    3360
aattttggtt ttgttgtgtt tgatgattct gagcctgttc agaaagtcct tagcaacagg    3420
cccatcatgt tcagaggtga ggtccgtctg aatgtcgaag agaagaagac tcgagctgcc    3480
agggaaggcg accgacgaga taatcgcctt cggggacctg gaggccctcg aggtgggctg    3540
ggtggtggaa tgagaggccc tccccgtgga ggcatggtgc agaaaccagg atttggagtg    3600
ggaaggggc ttgcgccacg gcagtgataa                                     3630
```

<210> SEQ ID NO 70
<211> LENGTH: 1066
<212> TYPE: PRT
<213> ORGANISM: Artificial Sequence
<220> FEATURE:
<223> OTHER INFORMATION: Synthetic polypeptide

<400> SEQUENCE: 70

```
Met Lys Met Asp Lys Lys Thr Ile Val Trp Phe Arg Arg Asp Leu Arg
1               5                   10                  15

Ile Glu Asp Asn Pro Ala Leu Ala Ala Ala His Glu Gly Ser Val
                20                  25                  30

Phe Pro Val Phe Ile Trp Cys Pro Glu Glu Glu Gly Gln Phe Tyr Pro
            35                  40                  45

Gly Arg Ala Ser Arg Trp Trp Met Lys Gln Ser Leu Ala His Leu Ser
```

-continued

```
             50                  55                  60
Gln Ser Leu Lys Ala Leu Gly Ser Asp Leu Thr Leu Ile Lys Thr His
65                  70                  75                  80

Asn Thr Ile Ser Ala Ile Leu Asp Cys Ile Arg Val Thr Gly Ala Thr
                    85                  90                  95

Lys Val Val Phe Asn His Leu Tyr Asp Pro Val Ser Leu Val Arg Asp
                    100                 105                 110

His Thr Val Lys Glu Lys Leu Val Glu Arg Gly Ile Ser Val Gln Ser
                    115                 120                 125

Tyr Asn Gly Asp Leu Leu Tyr Glu Pro Trp Glu Ile Tyr Cys Glu Lys
                    130                 135                 140

Gly Lys Pro Phe Thr Ser Phe Asn Ser Tyr Trp Lys Lys Cys Leu Asp
145                 150                 155                 160

Met Ser Ile Glu Ser Val Met Leu Pro Pro Trp Arg Leu Met Pro
                    165                 170                 175

Ile Thr Ala Ala Ala Glu Ala Ile Trp Ala Cys Ser Ile Glu Glu Leu
                    180                 185                 190

Gly Leu Glu Asn Glu Ala Glu Lys Pro Ser Asn Ala Leu Leu Thr Arg
                    195                 200                 205

Ala Trp Ser Pro Gly Trp Ser Asn Ala Asp Lys Leu Leu Asn Glu Phe
                    210                 215                 220

Ile Glu Lys Gln Leu Ile Asp Tyr Ala Lys Asn Ser Lys Lys Val Val
225                 230                 235                 240

Gly Asn Ser Thr Ser Leu Leu Ser Pro Tyr Leu His Phe Gly Glu Ile
                    245                 250                 255

Ser Val Arg His Val Phe Gln Cys Ala Arg Met Lys Gln Ile Ile Trp
                    260                 265                 270

Ala Arg Asp Lys Asn Ser Glu Gly Glu Glu Ser Ala Asp Leu Phe Leu
                    275                 280                 285

Arg Gly Ile Gly Leu Arg Glu Tyr Ser Arg Tyr Ile Cys Phe Asn Phe
                    290                 295                 300

Pro Phe Thr His Glu Gln Ser Leu Leu Ser His Leu Arg Phe Phe Pro
305                 310                 315                 320

Trp Asp Ala Asp Val Asp Lys Phe Lys Ala Trp Arg Gln Gly Arg Thr
                    325                 330                 335

Gly Tyr Pro Leu Val Asp Ala Gly Met Arg Glu Leu Trp Ala Thr Gly
                    340                 345                 350

Trp Met His Asn Arg Ile Arg Val Ile Val Ser Ser Phe Ala Val Lys
                    355                 360                 365

Phe Leu Leu Leu Pro Trp Lys Trp Gly Met Lys Tyr Phe Trp Asp Thr
370                 375                 380

Leu Leu Asp Ala Asp Leu Glu Cys Asp Ile Leu Gly Trp Gln Tyr Ile
385                 390                 395                 400

Ser Gly Ser Ile Pro Asp Gly His Glu Leu Asp Arg Leu Asp Asn Pro
                    405                 410                 415

Ala Leu Gln Gly Ala Lys Tyr Asp Pro Glu Gly Glu Tyr Ile Arg Gln
                    420                 425                 430

Trp Leu Pro Glu Leu Ala Arg Leu Pro Thr Glu Trp Ile His His Pro
                    435                 440                 445

Trp Asp Ala Pro Leu Thr Val Leu Lys Ala Ser Gly Val Glu Leu Gly
                    450                 455                 460

Thr Asn Tyr Ala Lys Pro Ile Val Asp Ile Asp Thr Ala Arg Glu Leu
465                 470                 475                 480
```

```
Leu Ala Lys Ala Ile Ser Arg Thr Arg Glu Ala Gln Ile Met Ile Gly
            485                 490                 495

Ala Ala Ala Arg Asp Pro Pro Val Ala Thr Met Val Ser Lys Gly Glu
            500                 505                 510

Glu Asp Asn Met Ala Ile Ile Lys Glu Phe Met Arg Phe Lys Val His
            515                 520                 525

Met Glu Gly Ser Val Asn Gly His Glu Phe Glu Ile Glu Gly Glu Gly
            530                 535                 540

Glu Gly Arg Pro Tyr Glu Gly Thr Gln Thr Ala Lys Leu Lys Val Thr
545                 550                 555                 560

Lys Gly Gly Pro Leu Pro Phe Ala Trp Asp Ile Leu Ser Pro Gln Phe
                565                 570                 575

Met Tyr Gly Ser Lys Ala Tyr Val Lys His Pro Ala Asp Ile Pro Asp
            580                 585                 590

Tyr Leu Lys Leu Ser Phe Pro Glu Gly Phe Lys Trp Glu Arg Val Met
            595                 600                 605

Asn Phe Glu Asp Gly Gly Val Val Thr Val Thr Gln Asp Ser Ser Leu
            610                 615                 620

Gln Asp Gly Glu Phe Ile Tyr Lys Val Lys Leu Arg Gly Thr Asn Phe
625                 630                 635                 640

Pro Ser Asp Gly Pro Val Met Gln Lys Lys Thr Met Gly Trp Glu Ala
                645                 650                 655

Ser Ser Glu Arg Met Tyr Pro Glu Asp Gly Ala Leu Lys Gly Glu Ile
                660                 665                 670

Lys Gln Arg Leu Lys Leu Lys Asp Gly Gly His Tyr Asp Ala Glu Val
                675                 680                 685

Lys Thr Thr Tyr Lys Ala Lys Lys Pro Val Gln Leu Pro Gly Ala Tyr
            690                 695                 700

Asn Val Asn Ile Lys Leu Asp Ile Thr Ser His Asn Glu Asp Tyr Thr
705                 710                 715                 720

Ile Val Glu Gln Tyr Glu Arg Ala Glu Gly Arg His Ser Thr Gly Gly
                725                 730                 735

Met Asp Glu Leu Tyr Lys Thr Glu Pro Gln Glu Glu Ser Glu Glu Glu
            740                 745                 750

Val Glu Glu Pro Glu Glu Arg Gln Gln Thr Pro Glu Val Val Pro Asp
            755                 760                 765

Asp Ser Gly Thr Phe Tyr Asp Gln Ala Val Val Ser Asn Asp Met Glu
770                 775                 780

Glu His Leu Glu Glu Pro Val Ala Glu Pro Glu Asp Pro Glu Pro Glu
785                 790                 795                 800

Glu Pro Glu Gln Glu Pro Val Ser Glu Ile Glu Glu Lys Pro Glu
                805                 810                 815

Pro Val Leu Glu Glu Thr Ala Pro Glu Asp Ala Gln Lys Ser Ser Ser
            820                 825                 830

Pro Ala Pro Ala Asp Ile Ala Gln Thr Val Gln Glu Asp Leu Arg Thr
            835                 840                 845

Phe Ser Trp Ala Ser Val Thr Ser Lys Asn Leu Pro Pro Ser Gly Ala
850                 855                 860

Val Pro Val Thr Gly Ile Pro Pro His Val Val Lys Val Pro Ala Ser
865                 870                 875                 880

Gln Pro Arg Pro Glu Ser Lys Pro Glu Ser Gln Ile Pro Pro Gln Arg
                885                 890                 895
```

```
Pro Gln Arg Asp Gln Arg Val Arg Glu Gln Arg Ile Asn Ile Pro Pro
                900                 905                 910

Gln Arg Gly Pro Arg Pro Ile Glu Ala Gly Glu Gln Gly Asp Ile
        915                 920                 925

Glu Pro Arg Arg Met Val Arg His Pro Asp Ser His Gln Leu Phe Ile
    930                 935                 940

Gly Asn Leu Pro His Glu Val Asp Lys Ser Glu Leu Lys Asp Phe Phe
945                 950                 955                 960

Gln Ser Tyr Gly Asn Val Val Glu Leu Arg Ile Asn Ser Gly Gly Lys
                965                 970                 975

Leu Pro Asn Phe Gly Phe Val Val Phe Asp Asp Ser Glu Pro Val Gln
            980                 985                 990

Lys Val Leu Ser Asn Arg Pro Ile Met Phe Arg Gly Glu Val Arg Leu
        995                 1000                1005

Asn Val Glu Glu Lys Lys Thr Arg Ala Ala Arg Glu Gly Asp Arg
    1010                1015                1020

Arg Asp Asn Arg Leu Arg Gly Pro Gly Pro Arg Gly Gly Leu
    1025                1030                1035

Gly Gly Gly Met Arg Gly Pro Pro Arg Gly Gly Met Val Gln Lys
    1040                1045                1050

Pro Gly Phe Gly Val Gly Arg Gly Leu Ala Pro Arg Gln
    1055                1060                1065

<210> SEQ ID NO 71
<211> LENGTH: 3204
<212> TYPE: DNA
<213> ORGANISM: Artificial Sequence
<220> FEATURE:
<223> OTHER INFORMATION: Synthetic polynucleotide

<400> SEQUENCE: 71
atgaagatgg acaaaaagac tatagtttgg tttagaagag acctaaggat tgaggataat    60
cctgcattag cagcagctgc tcacgaagga tctgttttc  ctgtcttcat ttggtgtcct   120
gaagaagaag acagttttta tcctggaaga gcttcaagat ggtggatgaa acaatcactt   180
gctcacttat ctcaatcctt gaaggctctt ggatctgacc tcactttaat caaaacccac   240
aacacgattt cagcgatctt ggattgtatc cgcgttaccg tgctacaaa  agtcgtcttt   300 aaccacctct atgatcctgt ttcgttagtt cgggaccata ccgtaaagga gaagctggtg   360
gaacgtggga tctctgtgca aagctacaat ggagatctat tgtatgaacc gtgggagata   420
tactgcgaaa agggcaaacc ttttacgagt ttcaattctt actggaagaa atgcttagat   480
atgtcgattg aatccgttat gcttcctcct ccttggcggt tgatgccaat aactgcagcg   540
gctgaagcga tttgggcgtg ttcgattgaa gaactaggc  tggagaatga ggccgagaaa   600
ccgagcaatg cgttgttaac tagagcttgg tctccaggat ggagcaatgc tgataagtta   660
ctaaatgagt tcatcgagaa gcagttgata gattatgcaa agaacagcaa gaaagttgtt   720
gggaattcta cttcactact ttctccgtat ctccatttcg gggaaataag cgtcagacac   780
gttttccagt gtgcccggat gaaacaaatt atatgggcaa agataagaa  cagtgaagga   840 gaagaaagtg cagatctttt tcttagggga atcggtttaa gagagtattc tcggtatata   900
tgtttcaact tcccgtttac tcacgagcaa tcgttgttga tcatcttcg  gttttccct    960 tgggatgctg atgttgataa gttcaaggcc tggagacaag caggaccgg  ttatccgttg  1020 gtggatgccg aatgagaga gctttgggct accggatgga tgcataacag aataagagtg  1080
```

|   |   |   |
|---|---|---|
| attgtttcaa gctttgctgt gaagtttctt ctccttccat ggaaatgggg aatgaagtat | 1140 |
| ttctgggata cacttttgga tgctgatttg gaatgtgaca tccttggctg cagtatatc | 1200 |
| tctgggagta tccccgatgg ccacgagctt gatcgcttgg acaatcccgc gttacaaggc | 1260 |
| gccaaatatg acccagaagg tgagtacata aggcaatggc ttcccgagct tgcgagattg | 1320 |
| ccaactgaat ggatccatca tccatgggac gctcctttaa ccgtactcaa agcttctggt | 1380 |
| gtggaactcg gaacaaacta tgcgaaaccc attgtagaca tcgacacagc tcgtgagcta | 1440 |
| ctagctaaag ctatttcaag aacccgtgaa gcacagatca tgatcggagc agcagcccgg | 1500 |
| gatccaccgg tcgccaccat ggtgagcaag ggcgaggagg ataacatggc catcatcaag | 1560 |
| gagttcatgc gcttcaaggt gcacatggag ggctccgtga acggccacga gttcgagatc | 1620 |
| gagggcgagg gcgagggccg cccctacgag ggcacccaga ccgccaagct gaaggtgacc | 1680 |
| aagggtggcc ccctgccctt cgcctgggac atcctgtccc ctcagttcat gtacggctcc | 1740 |
| aaggcctacg tgaagcaccc cgccgacatc cccgactact tgaagctgtc cttccccgag | 1800 |
| ggcttcaagt gggagcgcgt gatgaacttc gaggacggcg gcgtggtgac cgtgacccag | 1860 |
| gactcctccc tgcaggacgg cgagttcatc tacaaggtga agctgcgcgg caccaacttc | 1920 |
| ccctccgacg gccccgtaat gcagaagaag accatgggct gggaggcctc ctccgagcgg | 1980 |
| atgtaccccg aggacggcgc cctgaagggc gagatcaagc agaggctgaa gctgaaggac | 2040 |
| ggcggccact acgacgctga ggtcaagacc acctacaagg ccaagaagcc cgtgcagctg | 2100 |
| cccggcgcct acaacgtcaa catcaagttg gacatcacct cccacaacga ggactacacc | 2160 |
| atcgtggaac agtacgaacg cgccgagggc cgccactcca ccggcggcat ggacgagctg | 2220 |
| tacaagactg agcctcagga ggagtctgaa gaagaagtag aggaacctga agaaagacag | 2280 |
| caaacacctg aggtggtacc tgatgattct ggaactttct atgatcaggc agttgtcagt | 2340 |
| aatgacatgg aagaacattt agaggagcct gttgctgaac cagagcctga tcctgaacca | 2400 |
| gaaccagaac aagaacctgt atctgaaatc aagaggaaa agcctgagcc agtattagaa | 2460 |
| gaaactgccc ctgaggatgc tcagaagagt tcttctccag cacctgcaga catagctcag | 2520 |
| acagtacagg aagacttgag gacatttttct tgggcatctg tgaccagtaa gaatcttcca | 2580 |
| cccagtggag ctgttccagt tactgggata ccacctcatg ttgttaaagt accagcttca | 2640 |
| cagccccgtc cagagtctaa gcctgaatct cagattccac cacaaagacc tcagcgggat | 2700 |
| caaagagtgc gagaacaacg aataaatatt cctccccaaa ggggacccag accaatccgt | 2760 |
| gaggctggtg agcaaggtga cattgaaccc cgaagaatgg tgagcaccc tgacagtcac | 2820 |
| caactcttca ttggcaacct gcctcatgaa gtggacaaat cagagcttaa agatttcttt | 2880 |
| caaagttatg gaaacgtggt ggagttgcgc attaacagtg gtgggaaatt acccaatttt | 2940 |
| ggttttgttg tgtttgatga ttctgagcct gttcagaaag tccttagcaa caggcccatc | 3000 |
| atgttcagag gtgaggtccg tctgaatgtc gaagagaaga gactcgagc tgccagggaa | 3060 |
| ggcgaccgac gagataatcg ccttcgggga cctggaggcc ctcgaggtgg gctgggtggt | 3120 |
| ggaatgagag gccctccccg tggaggcatg gtgcagaaac caggatttgg agtgggaagg | 3180 |
| gggcttgcgc cacggcagtg ataa | 3204 |

<210> SEQ ID NO 72
<211> LENGTH: 498
<212> TYPE: PRT
<213> ORGANISM: Artificial sequence
<220> FEATURE:
<223> OTHER INFORMATION: Synthetic polypeptide

<400> SEQUENCE: 72

Met Lys Met Asp Lys Thr Ile Val Trp Phe Arg Arg Asp Leu Arg
1               5                   10                  15

Ile Glu Asp Asn Pro Ala Leu Ala Ala Ala His Glu Gly Ser Val
            20                  25                  30

Phe Pro Val Phe Ile Trp Cys Pro Glu Glu Gly Gln Phe Tyr Pro
        35                  40                  45

Gly Arg Ala Ser Arg Trp Trp Met Lys Gln Ser Leu Ala His Leu Ser
    50                  55                  60

Gln Ser Leu Lys Ala Leu Gly Ser Asp Leu Thr Leu Ile Lys Thr His
65                  70                  75                  80

Asn Thr Ile Ser Ala Ile Leu Asp Cys Ile Arg Val Thr Gly Ala Thr
                85                  90                  95

Lys Val Val Phe Asn His Leu Tyr Asp Pro Val Ser Leu Val Arg Asp
            100                 105                 110

His Thr Val Lys Glu Lys Leu Val Glu Arg Gly Ile Ser Val Gln Ser
        115                 120                 125

Tyr Asn Gly Asp Leu Leu Tyr Glu Pro Trp Glu Ile Tyr Cys Glu Lys
    130                 135                 140

Gly Lys Pro Phe Thr Ser Phe Asn Ser Tyr Trp Lys Lys Cys Leu Asp
145                 150                 155                 160

Met Ser Ile Glu Ser Val Met Leu Pro Pro Trp Arg Leu Met Pro
                165                 170                 175

Ile Thr Ala Ala Ala Glu Ala Ile Trp Ala Cys Ser Ile Glu Glu Leu
            180                 185                 190

Gly Leu Glu Asn Glu Ala Glu Lys Pro Ser Asn Ala Leu Leu Thr Arg
        195                 200                 205

Ala Trp Ser Pro Gly Trp Ser Asn Ala Asp Lys Leu Leu Asn Glu Phe
    210                 215                 220

Ile Glu Lys Gln Leu Ile Asp Tyr Ala Lys Asn Ser Lys Val Val
225                 230                 235                 240

Gly Asn Ser Thr Ser Leu Leu Ser Pro Tyr Leu His Phe Gly Glu Ile
                245                 250                 255

Ser Val Arg His Val Phe Gln Cys Ala Arg Met Lys Gln Ile Ile Trp
            260                 265                 270

Ala Arg Asp Lys Asn Ser Glu Gly Glu Glu Ser Ala Asp Leu Phe Leu
        275                 280                 285

Arg Gly Ile Gly Leu Arg Glu Tyr Ser Arg Tyr Ile Cys Phe Asn Phe
    290                 295                 300

Pro Phe Thr His Glu Gln Ser Leu Leu Ser His Leu Arg Phe Phe Pro
305                 310                 315                 320

Trp Asp Ala Asp Val Asp Lys Phe Lys Ala Trp Arg Gln Gly Arg Thr
                325                 330                 335

Gly Tyr Pro Leu Val Asp Ala Gly Met Arg Glu Leu Trp Ala Thr Gly
        340                 345                 350

Trp Met His Asn Arg Ile Arg Val Ile Val Ser Ser Phe Ala Val Lys
    355                 360                 365

Phe Leu Leu Leu Pro Trp Lys Trp Gly Met Lys Tyr Phe Trp Asp Thr
370                 375                 380

Leu Leu Asp Ala Asp Leu Glu Cys Asp Ile Leu Gly Trp Gln Tyr Ile
385                 390                 395                 400

Ser Gly Ser Ile Pro Asp Gly His Glu Leu Asp Arg Leu Asp Asn Pro

```
                    405                 410                 415
Ala Leu Gln Gly Ala Lys Tyr Asp Pro Glu Gly Glu Tyr Ile Arg Gln
                420                 425                 430

Trp Leu Pro Glu Leu Ala Arg Leu Pro Thr Glu Trp Ile His His Pro
            435                 440                 445

Trp Asp Ala Pro Leu Thr Val Leu Lys Ala Ser Gly Val Glu Leu Gly
        450                 455                 460

Thr Asn Tyr Ala Lys Pro Ile Val Asp Ile Asp Thr Ala Arg Glu Leu
465                 470                 475                 480

Leu Ala Lys Ala Ile Ser Arg Thr Arg Gly Ala Gln Ile Met Ile Gly
                485                 490                 495

Ala Ala

<210> SEQ ID NO 73
<211> LENGTH: 822
<212> TYPE: PRT
<213> ORGANISM: Artificial sequence
<220> FEATURE:
<223> OTHER INFORMATION: Synthetic polypeptide

<400> SEQUENCE: 73

Met Lys Met Asp Lys Lys Thr Ile Val Trp Phe Arg Arg Asp Leu Arg
1               5                   10                  15

Ile Glu Asp Asn Pro Ala Leu Ala Ala Ala His Glu Gly Ser Val
            20                  25                  30

Phe Pro Val Phe Ile Trp Cys Pro Glu Glu Glu Gly Gln Phe Tyr Pro
        35                  40                  45

Gly Arg Ala Ser Arg Trp Trp Met Lys Gln Ser Leu Ala His Leu Ser
    50                  55                  60

Gln Ser Leu Lys Ala Leu Gly Ser Asp Leu Thr Leu Ile Lys Thr His
65                  70                  75                  80

Asn Thr Ile Ser Ala Ile Leu Asp Cys Ile Arg Val Thr Gly Ala Thr
                85                  90                  95

Lys Val Val Phe Asn His Leu Tyr Asp Pro Val Ser Leu Val Arg Asp
            100                 105                 110

His Thr Val Lys Glu Lys Leu Val Glu Arg Gly Ile Ser Val Gln Ser
        115                 120                 125

Tyr Asn Gly Asp Leu Leu Tyr Glu Pro Trp Glu Ile Tyr Cys Glu Lys
    130                 135                 140

Gly Lys Pro Phe Thr Ser Phe Asn Ser Tyr Trp Lys Lys Cys Leu Asp
145                 150                 155                 160

Met Ser Ile Glu Ser Val Met Leu Pro Pro Pro Trp Arg Leu Met Pro
                165                 170                 175

Ile Thr Ala Ala Ala Glu Ala Ile Trp Ala Cys Ser Ile Glu Glu Leu
            180                 185                 190

Gly Leu Glu Asn Glu Ala Glu Lys Pro Ser Asn Ala Leu Leu Thr Arg
        195                 200                 205

Ala Trp Ser Pro Gly Trp Ser Asn Ala Asp Lys Leu Leu Asn Glu Phe
    210                 215                 220

Ile Glu Lys Gln Leu Ile Asp Tyr Ala Lys Asn Ser Lys Lys Val Val
225                 230                 235                 240

Gly Asn Ser Thr Ser Leu Leu Ser Pro Tyr Leu His Phe Gly Glu Ile
                245                 250                 255

Ser Val Arg His Val Phe Gln Cys Ala Arg Met Lys Gln Ile Ile Trp
            260                 265                 270
```

```
Ala Arg Asp Lys Asn Ser Glu Gly Glu Ser Ala Asp Leu Phe Leu
        275                 280                 285

Arg Gly Ile Gly Leu Arg Glu Tyr Ser Arg Tyr Ile Cys Phe Asn Phe
    290                 295                 300

Pro Phe Thr His Glu Gln Ser Leu Leu Ser His Leu Arg Phe Pro
305                 310                 315                 320

Trp Asp Ala Asp Val Asp Lys Phe Lys Ala Trp Arg Gln Gly Arg Thr
                325                 330                 335

Gly Tyr Pro Leu Val Asp Ala Gly Met Arg Glu Leu Trp Ala Thr Gly
                340                 345                 350

Trp Met His Asn Arg Ile Arg Val Ile Val Ser Ser Phe Ala Val Lys
            355                 360                 365

Phe Leu Leu Leu Pro Trp Lys Trp Gly Met Lys Tyr Phe Trp Asp Thr
    370                 375                 380

Leu Leu Asp Ala Asp Leu Glu Cys Asp Ile Leu Gly Trp Gln Tyr Ile
385                 390                 395                 400

Ser Gly Ser Ile Pro Asp Gly His Glu Leu Asp Arg Leu Asp Asn Pro
                405                 410                 415

Ala Leu Gln Gly Ala Lys Tyr Asp Pro Glu Gly Glu Tyr Ile Arg Gln
            420                 425                 430

Trp Leu Pro Glu Leu Ala Arg Leu Pro Thr Glu Trp Ile His His Pro
    435                 440                 445

Trp Asp Ala Pro Leu Thr Val Leu Lys Ala Ser Gly Val Glu Leu Gly
    450                 455                 460

Thr Asn Tyr Ala Lys Pro Ile Val Asp Ile Asp Thr Ala Arg Glu Leu
465                 470                 475                 480

Leu Ala Lys Ala Ile Ser Arg Thr Arg Gly Ala Gln Ile Met Ile Gly
                485                 490                 495

Ala Ala Thr Glu Pro Gln Glu Glu Ser Glu Glu Val Glu Glu Pro
            500                 505                 510

Glu Glu Arg Gln Gln Thr Pro Glu Val Val Pro Asp Asp Ser Gly Thr
    515                 520                 525

Phe Tyr Asp Gln Ala Val Val Ser Asn Asp Met Glu Glu His Leu Glu
    530                 535                 540

Glu Pro Val Ala Glu Pro Glu Pro Asp Pro Glu Pro Glu Pro Glu Gln
545                 550                 555                 560

Glu Pro Val Ser Glu Ile Gln Glu Glu Lys Pro Glu Pro Val Leu Glu
                565                 570                 575

Glu Thr Ala Pro Glu Asp Ala Gln Lys Ser Ser Pro Ala Pro Ala
            580                 585                 590

Asp Ile Ala Gln Thr Val Gln Glu Asp Leu Arg Thr Phe Ser Trp Ala
            595                 600                 605

Ser Val Thr Ser Lys Asn Leu Pro Pro Ser Gly Ala Val Pro Val Thr
    610                 615                 620

Gly Ile Pro Pro His Val Val Lys Val Pro Ala Ser Gln Pro Arg Pro
625                 630                 635                 640

Glu Ser Lys Pro Glu Ser Gln Ile Pro Pro Gln Arg Pro Gln Arg Asp
                645                 650                 655

Gln Arg Val Arg Glu Arg Ile Asn Ile Pro Pro Gln Arg Gly Pro
            660                 665                 670

Arg Pro Ile Arg Glu Ala Gly Glu Gln Gly Asp Ile Glu Pro Arg Arg
    675                 680                 685
```

```
Met Val Arg His Pro Asp Ser His Gln Leu Phe Ile Gly Asn Leu Pro
    690                 695                 700
His Glu Val Asp Lys Ser Glu Leu Lys Asp Phe Phe Gln Ser Tyr Gly
705                 710                 715                 720
Asn Val Val Glu Leu Arg Ile Asn Ser Gly Gly Lys Leu Pro Asn Phe
                725                 730                 735
Gly Phe Val Val Phe Asp Asp Ser Glu Pro Val Gln Lys Val Leu Ser
            740                 745                 750
Asn Arg Pro Ile Met Phe Arg Gly Glu Val Arg Leu Asn Val Glu Glu
        755                 760                 765
Lys Lys Thr Arg Ala Ala Arg Glu Gly Asp Arg Asp Asn Arg Leu
770                 775                 780
Arg Gly Pro Gly Gly Pro Arg Gly Gly Leu Gly Gly Met Arg Gly
785                 790                 795                 800
Pro Pro Arg Gly Gly Met Val Gln Lys Pro Gly Phe Gly Val Gly Arg
                805                 810                 815
Gly Leu Ala Pro Arg Gln
            820

<210> SEQ ID NO 74
<211> LENGTH: 1066
<212> TYPE: PRT
<213> ORGANISM: Artificial sequence
<220> FEATURE:
<223> OTHER INFORMATION: Synthetic polypeptide

<400> SEQUENCE: 74

Met Lys Met Asp Lys Lys Thr Ile Val Trp Phe Arg Arg Asp Leu Arg
1               5                   10                  15
Ile Glu Asp Asn Pro Ala Leu Ala Ala Ala His Glu Gly Ser Val
                20                  25                  30
Phe Pro Val Phe Ile Trp Cys Pro Glu Glu Glu Gly Gln Phe Tyr Pro
            35                  40                  45
Gly Arg Ala Ser Arg Trp Trp Met Lys Gln Ser Leu Ala His Leu Ser
    50                  55                  60
Gln Ser Leu Lys Ala Leu Gly Ser Asp Leu Thr Leu Ile Lys Thr His
65                  70                  75                  80
Asn Thr Ile Ser Ala Ile Leu Asp Cys Ile Arg Val Thr Gly Ala Thr
                85                  90                  95
Lys Val Val Phe Asn His Leu Tyr Asp Pro Val Ser Leu Val Arg Asp
                100                 105                 110
His Thr Val Lys Glu Lys Leu Val Glu Arg Gly Ile Ser Val Gln Ser
            115                 120                 125
Tyr Asn Gly Asp Leu Leu Tyr Glu Pro Trp Glu Ile Tyr Cys Glu Lys
    130                 135                 140
Gly Lys Pro Phe Thr Ser Phe Asn Ser Tyr Trp Lys Lys Cys Leu Asp
145                 150                 155                 160
Met Ser Ile Glu Ser Val Met Leu Pro Pro Trp Arg Leu Met Pro
                165                 170                 175
Ile Thr Ala Ala Ala Glu Ala Ile Trp Ala Cys Ser Ile Glu Glu Leu
                180                 185                 190
Gly Leu Glu Asn Glu Ala Glu Lys Pro Ser Asn Ala Leu Leu Thr Arg
            195                 200                 205
Ala Trp Ser Pro Gly Trp Ser Asn Ala Asp Lys Leu Leu Asn Glu Phe
    210                 215                 220
```

```
Ile Glu Lys Gln Leu Ile Asp Tyr Ala Lys Asn Ser Lys Lys Val Val
225                 230                 235                 240

Gly Asn Ser Thr Ser Leu Leu Ser Pro Tyr Leu His Phe Gly Glu Ile
            245                 250                 255

Ser Val Arg His Val Phe Gln Cys Ala Arg Met Lys Gln Ile Ile Trp
        260                 265                 270

Ala Arg Asp Lys Asn Ser Glu Gly Glu Ser Ala Asp Leu Phe Leu
    275                 280                 285

Arg Gly Ile Gly Leu Arg Glu Tyr Ser Arg Tyr Ile Cys Phe Asn Phe
290                 295                 300

Pro Phe Thr His Glu Gln Ser Leu Leu Ser His Leu Arg Phe Phe Pro
305                 310                 315                 320

Trp Asp Ala Asp Val Asp Lys Phe Lys Ala Trp Arg Gln Gly Arg Thr
            325                 330                 335

Gly Tyr Pro Leu Val Asp Ala Gly Met Arg Glu Leu Trp Ala Thr Gly
                340                 345                 350

Trp Met His Asn Arg Ile Arg Val Ile Val Ser Phe Ala Val Lys
            355                 360                 365

Phe Leu Leu Leu Pro Trp Lys Trp Gly Met Lys Tyr Phe Trp Asp Thr
    370                 375                 380

Leu Leu Asp Ala Asp Leu Glu Cys Asp Ile Leu Gly Trp Gln Tyr Ile
385                 390                 395                 400

Ser Gly Ser Ile Pro Asp Gly His Glu Leu Asp Arg Leu Asp Asn Pro
                405                 410                 415

Ala Leu Gln Gly Ala Lys Tyr Asp Pro Glu Gly Glu Tyr Ile Arg Gln
            420                 425                 430

Trp Leu Pro Glu Leu Ala Arg Leu Pro Thr Glu Trp Ile His His Pro
        435                 440                 445

Trp Asp Ala Pro Leu Thr Val Leu Lys Ala Ser Gly Val Glu Leu Gly
    450                 455                 460

Thr Asn Tyr Ala Lys Pro Ile Val Asp Ile Asp Thr Ala Arg Glu Leu
465                 470                 475                 480

Leu Ala Lys Ala Ile Ser Arg Thr Arg Gly Ala Gln Ile Met Ile Gly
            485                 490                 495

Ala Ala Ala Arg Asp Pro Pro Val Ala Thr Met Val Ser Lys Gly Glu
                500                 505                 510

Glu Asp Asn Met Ala Ile Ile Lys Glu Phe Met Arg Phe Lys Val His
    515                 520                 525

Met Glu Gly Ser Val Asn Gly His Glu Phe Glu Ile Glu Gly Glu Gly
    530                 535                 540

Glu Gly Arg Pro Tyr Glu Gly Thr Gln Thr Ala Lys Leu Lys Val Thr
545                 550                 555                 560

Lys Gly Gly Pro Leu Pro Phe Ala Trp Asp Ile Leu Ser Pro Gln Phe
            565                 570                 575

Met Tyr Gly Ser Lys Ala Tyr Val Lys His Pro Ala Asp Ile Pro Asp
            580                 585                 590

Tyr Leu Lys Leu Ser Phe Pro Glu Gly Phe Lys Trp Glu Arg Val Met
        595                 600                 605

Asn Phe Glu Asp Gly Gly Val Val Thr Val Thr Gln Asp Ser Ser Leu
    610                 615                 620

Gln Asp Gly Glu Phe Ile Tyr Lys Val Lys Leu Arg Gly Thr Asn Phe
625                 630                 635                 640

Pro Ser Asp Gly Pro Val Met Gln Lys Lys Thr Met Gly Trp Glu Ala
```

-continued

```
                645                 650                 655
    Ser Ser Glu Arg Met Tyr Pro Glu Asp Gly Ala Leu Lys Gly Glu Ile
                    660                 665                 670

Lys Gln Arg Leu Lys Leu Lys Asp Gly Gly His Tyr Asp Ala Glu Val
                    675                 680                 685

Lys Thr Thr Tyr Lys Ala Lys Lys Pro Val Gln Leu Pro Gly Ala Tyr
                    690                 695                 700

Asn Val Asn Ile Lys Leu Asp Ile Thr Ser His Asn Glu Asp Tyr Thr
    705                 710                 715                 720

Ile Val Glu Gln Tyr Glu Arg Ala Glu Gly Arg His Ser Thr Gly Gly
                    725                 730                 735

Met Asp Glu Leu Tyr Lys Thr Glu Pro Gln Glu Ser Glu Glu
                    740                 745                 750

Val Glu Glu Pro Glu Glu Arg Gln Gln Thr Pro Glu Val Val Pro Asp
                    755                 760                 765

Asp Ser Gly Thr Phe Tyr Asp Gln Ala Val Val Ser Asn Asp Met Glu
                    770                 775                 780

Glu His Leu Glu Glu Pro Val Ala Glu Pro Glu Asp Pro Glu Pro
    785                 790                 795                 800

Glu Pro Glu Gln Glu Pro Val Ser Glu Ile Gln Glu Glu Lys Pro Glu
                    805                 810                 815

Pro Val Leu Glu Glu Thr Ala Pro Glu Asp Ala Gln Lys Ser Ser Ser
                    820                 825                 830

Pro Ala Pro Ala Asp Ile Ala Gln Thr Val Gln Glu Asp Leu Arg Thr
                    835                 840                 845

Phe Ser Trp Ala Ser Val Thr Ser Lys Asn Leu Pro Pro Ser Gly Ala
                    850                 855                 860

Val Pro Val Thr Gly Ile Pro Pro His Val Val Lys Val Pro Ala Ser
    865                 870                 875                 880

Gln Pro Arg Pro Glu Ser Lys Pro Glu Ser Gln Ile Pro Pro Gln Arg
                    885                 890                 895

Pro Gln Arg Asp Gln Arg Val Arg Glu Gln Arg Ile Asn Ile Pro Pro
                    900                 905                 910

Gln Arg Gly Pro Arg Pro Ile Arg Glu Ala Gly Glu Gln Gly Asp Ile
                    915                 920                 925

Glu Pro Arg Arg Met Val Arg His Pro Asp Ser His Gln Leu Phe Ile
                    930                 935                 940

Gly Asn Leu Pro His Glu Val Asp Lys Ser Glu Leu Lys Asp Phe Phe
    945                 950                 955                 960

Gln Ser Tyr Gly Asn Val Val Glu Leu Arg Ile Asn Ser Gly Gly Lys
                    965                 970                 975

Leu Pro Asn Phe Gly Phe Val Val Phe Asp Asp Ser Glu Pro Val Gln
                    980                 985                 990

Lys Val Leu Ser Asn Arg Pro Ile  Met Phe Arg Gly Glu  Val Arg Leu
                    995                1000                1005

Asn Val  Glu Glu Lys Lys Thr  Arg Ala Ala Arg Glu  Gly Asp Arg
                   1010                1015                1020

Arg Asp  Asn Arg Leu Arg Gly  Pro Gly Gly Pro Arg  Gly Gly Leu
                   1025                1030                1035
```

```
Gly Gly  Gly Met Arg Gly Pro  Pro Arg Gly Gly Met  Val Gln Lys
    1040                 1045              1050

Pro Gly  Phe Gly Val Gly Arg  Gly Leu Ala Pro Arg  Gln
    1055                 1060              1065
```

FUSION PROTEIN AND NUCLEIC ACID MOLECULE FOR LIGHT-DEPENDENT STRESS GRANULE ASSEMBLY

BACKGROUND

Stress granules are non-membranous assemblies of mRNA and protein (mRNP) that form when translation initiation is limiting, which occurs during many stress responses including glucose starvation, heat stress, osmotic stress, and oxidative stress. Stress granules are thought to influence mRNA function, localization, and to affect signaling pathways. Normally, stress granule formation is a dynamic, reversible process that relies on particular RNA-binding proteins that harbor self-interacting domains of low sequence complexity (LC domains). However, a disturbance in the assembly and/or dynamics of these structures is closely associated with a wide array of human diseases, including cancer, infectious diseases and neurodegenerative diseases such as Alzheimer's, Huntington's, Parkinson's, frontotemporal dementia (FTD), and amyotrophic lateral sclerosis (ALS).

The GTPase-Activating Protein SH3 Domain-Binding Proteins (G3BPs), G3BP1, G3BP2a and G3BP2b, are important regulators of stress granule dynamics. G3BP1 has been reported to play a critical role in the secondary aggregation step of stress granule formation, and has been used as a reliable marker of stress granules. The misregulation of stress granule dynamics has been reported in many forms of ALS. G3BP1 is critical for neuronal survival since G3BP1 null mice demonstrate widespread neuronal cell death in the central nervous system. Although single knockout of either G3BP1 or G3BP2 partially reduces the number of stress granule-positive cells induced under stress conditions, the knockout of both genes eliminates stress granule assembly.

To facilitate the analysis of G3BP function, G3BP1 has been fused to, e.g., Green Fluorescent Protein (GFP). However, G3BP fusion proteins for selectively inducing stress granule formation have not been described. Rather, conventional approaches of using sodium azide, arsenite, osmotic (e.g., sorbitol), hypoxia, and heat shock are disclosed for stimulating stress granule assembly. Notably, these toxic conditions confound studies for assessing the role of stress granules in diseases such as ALS, FTD, and cancer. Therefore, there is a need in the art for a noninvasive method of inducing stress granule formation in cells.

SUMMARY OF THE INVENTION

The present invention provides a nucleic acid molecule encoding a fusion protein composed of (a) plant cryptochrome (CRY) at the amino terminus of the fusion protein, and (b) GTPase-Activating Protein SH3 Domain-Binding Protein (G3BP). In some embodiments, the CRY lacks the Cryptochrome C-terminal Extension (CCE) domain and has an amino acid sequence of, e.g., SEQ ID NO:59, SEQ ID NO:65 or SEQ ID NO:72. In other embodiments, the G3BP lacks an N-terminal Nuclear Transport Factor 2 (NTF2)-like domain and has the amino acid sequence of, e.g., SEQ ID NO:25 or SEQ ID NO:28. In further embodiments, the fusion protein includes a reporter protein. In yet other embodiments, the fusion protein has the amino acid sequence of SEQ ID NO:68, SEQ ID NO:70 or SEQ ID NO:74. A vector containing the nucleic acid molecule and cell harboring the vector are also provided, as is a method for inducing stress granule formation in a cell by expressing the nucleic acid molecule in a cell and exposing the cell to light in the range of 365 to 550 nm.

BRIEF DESCRIPTION OF THE DRAWINGS

FIGS. 1A-1B depict an amino acid sequence alignment of human G3BP1 (P1), G3BP2a (P2A) and G3BP2b (P2B) proteins. N-terminal Nuclear Transport Factor 2 (NTF2)-like domains are underlined. Boxes indicate ribonucleoprotein (RNP) motifs RNP1 and RNP2 of the RNA Recognition Motif (RRM). "*" indicate arginine-glycine-rich boxes.

FIGS. 2A-2C depict an amino acid sequence alignment of rat (*Rattus norvegicus*), mouse (*Mus musculus*), cow (*Bos taurus*), monkey (*Macaca mulatta*), human (*Homo sapiens*), chimp (*Pan troglodytes*) and dog (*Canis lupus*) G3BP1 proteins. NTF2-like domains are underlined. "*" indicates identical residues across species. ":" and "." indicate conserved residues and "-" indicates a gap.

FIGS. 3A-3D depict an amino acid sequence alignment of rat (*Rattus norvegicus*), mouse (*Mus musculus*), cow (*Bos Taurus*), monkey (*Macaca mulatta*), human (*Homo sapiens*), chimp (*Pan troglodytes*) and dog (*Canis lupus*) G3BP2a ("A") and G3BP2b ("B") proteins. NTF2-like domains are underlined. "*" indicates identical residues across species. ":" and "." indicate conserved residues and "-" indicates a gap.

FIGS. 4A-4F depict an amino acid sequence alignment of cryptochrome (CRY) proteins from plants. OS1 and OS2, *Oryza sativa* CRY1 and CRY2, respectively; SB1 and SB2, *Sorghum bicolor* CRY1 and CRY2, respectively; AT1 and AT2, *Arabidopsis thaliana* CRY1 and CRY2, respectively; LE1, *Lycopersicon* esculentum CRY1; GM1 and GM2, *Glycine max* CRY1 and CRY2, respectively; and PP1, *Physcomitrella* patens CRY1. "*" indicates identical residues across species. ":" and "." indicate conserved residues and "-" indicates a gap. The characters "F" and "M" above sequences indicate residues known to interact with flavin adenine dinucleotide (FAD) or methenyltetrahydrofolate (MTHF), respectively. "$" indicates trp-triad residues and filled bar indicates the approximate junction between photolyase homology region (PHR) and the Cryptochrome C-terminal Extension (CCE) domains.

DETAILED DESCRIPTION OF THE INVENTION

Analysis of stress granules in disease is confounded by the conditions conventionally required to induce stress granule formation. A rapid, uniform and non-toxic approach for induction of stress granules has now been identified. In accordance with this invention, G3BP is fused with a cryptochrome dimerization domain, thereby providing stress granule formation in response to a brief pulse of blue light. Accordingly, this invention is a fusion protein composed of a plant cryptochrome (CRY) and G3BP, as well as a method for inducing stress granule formation in a cell by exposing a cell expressing the fusion protein to light.

As is conventional in the art, the term "fusion protein" refers to a protein composed of a plurality of polypeptide components, that while typically unjoined in their native state, are joined by their respective amino and carboxyl termini through a peptide linkage to form a single continuous polypeptide. Fusion proteins may be a combination of two, three or even four or more different proteins. The term fusion protein includes, but is not limited to, a fusion protein with two or three heterologous amino acid sequences; immunologically tagged proteins; and fusion proteins with detectable fusion partners, e.g., reporter proteins such as a fluorescent protein, β-galactosidase, luciferase, and the like. Ideally, a fusion protein comprises or consists essentially of all or a portion of G3BP that is capable of mediating stress granule formation, directly or indirectly linked at its N-terminus to a plant cryptochrome. In certain embodiments, the N-terminal NTF2-like domain of G3BP is replaced or substituted with a plant cryptochrome; or a plant cryptochrome and a reporter protein.

It has been shown that knockout of either G3BP1 or G3BP2 reduces stress granule formation and that knockout of both G3BP1 and G3BP2 eliminates stress granule assembly (Matsuki, et al. (2013) Genes Cells 18(2):135-46). Accordingly, for the purposes of this invention "GTPase-Activating Protein SH3 Domain-Binding Protein" or "G3BP" is intended to include the proteins G3BP1, G3BP2a, and G3BP2b. G3BP2a and G3BP2b are encoded by the same gene and represent alternatively spliced isoforms that differ by an insertion of 99 base pairs in the central region of G3BP2a giving rise to the presence of five SH3-binding domains in G3BP2b compared to four domains in the G3BP2a protein. The amino acid sequence of wild-type human G3BP1 (SEQ ID NO:1) is known in the art and available under GENBANK Accession Nos. NP_005745 and NP_938405 (See FIG. 1A-1B). Likewise, the amino acid sequences of wild-type human G3BP2a (SEQ ID NO:2) and human G3BP2b (SEQ ID NO:3) are known in the art and available under GENBANK Accession Nos. NP_036429 and NP_987100, respectively (See FIG. 1A-1B).

G3BP1, G3BP2a, and G3BP2b are highly conserved across species (see FIG. 2A-2C and FIG. 3A-3D). For example, there is 65% identity and 74% sequence similarity between G3BP1 and G3BP2a proteins in mice and humans. In this respect, this invention also includes the use of both human and non-human G3BP proteins in the fusion protein described herein. In particular, this invention includes G3BP proteins from various animals including chimpanzee, mouse, rat, and the like. Preferably, the animal is a mammal. Examples of wild-type mammalian G3BP proteins are known in the art and available under the GENBNAK Accession Nos. provided in Table 1.

TABLE 1

| Animal | GENBANK Accession No. | |
| --- | --- | --- |
|  | G3BP1 | G3BP2 |
| Pan troglodytes | JAA44555 | JAA39401 |
|  |  | JAA39402 |
| Macaca mulatta | NP_001248671 | AFE81132 |
|  |  | NP_001248697 |
| Canis lupus | XP_867372 | XP_022269103 |
|  |  | XP_022269104 |
| Mus musculus | NP_038744 | NP_001074266 |
|  |  | NP_001074265 |
| Bos taurus | NP_001032700 | NP_001039920 |
|  |  | XP_015327172 |
| Rattus norvegicus | NP_598249 | EDL88604 |
|  |  | NP_001014011 |

Exemplary mammalian G3BP1 and G3BP2 proteins of use in the fusion protein of this invention are presented in FIG. 2A-2C and FIG. 3A-3D, respectively, and include a G3BP1 of SEQ ID NO:1, 4, 5, 6, 7, 8 or 9 or a G3BP2 of SEQ ID NO:2, 3, 10, 11, 12, 13, 14, 15, 16, 17, 18, 19, 20 or 21. In particular embodiments, the fusion protein of the invention includes a human G3BP1 protein of SEQ ID NO:1, or human G3BP2 protein of SEQ ID NO:2, 3 or 22.

Wild-type G3BP proteins feature a highly conserved N-terminal Nuclear Transport Factor 2 (NTF2)-like domain. The NTF2-like domain has been implicated in several G3BP functions including dimerization and stress granule assembly (Tourriére, et al. (2003) J. Cell Biol. 160:823-831). In addition, the G3BP NTF2-like domain has been suggested to play a role in nuclear shuttling. This suggestion is based on findings of G3BP1 and G3BP2 both in the cytoplasm and in the nucleus (Barnes, et al. (2002) Cancer Res. 62:1251-1255; French, et al. (2002) Histochem. J. 34:223-231). Also, NTF2-like domain deletion mutants of G3BP2a have been shown to be exclusively localized to the cytoplasm (Prigent, et al. (2000) J. Biol. Chem. 275:36441-36449). In accordance with certain embodiments of this invention, the NTF2-like domain of G3BP is absent in the instant fusion protein. Accordingly, "G3BP lacking an NTF2-like domain" refers to the deletion or removal of the NTF2-like domain of G3BP. As is known in the art, the NTF2-like domain of G3BP is located within the N-terminal ~140 amino acid residues of G3BP (see FIG. 1A-1B). Accordingly, "G3BP lacking an NTF2-like domain" refers to deletion of, e.g., residues 1-139, 7-135, 11-134, 1-142, 7-142, 11-142 or 11-139 of a wild-type G3BP1, G3BP2a or G3BP2b protein.

G3BP C-termini have two motifs traditionally associated with RNA binding. These include a canonical RNA Recognition Motif (RRM) and loosely conserved RGG (arginine-glycine rich) boxes. The RRM domain is composed of two short, loosely conserved motifs, RNP1 (LFIGNL; SEQ ID NO:23) and RNP2 (PNFGFVVF; SEQ ID NO:24), separated by 30 to 33 amino acid residues and has been shown to bind to RNA molecules (U.S. Pat. No. 8,268,550; Pin, et al. (2017) Acta Veterinaria et Zootechnica Sinica 48(3):515-521). RGG domains (RGP, RGG, GGG and GRG) located at the C-terminus of G3BP are often found in RNA-binding proteins and may confer cooperative binding to RRM motifs. Therefore, in accordance with the fusion protein of this invention, a "G3BP lacking an NTF2-like domain" refers to a G3BP having an RNA Recognition Motif comprising the amino acid sequence of SEQ ID NO:23 and SEQ ID NO:24, and five or six arginine-glycine rich boxes. An exemplary human G3BP1 protein lacking an NTF2-like domain, which is of particular use in the fusion protein of this invention is provided under SEQ ID NO:25. Exemplary human G3BP2 proteins lacking an NTF2-like domain, which are of particular use in the fusion protein of this invention are provided under SEQ ID NOs:26, and 28. Exemplary non-human mammalian G3BP1 proteins lacking an NTF2-like domain are provided under SEQ ID NOs:29, 30, 31, 32, 33, 34 and 35. Exemplary non-human mammalian G3BP2 proteins lacking an NTF2-like domain are provided under SEQ ID NOs:35, 36, 37, 38, 39, 40, 41, 42, 43, 44, 45 and 46. In particular embodiments, the fusion protein of the invention includes a G3BP1 protein of SEQ ID NO:25.

Notably, it has been shown that G3BP1 lacking the N-terminal NTF2-like domain does not induce stress granule formation (Takahashi, et al. (2013) Mol. Cell Biol. 33:815-829; Tourriere, et al. (2003) J. Cell Biol. 160:823-31). However, as described herein, a fusion protein including (a) a cryptochrome at the amino terminus and (b) a G3BP lacking an NTF2-like domain at the carboxy terminus restores stress granule formation and imparts light-sensitivity to G3BP. Similarly, fusion of a cryptochrome to a full length G3BP retains stress granule formation and imparts light-sensitivity to G3BP. Accordingly, the fusion protein of this invention includes a cryptochrome, in particular a plant cryptochrome, for providing light-sensitive G3BP-mediated stress granule formation.

"Cryptochrome" or "CRY" is an ultraviolet-A/blue light photoreceptor found in plants, insects, fish, amphibians, mammals and fungi. Cryptochromes are composed of two major domains, the N-terminal PHR (for Photolyase-Homologous Region) domain of about 500 residues, and the C-terminal extension CCE (for Cryptochrome C-terminal Extension) domain, which varies in length (FIG. 4A-4F). The PHR domain is required for chromophore-binding and homo-dimerization (Sang, et al. (2005) *Plant Cell* 17:1569-84; Yu, et al. (2007) *Proc. Natl. Acad. Sci. USA* 104:7289-94), whereas CCE is an effector domain of cryptochrome (Yang, et al. (2000) *Cell* 103:815-827; Wang, et al. (2001) *Science* 294:154-158).

For the purposes of this invention, "cryptochrome" or "CRY" is intended to include the proteins CRY1, CRY2 and CRY3. While CRY proteins from fungi, insects or animals can be used in the fusion protein of this invention, preferably the CRY protein is a plant CRY protein. Plant CRY proteins include, but are not limited to, CRY1 and CRY2 proteins from *Chlamydomonas reinhardtii, Physcomitrella patens, Adiantum capillus-veneris, Arabidopsis thaliana, Lycopersicon esculentum, Sorghum bicolor, Oryza sativa, Glycine max* and *Sinapis alba* (Lin & Todo (2005) *Genome Biology* 6:220)(Table 2).

TABLE 2

| Plant | GENBANK Accession No. | |
|---|---|---|
| | CRY1 | CRY2 |
| *Physcomitrella patens* | XP_001751763 | — |
| *Arabidopsis thaliana* | NP_567341 | NP_171935 |
| *Lycopersicon esculentum* | NP_001234667 | — |
| *Sorghum bicolor* | XP_002436988 | AAV97867 |
| *Oryza sativa* | BAD17529 | BAD23780 |
| *Glycine max* | NP_001242152 | NP_001235220 |

CRY1 = DSPD, PHLL1;
CRY2 = KIAA0658, PHLL2.

The CRY PHR domain is composed of sequential α/β subdomains and α-helix subdomains, large parts of which cover the chromophore binding sites of 5,10-methenyltetrahydrofolate (MTHF) and flavin adenine dinucleotide (FAD). In addition to the roles of binding chromophores to perceive light and get photoactivated, the PHR domain mediates self-dimerization and blue light-induced autophosphorylation, both of which are essential for CRY activity. The FAD-binding pocket of cryptochrome is the most conserved region within the PHR domain (see FIG. 4C-4D). In addition, W324, W377, and W400 of the trp-triad residues, which are required for photoreduction, are also conserved (see FIG. 4C-4D). Accordingly, in certain embodiments, the CRY used in the fusion protein of this invention includes a PHR domain required for binding chromophores, self-dimerization and blue light-induced autophosphorylation.

Although the CCE domains of plant cryptochromes share little sequence similarity with the CCE domains of animal cryptochromes, plant cryptochromes from different species do share a common sequence DAS motif in their CCE's (Lin & Shalitin (2003) *Annu. Rev. Plant Biol.* 54:81469-496). Cryptochromes from liverwort, moss, and fern all possess various versions of the DAS motif (Lin & Shalitin, 2003). Computational analyses of secondary structures of CCEs from *Arabidopsis* and human cryptochromes predict that this domain is intrinsically unstructured. The unstructured nature of the CCE domain of *Arabidopsis* CRY1 (the C-terminal 180 residues; see FIG. 4E-4F) has been confirmed by the circular dichroism and NMR analyses. It has been suggested that the CCE domains of cryptochromes act as effector modules by undergoing light-induced folding or unfolding to alter their interaction with the PHR domain and to change the overall conformation of the photoreceptors.

It has now been found that a CRY protein lacking a CCE domain is sufficient to facilitate light-dependent, G3BP-mediated stress granule formation. Therefore, the CRY protein used in the fusion protein of this invention may be a full length CRY protein (e.g., SEQ ID NO:47, 48, 49, 50, 51, 52, 53, 54, 55 or 56) or more particularly a truncated CRY protein lacking a CCE domain. In particular embodiments, the CRY of the fusion protein of this invention comprises, consists essentially of, or consists of the N-terminal PHR domain of a CRY protein. In other embodiments, the CRY protein is an Arabidopsis CRY2 protein with an E490G mutation. Exemplary CRY proteins lacking a CCE domain are provided in SEQ ID NO:57, 58, 59, 60, 61, 62, 63, 64, 65, 66 and 72. In particular embodiments, the fusion protein of the invention includes a CRY2 protein of SEQ ID NO:59, SEQ ID NO:65 or SEQ ID NO:72. In certain embodiments, the fusion protein of this invention has the amino acid sequence set forth in SEQ ID NO:67 or SEQ ID NO:73.

In some embodiments, the fusion protein of this invention also includes a reporter protein. As is conventional in the art, a reporter protein is a protein that can allow for the detection, quantification, localization and/or isolation of a protein of interest. Ideally, a reporter protein of use in this invention is a fluorescent protein or a combination of fluorescent proteins. The fluorescent protein can be or include an ultraviolet fluorescent protein, a blue fluorescent protein, a cyan fluorescent protein, a green fluorescent protein, a yellow fluorescent protein, an orange fluorescent protein, a red fluorescent protein, a far-red fluorescent protein, a near infrared fluorescent protein, an infrared fluorescent protein, a sapphire-type fluorescent protein, a long Stokes shift fluorescent protein, a switchable fluorescent protein, or any combination thereof. In some embodiments, the fluorescent protein has an excitation wavelength that overlaps with the response range of the CRY protein of the instant fusion protein. In other embodiments, the fluorescent protein has an excitation wavelength that does not overlap with the response range of the CRY protein of the instant fusion protein. Notably, CRYs are active principally in the range of 365 to 550 nm, with a maximal response in the range of 390 to 480 nm. Examples of suitable fluorescent proteins are provided in Table 3.

TABLE 3

| Fluorescent Protein | Excitation max (nm) | Emission max (nm) |
|---|---|---|
| Blue Fluorescent Proteins | | |
| Azurite | 384 | 450 |
| EBFP | 383 | 445 |
| EBFP2 | 383 | 448 |
| Y66H | 382 | 459 |
| Cyan Fluorescent Proteins | | |
| ECFP | 439 | 476 |
| AmCyan1 | 458 | 489 |

TABLE 3-continued

| Fluorescent Protein | Excitation max (nm) | Emission max (nm) |
|---|---|---|
| Cerulean | 433 | 475 |
| CyPet | 435 | 477 |
| mTFP1 | 462 | 492 |
| TagCFP | 458 | 480 |
| Green Fluorescent Proteins | | |
| AcGFP | 480 | 505 |
| Azami Green | 492 | 505 |
| Emerald | 487 | 509 |
| GFP | 395 | 509 |
| Stemmer | 395 | 509 |
| TagGFP | 482 | 505 |
| T-Sapphire | 399 | 511 |
| TurboGFP | 482 | 502 |
| ZsGreen | 493 | 505 |
| Yellow Fluorescent Proteins | | |
| EYFP | 514 | 527 |
| mBanana | 540 | 553 |
| mCitrine | 516 | 529 |
| TagYFP | 508 | 524 |
| Topaz | 514 | 527 |
| Venus | 515 | 528 |
| YPet | 517 | 530 |
| Orange Fluorescent Proteins | | |
| RFP | 558 | 583 |
| Tomato | 554 | 581 |
| Kusbira Orange | 548 | 559 |
| mOrange | 548 | 562 |
| mTangerine | 568 | 585 |
| Red Fluorescent Proteins | | |
| AsRed2 | 576 | 592 |
| HcRed1 | 588 | 618 |
| JRed | 584 | 610 |
| mApple | 568 | 592 |
| mCherry | 587 | 610 |
| mPlum | 590 | 649 |
| mRaspberry | 598 | 625 |
| mRFP1 | 584 | 607 |
| mRuby | 558 | 605 |
| mStrawberry | 574 | 596 |

Reporter proteins other than fluorescent reporter proteins can be employed in addition to or in the alternative to fluorescent reporter proteins. For example, antibodies, antibody fragments, peptide tags (e.g., His6x, FLAG), enzymes, or the like, or any combination thereof can be used. The reporter protein can be fused (in-frame) to the N-terminus (e.g., Reporter-CRY-G3BP) or C-terminus (e.g., CRY-G3BP-Reporter) of the fusion protein or be inserted between the CRY and G3BP proteins (e.g., CRY-Reporter-G3BP). Exemplary fusion proteins including a reporter protein are set forth in SEQ ID NO:68, SEQ ID NO:70 and SEQ ID NO:74.

The fusion protein of this invention can be prepared by conventional recombinant DNA methods. In general, this includes isolating the nucleic acid molecule encoding the G3BP and CRY proteins of interest (e.g., by restriction enzyme digestion or PCR amplification); inserting the coding sequence of G3BP and CRY (in frame) into a suitable vector, e.g., an expression vector that includes the requisite sequences for protein expression (e.g., promoter, terminator, etc.); and introducing the vector into a suitable host cell, e.g., to express the fusion protein. In certain embodiments, this invention provides a nucleic acid molecule encoding a CRY-G3BP fusion protein, a vector including said nucleic acid molecule and a host cell harboring said vector.

The terms "nucleic acid molecule" and "polynucleotide" are used interchangeably and refer to a polymeric form of nucleotides of any length, either deoxyribonucleotides or ribonucleotides, or analogs thereof. Non-limiting examples of nucleic acid molecules include a gene, a gene fragment, exons, introns, messenger RNA (mRNA), transfer RNA, ribosomal RNA, cDNA, recombinant polynucleotides, branched polynucleotides, plasmids, vectors, isolated DNA of any sequence, control regions, isolated RNA of any sequence, nucleic acid probes, and primers. The nucleic acid molecule may be linear or circular.

In particular, the nucleic acid molecule of the invention encodes the fusion protein disclosed herein. A "coding sequence" or a sequence that "encodes" a selected polypeptide, is a nucleic acid molecule which can be transcribed (in the case of DNA) and translated (in the case of mRNA) into a polypeptide, for example, in a host cell when placed under the control of appropriate regulatory sequences (or "control elements"). The boundaries of the coding sequence are typically determined by a start codon at the 5' (amino) terminus and a translation stop codon at the 3' (carboxy) terminus. A coding sequence can include, but is not limited to, cDNA from mRNA, genomic DNA sequences, and synthetic DNA sequences. A transcription termination sequence may be located 3' to the coding sequence. Other "control elements" may also be associated with a coding sequence. A DNA sequence encoding a polypeptide can be optimized for expression in a selected cell by using the codons preferred by the selected cell to represent the DNA copy of the desired polypeptide coding sequence. An exemplary coding sequence is set forth herein in SEQ ID NO:69 and 71.

To facilitate amplification and expression, the nucleic acid molecule encoding the fusion protein disclosed herein may be inserted into a vector. A "vector" is capable of transferring gene sequences to a host cell. Typically, "vector," "expression vector," and "gene transfer vector," mean any nucleic acid construct capable of directing the expression of a gene of interest and which can transfer gene sequences to host cells, which can be accomplished by genomic integration of all or a portion of the vector, or transient or inheritable maintenance of the vector as an extrachromosomal element. Thus, the term includes cloning, and expression vehicles, as well as integrating vectors.

A number of expression vectors for the expression of a nucleic acid molecule encoding a fusion protein of the invention are known in the art. Different examples of expression vectors are available for expression of the fusion protein in mammalian cells, insect cells, yeast cells, and bacterial cells. For example, the pEGFP-C1 mammalian vector (Invitrogen) contains a CMV promoter sequence, a nucleic acid sequence encoding green fluorescence protein, a multiple cloning site for insertion of nucleic acid sequence encoding the fusion protein. Additional non-limiting examples of publicly-available mammalian expression vectors include constitutive expression vectors GATEWAY® pDEST™26, pDEST™27, pDEST™40, and pDEST™47 (Invitrogen); adenoviral expression vectors (e.g., pAd/CM/V5-Dest GATEWAY® Vector Kit (Invitrogen); episomal expression vectors pCEP4 and pEBNA DEST (Invitrogen); lentiviral expression vectors (e.g., VIRAPOWER™ Bsd;

Invitrogen); and regulated expression vectors GATEWAY® pT-REX™-DEST 30 and pT-REX™-DEST 31 (Invitrogen). Non-limiting examples of bacterial expression vectors include GATEWAY® vectors pDEST™14, pDEST™15, pDEST™17, pDEST™24, pET-DEST42; pEM7/Bsd; pEM7/Zeo; pRSET A, B, & C; pRSET-BFP; pRSET-CFP; pRSET-EmGFP; pTrcHis A, B, & C; and pTrcHis2 A, B, & C vectors (Invitrogen). Non-limiting examples of yeast expression vectors include pAO815; pGAPZ A, B, & C; pPIC3.5K; pPIC9K; pTEFl/Bsd; pTEFl/Zeo; pYC2/CT; pYES2; pYES2/CT; and pYES3/CT (Invitrogen). Non-limiting examples of insect and baculovirus expression vectors include GATEWAY® vectors pDEST™10, pDEST™20, pDEST™8, pMT-DEST™48; pAC5.1/V5-His A, B, & C; pFastBac Dual; and pIB/V5-His-DEST (Invitrogen).

The expression vectors used to express a fusion protein may include one or more (e.g., 1, 2 or 3) constitutive promoter sequences and/or one or more (e.g., 1, 2 or 3) inducible promoter sequences. Non-limiting examples of constitutive promoter sequences include bacterial promoters (e.g., *E. coli* $a^{70}$, $\sigma^8$, $\sigma^{32}$, or $\sigma^{54}$ promoters; *B. subtilis* $\sigma^A$ or $\sigma^B$ promoters; T7 RNA polymerase-based promoters; and a bacteriophage SP6 promoter), yeast promoters (e.g., pCyc, pAdh, pSte5, ADH1, cyc70, cyc43, cyc28, pPGK1, pCYC, and GPD (TDH3) promoters), and mammalian promoters (e.g., cytomegalovirus immediate early gene-based promoters, SV40 early promoter, and Rous sarcoma virus promoter). Non-limiting examples of inducible promoter sequences include alcohol dehydrogenase I gene promoters, tetracycline-responsive promoter systems, glucocorticoid receptor promoters, estrogen receptor promoter, ecdysone receptor promoters, metallothionein-based promoters, and T7-polymerase based promoters. Several different mammalian expression vectors available that allow for the inducible expression of a nucleic acid sequence (e.g., a fusion protein) are publicly available including pTET-ON Advanced (Clontech), pERV3 (Stratagene), pNEBR-Rl (New England Bio-Labs), and pCMV5-CymR (Qbiogene).

One or more nucleic acid molecules encoding a fusion protein of the invention may be introduced into a transgenic cell or host cell using methods known in the art, including, but not limited to electroporation, microinjection, lipid-mediated transfection (e.g., liposomal delivery systems), calcium phosphate-mediated transfection, DEAE dextran-mediated transfection, DNA transfection by biolistics, DNA transfection mediated by polybrene, and virus-mediated transduction.

Any type of cell or host cell can be used in accordance with this invention, including, but not limited to, a mammalian cell (e.g., a human, mouse, rat, monkey, or rabbit cell), a yeast cell, a bacterial cell, or an insect cell. A mammalian cell that expresses a fusion protein of the invention may include a primary cell such as a fibroblast, an epithelial cell, an endothelial cell, a smooth muscle cell, a hepatocyte, a kidney cell, and a lymphocyte. Additional examples of suitable mammalian cell lines include COS-7 monkey kidney cells, CV-1, L-cells, C127 cells, 3T3 cells, Chinese hamster ovary (CHO) cells, human embryonic kidney (HEK) cells, HeLa cells (e.g., HeLa S3 or HeLa Kyoto cells), 293 cells, 293T cells, N2A, U2OS, HUH7 and BHK cell lines. A variety of cells are commercially available for the expression of recombinant proteins, including, but not limited to, bacterial competent cells (e.g., BL21-AI™ ONE SHOT® cells, ONE SHOT®-BL21(DE3) cells, and ONE SHOT®-BL21(DE3) pLysE cells, (Invitrogen); and mammalian competent cells (e.g., MAXPAK Competent HeLa S3 cells, MAXPAK Competent CHO-K1 cells, and MAXPAK Competent HEK 293 cells (Genlantis)).

A transgenic cell that contains a nucleic acid molecule encoding the fusion protein of this invention may a stable cell line (e.g., a cell that has integrated the nucleic acid molecule encoding the fusion protein into one or more of its chromosomes). Alternatively, a transgenic cell may contain the nucleic acid molecule encoding the fusion protein in a plasmid or on an artificial chromosome, which replicates independently of the chromosomes of the cell.

A transgenic mammal may also be produced from a transgenic cell containing a nucleic acid molecule encoding the fusion protein of this invention. A transgenic animal may be a mouse, a rat, a bovine, an ovine, a caprine, a porcine, a horse, a rabbit, or a monkey. Methods for the production of a transgenic mammal from a transgenic cell are known in the art and include, without limitation, methods that require the transfer of a nucleus from a transgenic cell to an enucleated oocyte and/or the microinjection of one or more nucleic acids (e.g., a plasmid or an artificial chromosome) encoding the fusion proteins into an oocyte. Such genetically manipulated oocytes may then be transferred into a recipient female host to produce a transgenic mammal.

To facilitate the analysis of stress granule formation, this invention also provides a kit containing a nucleic acid, vector, and/or host cell encoding a fusion composed of a plant CRY at the amino terminus, and a G3BP. The kit may further contain materials describing the kit components and instructions for using the kit components. In addition, the kit can include reagents to, e.g., insert the nucleic acid molecule into a vector (e.g., restriction enzymes or ligase), introduce the vector into a host cell (e.g., transfection reagents), and/or amplify cells (e.g., growth medium).

As is known in the art, stress granules are dense aggregates in the cytosol composed of proteins and RNAs that appear when the cell is under stress. Stress granules contain polyadenylated RNA, small ribosomal subunits, translation initiation factors (eIF3, eIF4E, eIF4G), and RNA binding proteins (RBPs) such as TIA-1, HuR, PABP, G3BP and TTP that form following eIF2α phosphorylation. Given the light-responsiveness of the fusion protein disclosed herein, this invention also provides a method for inducing stress granule formation in a cell expressing a CRY-G3BP fusion protein (e.g., a fusion protein composed of a plant CRY at the amino terminus, and a G3BP lacking an N-terminal NTF2-like domain) in a cell and exposing the cell expressing the fusion protein to light so that stress granule formation in a cell is induced. In some embodiments, the cell is exposed to light in the range of 365 to 550 nm, or more preferably in the range of 390 to 480 nm.

This invention is of particular use in the analysis of stress granules involvement in diseases such as neurodegenerative disease, cancer and infectious disease. In this respect, the protein, nucleic acids, vectors, cells and method of this find use as basic research tools as well as in screening assays for compounds that modulate stress granule formation, assembly, disassembly, or nucleation; and/or ameliorate or treat a stress granule-related disease or disorder. For example, a cell expressing a fusion protein of this invention is treated with a library of compounds, exposed to blue light to induce stress granule assembly and formation/localization of stress granules is measured to determine whether one or more compounds modulate the assembly or location of stress granules. Localization of the fusion protein may be measured using, e.g., an antibody that specifically binds CRY or G3BP of the fusion protein or by fluorescence microscopy. An increase in the number of foci containing the fusion protein (e.g., intense immunostaining in distinct cellular structures) indicates an increase in the formation of stress granules. A decrease in the number of foci containing the fusion protein, likewise, indicates a decrease in the formation of stress granules. Agents that allow for the specific up-regulation of stress granule formation in cells are of use in providing increased resistance to toxic stress in a mammalian cell (e.g., for cell replacement therapies).

The following non-limiting examples are provided to further illustrate the present invention.

EXAMPLE 1: Fusion of Wild-Type G3BP1 (G3BP1$_{FL}$) with the Photolyase Homology Region of CRY2 (CRY$_{PHR}$) Leads to Stress Granule Formation N-terminal photolyase homology region (PHR) of *Arabidopsis thaliana* cryptochrome 2 (CRY2) simultaneously oligomerize upon blue light stimulation (Bugaj, et al. (2013) *Nature Methods* 10:249; Kennedy, et al. (2000) *Nature Methods* 7:973-5). Expression of CRY2$_{PHR}$-mCherry alone in mammalian cells induces negligible visible cluster after blue light activation (Lee, et al. (2014) *Nature Methods* 11:633-636). Fusing Intrinsically Disordered (IDR) proteins to CRY2 causes reversible droplets in living cells upon blue light stimulation (Shin, et al. (2017) *Cell* 168:159-171). This system, termed OptoDroplets, creates membraneless organelles by switching on light-activated-proteins. Initially, it was determined whether OptoDroplets of FUS and TDP43 could incorporate the stress granule component G3BP1 into the droplets. This analysis indicated that G3BP1 could not be incorporated into the FUS and TDP43 Optodroplets. Moreover, OptoDroplets of FUS and TDP43 were not positive for another stress granules marker PABPC1. This indicated the OptoFUS and OptoTDP43 were not stress granules.

Accordingly, the PHR domain of CRY2 fused to mCherry (CRY2$_{PHR}$-mCherry) was PCR-amplified from plasmid pCRY2PHR-mCherryN1 (Addgene) and fused to the N-terminus of full length G3BP1 (G3BP1$_{FL}$; ASU Biodesign) and stress granule formation by blue light induction as assessed. This analysis indicated that the CRY2$_{PHR}$-mCherry-G3BP1$_{FL}$ fusion protein could form granules with blue light. Moreover, the resulting stress granules stained positive for the stress granules marker PABPC1.

EXAMPLE 2: Replacement of NTF2-Like Domain of G3BP1 (G$^3$BP1$_{D1-142}$) With CRY$_{PHR}$ Leads to Stress Granule Formation G3BP is essential for stress granules assembly as condensate (Kedersha, et al. (2016) *J. Cell Biol.* 212:845). The NTF2-like domain of G3BP1 contributes to the stress granules formation by mediating oligomerization and mutual interaction with USP10 and Caprin1 (Kedersha, et al. (2016) *J. Cell Biol.* 212:845; Tourriere, et al. (2003) *J. Cell Biol.* 160:823). To reconstitute stress granules with a light inducible system, the NTF2-like domain of G3BP1 was deleted (residues 1-142; G3BP1$_{D1-142}$) and replaced with mCherry-tagged CRY$^2_{PHR}$.

It has been reported that CRY2$_{PHR}$ alone shows some nuclear bodies and little cytoplasm clustering upon blue light stimulation, while the CRY2$_{PHR}$ E490G (CRY2$_{olig}$) rapidly forms light-dependent clusters (Lee, et al. (2014) *Nature Methods* 11:633-636; Shin, et al. (2017) *Cell* 168: 159-171; Taslimi, et al. (2014) *Nat. Commun.* 5:4925). Consistent with previous reports, mCherry-tagged CRY2$_{PHR}$ formed some nuclear clusters but limited cytoplasmic cluster, while mCherry-tagged CRY2$_{olig}$ underwent clusters robustly upon identical activation condition in U2OS cells. Under identical blue light activation, the CRY2$_{PHR}$-mCherry-G3BP1$_{D1-142}$ fusion protein could assemble into granules rapidly (in seconds). Furthermore, these granules fused to form larger granules, which disassembled in minutes after removing the stimulation. This indicates the CRY2$_{PHR}$-mCherry-G3BP1$_{D1-142}$ granules were dynamic. To further elucidate the molecular dynamics of light-induced CRY2$_{PHR}$-mCherry-G3BP1$_{D1-142}$ granules, fluorescence recovery was assessed after photobleaching (FRAP) experiments by photo-bleaching the mCherry signal. CRY2$_{PHR}$-mCherry-G3BP1$_{D1-142}$ exhibited rapid recovery and a large mobile fraction. Taken together, these data indicate that light-dependent CRY2$_{PHR}$-mCherry-G3BP1$_{D1-142}$ granules are dynamic structures.

EXAMPLE 3: CRY2$_{PHR}$-mCherry-G3BP1$_{D1-142}$ Granules are Characteristic of Stress Granules It was subsequently determined whether these CRY2$_{PHR}$-mCherry-G3BP1$_{D1-142}$ granules were stress granules. First, stress granules marker GFP-TIA1 was co-expressed with the CRY2$_{PHR}$-mCherry-G3BP1$_{D1-142}$ fusion protein. With blue light activation, CRY2$_{PHR}$-mCherry-G3BP1$_{D1-142}$ assembled into granules and GFP-TIA1 was incorporated into these granules. As a control, it was observed that GFP-TIA1 could not be incorporated into CRY2$_{olig}$ clusters. Another stress granules component TDP43 was also incorporated into CRY2$_{PHR}$-mCherry-G3BP1$_{D1-142}$ granules. As such, the CRY2$_{PHR}$-mCherry-G3BP1$_{D1-142}$ granules were positive for stress granule proteins.

Stress granules are composed of proteins and mRNA (Kedersha, et al. (2016) *J. Cell Biol.* 212:845; Panas, et al. (2016) *J. Cell Biol.* 215:313-323). To investigate whether polyadenylated mRNA were present in CRY2$_{PHR}$-mCherry-G3BP1$_{D1-142}$ granules just as in canonical stress granules, FISH analysis was performed with a fluorescently conjugated oligo(dT) probe. This analysis indicated that mRNA was recruited into CRY2$_{PHR}$-mCherry-G3BP1$_{D1-142}$ granules but not CRY$_{FL}$ or CRY2$_{olig}$ clusters after blue light stimulation. Furthermore, CRY2$_{PHR}$-mCherry-G3BP1$_{D1-142}$ granules co-localized with endogenous TDP43 after photo-activation. These data indicate that photoactive CRY2$_{PHR}$-mCherry-G3BP1$_{D1-142}$ granules are canonical stress granules.

EXAMPLE 4: CRY2$_{PHR}$-mCherry-G3BP1$_{D1-142}$ Stress Granule Assembly is Dependent on Concentration and Blue Light Intensity It has been reported that light-activated OptoDroplet formation shows a threshold in both concentration and light intensity (Shin, et al. (2017) *Cell* 168:159-171). It was contemplated that CRY2$_{PHR}$-mCherry-G3BP1$_{D1-142}$ granule assembly kinetics was dependent on the local G3BP1 molecular concentration. With the CRY2 construct, the local G3BP1 molecular concentration could be controlled according to two independent methods, expression level and blue light intensity. To characterize the dynamic kinetics of CRY2$_{PHR}$-mCherry-G3BP1$_{D1-142}$ stress granules, blue light intensity was continuously increased to photoactive the CRY4$_{PHR}$-mCherry-G3BP1$_{D1-142}$ fusion protein beginning from weak laser power. Consistent with light-activated OptoDroplet formation, the assembly of CRY2$_{PHR}$-mCherry-G3BP1$_{D1-142}$ granules was largely dependent on blue light intensity. With low blue light power, no cells could form granules. Then with double blue light power, these cells with higher expression level formed limited granules. With further increasing blue light power, more granules assembled and granules assembled in these lower expressed level cells. Furthermore, $CRY2_{PHR}$-mCherry-$G3BP1_{D1-142}$ assembled quicker with higher blue light power. It was further observed that $CRY2_{PHR}$-mCherry-$G3BP1_{D1-142}$ showed the same assembly kinetics when the blue light was saturated.

It was subsequently determined whether expression level or protein concentration contributed to assembly of $CRY2_{PHR}$-mCherry-$G3BP1_{D1-142}$ granules. With fixed blue light intensity, the assembly kinetics were compared in cells with different $CRY2_{PHR}$-mCherry-$G3BP1_{D1-142}$ expression levels. With the lowest expression level of $CRY2_{PHR}$-mCherry-$G3BP1_{D1-142}$, the cells could not form granules. The cells with higher expression levels of $CRY2_{PHR}$-mCherry-$G3BP1_{D1-142}$ could form granules faster. These data indicated that the $CRY2_{PHR}$-mCherry-$G3BP1_{D1-142}$ granule assembly was both concentration and blue light intensity dependent. However, it was noted that $CRY2_{PHR}$-mCherry-$G3BP1_{D1-142}$ stress granule formation was independent of eIF2α phosphorylation and was in dynamic equilibrium with translating polysomes.

What is claimed is:

1. A nucleic acid molecule encoding a fusion protein comprising
   (a) a plant cryptochrome (CRY) protein at the amino terminus of the fusion protein, wherein the plant cryptochrome (CRY) has the amino acid sequence of SEQ ID NO:65, and wherein said plant cryptochrome (CRY) protein lacks CCE domain,
   (b) a fluorescent reporter protein, and
   (c) a GTPase-Activating Protein SH3 Domain-Binding Protein (G3BP) at the carboxy terminus of the fusion protein, wherein the GTPase-Activating Protein SH3 Domain-Binding Protein (G3BP) has the amino acid sequence of SEQ ID NO:25, and wherein said GTPase-Activating Protein SH3 Domain-Binding Protein (G3BP) lacks NTF2-like domain.

2. The nucleic acid molecule of claim 1, wherein the fusion protein comprises the amino acid sequence of SEQ ID NO:70.

3. A vector comprising the nucleic acid molecule of claim 1.

4. A cell harboring the vector of claim 3.

* * * * *